United States Patent
Hong et al.

(10) Patent No.: US 10,329,304 B2
(45) Date of Patent: Jun. 25, 2019

(54) COMPOUNDS AND METHODS FOR INHIBITION OF HEDGEHOG SIGNALING AND PHOSPHODIESTERASE

(71) Applicant: Vanderbilt University, Nashville, TN (US)

(72) Inventors: Charles C. Hong, Nolensville, TN (US); Charles H. Williams, Nashville, TN (US); Jonathan Hempel, Nashville, TN (US); T K Feaster, Nashville, TN (US); Don H. Rubin, Nashville, TN (US); Gary Sulikowski, Brentwood, TN (US); Jijun Hao, Biamond Bar, CA (US); Audrey Frist, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 0 days.

(21) Appl. No.: 15/452,551

(22) Filed: Mar. 7, 2017

(65) Prior Publication Data

US 2017/0190717 A1 Jul. 6, 2017

Related U.S. Application Data

(63) Continuation-in-part of application No. PCT/US2015/050024, filed on Sep. 14, 2015.

(60) Provisional application No. 62/049,735, filed on Sep. 12, 2014, provisional application No. 62/199,442, filed on Jul. 31, 2015, provisional application No. 62/304,513, filed on Mar. 7, 2016.

(51) Int. Cl.

| | |
|---|---|
| *C07D 495/14* | (2006.01) |
| *C07D 495/04* | (2006.01) |
| *C07D 409/12* | (2006.01) |
| *C07D 471/04* | (2006.01) |
| *C07D 333/38* | (2006.01) |
| *A61K 45/06* | (2006.01) |
| *A61K 9/00* | (2006.01) |
| *A61K 31/519* | (2006.01) |
| *A61K 31/5377* | (2006.01) |
| *A61K 31/517* | (2006.01) |
| *A61K 31/381* | (2006.01) |

(52) U.S. Cl.
CPC .......... *C07D 495/14* (2013.01); *A61K 9/0019* (2013.01); *A61K 9/0078* (2013.01); *A61K 31/381* (2013.01); *A61K 31/517* (2013.01); *A61K 31/519* (2013.01); *A61K 31/5377* (2013.01); *A61K 45/06* (2013.01); *C07D 333/38* (2013.01); *C07D 409/12* (2013.01); *C07D 471/04* (2013.01); *C07D 495/04* (2013.01)

(58) Field of Classification Search
CPC .. C07D 333/38; C07D 409/12; C07D 471/04; C07D 495/04; C07D 495/14; A61K 31/381; A61K 31/517; A61K 31/519; A61K 31/5377; A61K 45/06; A61K 9/0078

See application file for complete search history.

(56) References Cited

U.S. PATENT DOCUMENTS

| | | | |
|---|---|---|---|
| 8,481,553 B2 * | 7/2013 | Hansen | ................ A61K 31/167 514/262.1 |
| 2006/0025415 A1 | 2/2006 | Gonzalez et al. | |
| 2013/0225610 A1 | 8/2013 | Hansen et al. | |

FOREIGN PATENT DOCUMENTS

WO    2016040951 A1    3/2016

OTHER PUBLICATIONS

Tani, et al., Antifungal activities of novel non-azole molecules against S. cerevisiae and C. albicans, Eur. J. of Med. Chem., 47, 270-277 (2012).*
Pola, R., et al., The morphogen Sonic Hedgehog is an indirect angiogenic agent upregulating two families of angiogenic growth factors. Nat Med, 2001. 7(6): p. 706-11.
Powers, G. L.; Hammer, K. D. P.; Domenech, M.; Frantskevich, K.; Malinowski, R. L.; Bushman, W.; Beebe, D. J.; Marker, P. C. Mol. Cancer Res. 2015, 13, 149-160.
Pullamsetti, S. S. et al. Phosphodiesterase-4 promotes proliferation and angiogenesis of lung cancer by crosstalk with HIF. Oncogene (2012).doi:10.1038/onc.2012.136.
Rahnama, F., et al., Inhibition of GLI1 gene activation by Patched1. Biochem 1, 2006. 394(Pt 1): p. 19-26.
Reid, D., Sadjad, B. S., Zsoldos, Z. & Simon, A. LASSO—ligand activity by surface similarity order: a new tool for ligand based virtual screening. J. Comput. Aided Mol. Des. 22, 479-487 (2008).
Robarge, K. D.; Brunton, S. A.; Castanedo, G. M.; Cui, Y.; Dina, M. S.; Goldsmith, R.; Gould, S. E.; Guichert, O.; Gunzner, J. L.; Halladay, J.; Jia, W.; Khojasteh, C.; Koehler, M. F. T.; Kotkow, K.; La, H.; LaLonde, R. L.; Lau, K.; Lee, L.; Marshall, D.; Marsters, J. C., Jr.; Murray, L. J.; Qian, C.; Rubin, L. L.; Salphati,L.; Stanley, M. S.; Stibbard, J. H. A.; Sutherlin, D. P.; Ubhayaker, S.; Wang, S.; Wong, S.; Xie, M. Bioorganic & Medicinal Chemistry Letters 2009, 19, 5576-5581.
Rocque, W. J. et al. Detailed characterization of a purified type 4 phosphodiesterase, HSPDE4B2B: differentiation of high- and low-affinity (R)-rolipram binding. Protein Expr. Purif. 9, 191-202 (1997).
Rocque, W. J. et al. Human recombinant phosphodiesterase 4B2B binds (R)-rolipram at a single site with two affinities. Biochemistry 36, 14250-14261 (1997).
Rohatgi, R., Milenkovic, L. & Scott, M. P. Patched1 regulates hedgehog signaling at the primary cilium. Science 317, 372-376 (2007).
Rosow, D. E.; Liss, A. S.; Strobel, O.; Fritz, S.; Bausch, D.; Valsangkar, N. P.; Alsina, J.; Kulemann, B.; Park, J. K.; Yamaguchi, J.; LaFemina, J.; Thayer, S. P. Surgery 2012, 152, S19-S32.
Rudin, C. M.; Hann, C. L.; Laterra, J.; Yauch, R. L.; Callahan, C. A.; Fu, L.; Holcomb, T.; Stinson, J.; Gould, S. E.; Coleman, B.; LoRusso, P. M.; Hoff, Von, D. D.; de Sauvage, F. J.; Low; J. A. N Engl J Med 2009, 361, 1173-1178.

(Continued)

*Primary Examiner* — Erich A Leeser
(74) *Attorney, Agent, or Firm* — Stites & Harbison PLLC; Mandy Wilson Decker

(57) ABSTRACT

Compounds and compositions, and methods of use thereof, are provided and have utility in inhibiting hedgehog signaling and/or phosphodiesterase-4 activity.

13 Claims, 39 Drawing Sheets

(56) References Cited

OTHER PUBLICATIONS

Ryan, K. E. & Chiang, C. Hedgehog secretion and signal transduction in vertebrates. J. Biol. Chem. 287, 17905-17913 (2012).
Sanchez, P., et al., Inhibition of prostate cancer proliferation by interference with SONIC HEDGEHOG-GLII signaling. Proc Natl Acad Sci USA, 2004. 101(34): p. 12561-6.
Sasaki, H., et al., A binding site for Gli proteins is essential for HNF-3beta floor plate enhancer activity in transgenics and can respond to Shh in vitro. Development, 1997. 124(7): p. 1313-22.
Schneider, H. H., Schmiechen, R., Brezinski, M. & Seidler, J. Stereospecific binding of the antidepressant rolipram to brain protein structures. Eur. J. Pharmacol. 127, 105-115 (1986).
Schwend, T., Loucks, E. J. & Ahlgren, S. C. Visualization of Gli activity in craniofacial tissues of hedgehog-pathway reporter transgenic zebrafish. PLoS ONE 5, e14396 (2010).
Seldon PM, Barnes PJ, Meja K, Giembycz MA. Suppression of lipopolysaccharide-induced tumor necrosis factor-alpha generation from human peripheral blood monocytes by inhibitors of phosphodiesterase 4: interaction with stimulants of adenylyl cyclase. Mol Pharmacol. Oct. 1995;48(4):747-57.
Sengupta, R., Sun, T., Warrington, N. M. & Rubin, J. B. Treating brain tumors with PDE4 inhibitors. Trends Pharmacol. Sci. 32, 337-344 (2011).
Sharpe, H. J.; Pau, G.; Dijkgraaf, G. J.; Basset-Seguin, N.; Modrusan, Z.; Januario, T.; Tsui, V.; Durham, A. B.; Dlugosz, A. A.; Haverty, P. M.; Bourgon, R.; Tang, J. Y.; Sarin, K. Y.; Dirix, L.; Fisher, D. C.; Rudin, C. M.; Sofen, H.; Migden, M. R.; Yauch, R. L.; de Sauvage, F. J. Cancer Cell 2015, 27, 327-341.
Shame, H. J.; Wang, W.; Hannoush, R. N.; de Sauvage, F. J. Nat Chem Biol 2015, 11, 246-255.
Shultz, M. D. Bioorganic & Medicinal Chemistry Letters 2013, 23, 5980-5991.
Sinha, S. and J.K. Chen, Purmorphamine activates the Hedgehog pathway by targeting Smoothened. Nat Chem Biol, 2006. 2(1): p. 29-30.
Souness, J. E. et al. Evidence that cyclic AMP phosphodiesterase inhibitors suppress TNF alpha generation from human monocytes by interacting with a 'low-affinity' phosphodiesterase 4 conformer. Br. J. Pharmacol. 118, 649-658 (1996).
Stecca, B. and A. Ruiz i Altaba, Brain as a paradigm of organ growth: Hedgehog-Gli signaling in neural stem cells and brain tumors. J Neurobiol, 2005. 64(4): p. 476-90.
Stecca, B., et al., Melanomas require HEDGEHOG-GLI signaling regulated by interactions between GLI1 and the RAS-MEK/AKT pathways. Proc Natl Acad Sci USA, 2007. 104(14): p. 5895-900.
Still, W. C.; Kahn, M.; Mitra, A. J. Org. Chem. 1978, 43 (14), 2923-2925.
Sun, Y., Li, L., Lau, F., Beavo, J. A. & Clark, E. A. Infection of CD4+ memory T cells by HIV-1 requires expression of phosphodiesterase 4. J. Immunol. 165, 1755-1761 (2000).
Surace, E.M., et al., Inhibition of ocular neovascularization by Hedgehog blockade. Mol Ther, 2006. 13(3): p. 573-9.
Svärd, J.; Heby-Henricson, K.; Henricson, K. H.; Persson-Lek, M.; Rozell, B.; Lauth, M.; Bergström, A.; Ericson, J.; Toftgård, R.; Teglund, S. Developmental Cell 2006, 10, 187-197.
Taipale, J. and P.A. Beachy, The Hedgehog and Wnt signalling pathways in cancer. Nature, 2001. 411 (6835): p. 349-54.
Taipale, J., et al., Effects of oncogenic mutations in Smoothened and Patched can be reversed by cyclopamine. Nature, 2000. 406(6799): p. 1005-9.
Taipale, J.; Cooper, M. K.; Maiti, T.; Beachy, P. A. Nature 2002, 418, 892-896.
Tang, Y.; Gholamin, S.; Schubert, S.; Willardson, M. I.; Lee, A.; Bandopadhayay, P.; Bergthold, G.; Masoud, S.; Nguyen, B.; Vue, N.; Balansay, B.; Yu, F.; Oh, S.; Woo, P.; Chen, S.; Ponnuswami, A.; Monje, M.; Atwood, S. X.; Whitson, R. J.; Mitra, S.; Cheshier, S. H.; Qi, J.; Beroukhim, R.; Tang, J. Y.; Wechsler-Reya, R.; Oro, A. E.; Link, B. A.; Bradner, J. E.; Cho, Y.-J. Nat. Med. 2014, 20, 732-740.
Taskén, K. A. et al. Phosphodiesterase 4D and protein kinase a type II constitute a signaling unit in the centrosomal area. J. Biol. Chem. 276, 21999-22002 (2001).
Terrin, A. et al. PKA and PDE4D3 anchoring to AKAP9 provides distinct regulation of cAMP signals at the centrosome. J. Cell Biol. 198, 607-621 (2012).
Thayer, S.P., et al., Hedgehog is an early and late mediator of pancreatic cancer tumorigenesis. Nature, 2003. 425 (6960): p. 851-6.
Torphy, T. J. et al. Coexpression of human cAMP-specific phosphodiesterase activity and high affinity rolipram binding in yeast. J. Biol. Chem. 267, 1798-1804 (1992).
Tremblay, M. R.; Lescarbeau, A.; Grogan, M. J.; Tan, E.; Lin, G.; Austad, B. C.; Yu, L.-C.; Behnke, M. L.; Nair, S. J.; Hagel, M.; White, K.; Conley, J.; Manna, J. D.; Alvarez-Diez, T. M.; Hoyt, J.; Woodward, C. N.; Sydor, J. R.; Pink, M.; MacDougall, J.; Campbell, M. J.; Cushing, J.; Ferguson, J.; Curtis, M. S.; McGovern, K.; Read, M. A.; Palombella, V. J.; Adams, J.; Castro, A. C. Journal of Medicinal Chemistry 2009, 52, 4400-4418.
Tukachinsky, H. Lopez, L. V. & Salic, A. A mechanism for vertebrate Hedgehog signaling: recruitment to cilia and dissociation of SuFu-Gli complexes. J. Cell Biol. 191, 415-428 (2010).
Tuson, M., He, M. & Anderson, K. V. Protein kinase A acts at the basal body of the primary cilium to prevent Gli2 activation and ventralization of the mouse neural tube. Development 138, 4921-4930 (2011).
van Eeden, F. J. et al. Mutations affecting somite formation and patterning in the zebrafish, Danio rerio. Development 123, 153-164 (1996).
van Eeden, F.J., et al., Genetic analysis of fin formation in the zebra fish, Danio rerio. Development, 1996. 123: p. 255-62.
Wada, N. et al. Hedgehog signaling is required for cranial neural crest morphogenesis and chondrogenesis at the midline in the zebrafish skull. Development 132, 3977-3988 (2005).
Wang, B., Fallon, J. F. & Beachy, P. A. Hedgehog-regulated processing of Gli3 produces an anterior/posterior repressor gradient in the developing vertebrate limb. Cell 100, 423-434 (2000).
Watkins, D.N., et al., Hedgehog signalling within airway epithelial progenitors and in small-cell lung cancer. Nature, 2003. 422(6929): p. 313-7.
Wen, X. et al. Kinetics of hedgehog-dependent full-length Gli3 accumulation in primary cilia and subsequent degradation. Mol. Cell. Biol. 30, 1910-1922 (2010).
Wichterle, H., et al., Directed differentiation of embryonic stem cells into motor neurons. Cell, 2002.110(3): p. 385-97.
Williams C. H.; Hempel, J. E.; Hao, J.; Frist, A. Y.; Williams, M. M.; Fleming, J. T.; Sulikowski, G. A.; Cooper, M. K.; Chiang, C.; Hong, C. C. Cell Reports 2015, 11, 43-50.
Williams, J.A., et al., Identification of a small molecule inhibitor of the Hedgehog signaling pathway: effects on basal cell carcinoma-like lesions. Proc Natl Acad Sci USA, 2003. 100(8): p. 4616-21.
Wu, X, et al., A small molecule with osteogenesis-inducing activity in multipotent mesenchymal progenitor cells . .J Am Chern Soc, 2002. 124(49): p. 14520-1.
Houslay, M. D. & Adams, D. R. Putting the lid on phosphodiesterase 4. Nat. Biotechnol. 28, 38-40 (2010).
Houslay, M. D., Schafer, P. & Zhang, K. Y. J. Keynote review: phosphodiesterase-4 as a therapeutic target. Drug Discov. Today 10, 1503-1519 (2005).
Huang, P. & Schier, A. F. Dampened Hedgehog signaling but normal Wnt signaling in zebrafish without cilia. Development 136, 3089-3098 (2009).
Huang, Y.; Wolf, S.; Bista, M.; Meireles, L.; Camacho, C.; Holak, T. A; Dömling, A. "1,4-Thienodiazepine-2,5-diones via MCR (I): Synthesis, Virtual Space and p53-Mdm2 Activity" Chemical Biology & Drug Design, 2010, 76, 116-129.
Hui, C.-C.; Angers, S. Annu. Rev. Cell Dev. Biol. 2011, 27, 513-537.
Huitorel, P. From cilia and flagella to intracellular motility and back again: a review of a few aspects of microtubule-based motility. Biol. Cell 63, 249-258 (1988).
Hartikka, et al., Cyclic AMP, But Not Basic FGF, Increases the In Vitro Survival of Mesencephalic Dopaminergic Neurons and Pro-

(56) References Cited

OTHER PUBLICATIONS tects Them From MPP+-Induced Degeneration, 1992, Journal of Neuroscience Research 32: 190-201.
Hyman, J. M. et al. Small-molecule inhibitors reveal multiple strategies for Hedgehog pathway blockade. Proc. Natl. Acad. Sci. U.S.A. 106, 14132-14137 (2009).
Incardona, J.P., et al., The teratogenic Veratrum alkaloid cyclopamine inhibits sonic Hedgehog signal transduction. Development, 1998. 125(18): p. 3553-62.
Infante, P.; Alfonsi, R.; Botta, B.; Mori, M.; Di Marcotullio, L. Trends in Pharmacological Sciences 2015, 36, 547-558.
Ingham, P.W. and A.P. McMahon, Hedgehog signaling in animal development: paradigms and principles. Genes Dev, 2001. 15(23): p. 3059-87.
Ivachtchenko, A.; Kovalenko, S.; Tkachenko, O. V.; Parkhomenko, O. "Synthesis of Substituted Thienopyrimidine-4-ones" Journal of Combinatorial Chemistry, 2004, 6, 573-583.
Jacobitz, S., McLaughlin, M. M., Livi, G. P., Burman, M. & Torphy, T. J. Mapping the functional domains of human recombinant phosphodiesterase 4A: structural requirements for catalytic activity and rolipram binding. Mol. Pharmacol. 50, 891-899 (1996).
Jiang, J. & Struhl, G. Protein kinase A and hedgehog signaling in Drosophila limb development. Cell 80, 563-572 (1995).
Jimenez JL, Punzón C, Navarro J, Muñoz-Fernández MA, Fresno M. Phosphodiesterase 4 inhibitors prevent cytokine secretion by T lymphocytes by inhibiting nuclear factor-kappaB and nuclear factor of activated T cells activation. J Pharmacol Exp Ther. Nov. 2001;299(2):753-9.
Johnson, R.L., et al., Human homolog of patched, a candidate gene for the basal cell nevus syndrome. Science, 1996. 272(5268): p. 1668-71.
Jones, S., et al., Core Signaling Pathways in Human Pancreatic Cancers Revealed by Global Genomic Analyses. Science, 2008.
Kar, S.; Deb, M.; Sengupta, D.; Shilpi, A.; Bhutia, S. K.; Patra, S. K. Exp. Cell Res. 2012, 318, 1959-1972.
Karaman MW, Herrgard S, Treiber DK, et al. A quantitative analysis of kinase inhibitor selectivity. Nat. Biotechnol. 2008;26(1):127-132.
Karhadkar, S.S., et al., Hedgehog signalling in prostate regeneration, neoplasia and metastasis. Nature, 2004. 431 (7009): p. 707-12.
Kasper, M., et al., GLI transcription factors: mediators of oncogenic Hedgehog signalling. Eur J Cancer, 2006. 42(4): p. 437-45.
Kim, J.; Aftab, B. T.; Tang, J. Y.; Kim, D.; Lee, A. H.; Rezaee, M.; Kim, J.; Chen, B.; King, E. M.; Borodovsky, A.; Riggins, G. J.; Epstein, E. H.; Beachy, P. A.; Rudin, C. M. Cancer Cell 2013, 23, 23-34.
Klarenbeek, J. B., Goedhart, J., Hink, M. A., Gadella, T. W. J. & Jalink, K. A mTurquoise-Based cAMP Sensor for Both FLIM and Ratiometric Read-Out Has Improved Dynamic Range. PLoS ONE 6, e19170 (2011).
Lauth, M.; Bergström, A.; Shimokawa, T.; Toftgård, R. Proceedings of the National Academy of Sciences 2007, 104, 8455-8460.
Lawson, N.D., A.M. Vogel, and B.M. Weinstein, sonic Hedgehog and vascular endothelial growth factor act upstream of the Notch pathway during arterial endothelial differentiation. Dev Cell, 2002. 3(1): p. 127-36.
Liu, A., Wang, B. & Niswander, L. A. Mouse intraflagellar transport proteins regulate both the activator and repressor functions of Gli transcription factors. Development 132, 3103-3111 (2005).
Long J.; Li, B.; Rodriguez-Blanco, J.; Pastori, C.; Volmar, C.-H.; Wahlestedt, C.; Capobianco, A.; Bai, F.; Pei, X.-H.; Ayad, N. G.; Robbins, D. J. Journal of Biological Chemistry 2014, 289, 35494-35502.
Low, J. A.; de Sauvage, F. J. J. Clin. Oncol. 2010, 28, 5321-5326.
Mahindroo, N.; Punchihewa, C.; Fujii, N. Journal of Medicinal Chemistry 2009, 52, 3829-3845.
Marko D, Romanakis K, Zankl H, Fürstenberger G, Steinbauer B, Eisenbrand G. Induction of apoptosis by an inhibitor of cAMP-specific PDE in malignant murine carcinoma cells overexpressing PDE activity in comparison to their nonmalignant counterparts. Cell Biochem Biophys. 1998;28(2-3)15-101.

McCahill, A. et al. In resting COS1 cells a dominant negative approach shows that specific, anchored PDE4 cAMP phosphodiesterase isoforms gate the activation, by basal cyclic AMP production, of AKAP-tethered protein kinase A type II located in the centrosomal region. Cell. Signal. 17, 1158-1173 (2005).
McEwan, D. G. et al. Chemoresistant KM12C colon cancer cells are addicted to low cyclic AMP levels in a phosphodiesterase 4-regulated compartment via effects on phosphoinositide 3-kinase. Cancer Res. 67, 5248-5257 (2007).
McFerren, M.A., Useful plants of dermatology. VIII. The false hellebore (Veratrum californicum). J Am Acad Dermatol, 2006. 54(4): p. 7 18-20.
McMahon, A.P., P.W. Ingham, and C.J. Tabin, Developmental roles and clinical significance of Hedgehog signaling. Curr Top Dev Biol, 2003. 53: p. 1-114.
Metcalfe, C.; de Sauvage, F. J. Cancer Research 2011, 71, 5057-5061.
Miller-Moslin, K.; Peukert, S.; Jain, R. K.; McEwan, M. A.; Karki, R.; Llamas, L.; Yusuff, N.; He, F.; Li, Y.; Sun, Y.; Dai, M.; Perez, L.; Michael, W.; Sheng, T.; Lei, H.; Zhang, R.; Williams, J.; Bourret, A.; Ramamurthy, A.; Yuan, J.; Guo, R.; Matsumoto, M.; Vattay, A.; Maniara, W.; Amaral, A.; Dorsch, M.; Kelleher, J. F., III. Journal of Medicinal Chemistry 2009, 52, 3954-3968.
Munchhof, M. J.; Li, Q.; Shavnya, A.; Borzillo, G. V.; Boyden, T. L.; Jones, C. S.; LaGreca, S. D.; Martinez-Alsina, L.; Patel, N.; Pelletier, K.; Reiter, L. A.; Robbins, M. D.; Tkalcevic, G. T. ACS Med Chem Lett 2012, 3, 106-111.
Ng, J. M. Y.; Curran, T. Nature Reviews Cancer 2011, 11, 493-501.
Nikulina E, Tidwell JL, Dai HN, Bregman BS, Filbin MT. The phosphodiesterase inhibitor rolipram delivered after a spinal cord lesion promotes axonal regeneration and functional recovery. Proc Natl Acad Sci U S A. Jun. 8, 2004;101 (23):8786-90.
Noveen A, Jiang TX, Chuong CM. cAMP, an activator of protein kinase A, suppresses the expression of sonic hedgehog. Biochem Biophys Res Commun. Feb. 6, 1996;219(1):180-5.
Nusslein-Volhard, C. and E. Wieschaus, Mutations affecting segment number and polarity in Drosophila. Nature, 1980. 287(5785): p. 795-801.
Ogden, S. K. et al. G protein Galphai functions immediately downstream of Smoothened in Hedgehog signalling. Nature 456, 967-970 (2008).
Ohashi, T.; Oguro, Y.; Tanaka, T.; Shiokawa, Z.; Tanaka, Y.; Shibata, S.; Sato, Y.; Yamakawa, H.; Hattori, H.; Yamamoto, Y.; Kondo, S.; Miyamoto, M.; Nishihara, M.; Ishimura, Y.; Tojo, H.; Baba, A.; Sasaki, S. Bioorg Med Chem 2012, 20, 5507-5517.
Pan, S.; Wu, X.; Jiang, J.; Gao, W.; Wan, Y.; Cheng, D.; Han, D.; Liu, J.; Englund, N. P.; Wang, Y.; Peukert, S.; Miller-Moslin, K.; Yuan, J.; Guo, R.; Matsumoto, M.; Vattay, A.; Jiang, Y.; Tsao, J.; Sun, F.; Pferdekamper, A. C.; Dodd, S.; Tuntland, T.; Maniara, W.; Kelleher, J. F.; Yao, Y.-M.; Warmuth, M.; Williams, J.; Dorsch, M. ACS Med Chem Lett 2010, 1, 130-134.
Pan, Y., Bai, C. B., Joyner, A. L. & Wang, B. Sonic hedgehog signaling regulates Gli2 transcriptional activity by suppressing its processing and degradation. Mol. Cell. Biol. 26, 3365-3377 (2006).
Parsons, D.W., et al., An Integrated Genomic Analysis of Human Glioblastoma Multiforme. Science, 2008.
Pasca di Magliano, M. and M. Hebrok, Hedgehog signalling in cancer formation and maintenance. Nat Rev Cancer, 2003. 3(12): p. 903-11.
Pauls S, Zecchin E, Tiso N, Bortolussi M, Argenton F. Function and regulation of zebrafish nkx2.2a during development of pancreatic islet and ducts. Dev Biol. Apr. 15, 2007;304(2):875-90.
Peacock, C.D., et al., Hedgehog signaling maintains a tumor stem cell compartment in multiple myeloma. Proc Natl Acad Sci USA, 2007. 104(10): p. 4048-53.
Xie, J., et al., Activating Smoothened mutations in sporadic basal-cell carcinoma. Nature, 1998. 391(6662): p. 90-2.
Yauch, R. L. et al. Smoothened mutation confers resistance to a Hedgehog pathway inhibitor in medulloblastoma. Science 2009, 326, 572-574.
Yauch, R.L., et al., A paracrine requirement for Hedgehog signalling in cancer. Nature, 2008.

(56) References Cited

OTHER PUBLICATIONS

Yu PB, Hong CC, Sachidanandan C, et al. Dorsomorphin inhibits BMP signals required for embryogenesis and iron metabolism. Nat. Chem. Biol. 2008;4(1):33-41.

Zhang HT, Zhao Y, Huang Y, Dorairaj NR, Chandler LJ, O'Donnell JM. Inhibition of the phosphodiesterase 4 (PDE4) enzyme reverses memory deficits produced by infusion of the MEK inhibitor U0126 into the CA1 subregion of the rat hippocampus. Neuropsychopharmacology. Aug. 2004;29(8):1432-9.

Zhao, Y. Zhang, H.-T. & O'Donnell, J. M. Inhibitor binding to type 4 phosphodiesterase (PDE4) assessed using [3H] piclamilast and [3H]rolipram. J. Pharmacol. Exp. Ther. 305, 565-572 (2003).

Zilberberg L, ten Dijke P, Sakai LY, Rifkin DB. A rapid and sensitive bioassay to measure bone morphogenetic protein activity. BMC Cell Biol. 2007;8:41.

Hempel JE, Cadar AG, Hong CC. Bioorg Med Chem Lett. Apr. 15, 2016;26(8):1947-53.

Carney, et al., Drugging Hedgehog: signaling the-pathway to translation, Biology 2013, 11:37; 5 pages.

Alagarsamy, V.; Meena, S.; Ramseshu, K. V.; Solomon, V. R.; Thirumurugan, K.; Dhanabal, K.; Murugan, M. "Synthesis, Analgesic, Anti-Inflammatory, Ulcerogenic Index and Antibacterial Activities of Novel 2-Methylthio-3-substituted-5,6,7,8-tetrahydrobenzo (b) thieno[2,3-d]pyrimidin-4(3H)-ones" European Journal of Medicinal Chemistry, 2006, 41, 1293-1300.

Alagarsamy, V.; Rajesh, R.; Ramaseshu, M.; Vijaykumar, S.; Ramseshu, K. V.; Duraianandakumar, T. Biol. Pharm. Bull. 2004, 27, 652-656.

Ashton, M. J. et al. Selective type IV phosphodiesterase inhibitors as antiasthmatic agents. The syntheses and biological activities of 3-(cyclopentyloxy)-4-methoxybenzamides and analogues. J. Med. Chem. 37, 1696-1703 (1994).

Atwood, S. X.; Sarin, K. Y.; Whitson, R. J.; Li, J. R.; Kim, G.; Rezaee, M.; Ally, M. S.; Kim, J.; Yao, C.; Chang, A. L. S.; Oro, A. E.; Tang, J. Y. Cancer Cell 2015, 27, 342-353.

Ayers, K. L. & Thérond, P. P. Evaluating Smoothened as a G-protein-coupled receptor for Hedgehog signalling. Trends Cell Biol. 20, 287-298 (2010).

Baillie, G. S. Compartmentalized signalling: spatial regulation of cAMP by the action of compartmentalized phosphodiesterases. FEBS J. 276, 1790-1799 (2009).

Barad M, Bourtchouladze R, Winder DG, Golan H, Kandel E. Rolipram, a type IV-specific phosphodiesterase inhibitor, facilitates the establishment of long-lasting long-term potentiation and improves memory. Proc Natl Acad Sci U S A. Dec. 8, 1998;95(25):15020-5.

Barresi, M. J., Stickney, H. L. & Devoto, S. H. The zebrafish slow-muscle-omitted gene product is required for Hedgehog signal transduction and the development of slow muscle identity. Development 127, 2189-2199 (2000).

Barzi, M., Berenguer, J., Menendez, A., Alvarez-Rodriguez, R. & Pons, S. Sonic-hedgehog-mediated proliferation requires the localization of PKA to the cilium base. J. Cell. Sci. 123, 62-69 (2010).

Beachy, P.A., S.S. Karhadkar, and D.M. Berman, Tissue repair and stem cell renewal in carcinogenesis. Nature, 2004. 432(7015): p. 324-31.

Berman, D.M., et al., Medulloblastoma growth inhibition by Hedgehog pathway blockade. Science, 2002. 297(5586): p. 1559-61.

Berman, DM., et al., Widespread requirement for Hedgehog ligand stimulation in growth of digestive tract tumours. Nature, 2003. 425(6960): p. 846-51.

Burgin, A. B. et al. Design of phosphodiesterase 4D (PDE4D) allosteric modulators for enhancing cognition with improved safety. Nature Biotechnology 28, 63-70 (2010).

Chandrasekaran, A. et al. Identification and characterization of novel mouse PDE4D isoforms: molecular cloning, subcellular distribution and detection of isoform-specific intracellular localization signals. Cell. Signal. 20, 139-153 (2008).

Chen, J. K.; Taipale, J.; Cooper, M. K.; Beachy, P. A. Genes Dev. 2002, 16, 2743-2748.

Chen, J.K., et al., Small molecule modulation of Smoothened activity. Proc Natl Acad Sci U S A, 2002. 99(22): p. 14071-6.

Chen, W., S. Burgess, and N. Hopkins, Analysis of the zebrafish smoothened mutant reveals conserved and divergent functions of Hedgehog activity. Development, 2001. 128(12): p. 2385-96.

Chiang, C., et al., Cyclopia and defective axial patterning in mice lacking Sonic Hedgehog gene function. Nature, 1996. 383(6599): p. 407-13.

Chiang, C., et al., Essential role for Sonic Hedgehog during hair follicle morphogenesis. Dev Biol, 1999. 205(1): p. 1-9.

Clement, V., et al., HEDGEHOG-GLI1 signaling regulates human glioma growth, cancer stem cell self-renewal, and tumorigenicity. Curr Biol, 2007. 17(2): p. 165-72.

Cohen, M. M., Jr. Hedgehog signaling update. Am. J. Med. Genet. A 152A, 1875-1914 (2010).

Collier, L. S., Suyama, K., Anderson, J. H. & Scott, M. P. Drosophila Costal1 mutations are alleles of protein kinase A that modulate hedgehog signaling. Genetics 167, 783-796 (2004).

Concordet JP, Lewis KE, Moore JW, et al. Spatial regulation of a zebrafish patched homologue reflects the roles of sonic hedgehog and profein kinase A in neural tube and somite patterning. Development. 1996;122(9):2835-2846.

Cooper, M.K., et al., Teratogen-mediated inhibition of target tissue response to Shh signaling. Science, 1998. 280 (5369): p. 1603-7.

Corbit, K. C. et al. Vertebrate Smoothened functions at the primary cilium. Nature 437, 1018-1021 (2005).

Dockendorff, C.; Nagiec, M. M.; Weïwer, M.; Buhrlage, S.; Ting, A.; Nag, P. P.; Germain, A.; Kim, H.-J.; Youngsaye, W.; Scherer, C.; Bennion, M.; Xue, L.; Stanton, B. Z.; Lewis, T. A.; MacPherson, L.; Palmer, M.; Foley, M. A.; Perez, J. R.; Schreiber, S. L. ACS Med Chem Lett 2012, 3, 808-811.

Ekholm, D. et al. Cyclic nucleotide phosphodiesterases (PDE) 3 and 4 in normal, malignant, and HTLV-I transformed human lymphocytes. Biochem. Pharmacol. 58, 935-950 (1999).

Fabian MA, Biggs WH, Treiber DK, et al. A small molecule-kinase interaction map for clinical kinase inhibitors. Nat Biotech. 2005;23(3):329-336.

Favot L, Keravis T, Lugnier C. Modulation of VEGF-induced endothelial cell cycle protein expression through cyclic AMP hydrolysis by PDE2 and PDE4. Thromb Haemost. Sep. 2004;92(3):634-45.

Feldmann, G., et al., Blockade of Hedgehog signaling inhibits pancreatic cancer invasion and metastases: a new paradigm for combination therapy in solid cancers. Cancer Res, 2007. 67(5): p. 2187-96.

Fietz, M.J., et al., The Hedgehog gene family in Drosophila and vertebrate development. Dev Suppl, 1994: p. 43-51.

Firestone, A. J. et al. Small-molecule inhibitors of the AAA+ ATPase motor cytoplasmic dynein. Nature 484, 125-129 (2012).

Fondjo, E. S.; Döpp, D.; Henkel, G. Tetrahedron 2006, 62, 7121-7131.

Frank-Kamenetsky, M., et al., Small-molecule modulators of Hedgehog signaling: identification and characterization of Smoothened agonists and antagonists. 1 Biol, 2002. 1(2): p. 10.

Gailani, M.R. and A.E. Bale, Developmental genes and cancer: role of patched in basal cell carcinoma of the skin. J Natl Cancer Inst, 1997. 89(15): p. 1103-9.

Gailani, M.R., et al., The role of the human homologue of Drosophila patched in sporadic basal cell carcinomas. Nat Genet, 1996. 14(1): p. 78-81.

Gaspard, N., et al., An intrinsic mechanism of corticogenesis from embryonic stem cells. Nature, 2008.

Ge, X.; Milenkovic, L.; Suyama, K.; Hartl, T.; Purzner, T.; Winans, A.; Meyer, T.; Scott, M. P. eLife Sciences 2015, 4, e07068.

Gering, J., et al., Taking a patient safety approach to an integration of two hospitals. Jt Comm J Qual Patient Saf, 2005. 31(5): p. 258-66.

Gering, M. and R. Patient, Hedgehog signaling is required for adult blood stem cell formation in zebrafish embryos. Dev Cell, 2005. 8(3): p. 389-400.

Goldhoff, P. et al. Targeted inhibition of cyclic AMP phosphodiesterase-4 promotes brain tumor regression. Clin. Cancer Res. 14, 7717-7725 (2008).

Gudjonsson, J.E., et al., Lack of Evidence for Activation of the Hedgehog Pathway in Psoriasis. J Invest Dermatol, 2008.

(56) References Cited

OTHER PUBLICATIONS

Hahn, H., et al., Mutations of the human homolog of *Drosophila* patched in the nevoid basal cell carcinoma syndrome. Cell, 1996. 85(6): p. 841-51.

Hao J, Williams CH, Webb ME, Hong CC. Large scale zebrafish-based in vivo small molecule screen. J Vis Exp. 2010; (46). Available at: http://www.ncbi.nlm.nih.gov/pubmed/21248690. Accessed Nov. 8, 2011.

Haycraft, C. J. et al. Gli2 and Gli3 localize to cilia and require the intraflagellar transport protein polaris for processing and function. PLoS Genet. 1, e53 (2005).

Hesse, S.; Perspicace, E.; Kirsch, G. Tetrahedron Lett 2007, 48, 5261-5264.

Hirsinger, E., Stellabotte, F., Devoto, S. H. & Westerfield, M. Hedgehog signaling is required for commitment but not initial induction of slow muscle precursors. Dev. Biol. 275, 143-157 (2004).

Hoff, Von, D. D.; LoRusso, P. M.; Rudin, C. M.; Reddy, J. C.; Yauch, R. L.; Tibes, R.; Weiss, G. J.; Borad, M. J.; Hann, C. L.; Brahmer, J. R.; Mackey, H. M.; Lum, B. L.; Darbonne, W. C.; Marsters, J. C., Jr.; de Sauvage, F. J.; Low, J. A. N Engl J Med 2009, 361, 1164-1172.

Hong CC. Large-scale small-molecule screen using zebrafish embryos. Methods Mol. Biol. 2009;486:43-55.

Hosoya, T., et al., Naturally occurring small-molecule inhibitors of Hedgehog/ GLI-mediated transcription. Chembiochem, 2008. 9(7): p. 1082-92.

\* cited by examiner

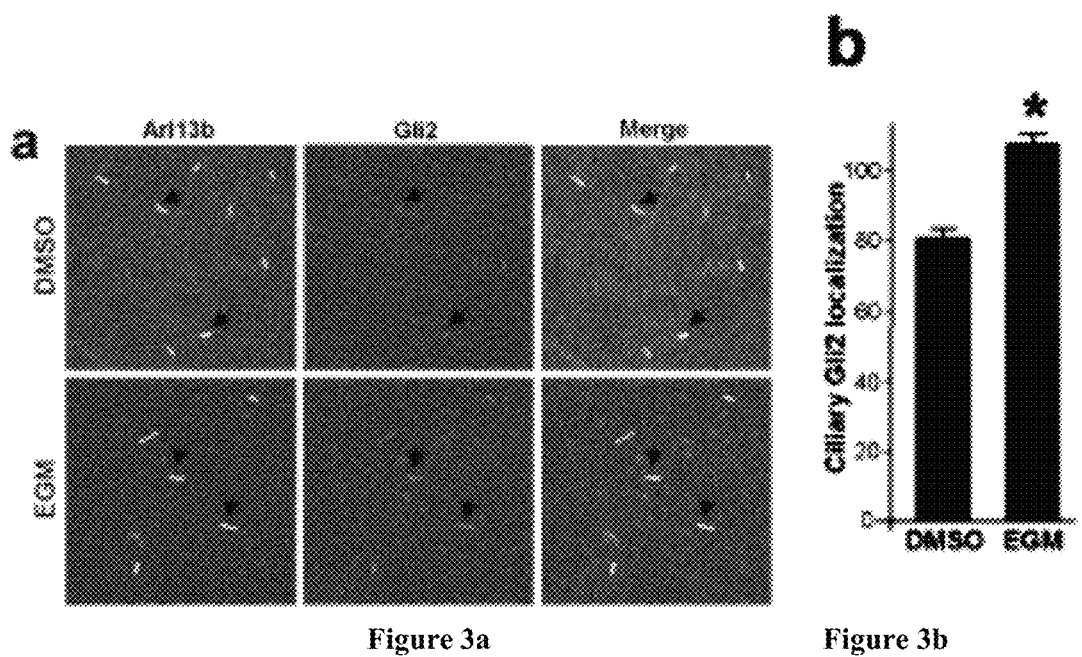
Figure 3a
Figure 3b
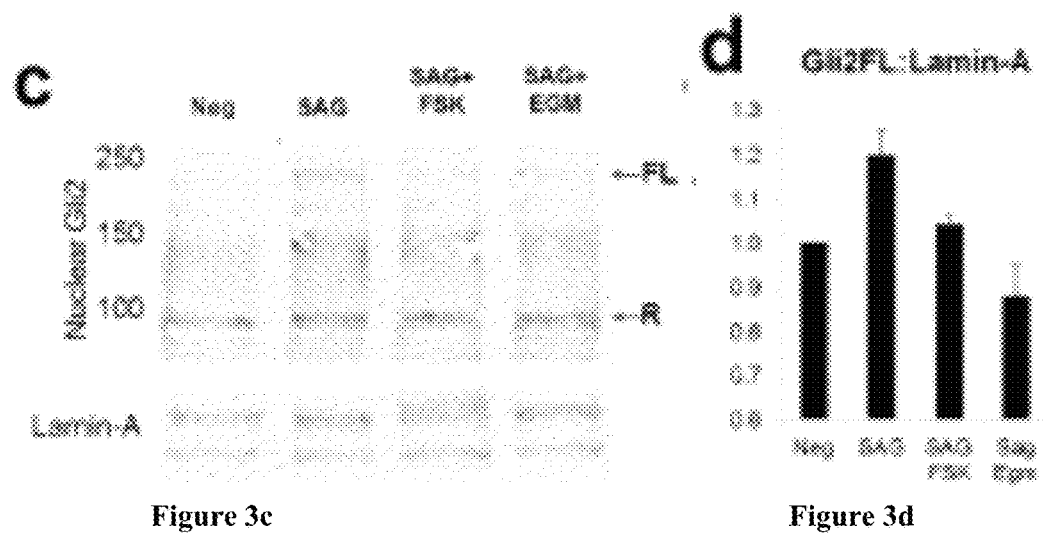
Figure 3c
Figure 3d
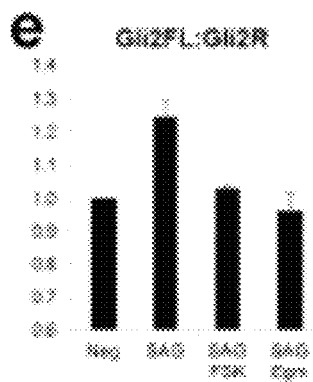
Figure 3e Eggmanone
3-(2-methylallyl)-2-((2-oxo-2-(thiophen-2-yl)ethyl)thio)-
5,6,7,8-tetrahydrobenzo[4,5]thieno[2,3-d]pyrimidin-
4(3H)-one.

IC50 for Hh reporter assay = 1.2 µM
IC50 for PDE4D3 inhibition = 2.4 µM

Descriptors: 0, 0, 0, 0, 0, 0, 0, 5, 0, 0, 0, 0, 15, 3, 0, 4, 14, 1, 1, 1, 2, 0, 2, 0

| Category | Target | PDB Code | LASSO Score |
|---|---|---|---|
| Metalloenzymes | PDE5, phosphodiesterase 5 | 1xp0 | 0.23 |
| Other Enzymes | COX-2, cyclooxygenase-2 | 1cx2 | 0.14 |
| Nuclear Hormone Receptors | GR, glucocorticoid receptor | 1m2z | 0.10 |
| Other Enzymes | AmpC, AmpC beta-lactamase | 1xgj | 0.09 |
| Kinases | P38 MAP, P38 mitogen activated protein | 1kv2 | 0.05 |
| Metalloenzymes | ACE, angiotensin-converting enzyme | 1o86 | 0.03 |
| Nuclear Hormone Receptors | PPARg, peroxisome proliferator activated receptor | 1fm9 | 0.03 |
| Other Enzymes | HIVRT, HIV reverse transcriptase | 1rt1 | 0.02 |
| Nuclear Hormone Receptors | RXRa, retinoic X receptor R | 1mvc | 0.02 |
| Serine Proteases | FXa, factor Xa | 1f0r | 0.02 |
| Kinases | PDGFrb, platelet derived growth factor receptor kinase | N/A | 0.02 |
| Kinases | SRC, tyrosine kinase SRC | 2src | 0.01 |

Figure 8

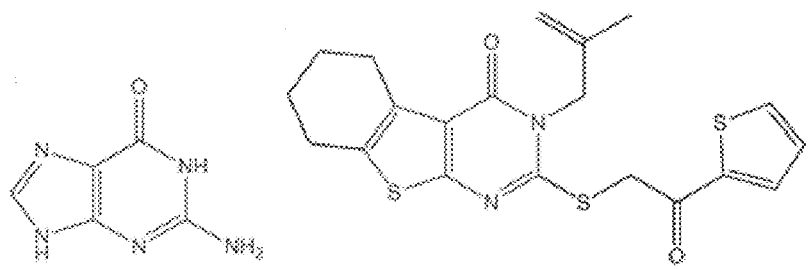

Figure 9

IP:anti-AKAP450
IB:anti-VSV

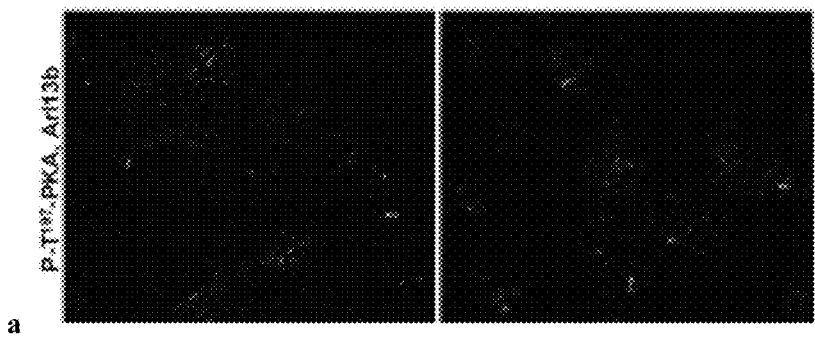
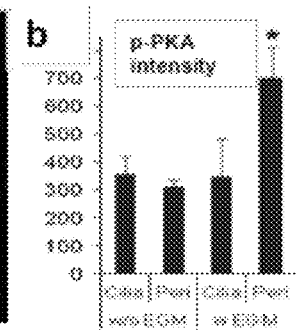
Figure 12a
Figure 12b
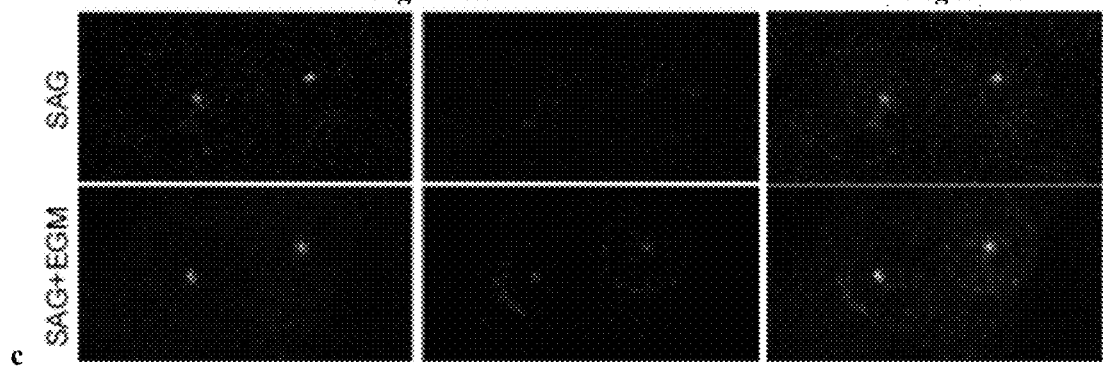
Figure 12c
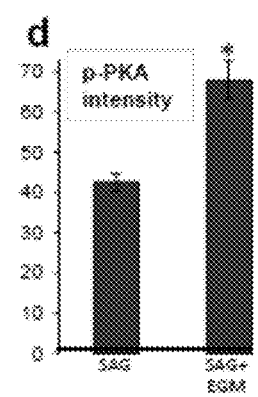
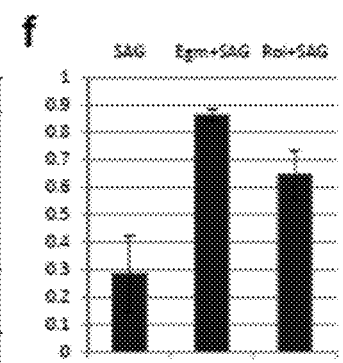
Figure 12d
Figure 12e
Figure 12f

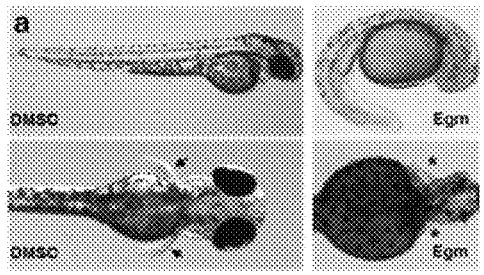
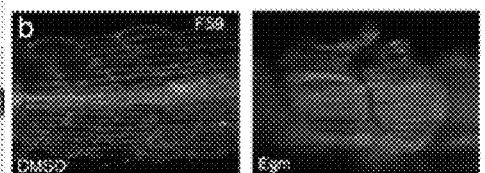
Figure 17a  Figure 17b
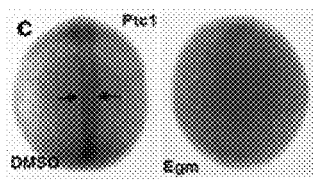
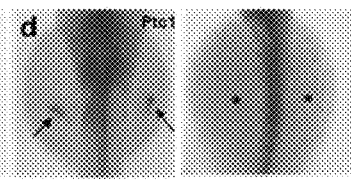
Figure 17c  Figure 17d
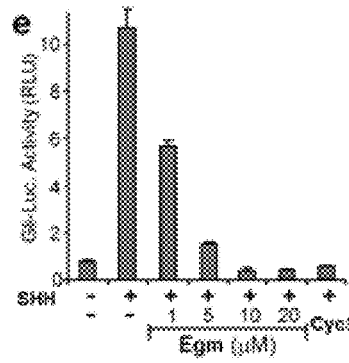
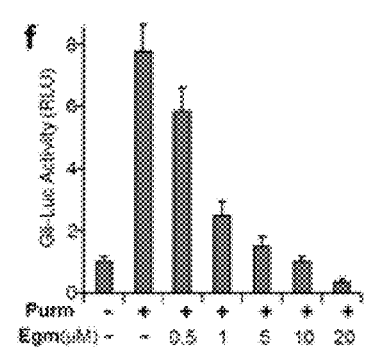
Figure 17e  Figure 17f
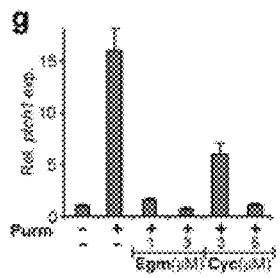
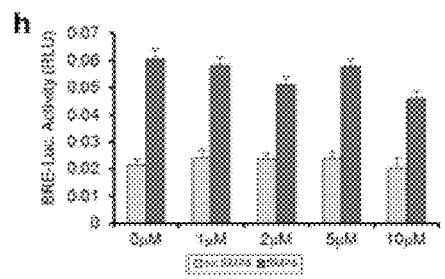
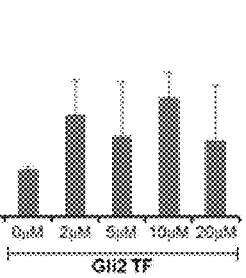
Figure 17g  Figure 17h  Figure 17i

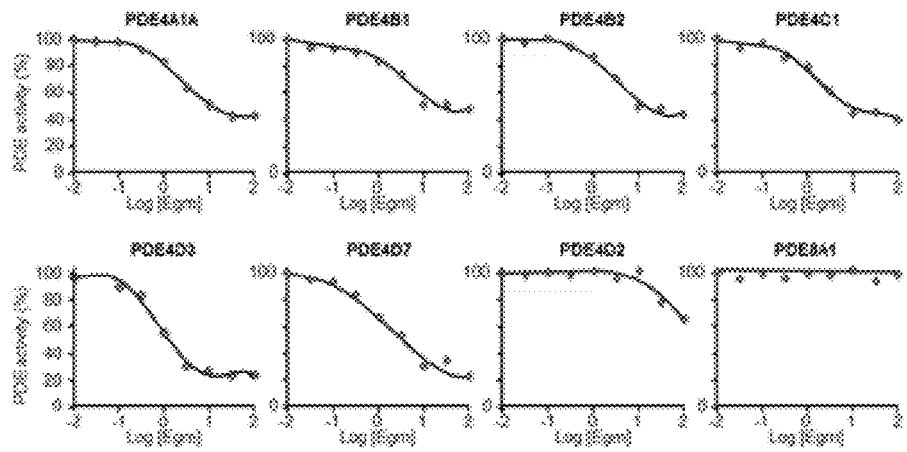
Figure 18a
Figure 18b
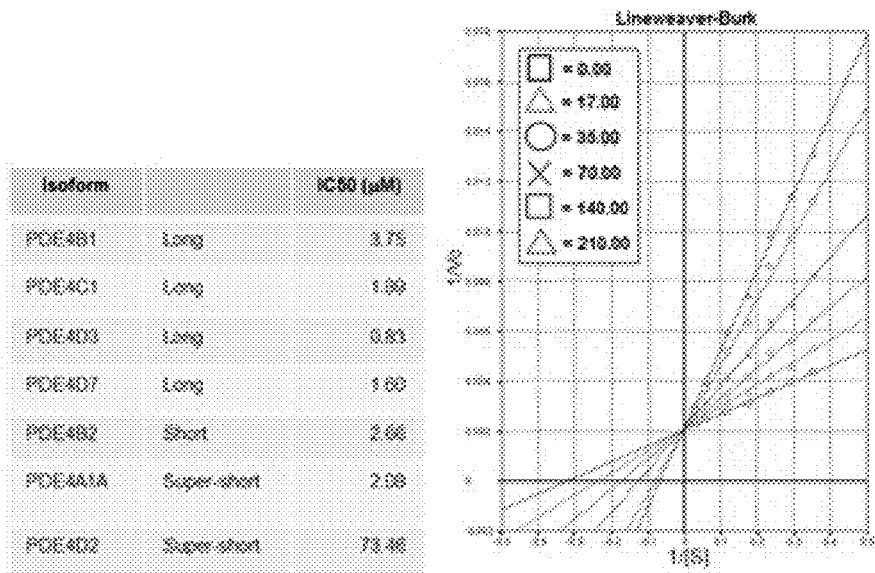
Figure 18c  Figure 18d

| Structure | Name | Hh Reporter Assay (IC50, μM) | In vitro PDE4D3 (IC50, μM) | Structure | Name | Hh Reporter Assay (IC50, μM) | In vitro PDE4D3 (IC50, μM) |
|---|---|---|---|---|---|---|---|
| 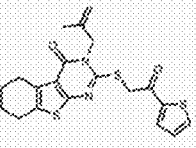 | EGM | 1.2 | 0.8 | 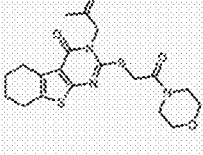 | EGM-7 | 10 | 16 |
| 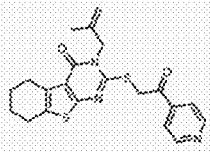 | EGM-2 | 2.5 | 1.6 | 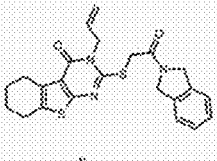 | EGM-8 | 12 | 2.8 |
| 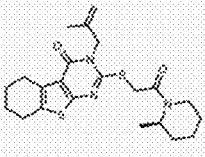 | EGM-3 | 3.0 | 1.4 | 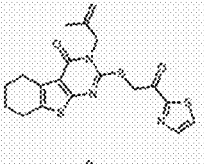 | EGM-9 | >25 | >25 |
| 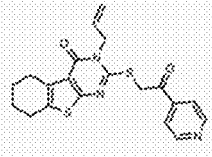 | EGM-4 | 5.0 | 3.2 | 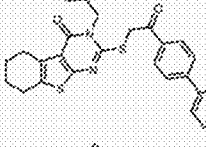 | EGM-10 | >25 | >25 |
| 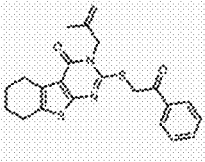 | EGM-5 | 7.4 | 6.4 | 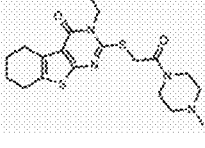 | EGM-11 | >25 | >25 |
| 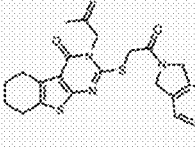 | EGM-6 | 19 | 8.4 | 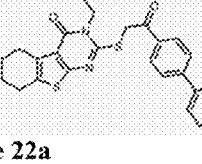 | EGM-12 | >25 | >25 |
Figure 22a

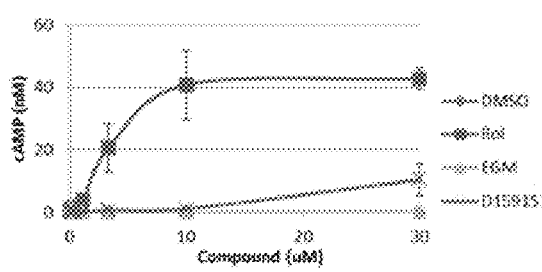
Figure 24a
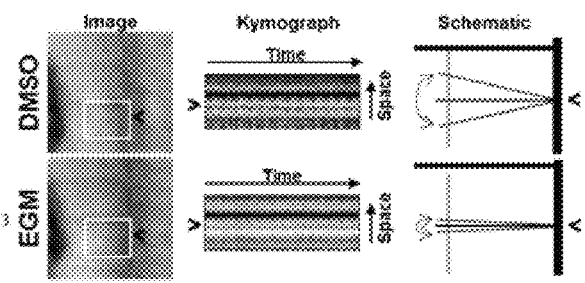
Figure 24b
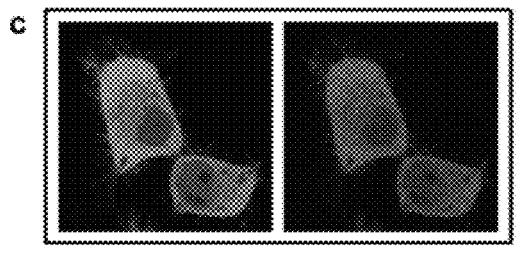
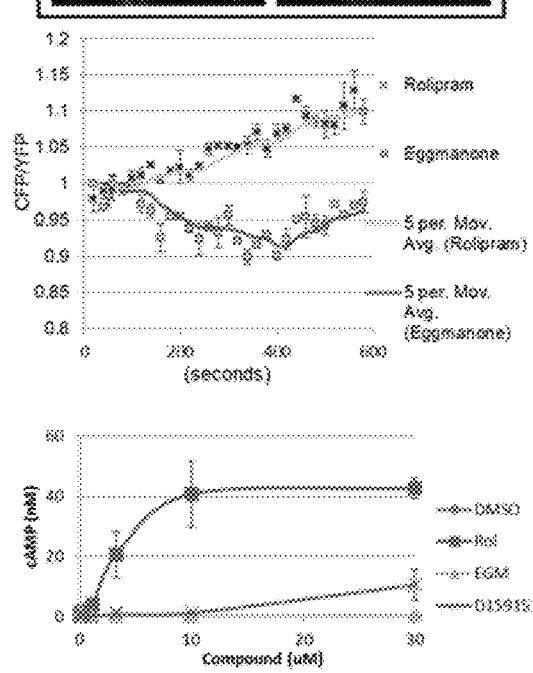
Figure 24c
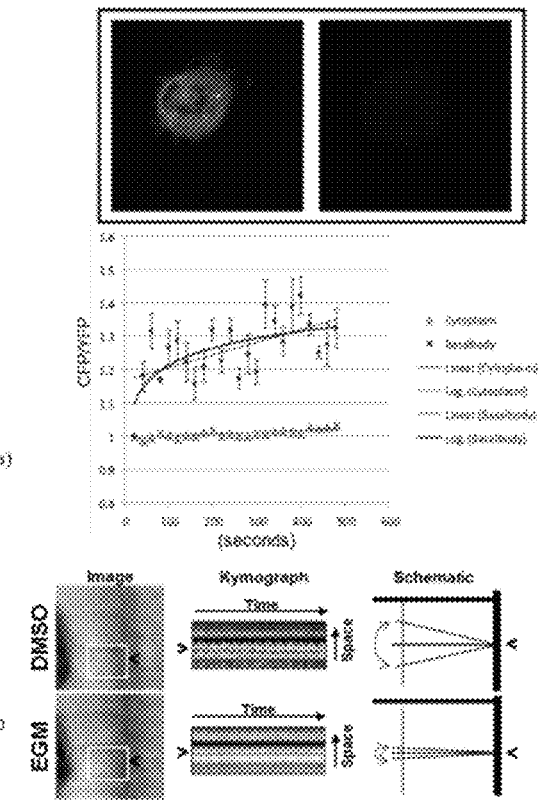
Figure 24d

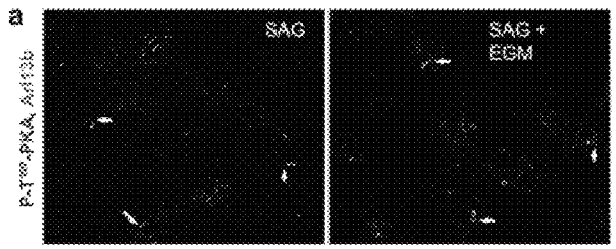
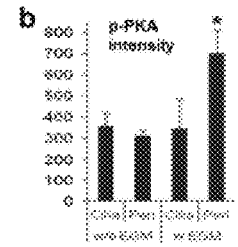
Figure 25a
Figure 25b
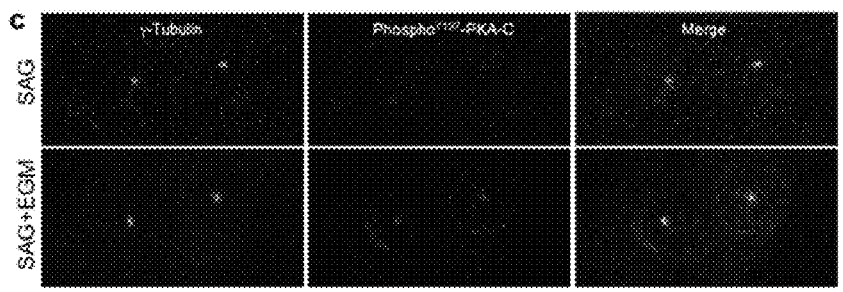
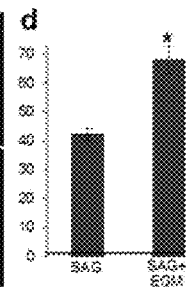
Figure 25c
Figure 25d
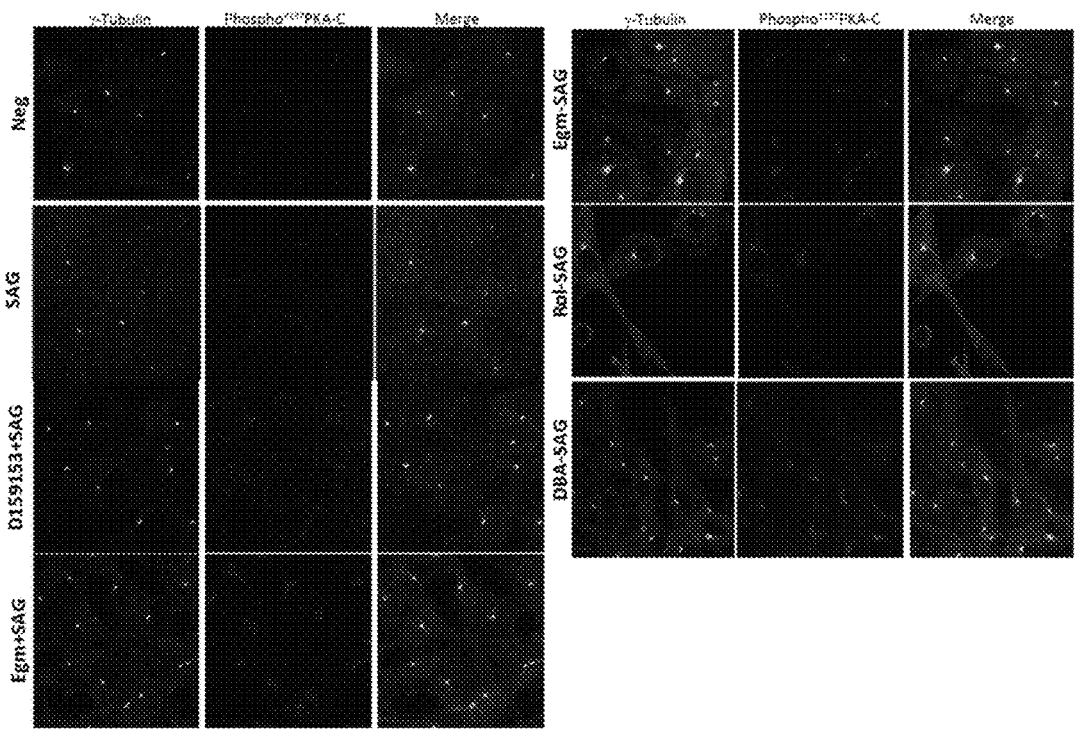
Figure 26

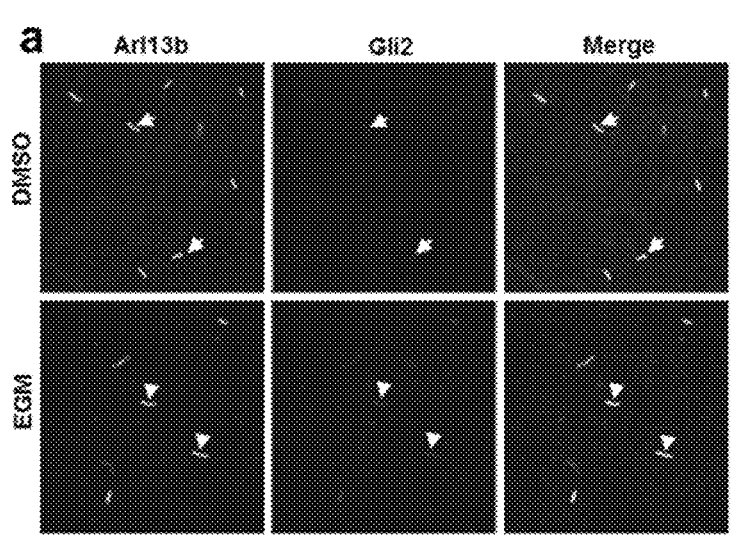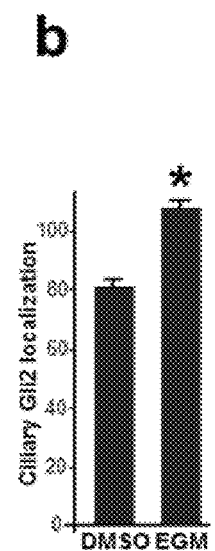
Figure 27a
Figure 27b
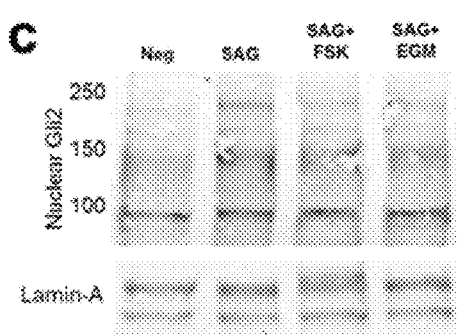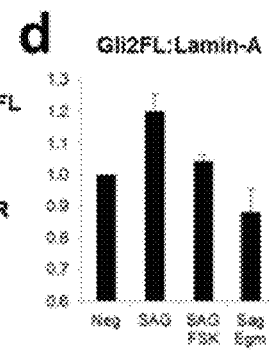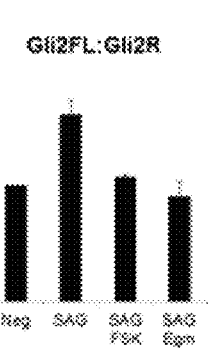
Figure 27c
Figure 27d
Figure 7e Ca bl: Diastolic Ca level, p=0.98 (n>20)
Ca T: Systolic Ca release, p=0.26 (n>20)
Ca Tau: SERCA function, p=0.44 (n>18)
Caff T: SR load, p=0.63 (n>18)

The Hedgehog Signaling Pathway

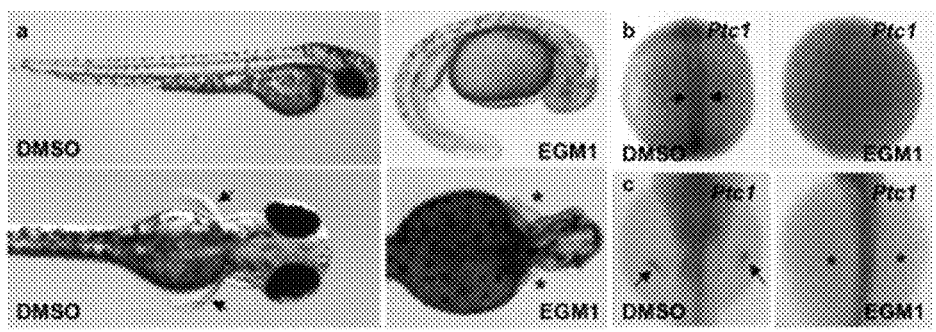
Figure 39b
Figure 39c
Figure 39a
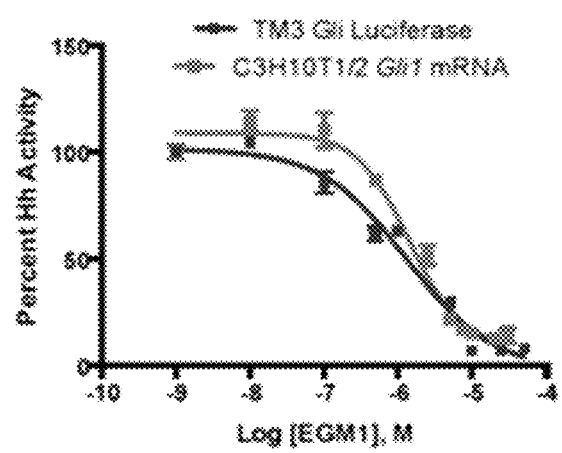
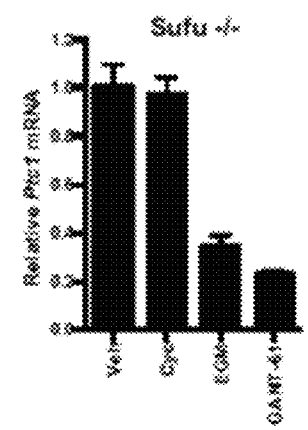
Figure 39d
Figure 39e

Synthesis and Derivatization of EGM1

SAR of Outer EGM1 Appendages

| | Y | R¹ | R² | TM3GliLuc EC$_{50}$ (µM)* | cLogP# |
|---|---|---|---|---|---|
| (1) | CH$_2$ | | | 1.35 | 5.1 |
| (2) | CH$_2$ | | | 3.02 | 4.6 |
| (3) | CH$_2$ | | | 2.96 | 4.8 |
| (4) | CH$_2$ | | | 0.478 | 4.3 |
| (5) | CH$_2$ | | | 1.58 | 4.8 |
| (6) | CH$_2$ | | | 12.6 | 5.2 |
| (7) | CH$_2$ | | | >20 | 3.9 |
| (8) | CH$_2$ | | | 8.49 | 5.3 |
| (9) | CH$_2$ | | | 18.2 | 3.3 |
| (10) | CH$_2$ | | | 6.31 | 4.4 |
| (11) | CH$_2$ | | | 10.5 | 4.0 |
| (12) | O | | | >20 | 4.1 |
| (13) | S | | | 2.51 | 4.7 |
| (14) | NH | | | 7.06 | 3.7 |

*Mean of at least two independent experiments performed in triplicate. # Calculated by Molinspiration Cheminformatics

Scaffold Hopping via Virtual Screening

- 98,000 compounds screened against EGM1 3D hypothesis via Suflex-Sim algorithm

- returned 20 non-EGM1-like hits with SS > 8.5

COMPOUNDS AND METHODS FOR INHIBITION OF HEDGEHOG SIGNALING AND PHOSPHODIESTERASE

RELATED APPLICATIONS

This application claims priority from International Patent Application No. PCT/US2015/050024, filed Sep. 14, 2015, which claims priority from U.S. Provisional Application Ser. No. 62/049,735 filed Sep. 12, 2014, and U.S. Provisional Application Ser. No. 62/199,442 filed Jul. 31, 2015, and claims priority from U.S. Provisional Patent Application No. 62/304,513, filed Mar. 7, 2016, the entire disclosures of which are incorporated herein by this reference.

GOVERNMENT INTEREST

This invention was made with government support under RO1HL104040 awarded by National Institutes of Health. The government has certain rights in the invention.

TECHNICAL FIELD

The presently-disclosed subject matter relates to compounds, compositions, and methods for inhibiting Hedgehog signaling. The presently-disclosed subject matter further relates to compounds, compositions, and methods for inhibiting phosphodiesterase 4.

INTRODUCTION

Hedgehog (Hh) signaling is one of the key regulators of both invertebrate and vertebrate development. During development, Hh signaling regulates a wide variety of processes, including patterning of body segments, organs, and appendages; chondrogenesis; myotome induction; and floor plate differentiation. In adult animals, Hh signaling regulates the survival of a variety of differentiated cell types, the proliferation of variety of adult stem cells, and the development of hair follicles.

In these various developmental processes, members of the Hh family of extracellular signaling molecules activate a membrane receptor complex. Initially, the binding of Hh to the transmembrane receptor Patched (Ptc) releases its inhibition of Smoothened (Smo), a distant cousin of the 7-transmembrane G-couple protein receptor family. The activation of Smo by Hh then initiates an intracellular signaling pathway that ultimately results in activation of Gli zinc-finger transcription factors, which are thought to mediate much of the cellular effects of Hh signaling.

In most subjects, the Hh signaling pathway is normally tightly regulated, becoming activated only in precise locations and at precise times. However, in other subjects, the aberrant activation of the Hh signaling pathway is associated with numerous types of malignancies, including basal cell carcinomas, medulloblastomas, melanomas, fibrosarcomas, rhabdomyosarcomas, glioblastomas, multiple myelomas and pancreatic cancers. Indeed, Hh signaling has been observed to promote tumorigenesis through both cell-autonomous and paracrine effects, and there is increasing recognition that Hh may play a key role in transforming adult stem cells into tumor stem cells and in maintaining tumor cell compartments. Consequently, in recent years, significant efforts have been spent developing small molecule inhibitors of the Hh pathway that are capable of being used in the treatment of cancer.

Despite the recent efforts, however, the large majority of Hedgehog signaling inhibitors target Smo and are subject to significant inhibitor-driven resistance mechanisms. Additionally, a large proportion of driver mutations of tumorigenesis occur at signaling nodes downstream of Smo, for which Smo antagonists are not predicted to show efficacy. Use of most of the small molecule inhibitors of the Hh pathway that have been developed to date has been limited by poor bioavailability and/or activity. Currently marketed Hedgehog signaling inhibitors (vismodegib and sonidegib) only antagonize the Smoothened receptor and treatment-driven resistance leads to a high rate of tumor recurrence. By inhibiting the pathway at nodes downstream of Smoothened, the possibility exists for avoiding resistance altogether, creating a second line treatment to the Smoothened antagonists, or a combination therapy with Smoothened antagonists. Therefore, the development of Hedgehog signaling inhibitors that function downstream of Smo would be of great significance to the clinical areas of Hedgehog-driven malignancies.

Accordingly, small molecule inhibitors of Hedgehog signaling that exhibit an increase in bioavailability and potency, would be both highly desirable and beneficial. Such inhibitors may find use in targeted treatment of basal cell carcinomas, medulloblastomas, pancreatic cancers, small cell lung cancers, breast cancers, glioblastomas, acute leukemias, and chronic myeloid leukemias.

SUMMARY

The presently-disclosed subject matter meets some or all of the above-identified needs, as will become evident to those of ordinary skill in the art after a study of information provided in this document.

This Summary describes several embodiments of the presently-disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this Summary or not. To avoid excessive repetition, this Summary does not list or suggest all possible combinations of such features.

The presently-disclosed subject matter includes a compound. In some embodiments, the compound is of the formula:

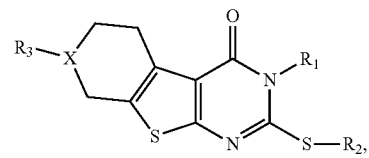

or pharmaceutically-acceptable salts thereof, wherein
X is selected from C, N, O, and S;
$R_1$ is selected from $CH_2CH_3$, $(CH_2)_2CH_3$,

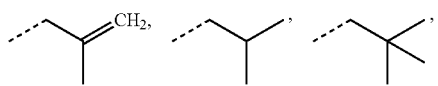

-continued
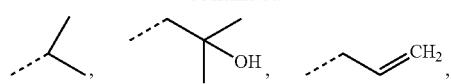
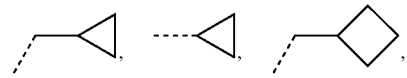
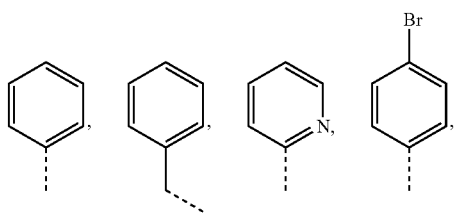
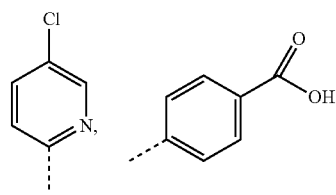 and ;
$R_2$ is selected from $CH_3$,
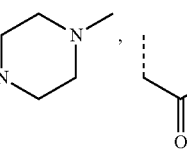, 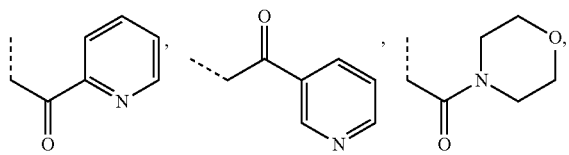
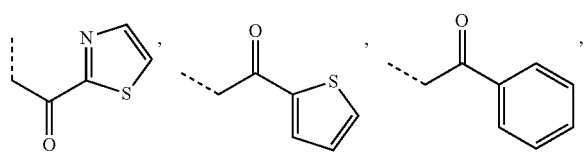
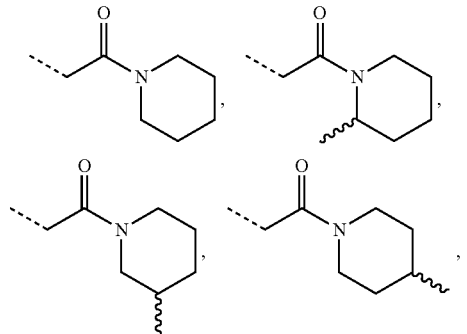
-continued
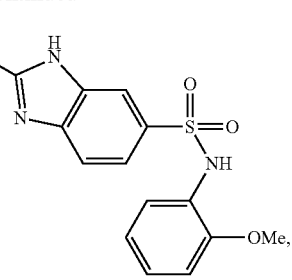
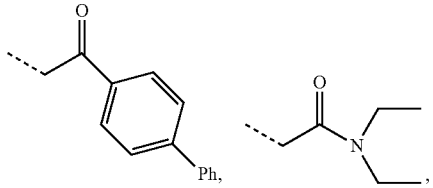
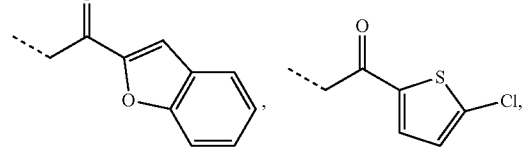
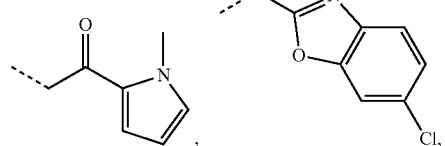
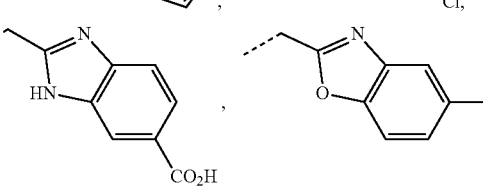
, 
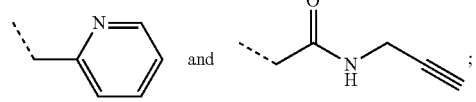
and
$R_3$ is selected from H, $CH_3$,
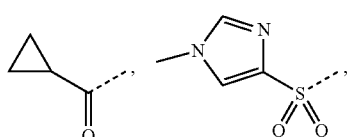
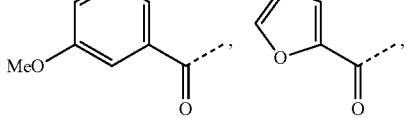

-continued
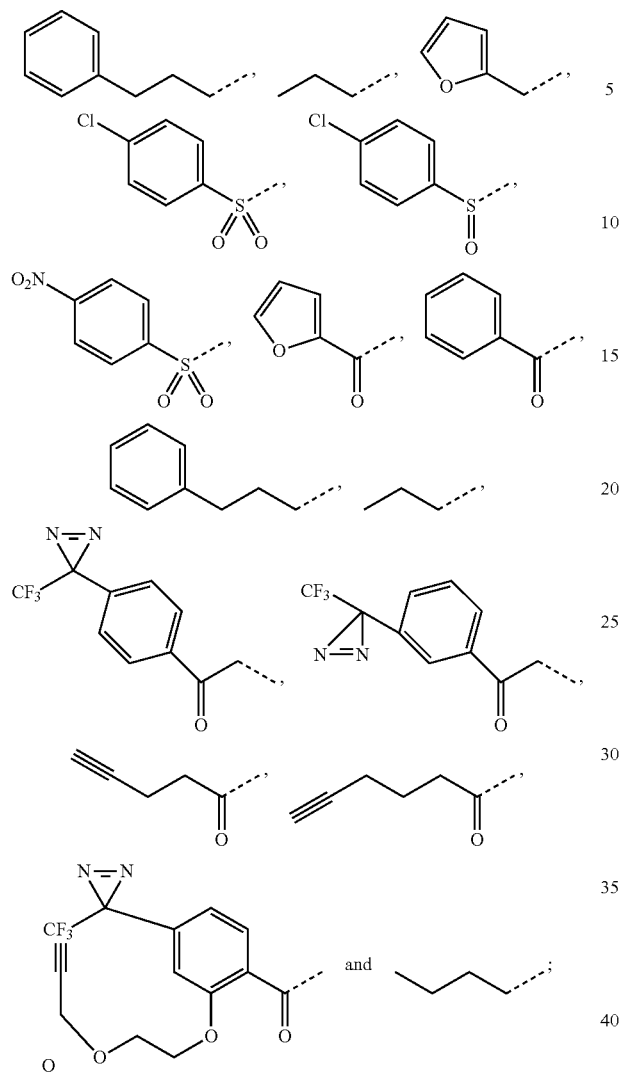
so long as when $R_2$ is
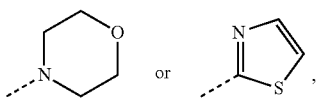
$R_1$ is not
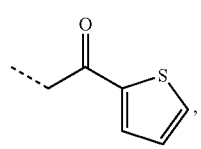
and so long as when $R_2$ is
X is C, and R3 is H, $R_1$ is not
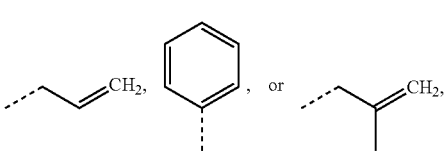
and
so long as when R2 is
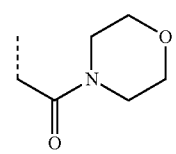
X is C and R3 is H, R1 is not
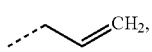
and
so long as when R2 is
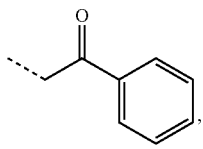
X is C and R3 is H, R1 is not
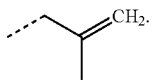
In some embodiments, the compound is according to a formula selected from the group consisting of:
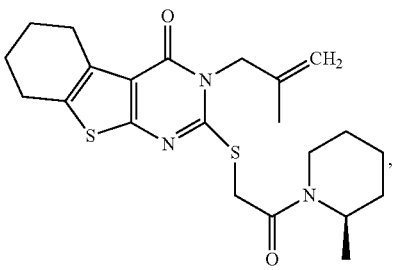
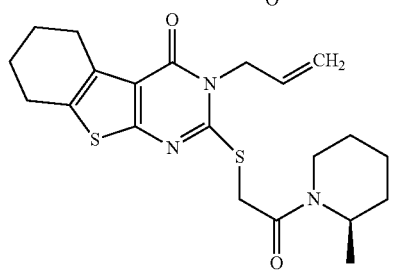

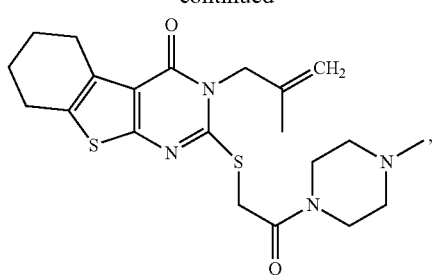
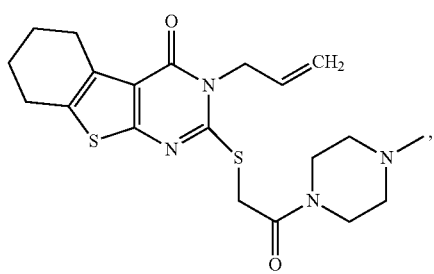
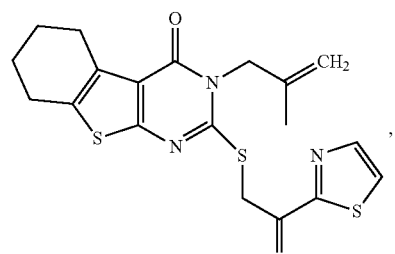
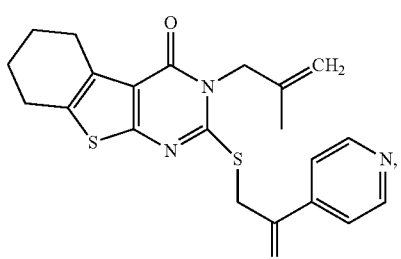
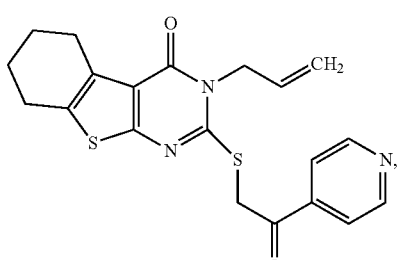
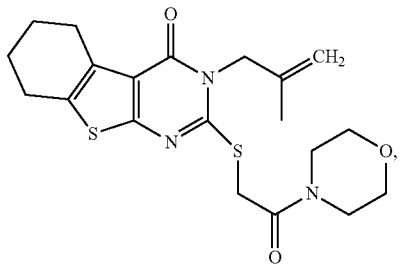
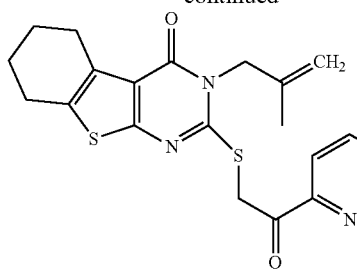, and
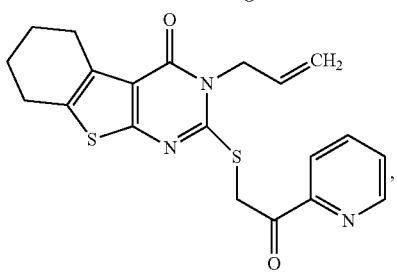,
or pharmaceutically-acceptable salts thereof.
In some embodiments, the compound is according to the formula:
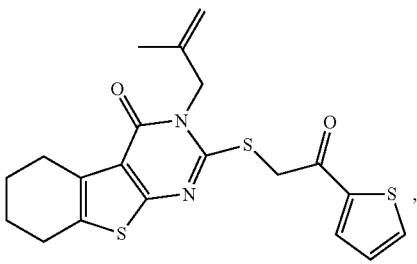,
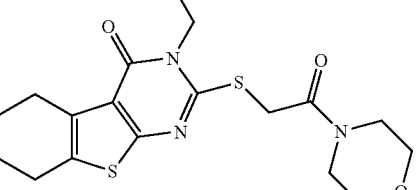,
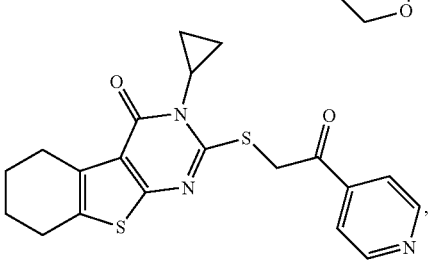,
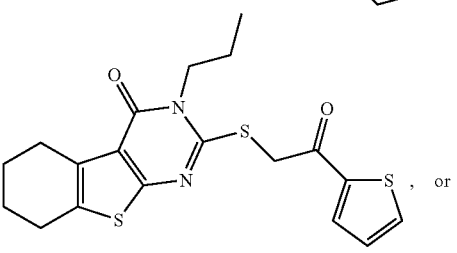, or -continued
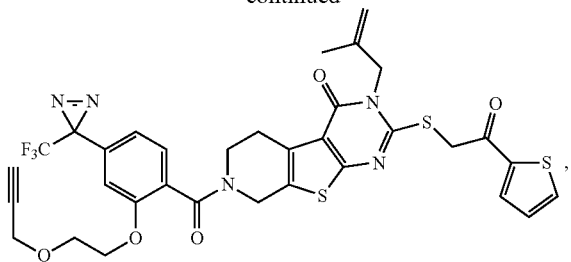
or pharmaceutically-acceptable salts thereof.
In some embodiments, the compound is according to the formula:
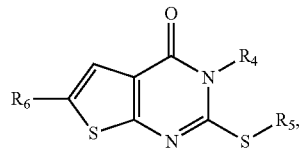
or pharmaceutically-acceptable salts thereof, wherein
$R_4$ is selected from
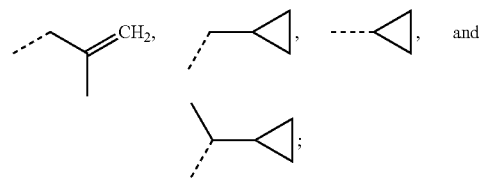
$R_5$ is selected from $CH_3$,
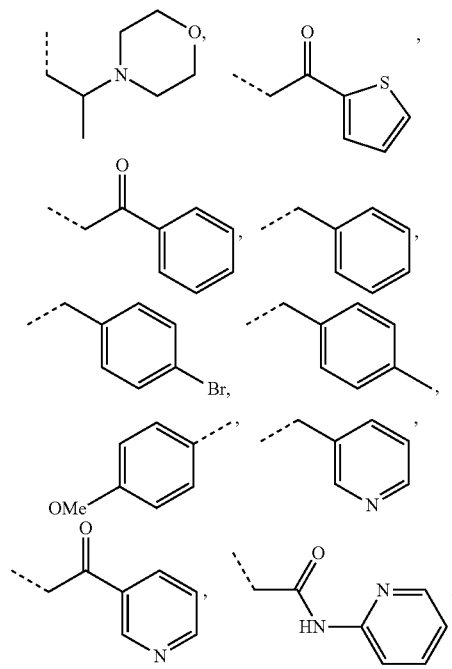
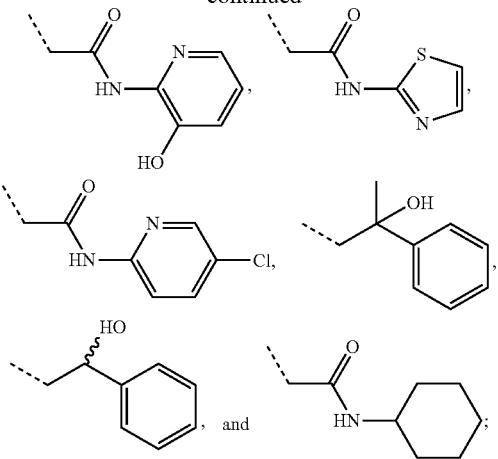
and
$R_6$ is selected from H,
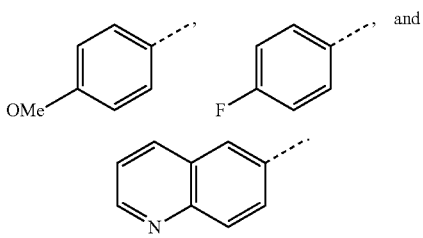
In some embodiments, the compound is selected from the group consisting of:
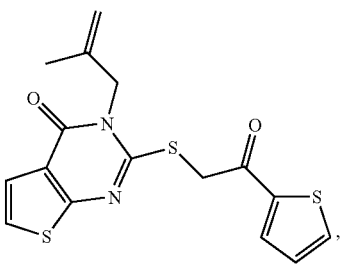
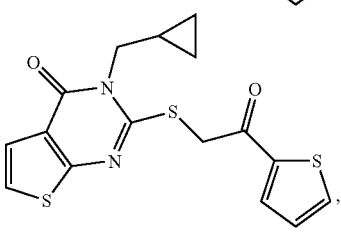
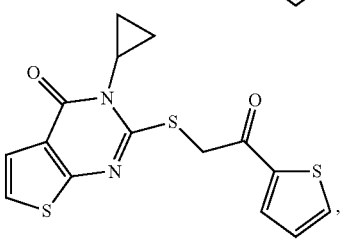

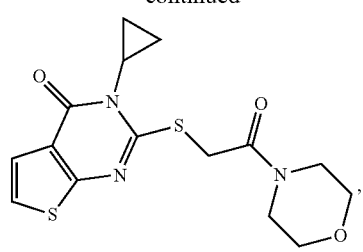
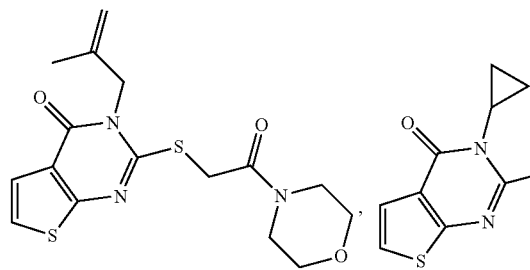
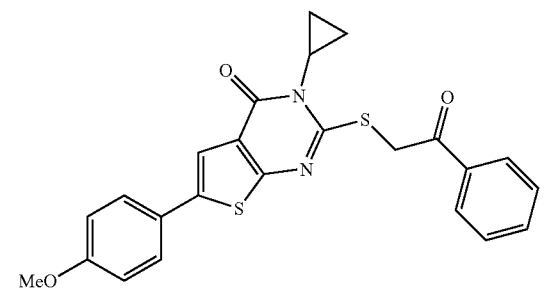
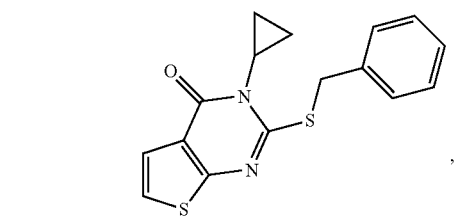
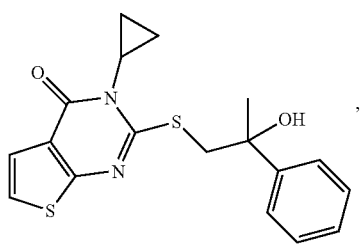
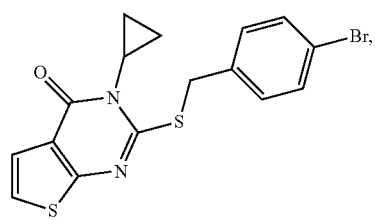
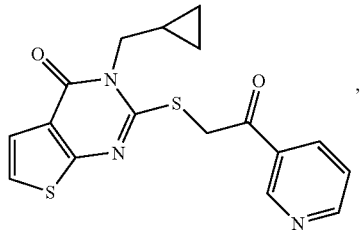
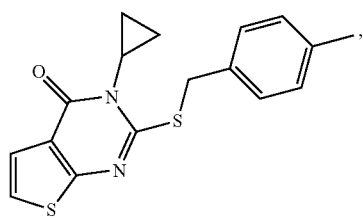
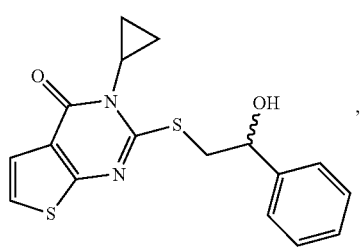
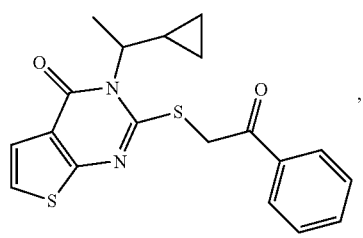
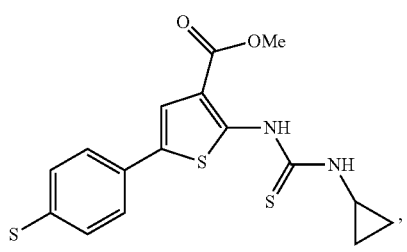

-continued
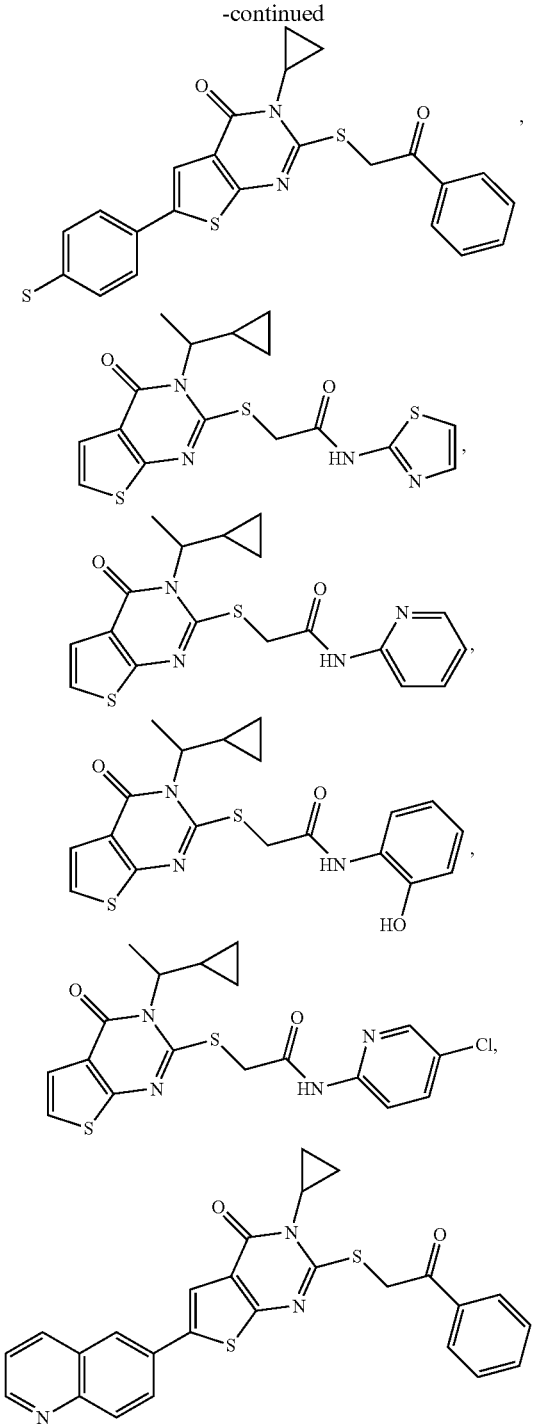
In some embodiments, the compound is of the formula:
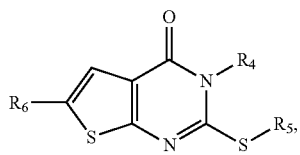
or pharmaceutically-acceptable salts thereof, wherein
$R_4$ is selected from
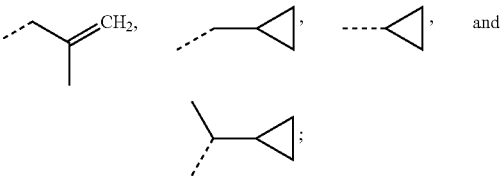
$R_5$ is selected from $CH_3$,
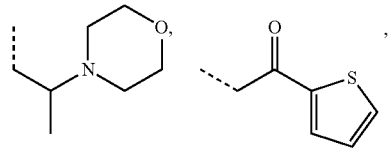
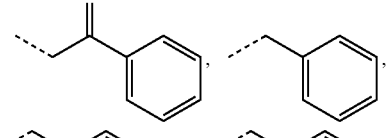
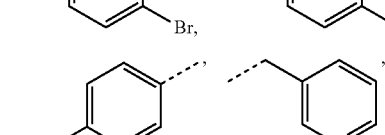
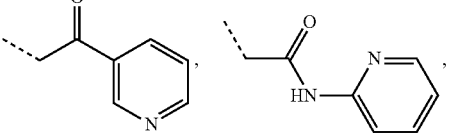
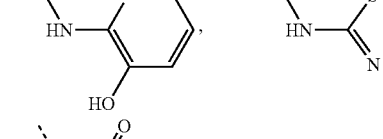
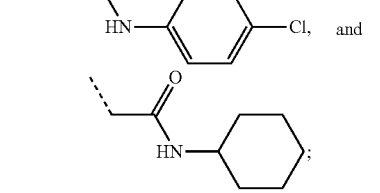
and
$R_6$ is selected from H,

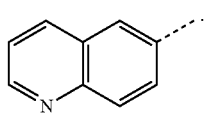
In some embodiments, the compound is of the formula:
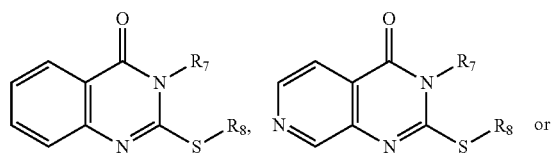
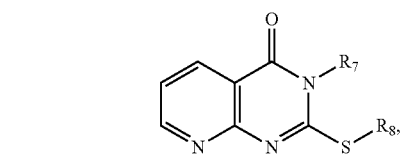
or pharmaceutically-acceptable salts thereof, wherein R₇ is selected from
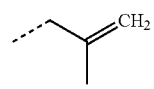 and 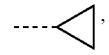,
and R₈ is
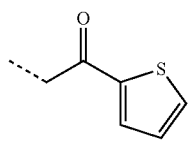 or 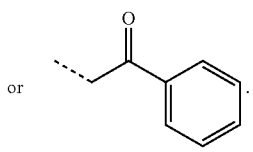.
In some embodiments, the compound is of the formula selected from
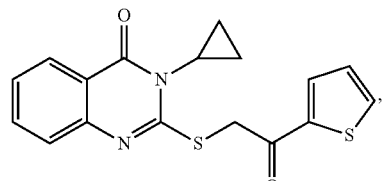
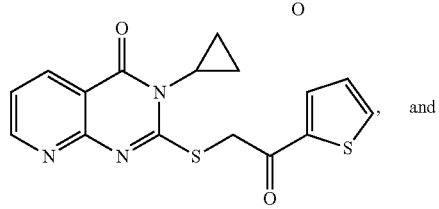 and
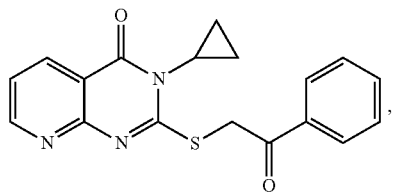,
or pharmaceutically acceptable salts thereof.
In some embodiments, the compound is of the formula:
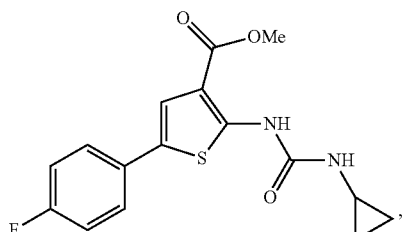
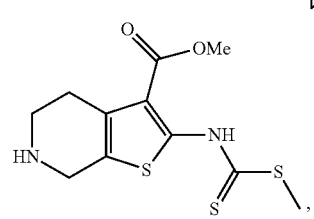,
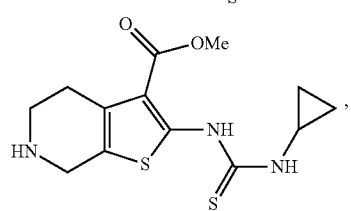,
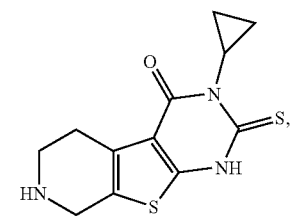,
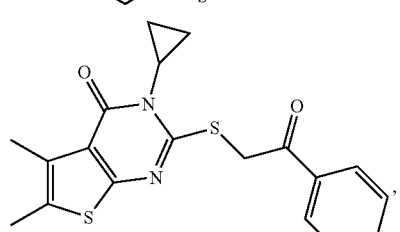,
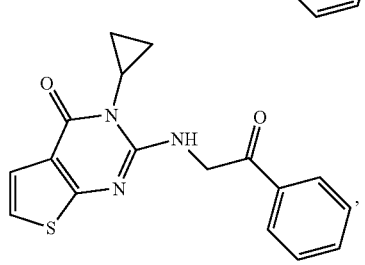, -continued

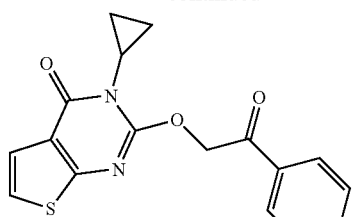

or

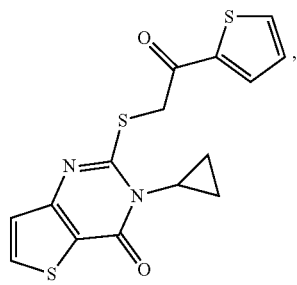 [SMILES: O=C(CSc1nc2ccsc2c(=O)n1C1CC1)c1cccs1]

or a pharmaceutically-acceptable salt thereof.

In some embodiments, the compound is of the formula:

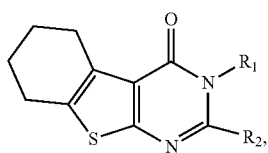

or pharmaceutically-acceptable salts thereof,
wherein
$R_1$ is selected from
H, and

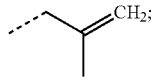

and
$R_2$ is selected from

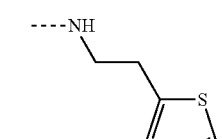 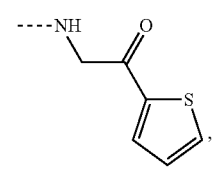

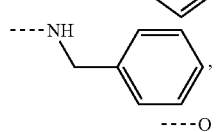 and

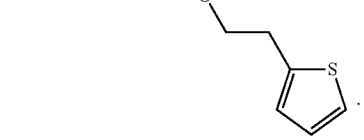

In some embodiments, the compound is of the formula:

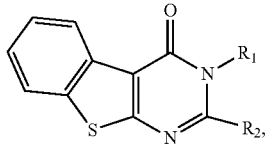

or pharmaceutically-acceptable salts thereof, wherein
$R_1$ is selected from

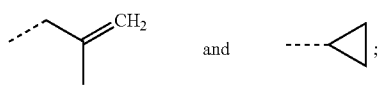 and 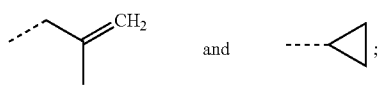 ;

and
$R_2$ is selected from

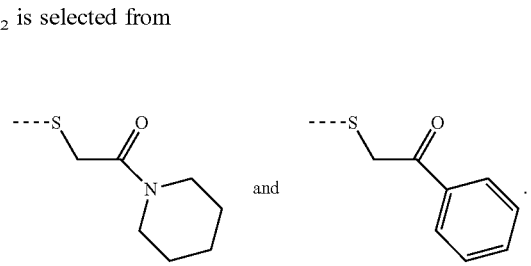

In some embodiments, the compound according to the formula selected from the group consisting of:

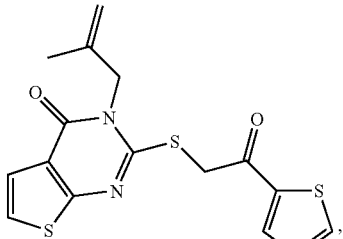

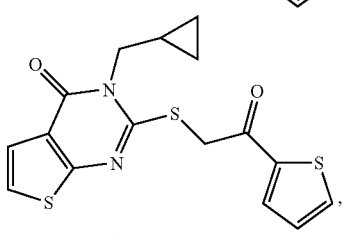

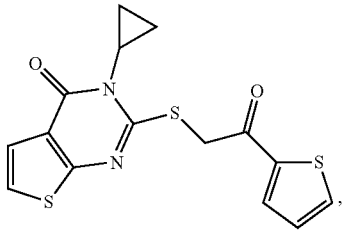

-continued
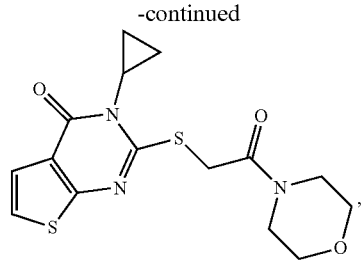
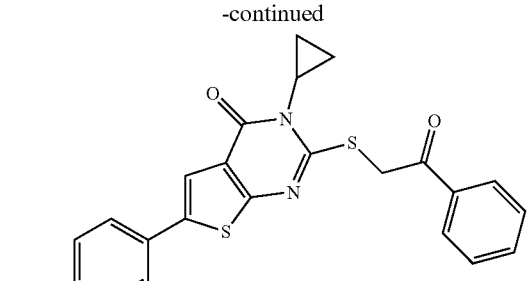
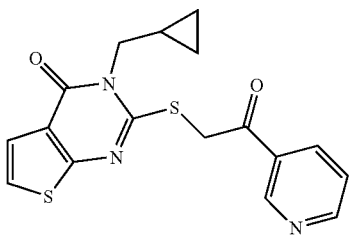
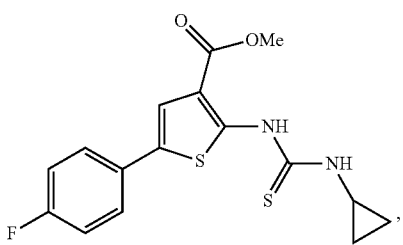
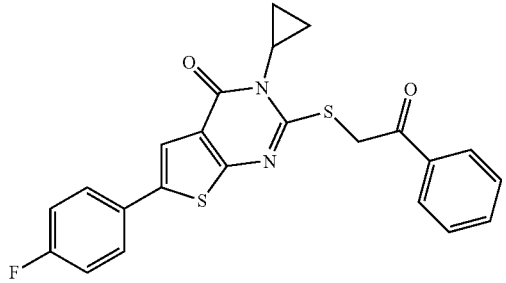
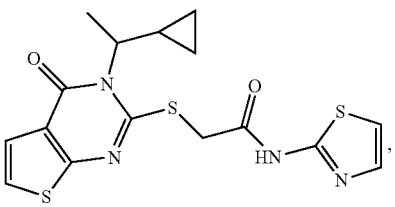
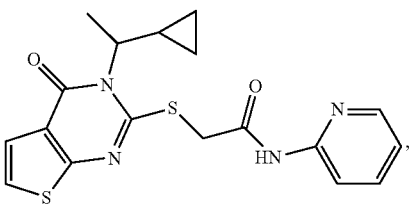
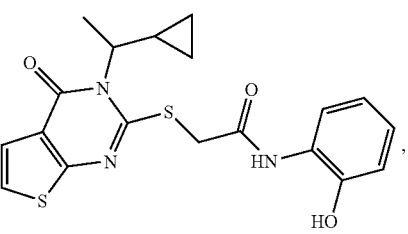

21
-continued

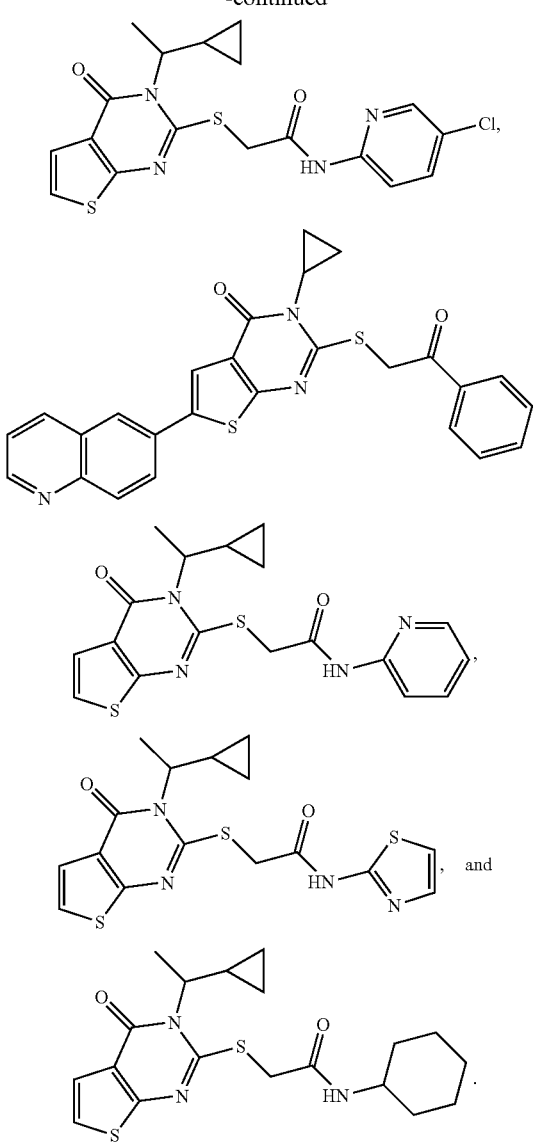

In some embodiments, the compound is of the formula

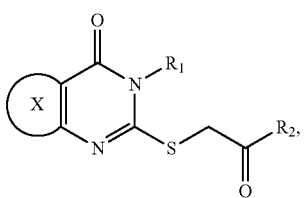

or pharmaceutically-acceptable salts thereof, wherein
X is selected from

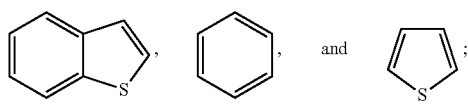

22

$R_1$ is selected from

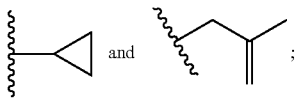

and
$R_2$ is selected from

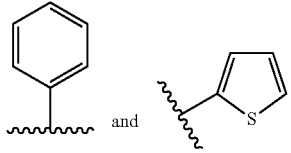

In some embodiments, the compound is of the formula:

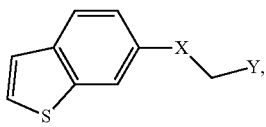

or pharmaceutically-acceptable salts thereof, wherein when X is S, Y is

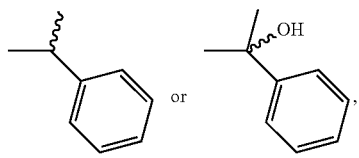

and when X is NH or O, Y is

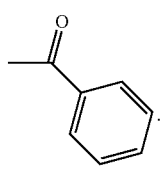

In some embodiments, the compound is a formula selected from the group consisting of

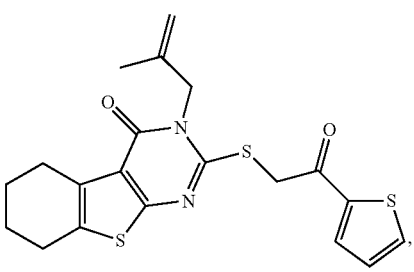

-continued

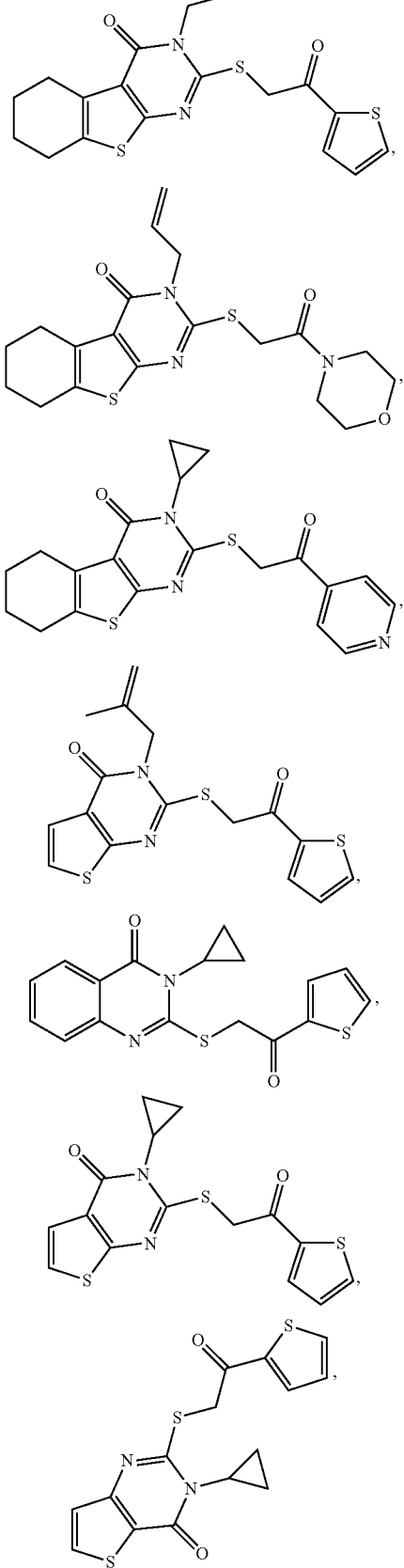

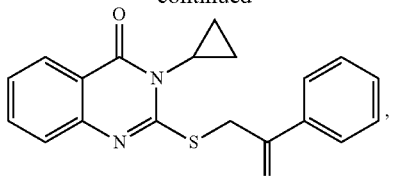

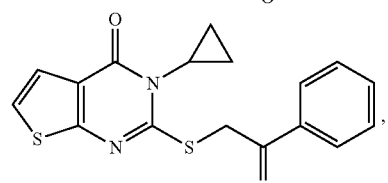

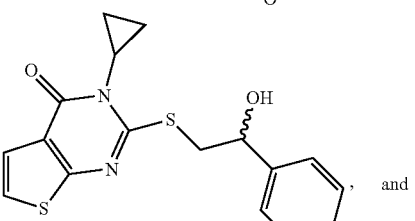

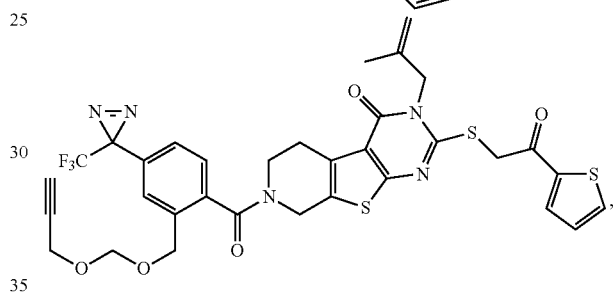

or pharmaceutically-acceptable salts thereof.

The presently-disclosed subject matter further includes a pharmaceutical composition. In some embodiments, the pharmaceutical composition includes a pharmaceutically-acceptable carrier; and a compound as disclosed herein. In some embodiments, the pharmaceutical composition further includes a second compound or composition having Hh signaling inhibition activity, PDE4 inhibition activity, anti-cancer or anti-tumor activity, anti-angiogenic activity, anti-metastatic activity, anti-heart failure activity, and/or anti-inflammation activity, or wherein the second compound or composition is useful for treating a condition of interest. In some embodiments, the second compound is a Smo antagonist. In some embodiments, the Smo antagonist is Vismodegib (GDC-0449, 1), Sonidegib (NVP-LDE225, 2), PF-04449913, IPI-926, BMS-833923, TAK-441, LY2940680, or itraconazole.

The presently-disclosed subject matter further includes a kit that comprises a compound or a pharmaceutical composition, as described herein, and a device for administration of the compound or composition. The presently-disclosed subject matter further provides a kit that comprises a compound or a pharmaceutical composition, as disclosed herein; and further comprising a second compound or composition having Hh signaling inhibition activity, PDE4 inhibition activity, anti-cancer or anti-tumor activity, anti-angiogenic activity, anti-metastatic activity, anti-heart failure activity, and/or anti-inflammation activity, or wherein the second compound or composition is useful for treating a condition of interest.

In some embodiments, the kit further comprises a second compound or composition and a device for administration of the compound or composition and/or a device for administration of the second compound or composition. In embodiments where the kit includes a device for administration of the compound(s) or composition(s) the device can be a nebulizer.

The presently-disclosed subject matter further includes methods. A method of inhibiting hedgehog signaling in a cell is provided and includes contacting a cell with an effective amount of a compound or pharmaceutical composition, as disclosed herein. In some embodiments, contacting the cell with the compound comprises administering the compound or composition to a subject.

In some embodiments, the administration is to a subject in need of treatment for a condition of interest. In some embodiments the condition of interest is related to heart failure. In other embodiments, the condition of interest is related to PDE4 activity, cancer, virus, angiogenesis, tumorigenisis or tumor activity, metastasis and/or inflammation. In some embodiments, the condition of interest is selected from basal cell carcinomas, medulloblastomas, pancreatic cancers, small cell lung cancers, breast cancers, glioblastomas, acute leukemias, and chronic myeloid leukemias.

A method of inhibiting phosphodiesterase-4 (PDE-4) in a cell is provided and includes contacting a cell with an effective amount of a compound or pharmaceutical composition, as disclosed herein. In some embodiments, contacting the cell with the compound comprises administering the compound or composition to a subject. In some embodiments, administration is to a subject in need of treatment for a condition of interest. In some embodiments, administration is intranasally or orally.

A method of treating a condition of interest is provided and includes contacting a cell with an effective amount of a compound or pharmaceutical composition, as disclosed herein. In some embodiments, contacting the cell with the compound comprises administering the compound or composition to a subject. In some embodiments, the administration is to a subject in need of treatment for a condition of interest.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are used, and the accompanying drawings of which:

(FIG. 1g) Left, Eggmanone inhibited PDE4 isoforms with the $IC_{50}$ range of 0.8 to 3.75 µM, except the super-short PDE4D2. Right, representation of PDE4 isoform structures. (FIG. 1h) Overexpression of wild-type PDE4D3 (D3WT) induced Hh reporter activity (*P=0.0026 versus pCS2 control), which was abolished by 5 µM Eggmanone (p<0.0001 versus D3WT). Overexpression of dominant-negative PDE4D3 (D3DN) decreased Hh reporter activity (**P=0.0121 versus pCS2).

(FIG. 2a) Rolipram increased total cellular cAMP levels, whereas Egm only caused small increase at concentrations above those required to inhibit Hh signaling. (FIG. 2b) Left, still images from high-speed video of zebrafish otic kinocilia. Middle, kymograph visualization demonstrates that cilia movement is markedly reduced following 2 µM Egm treatment. Right, schematic of motile kino-cilia (green, line of capture for kymograph). (FIG. 2c) Immunostaining for the basal body marker gamma-Tubulin (green) and the autophosphorylated PKA catalytic subunit (Phospho$^{Y197}$-PKA-C; red) in NIH3T3 cells stimulated with SAG (top) demonstrates a low baseline PKA activation; co-treatment with 5 µM Egm (middle) increases local PKA activation at the basal body and in areas immediately surrounding it; co-treatment with 10 µM Rolipram increases PKA activation more diffusely. (FIG. 2d) Intensity plot of immunostaining along a line bisecting the basal body and nucleus. (FIG. 2e) Correlation plot of p-PKA and gamma-Tubulin staining intensities.

FIG. 3a-3i include data and results of studies showing that Eggmanone causes dysregulation of cilia-to-nuclear trafficking of Gli2 and selectively kills Hh-dependent cells. (FIG. 3a) Immunostaining for the cilia marker Arl13b (green) and Gli2 (red) of NIH3T3 cells stimulated with SAG (20 nM) in the presence of 5 µM Egm or DMSO control. Egm treatment increased co-localization of Gli2 (yellow) in the primary cilia, arrows. (FIG. 3b) Quantitative analysis reveals that Egm significantly increased Gli2 localization in the cilia (n=10 for each condition; p=0.026, versus DMSO). (FIG. 3c) Representative western blot for Gli2 in nuclear fractions of NIH3T3 cells. Neg, unstimulated. SAG, stimulated with SAG (20 nM) for 60 minutes. SAG+FSK, co-treated with SAG and FSK (3004). SAG+EGM, co-treated with SAG and Egm (10 µM). Bottom, corresponding western blot for nuclear Lamin-A/C as loading controls. FL, full-length, active form of Gli2. R, proteolytically processed, repressor form of Gli2. (FIG. 3d) Quantitative analysis of the ratio of full length Gli2 to lamin-A in the nucleus reveals that SAG treatment increased abundance of full-length Gli2 in the nucleus, and this increase was abrogated by co-treatment with either FSK or Egm. (FIG. 3e) SAG treatment increased the nuclear ratio of full-length Gli2 (FL) to repressor Gli2 (R), which was abrogated by co-treatment with either FSK or Egm (For D and E, n=4 for each condition; p<0.05, versus SAG; ratio for each condition was normalized to the ratio of unstimulated controls). (FIG. 3f) Egm treatment (1004) led to rapid (within 24-hrs) decline in viability of SmoM2 cells but not NIH3T3 cells (n=3 for each data point; cell viability relative to DMSO-treated cells; *P<0.0001; **P=0.0021) (FIG. 3g) Relative cell viability of Daoy (medulloblastoma), RKO (colon cancer) and PC3 (prostate cancer) cells following 72-hour treatment with increasing concentrations of Egm (n=4, for each data point). Egm (10 µM) treatment of Daoy cells for 48-hours decreased cell proliferation, based on phospho-histone H3 (PH3) staining (FIG. 3h) and increased apoptosis, based on TUNEL staining (FIG. 3i).

FIG. 8 includes results from LASSO algorithm, including molecular surface descriptor of eggmanone.

FIG. 9 includes structures identified using LASSO algorithm.

(FIG. 10a) In vitro PDE activity assays across 11 PDE families reveals that Egm (10 µM) significantly inhibited only the PDE4 class. (FIG. 10b) Dose response curves of in vitro PDE assays.

(FIG. 11a) Left, vsv-tagged PDE4D3 (green). Middle, Arl13b immunostaining marks the primary cilium (red). Right, merged images. (FIG. 11b) NIH3T3 cells transfected with either VSV-PDE4D3 vector or empty vector control were treated with either DMSO or 5 uM eggmanone. Lysates were incubated with anti-AKAP450 antibody and complexes bound to Protein A/G beads. After immunoprecipitation, western blot probed with anti-VSV antibody demonstrated physical interaction between AKAP450 and PDE4D3. There is no difference between control and eggmanone treated cells.

FIGS. 12a-12f include data and results of studies showing that Eggmanone increases activation of cAMP-dependent protein kinase (PKA) at the cilium base, but not globally. (FIG. 12a) Immunostaining for the cilia marker Arl13b (green) and the autophosphorylated form of the PKA catalytic subunit (red) shows Egm treatment increases local PKA activation at the base of the primary cilia, corresponding to the basal body (n=16 for each condition, p=0.00014, versus SAG alone). (FIG. 12b) Quantitative analysis of (FIG. 12a); Immmunostaining of autophosphorylated (Thr-197) form of the PKA catalytic subunit (red) costained with cilia specific Arl13b (green) show that eggmanone treatment increases levels of phospho-PKA only in the periciliary domain, but not the cilium. (FIG. 12c) Immunostaining for the basal body marker gamma-Tubulin (green) and the autophosphorylated form of the PKA catalytic subunit (Phospho$^{Y197}$-PKA-C; red) in NIH3T3 cells stimulated with Hh pathway activator SAG demonstrates that co-treatment with Egm (5 µM) treatment increases local PKA activation in the basal body (yellow, merged). (FIG. 12d) Quantitative analysis of autophosphorylated PKA reveals that Egm treatment significantly increased PKA activation in the basal body (n=10 for each condition; p<0.05, versus SAG alone). (FIG. 12e) Correlation coefficients from studies in (FIG. 12c). (FIG. 12f) Graphic comparison of correlation coefficients found in FIG. 6e.

FIGS. 17a-17i includes data and images showing that Eggmanone specifically inhibits Hedgehog signaling. Zebrafish embryos treated with 2 µM EGM (Egm) starting at 4-hours post fertilization (hpf) exhibited range of phenotypes found in Hh pathway mutants, including ventral tail curvature, loss of pectoral fins (FIG. 17a), smaller eyes and when treated at 10 hpf (FIG. 17b) enlarged somites in place of normal chevron-shaped somites. Egm treatment abolished Hh-responsive ptch1 expression in adaxial cells at 12-hpf (FIG. 17c; arrow), and in the pectoral fin bud at 48-hpf (FIG. 17d; arrow). (FIG. 17e) Egm inhibited Sonic hedgehog (SHH)-responsive Gli-luciferase (Gli-Luc) reporter activity in a dose-dependent manner. Cyclopamine (Cyc) 5 uM for comparison (n=4 for each condition, results represented as mean RLU, relative luciferase units, +/−standard error; P-value <0.0184, starting at 1 µM). (FIG. 17f) Egm inhibited purmorphamine (Purm, 3 µM)-induced Gli-Luc reporter activity in a dose-dependent manner. (n=4; P-value <0.0054, starting at 0.5 μM). (FIG. 17g) Egm significantly inhibited ptch1 expression in response to purmorphamine in NIH3T3 fibroblasts (n=3 for each condition, expression normalized to GAPDH, P-value <0.003, starting at 1 μM) (FIG. 17h) Egm had no significant effects on BMP4-responsive reporter (BRE-luc) activity in C2Cl2BRA reporter cells. BRE-luc (BMP responsive element driven luciferase) cells were stimulated with BMP4 ligand. (FIG. 17i) Egm had no significant effect on Gli-luciferase reporter activity under Gli2 overexpression conditions.

FIGS. 18a-18d includes data and images showing that Eggmanone is a selective PDE4 inhibitor. (FIG. 18a) In vitro PDE activity assays across 11 PDE families reveal that Egm (10 and 50 μM) significantly inhibited only the PDE4 class (bold faced, highlighted). (FIG. 18b) Dose response curve for Egm inhibition of indicated PDE isoforms on in vitro assays. (FIG. 18c) Left, EGM inhibited PDE4 isoforms with the $IC_{50}$ range of 0.8 to 73.46 μM. Right, representation of PDE4 isoform structures. (FIG. 18d) Double reciprocal (Lineweaver-burke) plot indicates a competitive mode of inhibition.

FIGS. 22a and 22b includes data and showing that Hh inhibition requires PDE4 antagonism. (FIG. 22a) Results of Hh signaling reporter assays, and of PDE4D3 activity assay for eggmanone (EGM) and 12 analogs. A compound's ability to antagonize PDE4 correlates with it's ability to inhibit Hh signaling. (FIG. 22b) Overexpression of wildtype PDE4D3 (D3WT) induced Hh reporter activity (*P=0.0026 versus pCS2 control), which was abolished by 5 uM EGM (p<0.0001 versus D3WT). Overexpression of dominant negative PDE4D3 (D3DN) decreased Hh reporter activity (** P=0.0121 versus pCS2)

(FIG. 23a) The competitive PDE4 inhibitor rolipram (beige bars) inhibited Sonic hedgehog (SHH)-responsive Gli-luciferase (Gli-Luc) reporter activity, but, unlike eggmanone (Egm, blue bars), rolipram did not bring the reporter activity down to the baseline even at very high concentrations. (FIG. 23b) The allosteric PDE4 inhibitor D159153 (beige bars) did not inhibit Sonic hedgehog (SHH)-responsive Gli-luciferase (Gli-Luc) reporter activity even at very high concentrations (n=3 for each condition, results represented as mean RLU, relative luciferase units, +/−standard error).

FIGS. 24a-24d include data and graphs showing that Eggmanone causes local perturbations in cAMP levels without affecting global cellular cAMP content. (FIG. 24a) Eggmanone (EGM) treatment had no effect on total cellular cAMP content in NIH 3T3 cells, and the competitive PDE4 inhibitor rolipram and the allosteric PDE4 inhibitor D159153 substantially and moderately increased total cellular cAMP levels, respectively. (FIG. 24b) Left, still images from high-speed video of zebrafish otic kino-cilium. Middle, kymograph visualization demonstrates that cilium movement is markedly reduced following 2 μM EGM treatment. Right, schematic of motile kino-cilium (green, line of capture for kymograph). (FIG. 24c) Top, NIH3T3 cells expressing m TurquoiseΔ-Epac(CD, ΔDEP)-cp173 Venus-Venus; Bottom, normalized mean kinetics of FRET change detected in response to 5 μM Rolipram or 5 μM EGM (n=3). (FIG. 24d) Top, NIH3T3 cells expressing PKAC-YFP and PKARII-CFP; Bottom, normalized mean kinetics of FRET change detected in response to 5 μM EGM (n=2). FRET values are the mean calculated within an ROI drawn to include the entire cytosolic area or the centrosome.

FIGS. 25a-25d includes images and graphs showing that Eggmanone (EGM) treatment results in PKA activation restricted to the basal bodies. (FIG. 25a) Immunostaining for the cilia marker Arl13b (green) and the autophosphorylated form of the PKA catalytic subunit (Phospho$^{Y197}$-PKA-C; red) in NIH3T3 cells stimulated with the Smo agonist SAG (left) demonstrates a low baseline PKA activation; co-treatment with 5 μM EGM (left) increases local PKA activation at the base of the primary cilia (n=16 for each condition, p=0.00014, versus SAG alone). (FIG. 25b) Quantitative analysis of (FIG. 25a). (FIG. 25c) Immunostaining for the basal body marker γ-Tubulin (green) and the autophosphorylated PKA catalytic subunit (Phospho$^{Y197}$-PKA-C; red) in NIH3T3 cells stimulated with SAG demonstrates that co-treatment with EGM (5 μM) dramatically increases PKA activation in the basal body (n=10 for each condition; p<0.05, versus SAG alone). (FIG. 25d) Quantitative analysis of (FIG. 25c).

FIG. 26 includes images showing that allosteric PDE4 inhibitor D159153 and cAMP analog dibutyril cAMP (DBA) induce spatially localized PKA activation in the basal body.

FIGS. 27a-27f include images and graphs showing that Eggmanone (EGM) causes selective dysregulation of Gli trafficking. (FIG. 27a) Immunostaining for the cilium marker Arl13b (green) and Gli2 (red) of NIH3T3 cells stimulated with SAG (20 nM) in the presence of 5 μM EGM or DMSO control. EGM treatment increased co-localization of Gli2 (yellow) in the primary cilium, arrows. (FIG. 27b) Quantitative analysis reveals that EGM significantly increased Gli2 localization in the cilium (n=10 for each condition; p=0.026, versus DMSO). (FIG. 27c) Representative western blot for Gli2 in nuclear fractions of NIH3T3 cells. Neg, unstimulated. SAG, stimulated with SAG (20 nM) for 60 minutes. SAG+FSK, co-treated with SAG and FSK (30 μM). SAG+EGM, co-treated with SAG and EGM (10 μM). Bottom, corresponding western blot for nuclear Lamin-A/C as loading controls. FL, full-length, active form of Gli2. R, proteolytically processed, repressor form of Gli2. (FIG. 27d) Quantitative analysis of the ratio of full length Gli2 to lamin-A in the nucleus reveals that SAG treatment increased abundance of full-length Gli2 in the nucleus, and this increase was abrogated by co-treatment with either FSK or EGM. (FIG. 27e) SAG treatment increased the nuclear ratio of full-length Gli2 (FL) to repressor Gli2 (R), which was abrogated by co-treatment with either FSK or EGM (For d and e, n=4 for each condition; p<0.05, versus SAG; ratio for each condition was normalized to the ratio of unstimulated controls). (FIG. 27l) Immunostaining for the cilium marker Arl13b (red) and IFT88 (green) of NIH3T3 cells stimulated with SAG (20 nM) in the presence of DMSO control (top), 100 μM ciliobrevin D (middle), or 5 μM EGM (bottom). Ciliobrevin D perturbed the localization of IFT88 in the cilium, but EGM did not affect IFT88 localization.

Figure 30:
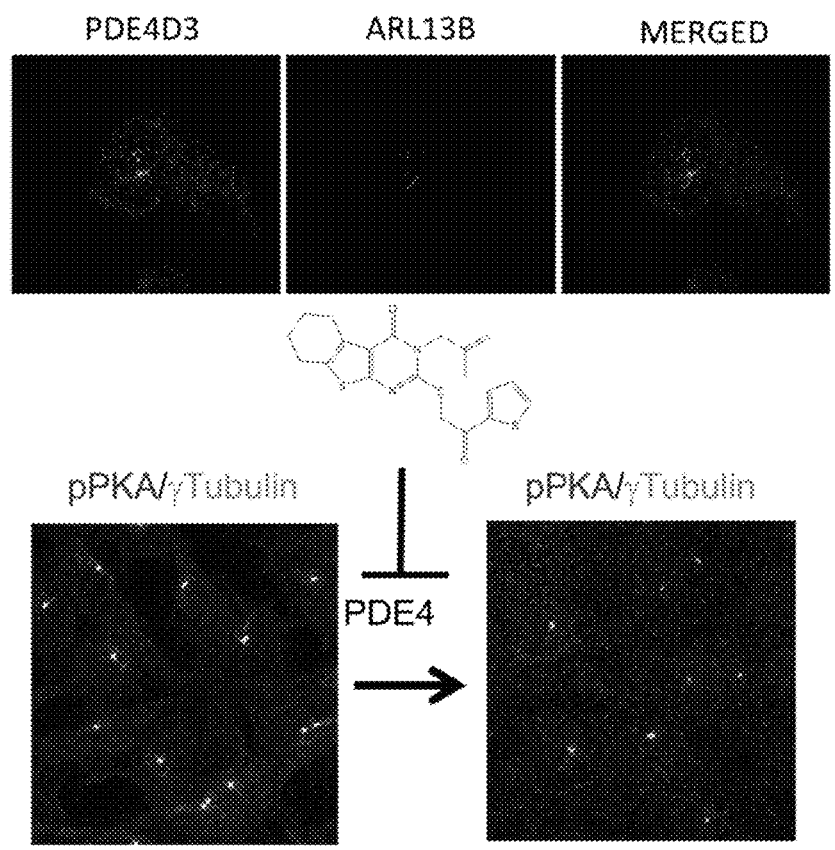

FIG. 30 includes images showing that addition of Egm causes local activation of PKA around PDE4 localization.

Figure 31:
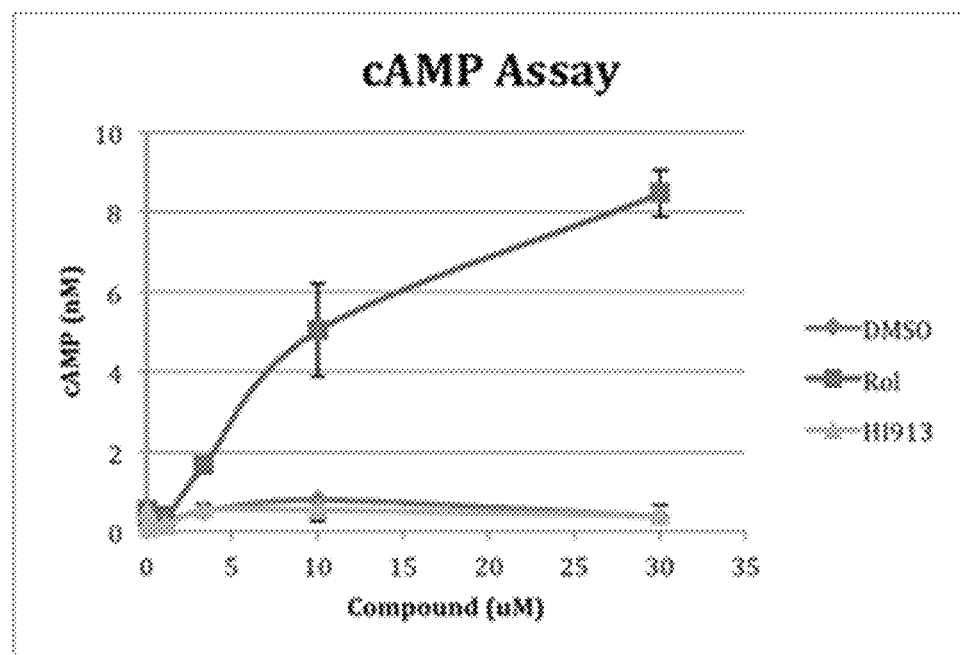

FIG. 31 includes a graph showing the concentration of total cAMP levels after administration with DMSO, Rolipram (Rol), and an embodied Egm (HI913).

Figure 32:
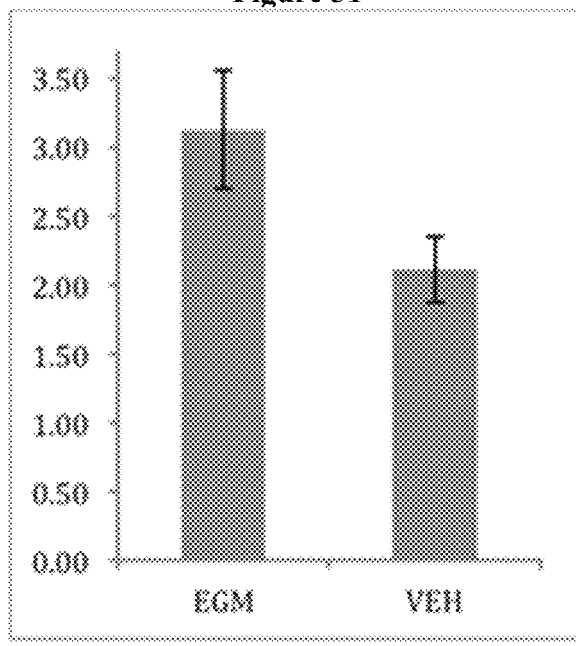

FIG. 32 includes a graph showing the effects of Egm on the contractibility of isolated mouse cardiomyocytes in comparison to a vehicle control (VEH).

Figure 33:
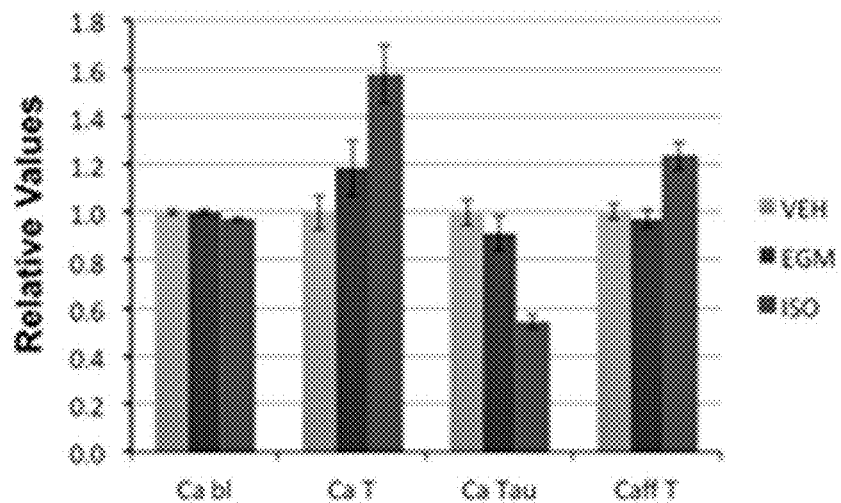

FIG. 33 includes a graph showing calcium handling results from mice that had been administered with VEH, EGM, or ISO.

Figure 34:
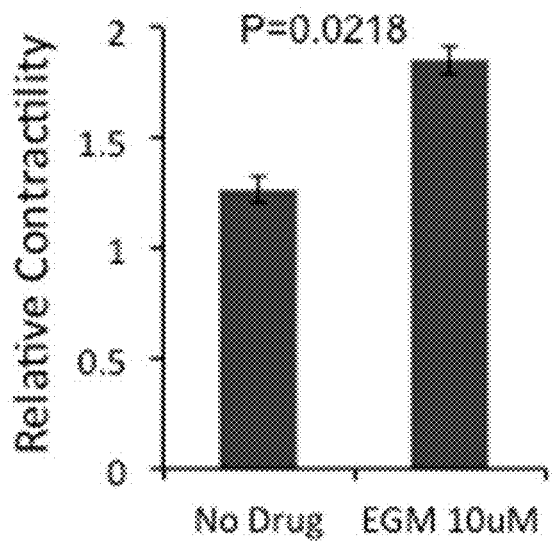

FIG. 34 includes a graph showing the effects of Egm on the contractibility of human cardiomyocytes derived from induced pluripotent stem cells (iPSCs).

Figure 35:
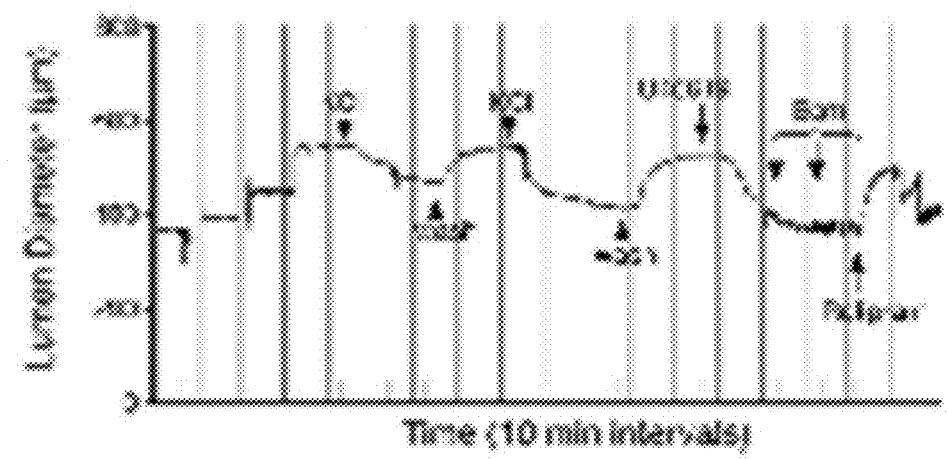

FIG. 35 includes a myograph of a cannulated mouse aorta showing that the addition of Egm results in little to no contraction or dilation of the vessel.

Figure 36:
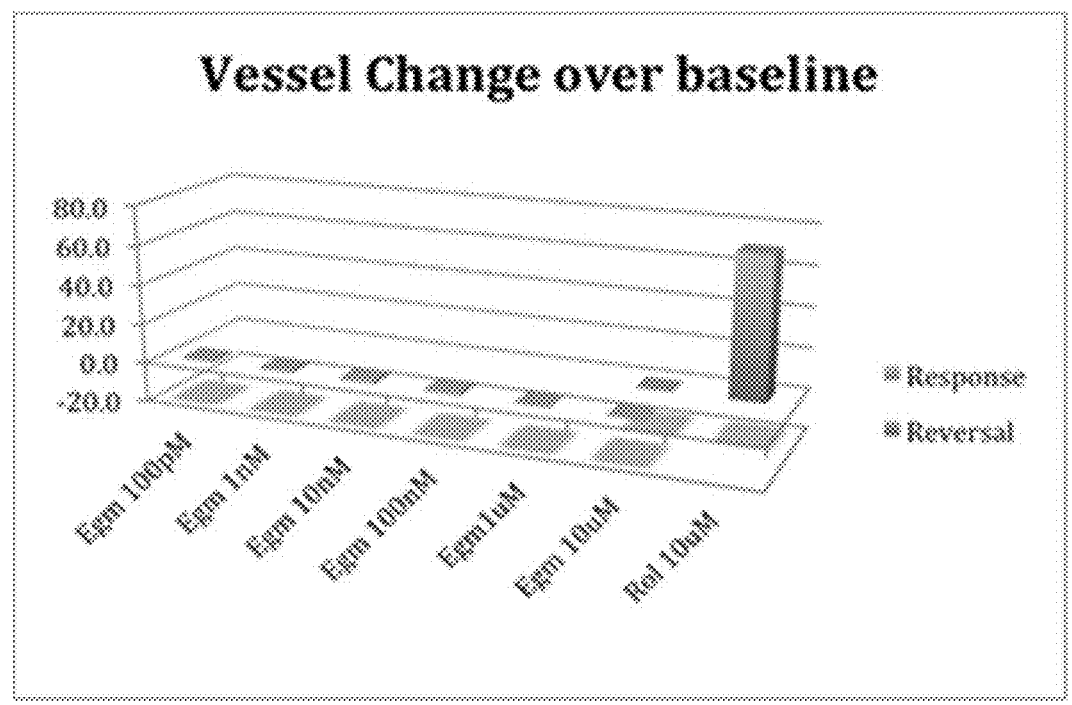

FIG. 36 includes a graph of an ascending aorta myography.

Figure 37:
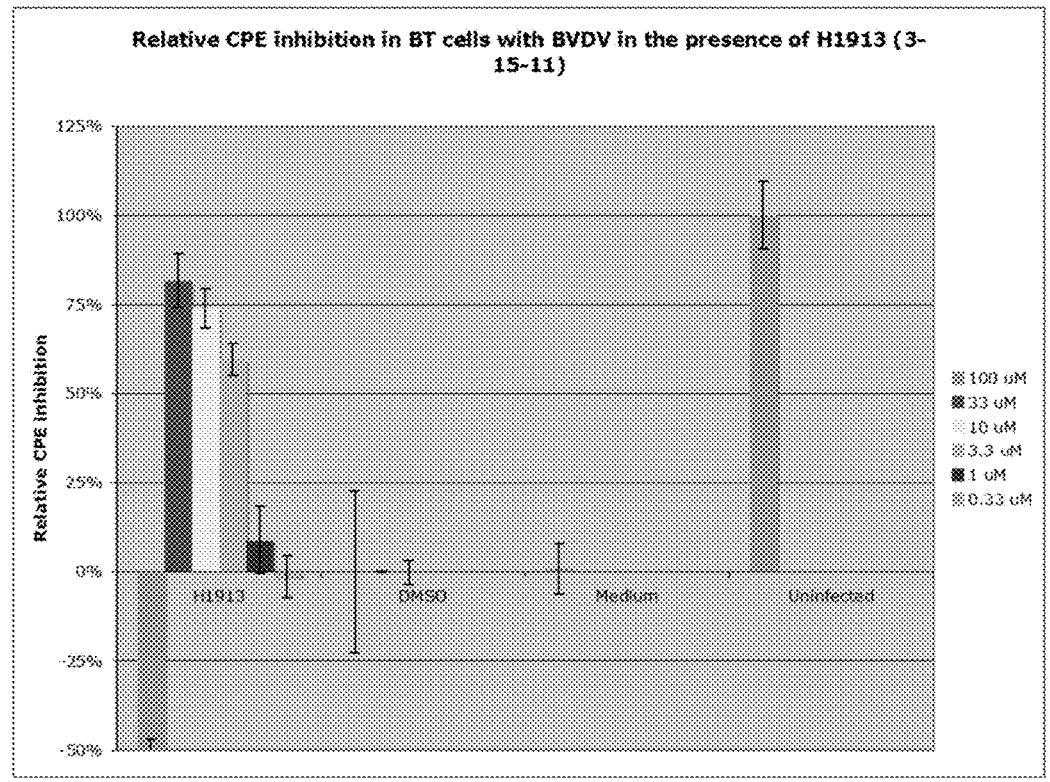

FIG. 37 includes a graph of relative cytotoxic effect in BT cells with Bovine Viral Diarrhea Virus, a surrogate for human hepatitis C virus in the present of H1913.

Figure 38:
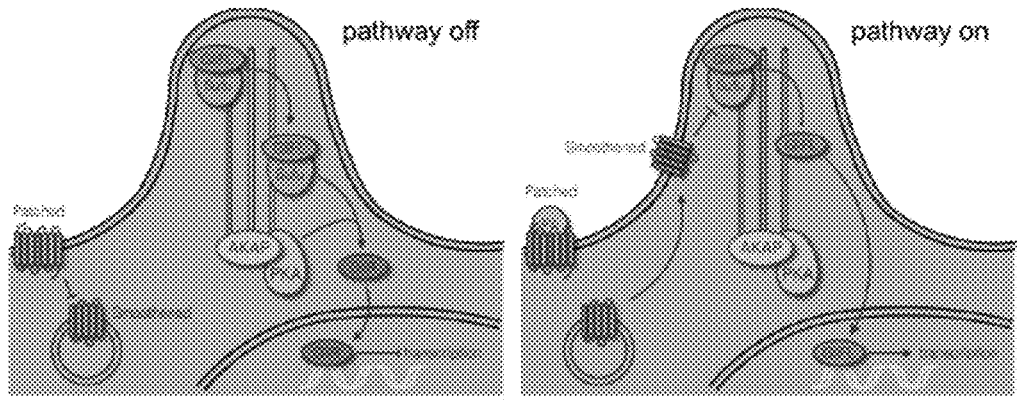
Figure 39F:
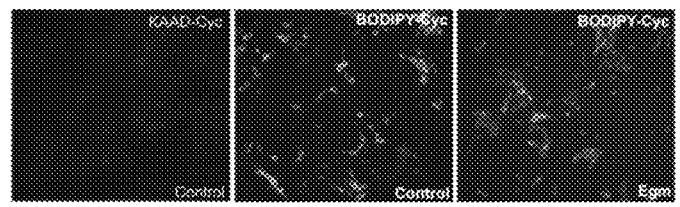
Figure 39G:
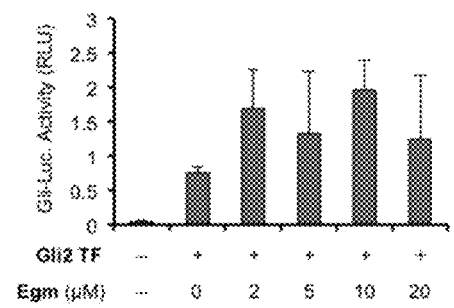

FIG. 38 includes a schematic of the Hedgehog Signaling Pathway.

FIGS. 39a-39g include data and images from discovery of EGM1 inhibiting Hedgehog signaling from an in vivo zebrafish phenotypic screen. (FIG. 39 (a)) includes images of zebrafish embryos treated with EGM1 exhibiting ventral tail curvature and loss of pectoral fins (FIG. 39 (b)) Egm treatment abolished Hh-responsive ptc1 expression in adaxial cells, and in the pectoral fin bud (FIG. 39 (c); arrow). (FIG. 39 (d)) graphs the concentration of EGM1 versus percent Hh activity, its cell-based inhibition profile. (FIG. 39 (e)) provides data of the relative percent of mRNA. (FIG. 39(f)) includes images where EGM1 was shown to not bind to the cyclopamine binding site of Smo as evidenced by its inability to displace a fluorescent analog of cylopamine from its binding site on Smo. (FIG. 39(g)) EGM1 could not overcome constitutive activation of signaling by overexpression of the Gli1 protein, thus indicating that EGM1 functioned between Sufu and Gli to effect Hh signaling inhibition.

Figure 4:
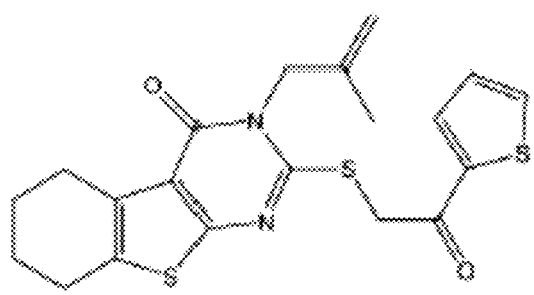
FIG. 4 includes the structure of Eggmanone identified in zebrafish-based screen for compounds that phenocopy hedgehog pathway mutants. Left, eggmanone, with IC50s for inhibition of Hh reporter activity and for PDE4D3 inhibition.
Figure 40A:
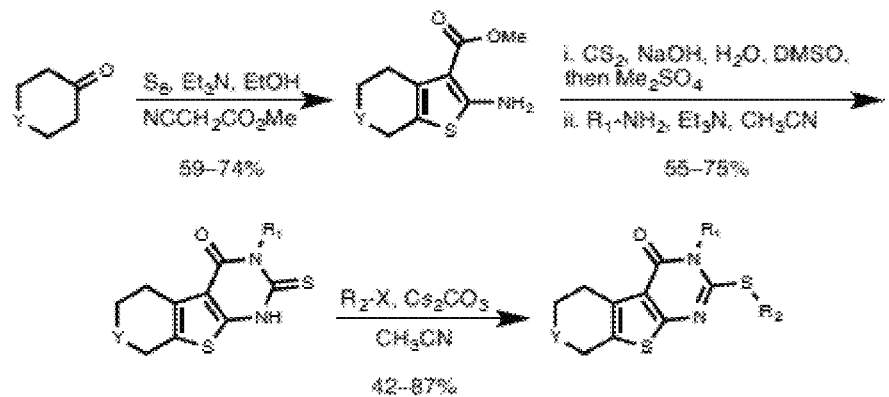
Figure 40B:
Figures 40C, 40D:
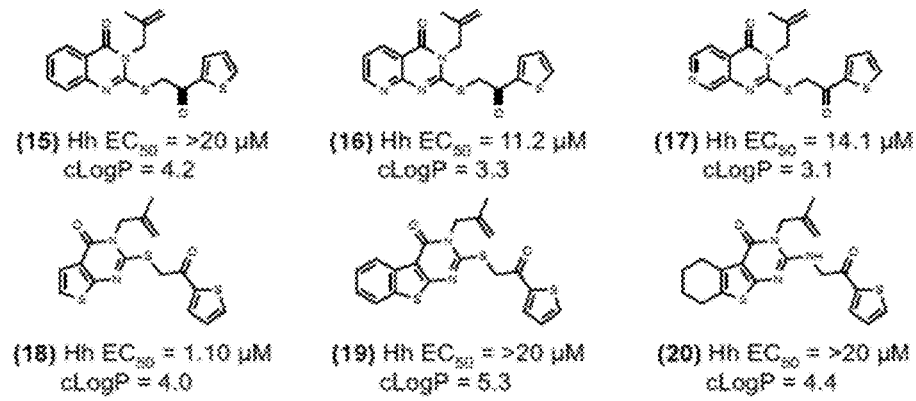

FIGS. 40a-4d Includes Synthesis and Characterization of EGM1 Compounds. (FIG. 40 (a)) includes a general reaction scheme for the synthesis and derivitization of EGM1. (FIG. 40 (b)) includes the Structure Activity Relationship (SAR) of Outer EGM1 Appendages. (FIG. 40 (c)) includes compounds with modifications to the EGM1 Core Scaffold. (FIG. 40 (d)) SAR-Informed Analog Evaluations.

Figure 41A:
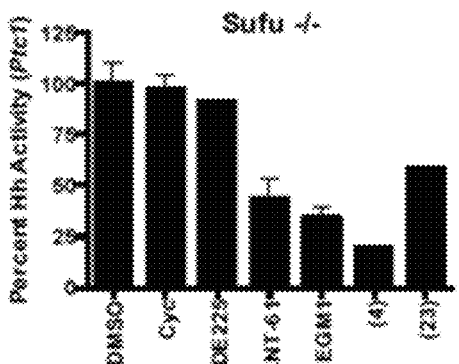
Figure 41B:
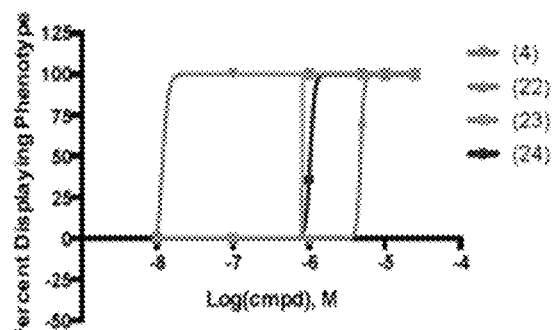
Figure 41C:
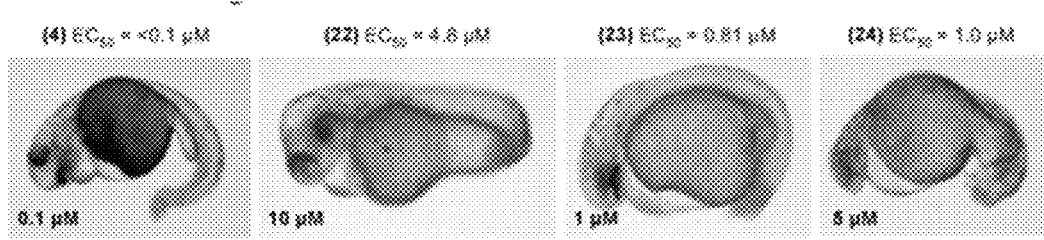

FIGS. 41a-41c include results of the mechanism of action validation for several EGM1 compounds. FIG. 41(a) charts percent Hh Activity (Pct1) based on administration of EGM1 compounds (4), (22), (23) and (24) as provided in FIG. 40. FIG. 41(b) includes the percent zebrafish displaying phenotype based on compound concentration. FIG. 41 (c) includes images of zebrafish and $EC_{50}$ based on compounds administered.

Figure 42:
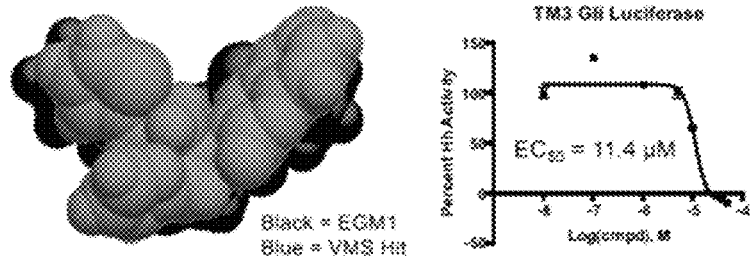

FIG. 42 provides a schematic of scaffold hopping via virtual screening. 98,000 compounds were screened against EGM1 3D hypothesis via the Suflex-Sim algorithm.

Figure 43:
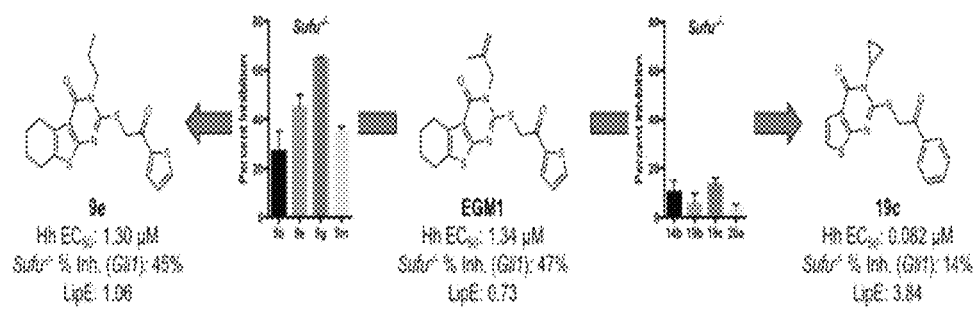

FIG. 43 includes data and results of in vivo phenotypic screening studies of EGM1 related structures.

Figure 44:
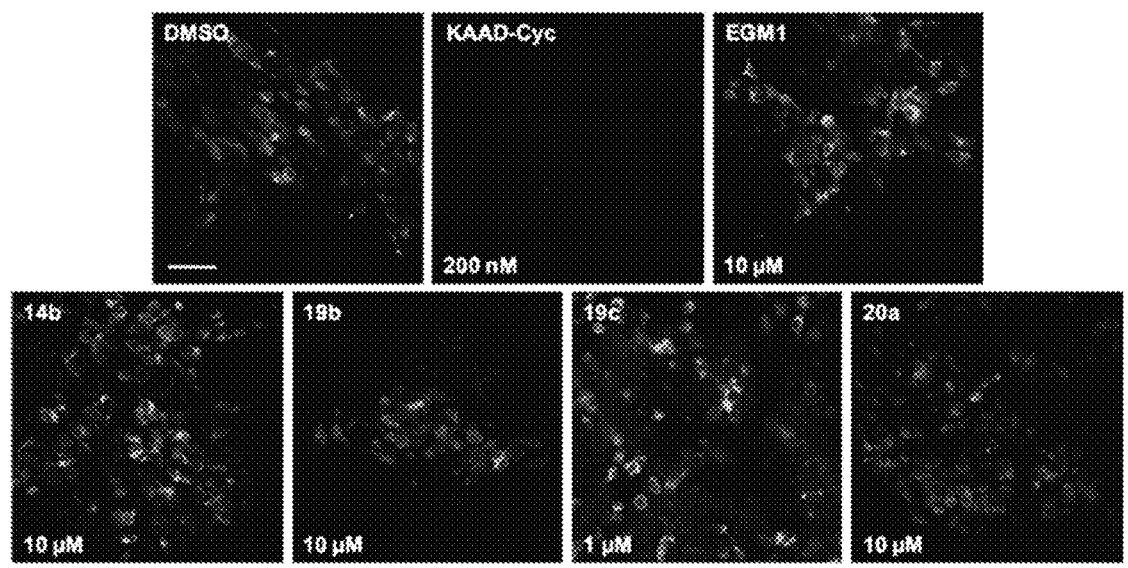

FIG. 44 includes images showing EGM1 analogs 14b, 19b, 19c and 20a lacking activity downstream of Sufu do not displace the binding of BODIPY-cyclopamine (5 nM) from its Smo binding site at the indicated concentrations, in contrast to KAAD-cyclopamine (200 nM). Green=BODIPY-cyclopamine; blue=DAPI. Scale bar=20 µm.

Figure 45A:
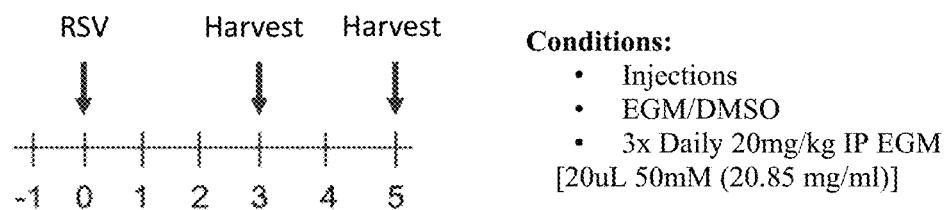
Figure 45B:
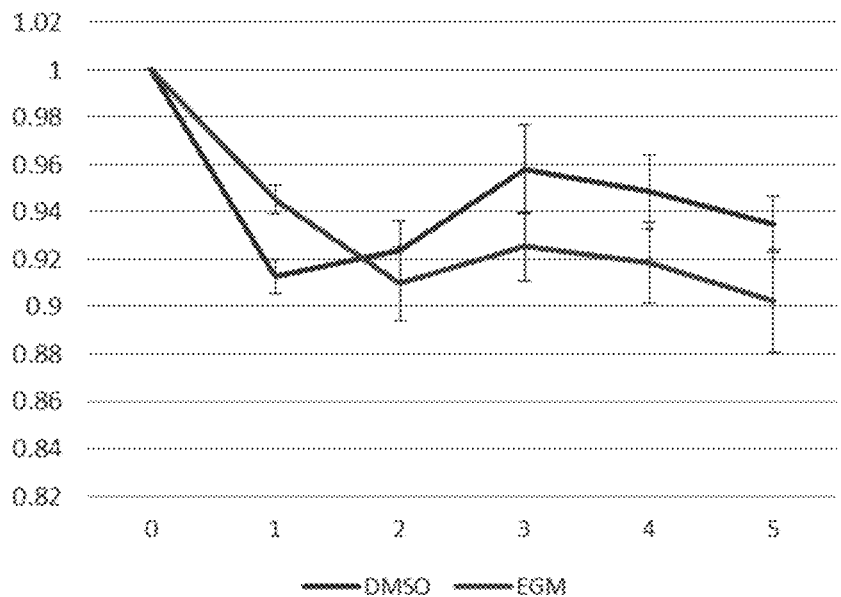
Figure 45C:
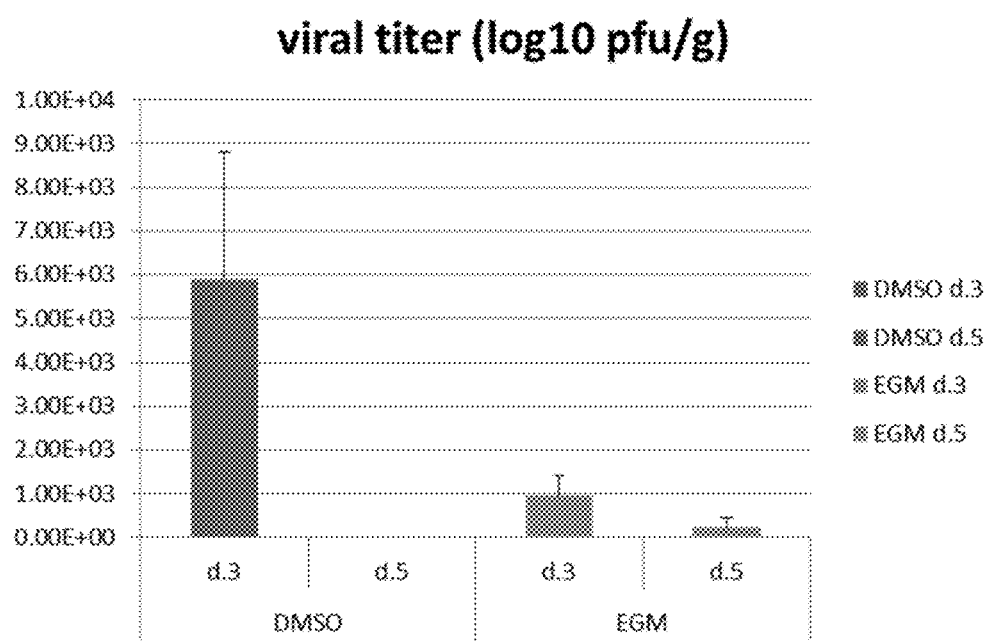

FIGS. 45a-45c include data and charts showing results of in vivo investigation of effects of EGM (Treatment) and Dimethyl sulphoxide ((DMSO) control) on RSV infection including (a) experimental conditions; (b) normalized daily body weight of mice after RSV infection and subsequent administration of DMSO and EGM; and (c) lung plaque assays measuring viral titer at days 3 and 5 subsequent to RSV infection and administration of DMSO and EGM.

DESCRIPTION OF EXEMPLARY EMBODIMENTS

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

The presently-disclosed subject matter meets some or all of the above-identified needs, as will become evident to those of ordinary skill in the art after a study of information provided in this document. To avoid excessive repetition, this Description does not list or suggest all possible combinations of such features.

The presently-disclosed subject matter includes compounds, pharmaceutical compositions, kits, and methods for using same. In some embodiments the compounds, pharmaceutical compositions, kits, and methods are useful for inhibiting hedgehog (Hh) signaling and/or inhibiting phosphodiesterase 4.

Chemical compounds having the structures set forth in Table 1A may be referred to herein with reference to the associated formula numbers, also set forth in Table 1A. Formula (1) is also referred to herein as Eggmanone.

TABLE 1A

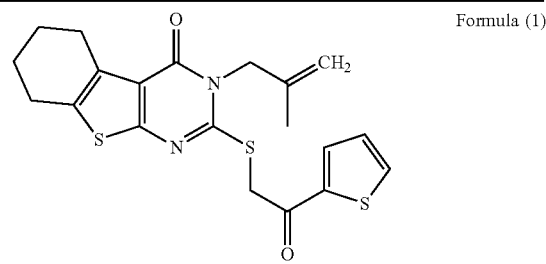

Formula (1)

TABLE 1A-continued
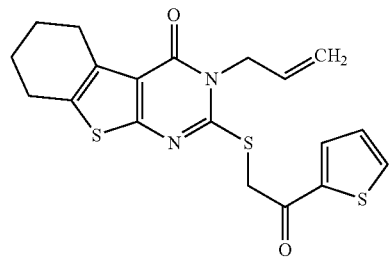 [SMILES: C=CCn1c(SCC(=O)c2cccs2)nc2sc3c(c2c1=O)CCCC3]
Formula (2)
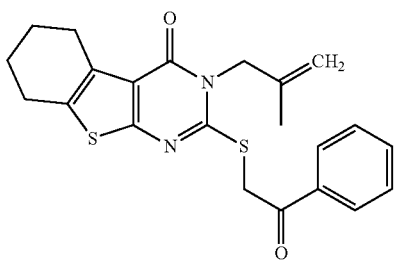 [SMILES: C=C(C)Cn1c(SCC(=O)c2ccccc2)nc2sc3c(c2c1=O)CCCC3]
Formula (3)
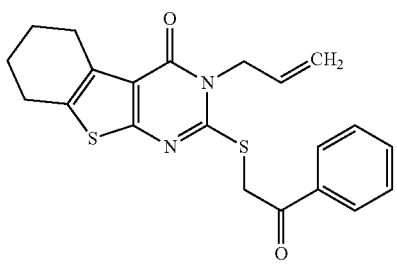
Formula (4)
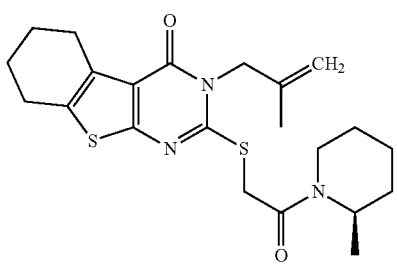 [SMILES: C=C(C)Cn1c(SCC(=O)N2CCCC[C@H]2C)nc2sc3c(c2c1=O)CCCC3]
Formula (5)
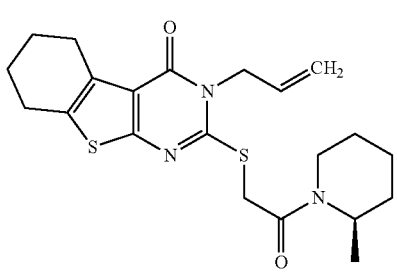 [SMILES: C=CCn1c(SCC(=O)N2CCCC[C@H]2C)nc2sc3c(c2c1=O)CCCC3]
Formula (6)
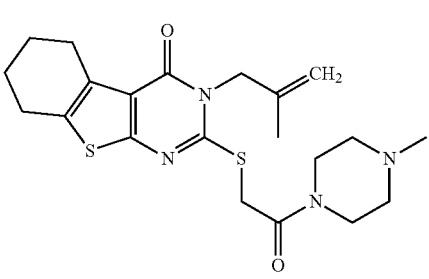 [SMILES: C=C(C)Cn1c(SCC(=O)N2CCN(C)CC2)nc2sc3c(c2c1=O)CCCC3]
Formula (7)
TABLE 1A-continued
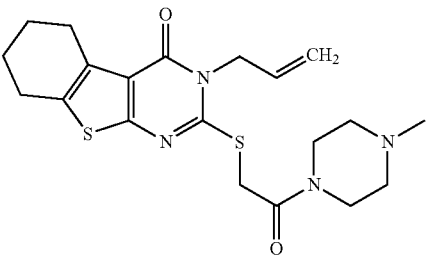 [SMILES: C=CCn1c(SCC(=O)N2CCN(C)CC2)nc2sc3c(c2c1=O)CCCC3]
Formula (8)
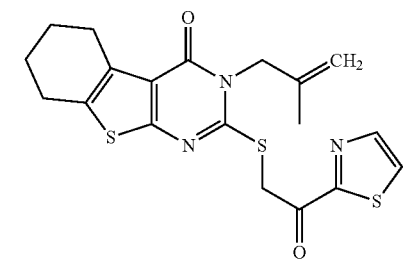 [SMILES: C=C(C)Cn1c(SCC(=O)c2nccs2)nc2sc3c(c2c1=O)CCCC3]
Formula (9)
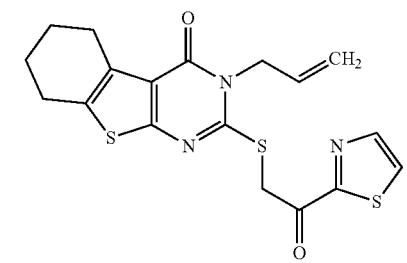
Formula (10)
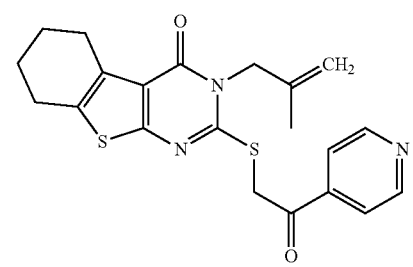 [SMILES: C=C(C)Cn1c(SCC(=O)c2ccncc2)nc2sc3c(c2c1=O)CCCC3]
Formula (11)
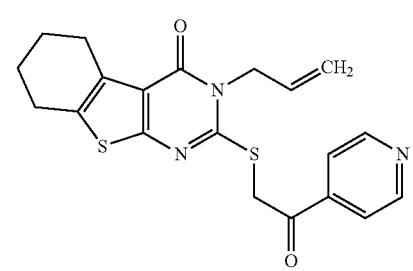 [SMILES: C=CCn1c(SCC(=O)c2ccncc2)nc2sc3c(c2c1=O)CCCC3]
Formula (12)
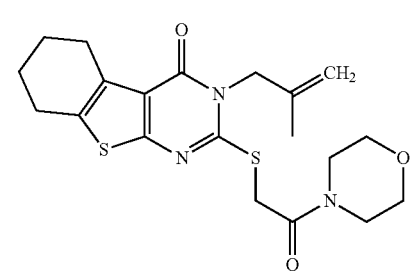 [SMILES: C=C(C)Cn1c(SCC(=O)N2CCOCC2)nc2sc3c(c2c1=O)CCCC3]
Formula (13)

TABLE 1A-continued

Formula (14)

Formula (15)

Formula (16)

Formula (17)

Formula (18)

Formula (19)

TABLE 1A-continued

Formula (20)

Compound

The presently-disclosed subject matter includes a compound having a structure represented by the formula:

or pharmaceutically-acceptable salts thereof, wherein X is selected from C, N, O, and S;

$R_1$ is selected from $CH_2CH_3$, $(CH_2)_2CH_3$, $R_2$ is selected from $CH_3$,

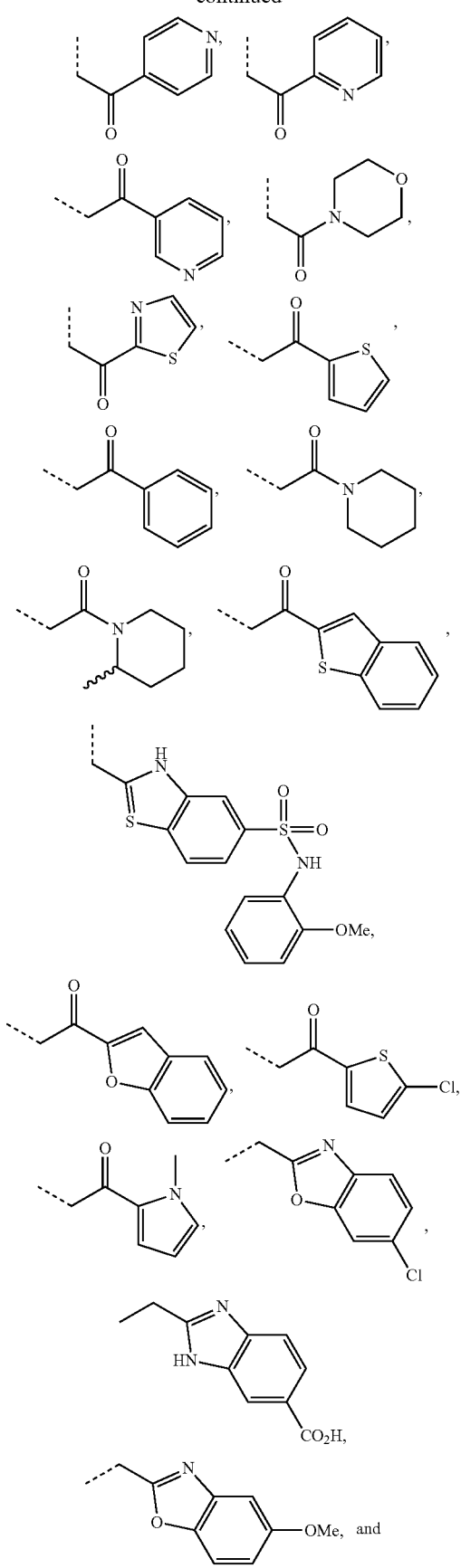
and
$R_3$ is selected from H, $CH_3$,
so long as when $R_2$ is
 or
,
$R_1$ is not
.
In some embodiments, the compound has a formula selected from the group set forth in Table 2, or pharmaceutically-acceptable salts thereof.

TABLE 2
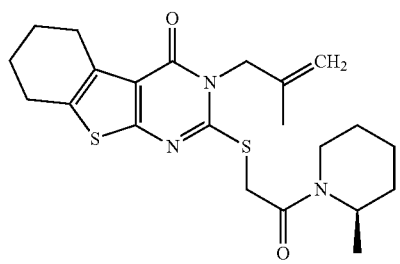 [SMILES: C=C(C)Cn1c(SCC(=O)N2CCCC[C@H]2C)nc2sc3c(c2c1=O)CCCC3]
Formula (5)
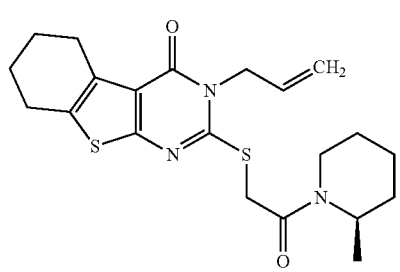 [SMILES: C=CCn1c(SCC(=O)N2CCCC[C@H]2C)nc2sc3c(c2c1=O)CCCC3]
Formula (6)
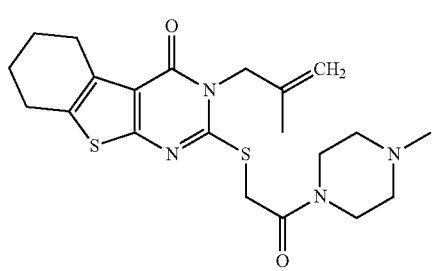 [SMILES: C=C(C)Cn1c(SCC(=O)N2CCN(C)CC2)nc2sc3c(c2c1=O)CCCC3]
Formula (7)
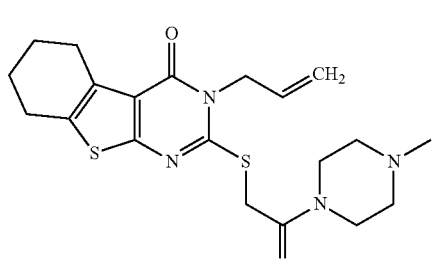
Formula (8)
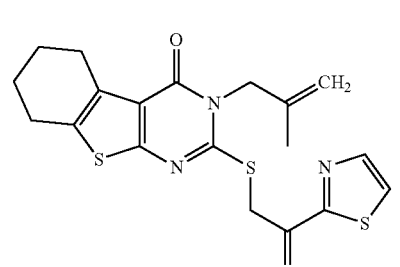
Formula (9)
TABLE 2-continued
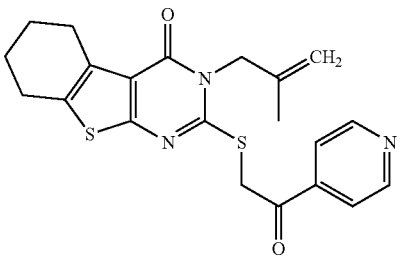 [SMILES: C=C(C)Cn1c(SCC(=O)c2ccncc2)nc2sc3c(c2c1=O)CCCC3]
Formula (11)
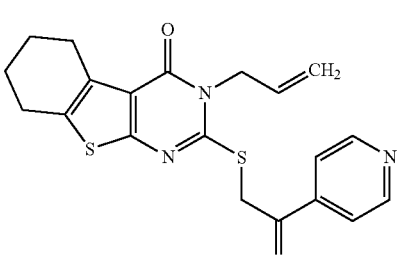
Formula (12)
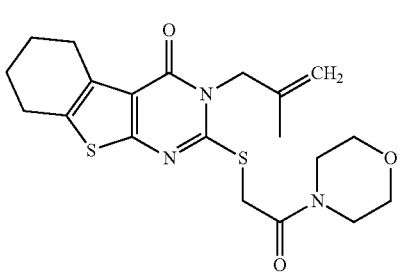 [SMILES: C=C(C)Cn1c(SCC(=O)N2CCOCC2)nc2sc3c(c2c1=O)CCCC3]
Formula (13)
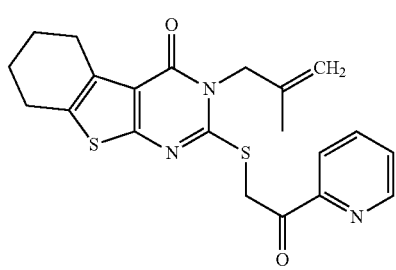 [SMILES: C=C(C)Cn1c(SCC(=O)c2ccccn2)nc2sc3c(c2c1=O)CCCC3]
Formula (15)
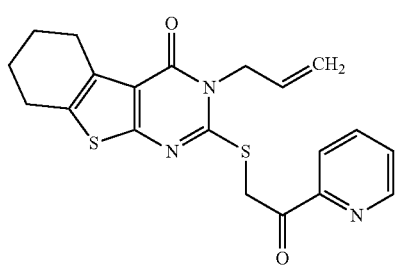
Formula (16)
In some embodiments, the compound has a formula selected from the group set forth in Table 1B, or pharmaceutically-acceptable salts thereof.

TABLE 1B
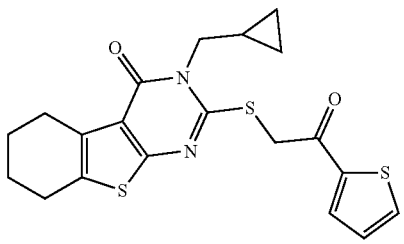 [SMILES: O=C(CSc1nc2sc3c(c2c(=O)n1CC1CC1)CCCC3)c1cccs1]
Formula (21)
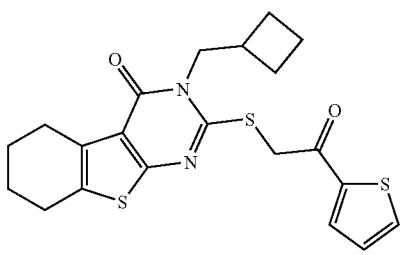 [SMILES: O=C(CSc1nc2sc3c(c2c(=O)n1CC1CCC1)CCCC3)c1cccs1]
Formula (22)
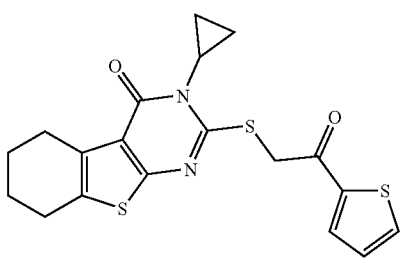 [SMILES: O=C(CSc1nc2sc3c(c2c(=O)n1C1CC1)CCCC3)c1cccs1]
Formula (23)
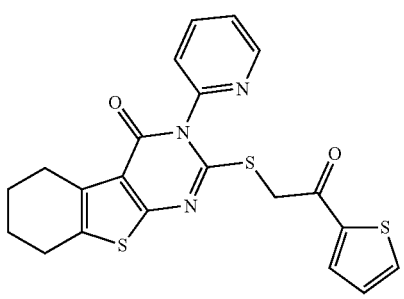 [SMILES: O=C(CSc1nc2sc3c(c2c(=O)n1-c1ccccn1)CCCC3)c1cccs1]
Formula (24)
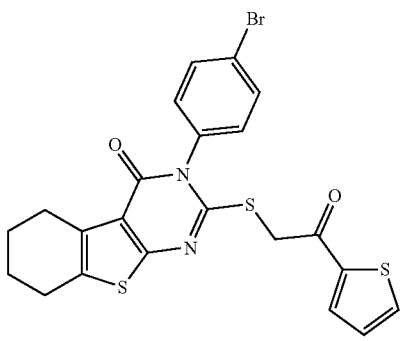 [SMILES: O=C(CSc1nc2sc3c(c2c(=O)n1-c1ccc(Br)cc1)CCCC3)c1cccs1]
Formula (25)

TABLE 1B-continued
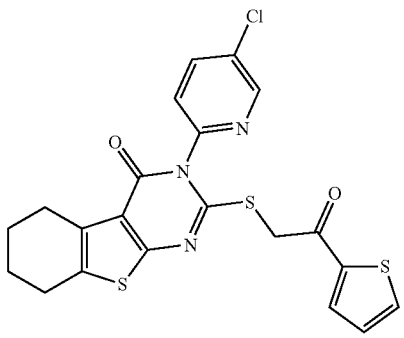 [SMILES: O=C(CSc1nc2sc3c(c2c(=O)n1-c1ccc(Cl)cn1)CCCC3)c1cccs1]
Formula (26)
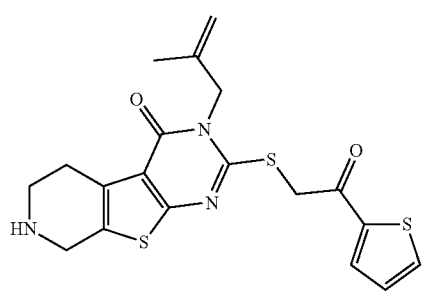 [SMILES: C=C(C)Cn1c(SCC(=O)c2cccs2)nc2sc3c(c2c1=O)CCNC3]
Formula (27)
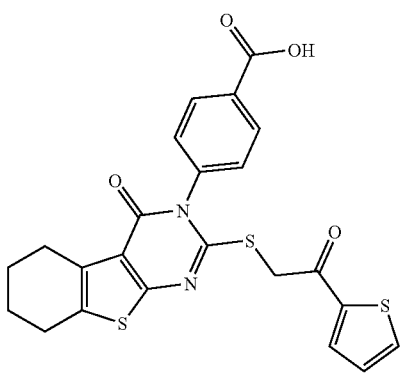 [SMILES: O=C(O)c1ccc(-n2c(SCC(=O)c3cccs3)nc3sc4c(c3c2=O)CCCC4)cc1]
Formula (28)
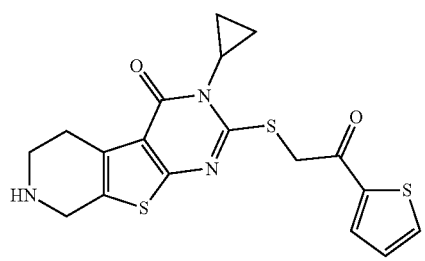 [SMILES: O=C(CSc1nc2sc3c(c2c(=O)n1C1CC1)CCNC3)c1cccs1]
Formula (29)
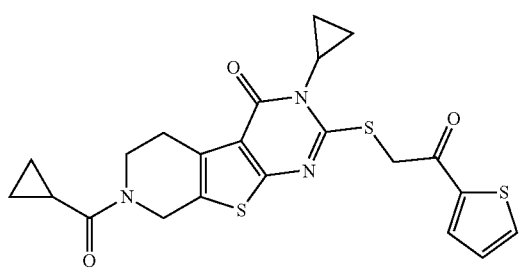 [SMILES: O=C(CSc1nc2sc3c(c2c(=O)n1C1CC1)CCN(C(=O)C1CC1)C3)c1cccs1]
Formula (30)

TABLE 1B-continued
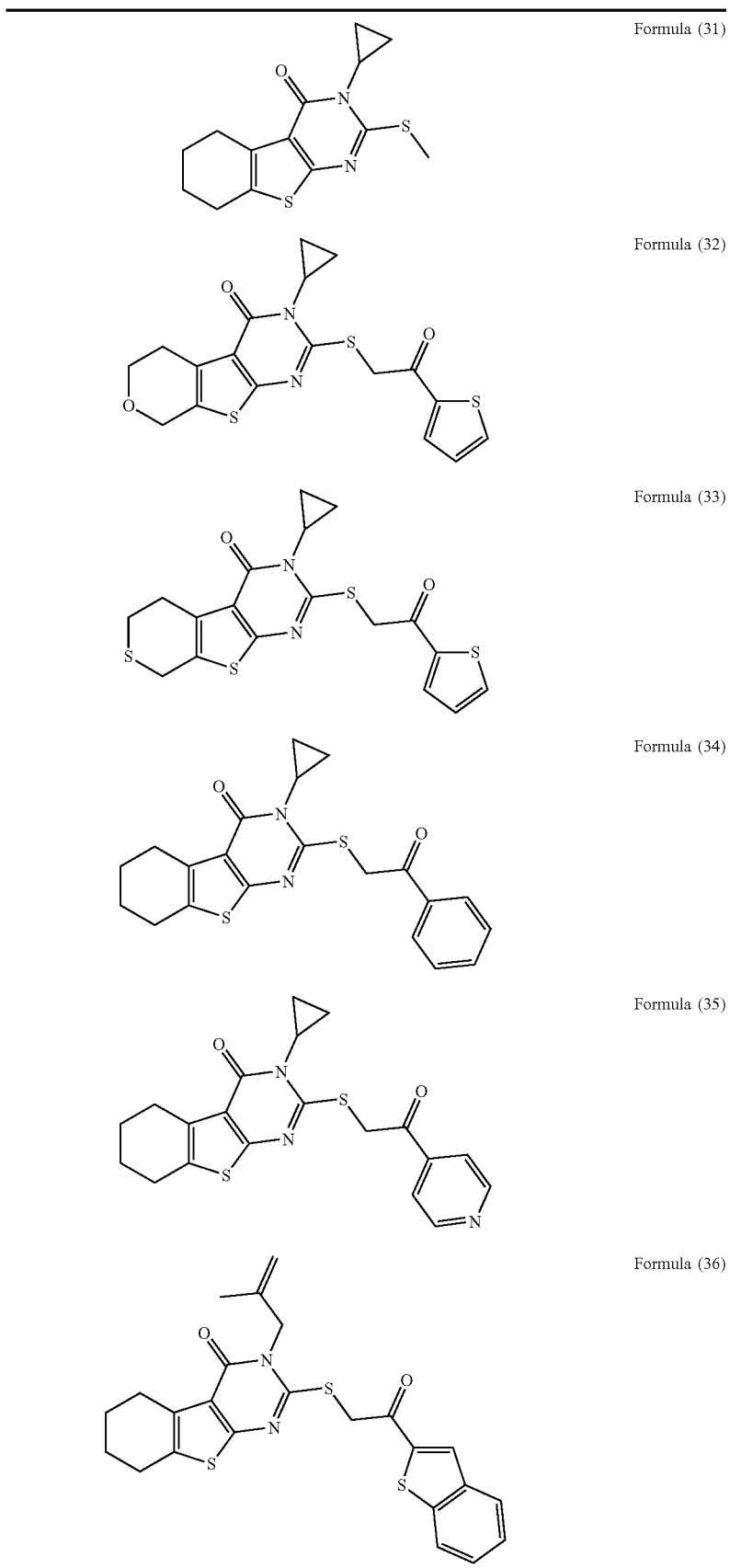
Formula (31)
Formula (32)
Formula (33)
Formula (34)
Formula (35)
Formula (36)

TABLE 1B-continued
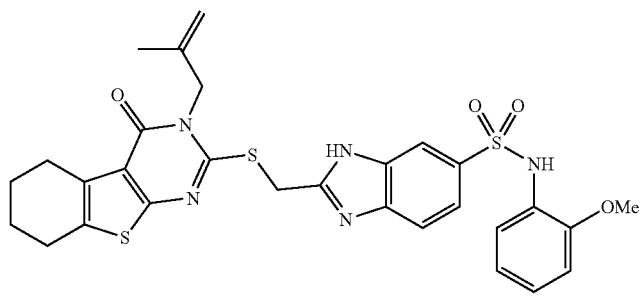
Formula (37)
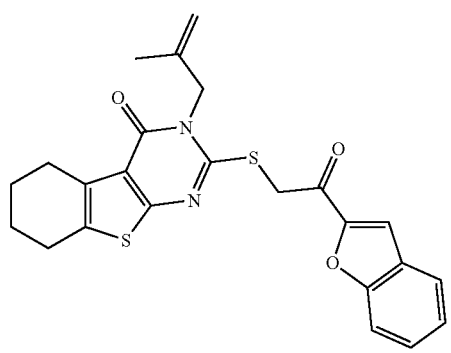 [SMILES: C=C(C)Cn1c(SCC(=O)c2cc3ccccc3s2)nc2sc3c(c2c1=O)CCCC3]
Formula (38)
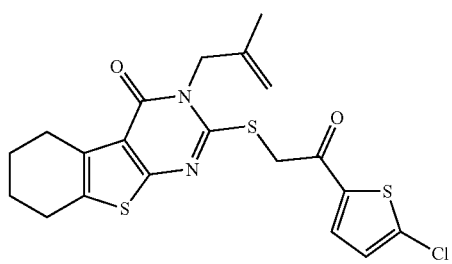 [SMILES: C=C(C)Cn1c(SCC(=O)c2ccc(Cl)s2)nc2sc3c(c2c1=O)CCCC3]
Formula (39)
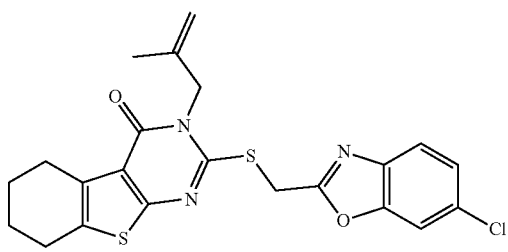 [SMILES: C=C(C)Cn1c(SCc2nc3ccc(Cl)cc3o2)nc2sc3c(c2c1=O)CCCC3]
Formula (40)
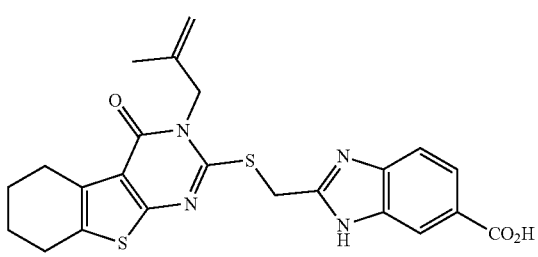 [SMILES: C=C(C)Cn1c(SCc2nc3ccc(C(=O)O)cc3[nH]2)nc2sc3c(c2c1=O)CCCC3]
Formula (41)

TABLE 1B-continued
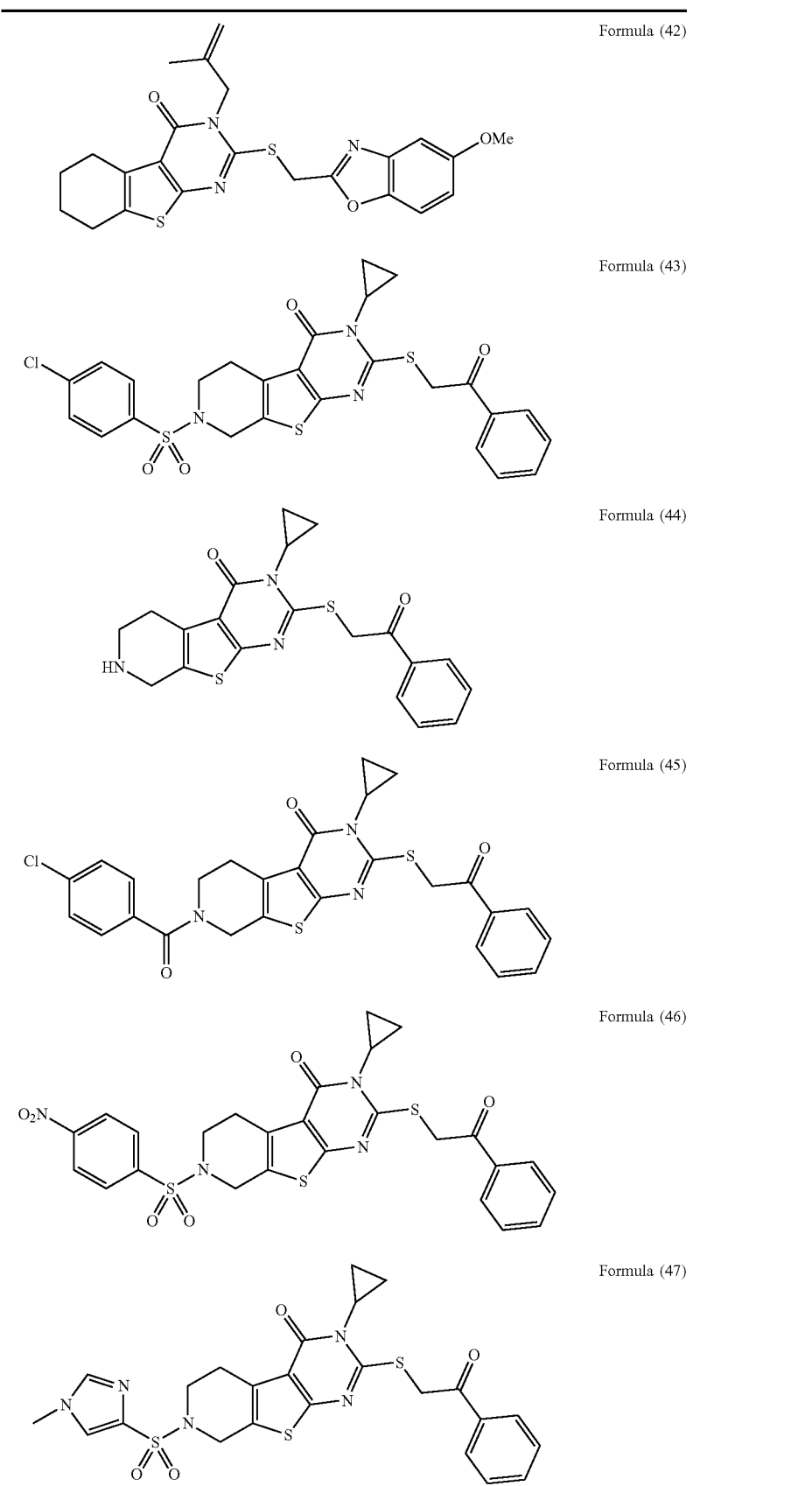
Formula (42)
Formula (43)
Formula (44)
Formula (45)
Formula (46)
Formula (47)

TABLE 1B-continued
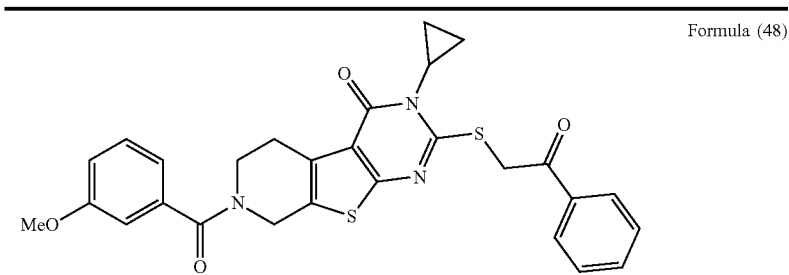
Formula (48)
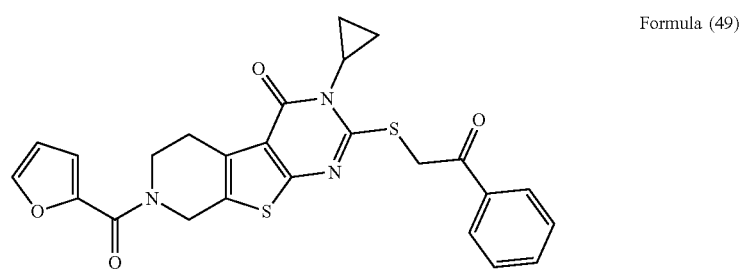
Formula (49)
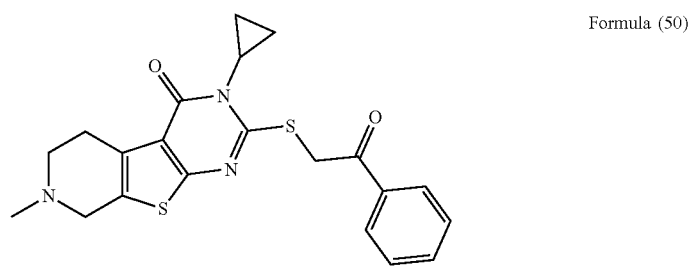
Formula (50)
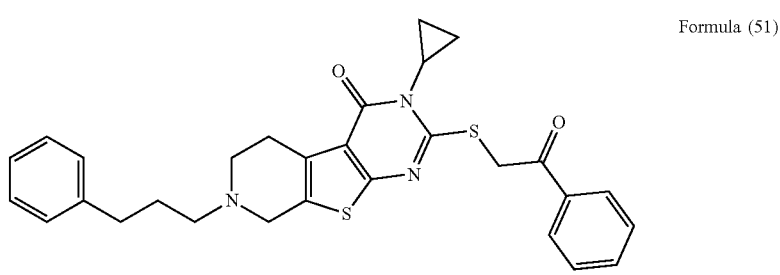
Formula (51)
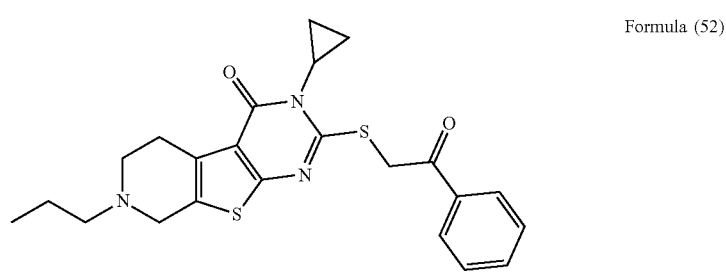
Formula (52)
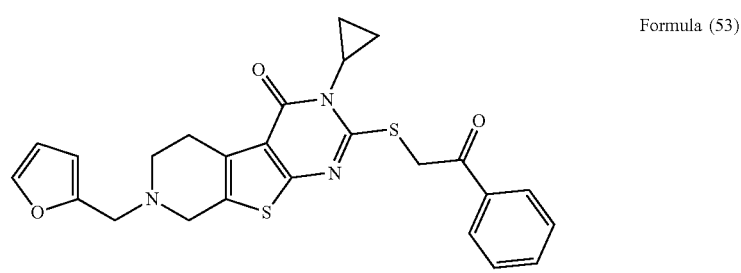
Formula (53)

TABLE 1B-continued

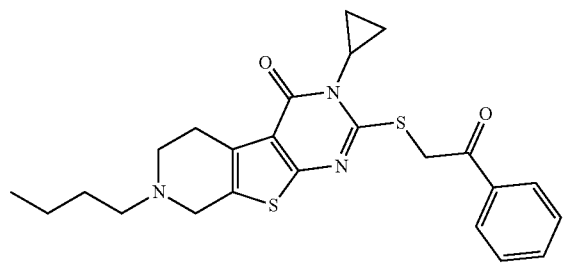 [SMILES: CCCCN1CCc2c(sc3nc(SCC(=O)c4ccccc4)n(C4CC4)c(=O)c23)C1]

Formula (54)

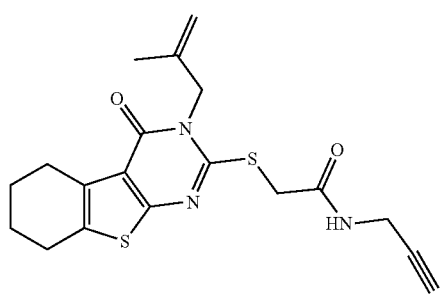 [SMILES: C#CCNC(=O)CSc1nc2sc3c(c2c(=O)n1CC(=C)C)CCCC3]

Formula (55)

In some embodiments, the compound has a formula selected from the group consisting of

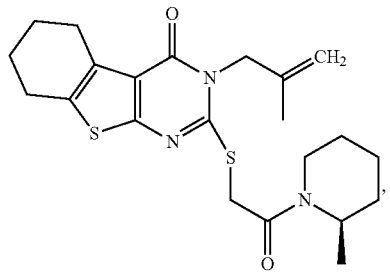 [SMILES: C=C(C)Cn1c(SCC(=O)N2CCCC[C@H]2C)nc2sc3c(c2c1=O)CCCC3]

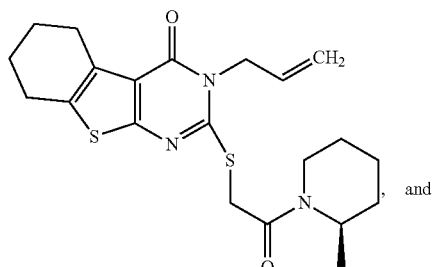

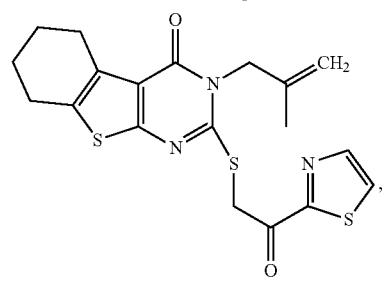

or pharmaceutically-acceptable salts thereof.

In some embodiments, the compound has the formula:

or pharmaceutically-acceptable salts thereof. In some embodiments, the compound has the formula:

or pharmaceutically-acceptable salts thereof. In some embodiments, the compound has the formula:

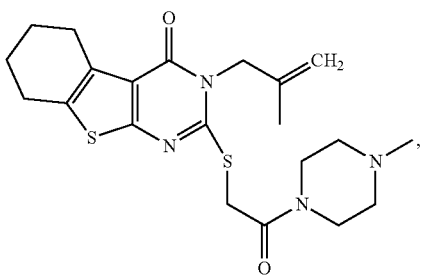 [SMILES: C=C(C)Cn1c(SCC(=O)N2CCN(C)CC2)nc2sc3c(c2c1=O)CCCC3]

or pharmaceutically-acceptable salts thereof. In some embodiments, the compound has the formula:

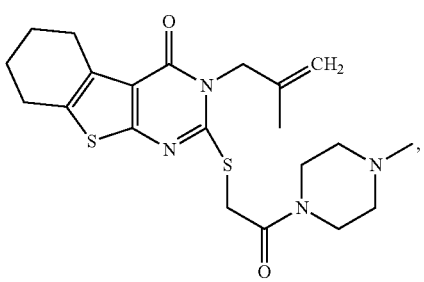 [SMILES: C=C(C)Cn1c(SCC(=O)N2CCN(C)CC2)nc2sc3c(c2c1=O)CCCC3]

or pharmaceutically-acceptable salts thereof. In some embodiments, the compound has the formula:

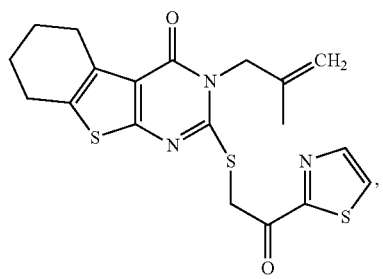 [SMILES: C=C(C)Cn1c(SCC(=O)c2nccs2)nc2sc3c(c2c1=O)CCCC3]

or pharmaceutically-acceptable salts thereof. In some embodiments, the compound has the formula:

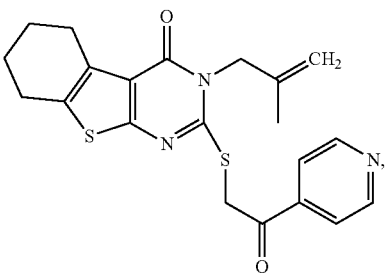 [SMILES: C=C(C)Cn1c(SCC(=O)c2ccncc2)nc2sc3c(c2c1=O)CCCC3]

or pharmaceutically-acceptable salts thereof. In some embodiments, the compound has the formula:

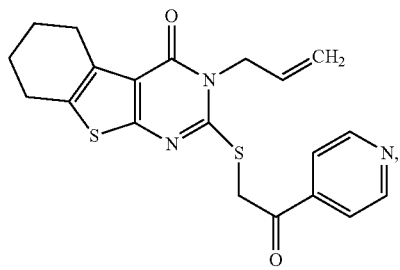 [SMILES: C=CCn1c(SCC(=O)c2ccncc2)nc2sc3c(c2c1=O)CCCC3]

or pharmaceutically-acceptable salts thereof. In some embodiments, the compound has the formula:

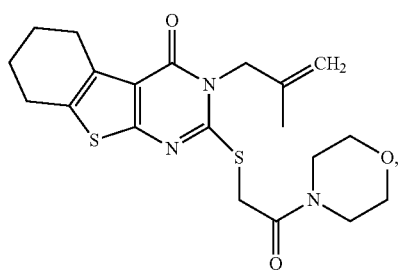 [SMILES: C=C(C)Cn1c(SCC(=O)N2CCOCC2)nc2sc3c(c2c1=O)CCCC3]

or pharmaceutically-acceptable salts thereof. In some embodiments, the compound has the formula:

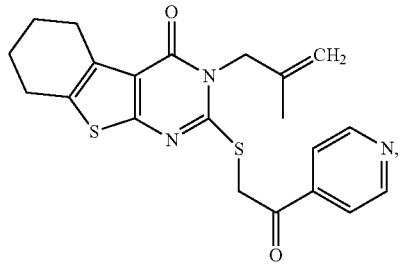 [SMILES: C=C(C)Cn1c(SCC(=O)c2ccncc2)nc2sc3c(c2c1=O)CCCC3]

or pharmaceutically-acceptable salts thereof. In some embodiments, the compound has the formula:

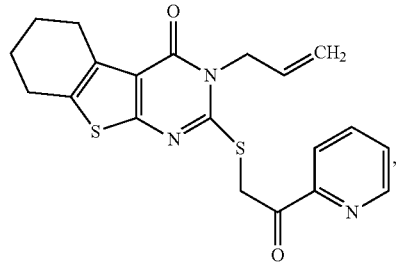 [SMILES: C=CCn1c(SCC(=O)c2ccccn2)nc2sc3c(c2c1=O)CCCC3]

or pharmaceutically-acceptable salts thereof.

In yet other embodiments, the compound has a structure of the formula:

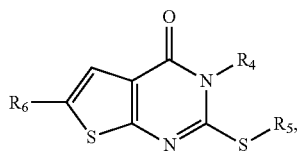
or pharmaceutically-acceptable salts thereof, wherein R₄ is selected from
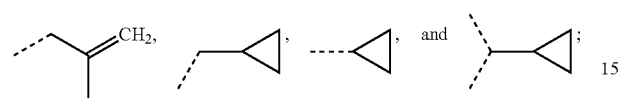
R₅ is selected from CH₃,
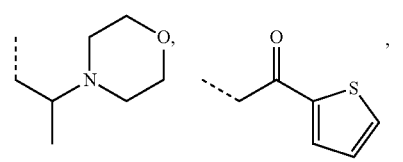
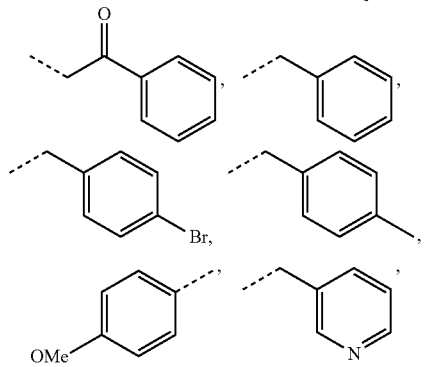
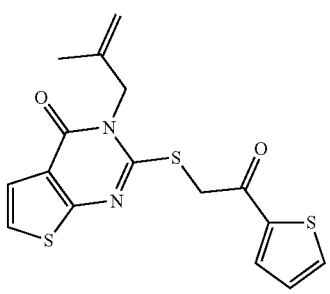 [SMILES: C=C(C)Cn1c(SCC(=O)c2cccs2)nc2sccc2c1=O]
and
R₆ is selected from H,
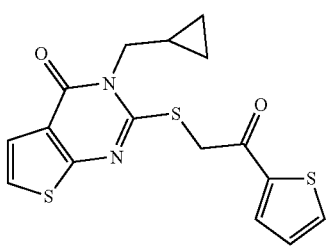 [SMILES: O=C(CSc1nc2sccc2c(=O)n1CC1CC1)c1cccs1]
In some embodiments, the compound has a formula selected from the group set forth in Table 1C, or pharmaceutically-acceptable salts thereof.
TABLE 1C TABLE 1C-continued
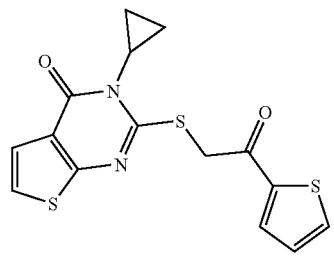 [SMILES: O=C(CSc1nc2sccc2c(=O)n1C1CC1)c1cccs1]
Formula (58)
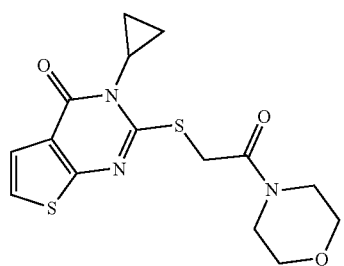 [SMILES: O=C(CSc1nc2sccc2c(=O)n1C1CC1)N1CCOCC1]
Formula (59)
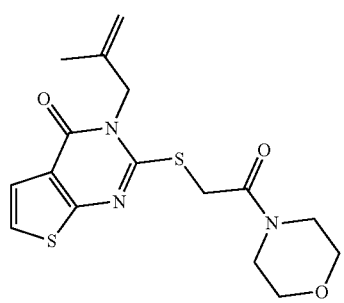 [SMILES: C=C(C)Cn1c(SCC(=O)N2CCOCC2)nc2sccc2c1=O]
Formula (60)
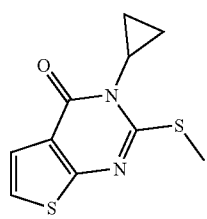
Formula (61)
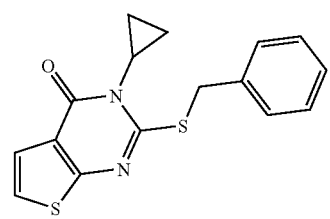 [SMILES: O=c1c2ccsc2nc(SCc2ccccc2)n1C1CC1]
Formula (62)
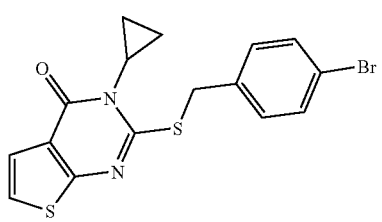 [SMILES: O=c1c2ccsc2nc(SCc2ccc(Br)cc2)n1C1CC1]
Formula (63)

TABLE 1C-continued
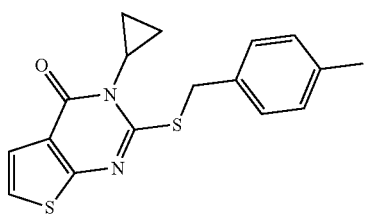 [SMILES: Cc1ccc(CSc2nc3sccc3c(=O)n2C2CC2)cc1]
Formula (64)
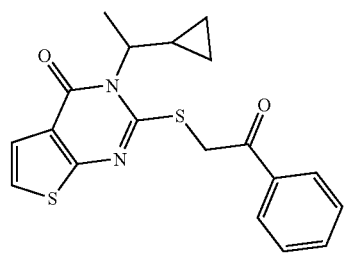 [SMILES: CC(C1CC1)n1c(SCC(=O)c2ccccc2)nc2sccc2c1=O]
Formula (65)
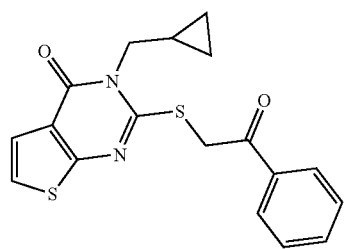 [SMILES: O=C(CSc1nc2sccc2c(=O)n1CC1CC1)c1ccccc1]
Formula (66)
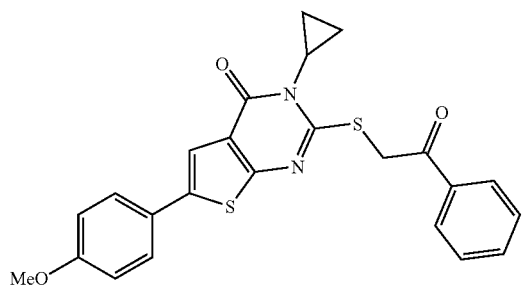 [SMILES: COc1ccc(-c2cc3c(=O)n(C4CC4)c(SCC(=O)c4ccccc4)nc3s2)cc1]
Formula (67)
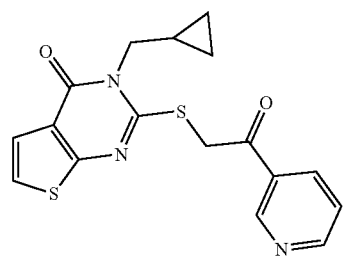 [SMILES: O=C(CSc1nc2sccc2c(=O)n1CC1CC1)c1cccnc1]
Formula (68)
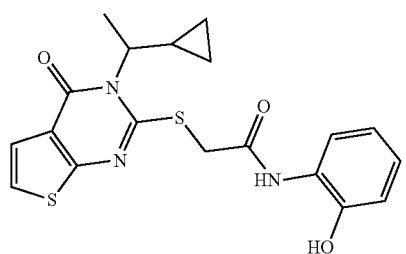 [SMILES: CC(C1CC1)n1c(SCC(=O)Nc2ccccc2O)nc2sccc2c1=O]
Formula (69)

TABLE 1C-continued
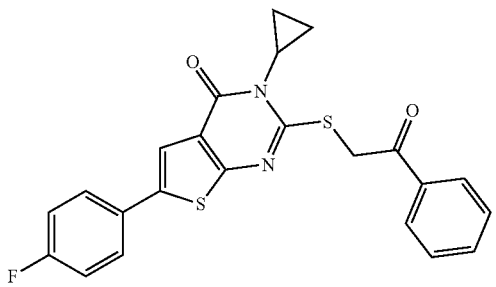 [SMILES: O=C(CSc1nc2sc(-c3ccc(F)cc3)cc2c(=O)n1C1CC1)c1ccccc1]
Formula (70)
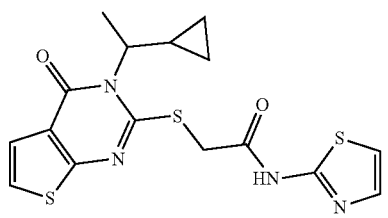 [SMILES: CC(C1CC1)n1c(SCC(=O)Nc2nccs2)nc2sccc2c1=O]
Formula (71)
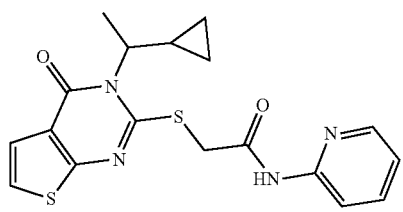 [SMILES: CC(C1CC1)n1c(SCC(=O)Nc2ccccn2)nc2sccc2c1=O]
Formula (72)
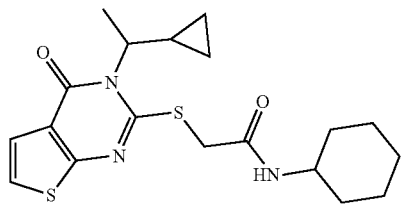 [SMILES: CC(C1CC1)n1c(SCC(=O)NC2CCCCC2)nc2sccc2c1=O]
Formula (73)
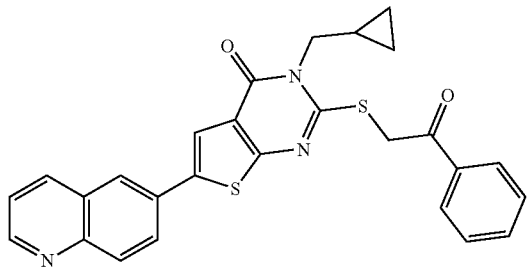 [SMILES: O=C(CSc1nc2sc(-c3ccc4ncccc4c3)cc2c(=O)n1CC1CC1)c1ccccc1]
Formula (74)
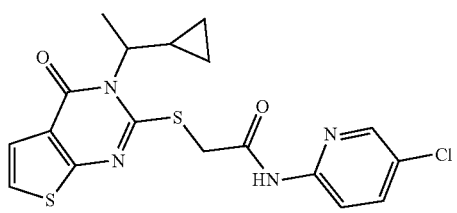 [SMILES: CC(C1CC1)n1c(SCC(=O)Nc2ccc(Cl)cn2)nc2sccc2c1=O]
Formula (75)
In other embodiments, the compound has a structure of the formula:

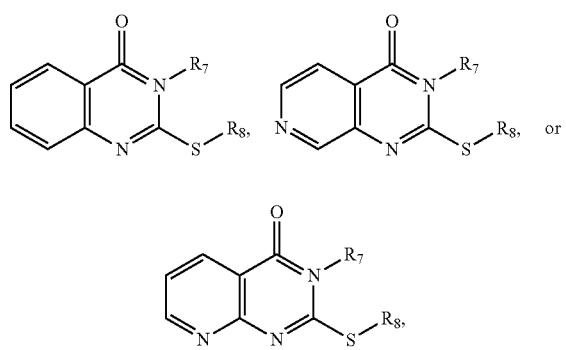

or pharmaceutically-acceptable salts thereof, wherein R₇ is selected from

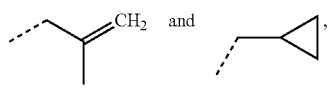

and R₈ is

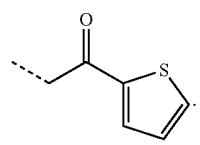

In yet further embodiments, the compound has a formula selected from the group set forth in Table 1D, or pharmaceutically-acceptable salts thereof.

TABLE 1D

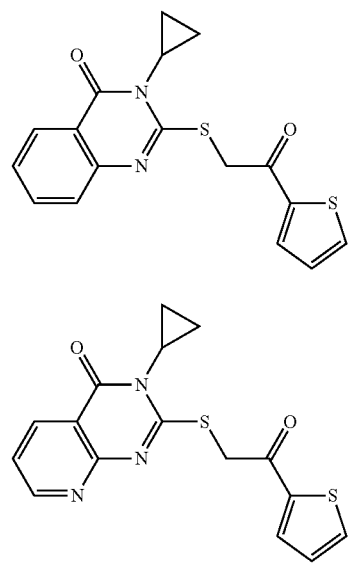

Formula (76)

Formula (77)

TABLE 1D-continued

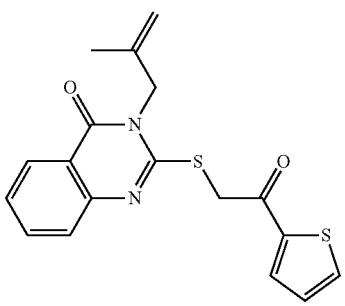 [SMILES: C=C(C)Cn1c(SCC(=O)c2cccs2)nc2ccccc2c1=O]

Formula (78)

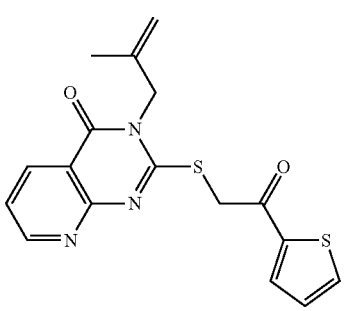

Formula (79)

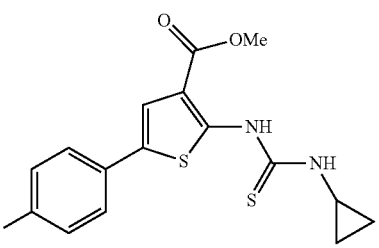

Formula (80)

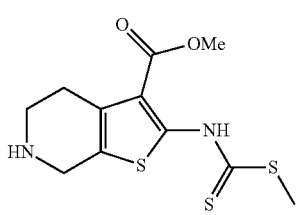 [SMILES: COC(=O)c1c(NC(=S)SC)sc2c1CCNC2]

Formula (81)

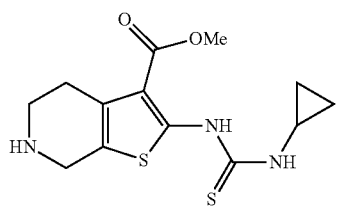 [SMILES: COC(=O)c1c(NC(=S)NC2CC2)sc2c1CCNC2]

Formula (82)

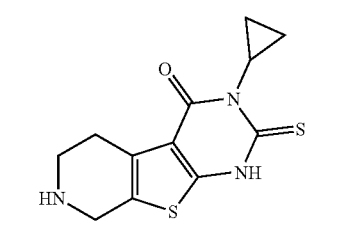 [SMILES: O=c1c2c3c(sc2[nH]c(=S)n1C1CC1)CNCC3]

Formula (83)

In yet further embodiments, the compound has a formula selected from the group set forth in Table 1E, or pharmaceutically-acceptable salts thereof.

TABLE 1E
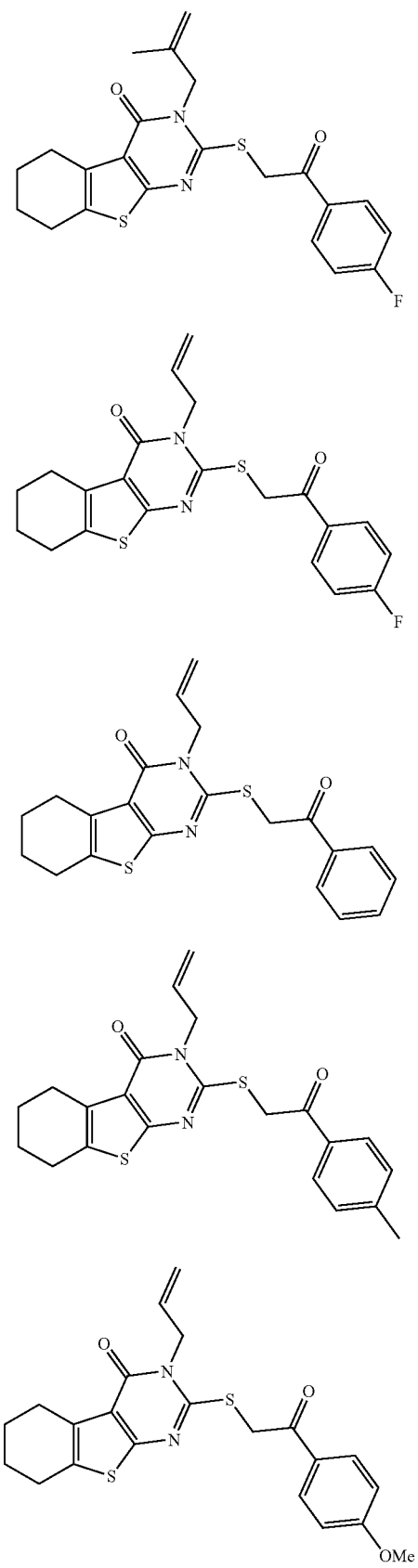
Formula (84)
Formula (85)
Formula (86)
Formula (87)
Formula (88)
TABLE 1E-continued
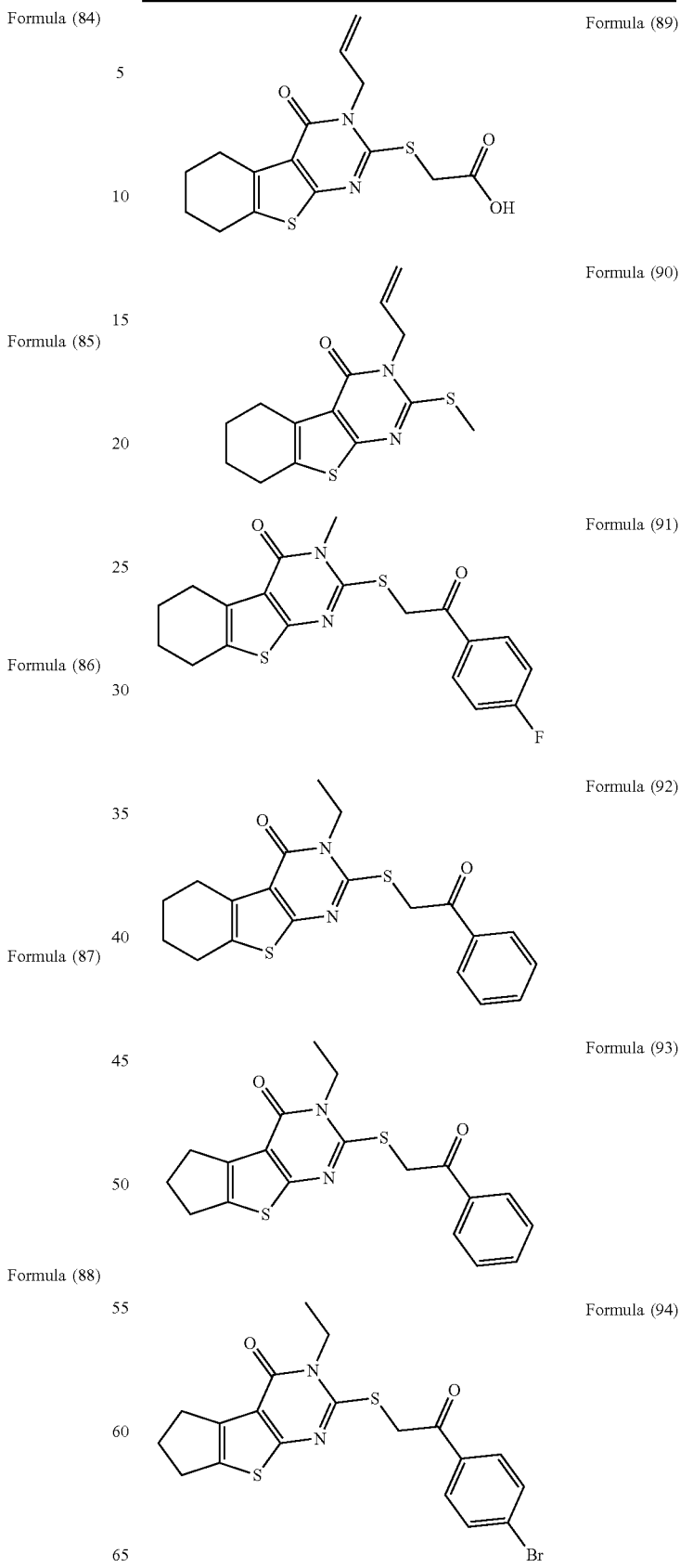
Formula (89)
Formula (90)
Formula (91)
Formula (92)
Formula (93)
Formula (94)

TABLE 1E-continued
Formula (95)
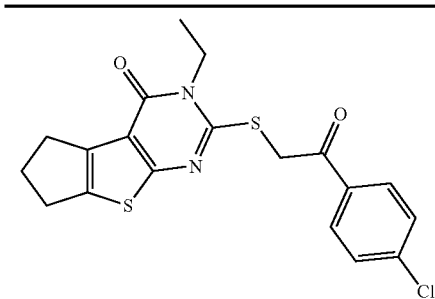
Formula (96)
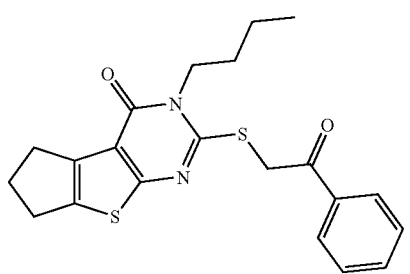 [SMILES: CCCCn1c(SCC(=O)c2ccccc2)nc2sc3c(c2c1=O)CCC3]
Formula (97)
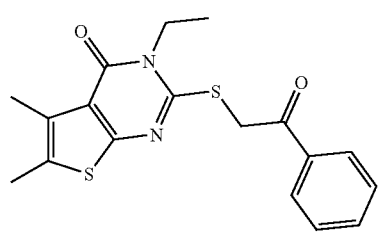 [SMILES: CCn1c(SCC(=O)c2ccccc2)nc2sc(C)c(C)c2c1=O]
Formula (98)
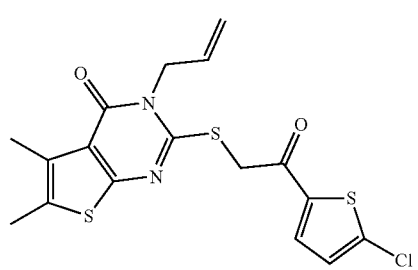 [SMILES: C=CCn1c(SCC(=O)c2ccc(Cl)s2)nc2sc(C)c(C)c2c1=O]
Formula (99)
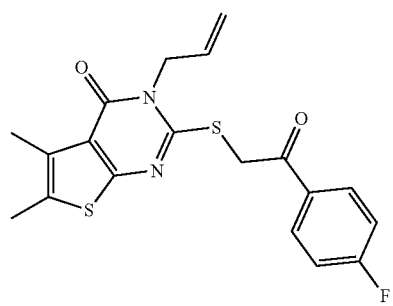 [SMILES: C=CCn1c(SCC(=O)c2ccc(F)cc2)nc2sc(C)c(C)c2c1=O]
Formula (100)
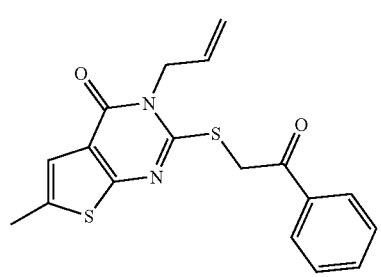 [SMILES: C=CCn1c(SCC(=O)c2ccccc2)nc2sc(C)cc2c1=O]
TABLE 1E-continued
Formula (101)
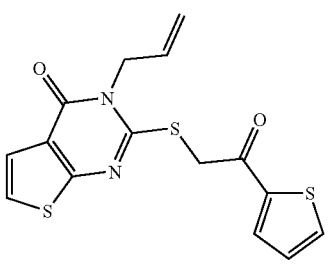 [SMILES: C=CCn1c(SCC(=O)c2cccs2)nc2sccc2c1=O]
Formula (102)
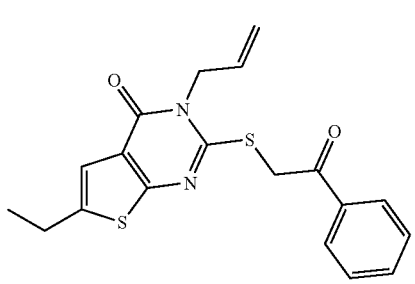 [SMILES: C=CCn1c(SCC(=O)c2ccccc2)nc2sc(CC)cc2c1=O]
Formula (103)
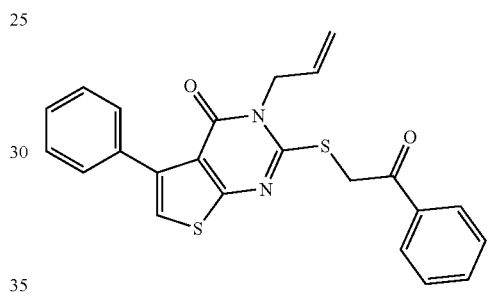
In yet further embodiments, the compound has a formula selected from the following:
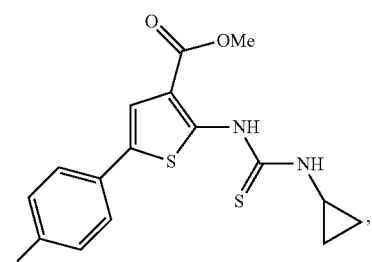
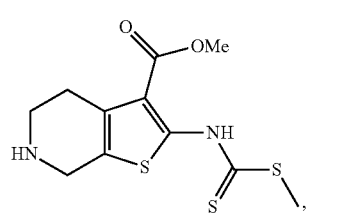
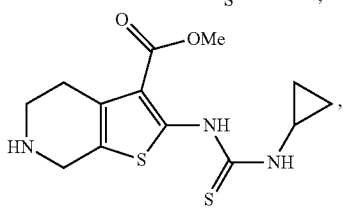

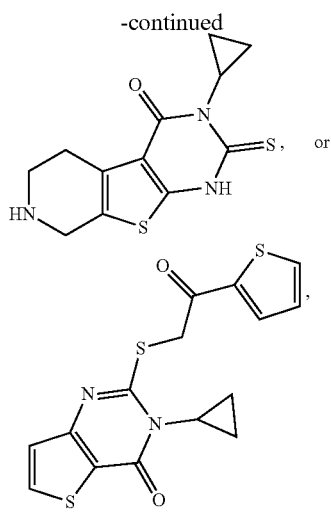

or a pharmaceutically-acceptable salts thereof.

In yet further embodiments, the compound has a formula set forth herein, including in the Examples.

Pharmaceutical Compositions

The presently-disclosed subject matter further includes pharmaceutical compositions of the compounds as disclosed herein, and further includes a pharmaceutically-acceptable carrier. In this regard, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose.

Suitable formulations include aqueous and non-aqueous sterile injection solutions that can contain antioxidants, buffers, bacteriostats, bactericidal antibiotics and solutes that render the formulation isotonic with the bodily fluids of the intended recipient; and aqueous and non-aqueous sterile suspensions, which can include suspending agents and thickening agents.

The compositions can take such forms as suspensions, solutions or emulsions in oily or aqueous vehicles, and can contain formulatory agents such as suspending, stabilizing and/or dispersing agents. Alternatively, the active ingredient can be in powder form for constitution with a suitable vehicle, e.g., sterile pyrogen-free water, before use.

The formulations can be presented in unit-dose or multi-dose containers, for example sealed ampoules and vials, and can be stored in a frozen or freeze-dried (lyophilized) condition requiring only the addition of sterile liquid carrier immediately prior to use.

For oral administration, the compositions can take the form of, for example, tablets or capsules prepared by a conventional technique with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycollate); or wetting agents (e.g., sodium lauryl sulphate). The tablets can be coated by methods known in the art.

Liquid preparations for oral administration can take the form of, for example, solutions, syrups or suspensions, or they can be presented as a dry product for constitution with water or other suitable vehicle before use. Such liquid preparations can be prepared by conventional techniques with pharmaceutically acceptable additives such as suspending agents (e.g., sorbitol syrup, cellulose derivatives or hydrogenated edible fats); emulsifying agents (e.g. lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations can also contain buffer salts, flavoring, coloring and sweetening agents as appropriate. Preparations for oral administration can be suitably formulated to give controlled release of the active compound. For buccal administration the compositions can take the form of tablets or lozenges formulated in conventional manner.

The compounds can also be formulated as a preparation for implantation or injection. Thus, for example, the compounds can be formulated with suitable polymeric or hydrophobic materials (e.g., as an emulsion in an acceptable oil) or ion exchange resins, or as sparingly soluble derivatives (e.g., as a sparingly soluble salt).

The compounds can also be formulated in rectal compositions (e.g., suppositories or retention enemas containing conventional suppository bases such as cocoa butter or other glycerides), creams or lotions, or transdermal patches.

In some embodiments, the pharmaceutical composition includes a compound as disclosed herein or pharmaceutically-acceptable salts thereof.

In some embodiments, the pharmaceutical composition includes a compound of Formula (1), or pharmaceutically-acceptable salts thereof. In some embodiments, the pharmaceutical composition includes a the compound of Formula (3), or pharmaceutically-acceptable salts thereof. In some embodiments, the pharmaceutical composition includes a the compound of Formula (5), or pharmaceutically-acceptable salts thereof. In some embodiments, the pharmaceutical composition includes a the compound of Formula (6), or pharmaceutically-acceptable salts thereof. In some embodiments, the pharmaceutical composition includes a the compound of Formula (7), or pharmaceutically-acceptable salts thereof. In some embodiments, the pharmaceutical composition includes a the compound of Formula (8), or pharmaceutically-acceptable salts thereof. In some embodiments, the pharmaceutical composition includes a the compound of Formula (9), or pharmaceutically-acceptable salts thereof. In some embodiments, the pharmaceutical composition includes a the compound of Formula (11), or pharmaceutically-acceptable salts thereof. In some embodiments, the pharmaceutical composition includes a the compound of Formula (12), or pharmaceutically-acceptable salts thereof. In some embodiments, the pharmaceutical composition includes a the compound of Formula (13), or pharmaceutically-acceptable salts thereof. In some embodiments, the pharmaceutical composition includes a the compound of Formula (15), or pharmaceutically-acceptable salts thereof. In some embodiments, the pharmaceutical composition includes a the compound of Formula (16), or pharmaceutically-acceptable salts thereof. In some embodiments, the pharmaceutical composition includes a the compound of any of Formula (1) to Formula (83).

As disclosed herein, compounds and compositions of the presently-disclosed subject matter are inhibitors of hedgehog signaling and inhibitors of PDE4. Such inhibitors have further utilities as described herein, which include, but are not limited to, anti-cancer or anti-tumor activity, anti-angiogenic activity, anti-metastatic activity, and/or anti-inflammation activity, and utility for treating certain conditions of interest. In this regard, in some embodiments, the pharmaceutical composition can further include a second compound or composition having Hh signaling inhibition activity, PDE4 inhibition activity, anti-cancer or anti-tumor activity, anti-angiogenic activity, anti-metastatic activity, and/or anti-inflammation activity, or wherein the second compound or composition is useful for treating a condition of interest. In some embodiments, the addition of the second compound or composition provides for a synergistic response. In some embodiments the second compound is a Smo antagonist. In some embodiments the Smo antagonist is Vismodegib (GDC-0449, 1), Sonidegib (NVP-LDE225, 2), PF-04449913, IPI-926, BMS-833923, TAK-441, LY2940680, and itraconazole Kits The presently-disclosed subject matter further includes kits, including a compound or pharmaceutical composition. In some embodiments, the kit can include a compound or pharmaceutical composition, as described herein, packaged together with a second compound or composition, a treatment device, and/or an administration device.

In some embodiments, the kit includes a compound, or a pharmaceutical composition including a compound as disclosed herein.

In some embodiments, a kit can include a compound or pharmaceutical composition as described herein, packaged together with a device useful for administration of the compound or composition. As will be recognized by those or ordinary skill in the art, the appropriate administration aiding device will depend on the formulation of the compound or composition that is selected and/or the desired administration site. For example, if the formulation of the compound or composition is appropriate for injection in a subject, the device could be a syringe. For another example, if the desired administration site is cell culture media, the device could be a sterile pipette.

As disclosed herein, compounds and compositions of the presently-disclosed subject matter are inhibitors of hedgehog signaling and, in some aspects, inhibitors of PDE4. n some embodiments, the composition is an inhibitor of PDE4 and hedgehog signaling, in other embodiments, the composition is an inhibitor of hedgehog signaling independent of PDE4 inhibition. Such inhibitors have further utilities as described herein, which include, but are not limited to, anti-cancer or anti-tumor activity, anti-angiogenic activity, anti-metastatic activity, and/or anti-inflammation activity, and utility for treating certain conditions of interest. In this regard, in some embodiments, the kit can further include a second compound or composition having Hh signaling inhibition activity, PDE4 inhibition activity, anti-cancer or anti-tumor activity, anti-angiogenic activity, anti-metastatic activity, and/or anti-inflammation activity, or wherein the second compound or composition is useful for treating a condition of interest. In some embodiments, the addition of the second compound or composition provides for a synergistic response.

The presently-disclosed subject matter further includes kits comprising a reagent to carry out a method as described hereinbelow.

Methods

The presently-disclosed subject matter further includes methods. A method of inhibiting hedgehog signaling is provided. In some embodiments, the method includes contacting a cell with an effective amount of a compound or pharmaceutical composition as disclosed herein. In some embodiments, contacting the cell with the compound or composition comprises administering the compound or composition to a subject. In some embodiments, the administration is to a subject in need of treatment for a condition of interest. Examples of relevant conditions of interest associated with inhibition of hedgehog signaling are set forth hereinbelow.

Also provided is a method of inhibiting phosphodiesterase-4. In some embodiments, the method includes contacting a cell with an effective amount of a compound or pharmaceutical composition as disclosed herein. In some embodiments, contacting the cell with the compound or composition comprises administering the compound or composition to a subject. In some embodiments, the administration is to a subject in need of treatment for a condition of interest. Examples of relevant conditions of interest associated with inhibition of PDE4 activity are set forth hereinbelow.

Also provided is a method of treating a condition of interest. In some embodiments, the method includes contacting a cell with an effective amount of a compound or pharmaceutical composition as disclosed herein. In some embodiments, contacting the cell with the compound or composition comprises administering the compound or composition to a subject. In some embodiments, the administration is to a subject in need of treatment for a condition of interest. Examples of relevant conditions of interest associated with inhibition of Hh signaling and/or inhibition of PDE4 activity are set forth hereinbelow.

As will be recognized by one of ordinary skill in the art, the term "inhibiting" or "inhibition" does not refer to the ability to completely inactivate all target biological activity in all cases. Rather, the skilled artisan will understand that the term "inhibiting" refers to decreasing biological activity of a target, such as a decreasing Hh signaling or decreasing PDE4 activity, such as can occur with a ligand binding site of the target, or protein in a biochemical pathway of the target, is blocked, or when a non-native complex with the target, or protein in a biochemical pathway of the target, is formed. Such decrease in biological activity can be determined relative to a control, wherein an inhibitor is not administered and/or placed in contact with the target. For example, in some embodiments, a decrease in activity relative to a control can be about a 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% decrease. The term "inhibitor" refers to a compound of composition that inactivates or decreases the biological activity of a target, such as Hh signaling pathway or PDE4 activity.

The terms "treatment" or "treating" refer to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

The terms "subject" or "subject in need thereof" refer to a target of administration, which optionally displays symptoms related to a particular disease, pathological condition, disorder, or the like. The subject of the herein disclosed methods can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. A patient refers to a subject afflicted with a disease or disorder. The term "patient" includes human and veterinary subjects.

The term "administering" refers to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, and parenteral administration, including injectable such as intravenous administration, intra-arterial administration, intramuscular administration, and subcutaneous administration. Administration can include use of a device, including, for example, needles, nebulizers, and droppers. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

The term "effective amount" refers to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

Uses and Conditions of Interest

As disclosed herein, compounds and compositions of the presently-disclosed subject matter are inhibitors of hedgehog signaling via inhibition of PDE4, without global perturbations in cAMP levels. Rather, surprisingly and unexpectedly, the compounds and compositions disclosed herein selectively raise cAMP levels in the basal body, such that the compounds and compositions might be considered organelle-targeted. As such, the compounds and compositions of the presently-disclosed subject matter have utilities in connection with inhibition of the hedgehog pathway, and utilities in connection with inhibition of PDE4 activity.

Inhibiting Hedgehog Signaling

The presently-disclosed subject matter includes methods of inhibiting hedgehog signaling in a cell, comprising contacting a cell with an effective amount of a Hh signaling inhibitor. In some embodiments, the presently-disclosed subject matter includes methods of inhibiting Hh signaling in a cell, comprising administering an effective amount of a Hh signaling inhibitor to a subject. In some embodiments, the subject is in need of a treatment for a condition of interest. In some embodiments, the Hh signaling inhibitor is a compound or pharmaceutical composition as disclosed hereinabove. In some embodiments, the presently-disclosed subject matter includes methods of treating a condition of interest, including conditions as identified herein.

With regard to targeting hedgehog signaling, methods of the presently-disclosed invention can be useful in treating conditions involving neoplastic or hyperplastic transformations, conditions related to tissue homeostasis, and anti-angiogenesis treatment to target cancers.

Treatment of Neoplastic or Hyperplastic Transformations.

Constitutive Hh signal activation, due to mutations that activate the pathway, is implicated in numerous neoplastic or hyperplastic conditions. For instance, constitutive activation of Hh pathway has been shown to play critical roles in tumorigenesis in malignant medulloblastoma (the most common brain tumor in children), neuroectodermal tumors, ependymomas, tumors associated with Gorlin syndrome (also known as Basal Cell Nevus Syndrome, a hereditary syndrome conferring high risk of skin and brain cancers, including basal cell carcinoma, medulloblastoma, and meningioma), sporadic basal cell carcinoma (the most common form of skin cancer), rhabdomyosarcoma, glioblastoma, renal carcinoma, thyroid carcinoma, bone cancers, chondrosarcoma, breast cancer, urogenital cancers (including prostate cancer), adrenal cancers, gastrointestinal cancers, pancreatic cancers, and lung cancers (small cell lung cancer, squamous cell cancer, and adenocarcinomas). With regard to medulloblastoma, for example, the compounds and compositions disclosed herein have particular utility because they are hedgehog signaling inhibitors that do not target smoothened. These compounds and compositions can selectively kill cells over-expressing oncogenic, drug-resistant forms of smoothened. In the medulloblastoma field, drug resistance to smoothened antagonists are quickly becoming recognized as an important problem.

Proliferation of these cancer cells requires Hh signaling, and blocking Hh pathways has been shown to inhibit cancer cell proliferation and to reduce tumor size in Xenograft models. In addition to direct promotion of tumorigenesis, Hh pathway has been shown to be required in tissue mesenchyme surrounding pancreatic cancers to support tumor growth by a paracrine effects. Moreover, in animal models, blocking Hh signaling has been shown to suppress metastasis of pancreatic and prostate cancers.

As such, compounds and composition disclosed herein, which are inhibitors of Hh signaling, can have utility in treating cancers in which underlying the neoplastic transformation is caused, maintained or characterized by persistent Hh activation.

In some embodiments, methods of the presently-disclosed subject matter make use of compounds and composition disclosed herein for treatment of a cancer, such as a cancer identified above. In some embodiments, the cancer can be basal cell carcinoma, breast, cervical, colon, melanoma, prostate, pancreatic, medulloblastoma, small cell lung, or squamous lung. The status of Hh activation in particular tumor types can be found in publically-available resource, such as the Broad-Novartis Cancer Cell Line Encyclopedia, which can be accessed online (http://www.broadinstitute.org/ccle/). In some embodiments, the cancer can be: acute B-cell, acute myeloid leukemia (AML), B-cell acute lymphoblastic (ALL-B cell), bile duct cancer, Burkitt's lyphoma, chondrosarcoma, chronic myeloid leukemia (CML), colorectal, DLBCL lymphoma, endometrial, esophageal, Ewings sarcoma, glioma, Hodgkin's lymphoma, leukemia, liver, lung (including small cell (SCLC) and non-small cell type (NSCLC)), medulloblastoma, melanoma, mesothelioma, multiple myeloma, neuroblastoma, osteosarcoma, ovarian, pancreatic, prostate, renal, stomach, thyroid, T-cell acute lymphoblastic leukemia (ALL-T cell), or urinary tract.

In some embodiment, the cancer can be a cancer in which tumor profiling indicates Hh signal activation. Such cancers can be identified, for example, based on the overexpression of Hh pathway markers such as Gli1, Gli2, Gli3, Ptch1, and Ptch2 genes. The status of Hh activation in tumors of an individual subject can be determined, for example, by molecular profiling and accessed through portals such as My Cancer Genome (http://www.mycancergenome.org/). As such, some embodiments of the presently-disclosed subject matter provide for a personalized approach to determining a pathway signature of an individual subject's neoplasm. In some embodiments, for example, if sequence and expression profile analysis indicate that Hh signaling is activated in a particular subject's tumor, Hh inhibitors, including compounds and compositions of the presently-disclosed subject matter, can be a used to treat the cancer.

Anti-Angiogenesis Therapy.

An important hallmark of cancer cells is rapid accumulation of mutations within rapidly dividing cell populations. These mutations allow subpopulation of cancer cells to develop resistance to chemotherapeutic agents and thus escape therapy. In the absence of angiogenesis, the growth of tumors is limited by mismatch between oxygen/nutrient supply and demand such that tumors cannot grow beyond a certain size (typically <2 mm$^3$). Tumor angiogenesis is essential for transition into clinically significant large tumors as well as metastasis. Since blood vessels within tumors are typically comprised of noncancerous endothelial cells, targeting endothelial cells with anti-angiogenic molecules is an attractive method to block tumor growth, metastasis and drug resistance. Because Hh signaling plays a critical paracrine role in promoting angiogenesis, Hh signaling inhibitors, such as the compound and compositions as disclosed herein, can also be used as an anti-angiogenesis therapy for variety of cancers.

Conditions Related to Tissue Homeostasis.

The Hh pathway plays a key role in postnatal tissue homeostasis and regeneration. For example, in animal models, Hh pathway has been shown become activated after tissue injury, for instance of retina, bile duct, lung, bone and prostate. Hh pathway plays an important role regulating hair follicle, bone marrow, CNS, and benign prostate hyperplasia. As such, Hh signaling inhibitors, such as the compound and compositions as disclosed herein, can also be used as a part of treatment for neuroproliferative diseases, benign prostate hyperplasia, bone marrow proliferative disease and leukemia, osteopetrosis and hair overgrowth.

Furthermore, compounds and compositions as disclosed herein can also be useful in methods of stem cell differentiation.

Inhibiting PDE4 Activity

The presently-disclosed subject matter includes methods of inhibiting PDE4 Activity in a cell, comprising contacting a cell with an effective amount of a PDE4 inhibitor. In some embodiments, the presently-disclosed subject matter includes methods of inhibiting PDE4 in a cell, comprising administering an effective amount of a PDE4 inhibitor to a subject. In some embodiments, the subject is in need of a treatment for a condition of interest. In some embodiments, the PDE4 inhibitor is a compound or pharmaceutical composition as disclosed hereinabove. In some embodiments, the presently-disclosed subject matter includes methods of treating a condition of interest, including conditions as identified herein.

With regard to targeting PDE4 activity, methods of the presently-disclosed invention can be useful in treating conditions involving inflammation, making use of PDE4 inhibitors as an anti-tumor, anti-angiogenic, or anti-metastatic agents, making use of PDE4 inhibitors to target the central nervous system, and making use of PDE4 inhibitors as anti-viral agents.

Targeting Inflammation.

TNF-α is an important target in numerous diseases including rheumatoid arthritis, Crohn's disease and psoriasis inhibition of PDE4 in monocytes and T-cells prevents TNF-α production. Furthermore inhibition of PDE4 in neutrophils, which play a pivotal role in chronic obstructive pulmonary disease (COPD) and severe asthma, prevents multiple neutrophil responses, including chemotaxis, adhesion and production of IL-8. Furthermore PDE4 inhibitor CP80,633 suppressed T cell proliferation and production of IL-2, IL-5 and TNF-α. As such, the compounds and compositions disclosed herein can be used in anti-inflammatory treatment.

Anti-Tumor, Anti-Angiogenic, Anti-Metastatic Agents.

As disclosed herein, compounds and compositions of the presently-disclosed subject matter have anti-proliferative effects in various cancer cell lines. It is also documented that PDE4 inhibitors have antiproliferative activity against murine carcinoma cells. In addition to anti proliferative effects inhibition of PDE4 has been linked to inhibition of VEGF (Vascular endothelial growth factor) which is essential for angiogenesis. Furthermore, PDE4 inhibition could have anti-metastatic effects due to its inhibition of Rho-driven migration of fibroblasts. PDE4 inhibition can also find utility in the context of pathological angiogenesis, including macular degeneration and diabetic retinopathy. As such, the compounds and compositions disclosed herein can be used as anti-tumor, anti-angiogenic, anti-metastatic, agents.

Targeting Central Nervous System.

PDE4 is expressed in various neuronal cell types in the CNS. Indeed, Rolipram does show some efficacy in several preclinical models for depression, memory deficit, Alzheimer's disease, and spinal cord injury. Furthermore PDE4 inhibition has been shown to be beneficial and effective in the MPTP mouse model of Parkinson's disease via a direct neuroprotective effect. Additionally inhibition of PDE4 improves both the working memory and reference memory caused by NMDA receptor antagonists. As such, the compounds and compositions disclosed herein can be used in the treatment of CNS disorders and neuropsychiatric disorders, such as depression, memory deficits, Alzheimers' disease, spinal cord injury, and Parkinson's disease.

Anti-Viral Agents.

PDE4 was found to be functionally up-regulated in human T-lymphotropic virus-infected T-cells and may contribute to the virus-induced proliferation. Furthermore, selective blocking of PDE4 activity inhibited IL-2R expression and thereby led to abolishing HIV-1 DNA nuclear import in memory T cells. Additionally there have been recent implications of PDE4 playing major important roles in the infection process of respiratory syncytial virus (RSV), Dengue, and cowpox. As disclosed herein, compounds and compositions of the presently-disclosed subject matter have antiviral effects on, RSV, Influenza, Dengue, and Bovine Viral Diarrhea Virus (BVDV). As such, the compounds and compositions disclosed herein can be used as anti-viral agents.

The compounds and compositions disclosed herein can also be used in the treatment of conditions in which side effects of existing competitive PDE4 inhibitors have limited treatment options and have prompted need for development of alternative PDE4 inhibitors.

Treatments Related to Heart Failure

Heart failure (HF) is a common condition affecting over 5.8 million Americans, and the prevalence of HF is expected increase dramatically over the next 20 years. Presently, one in 5 Americans has lifetime risk of HF. HF is primary reason for hospitalization in US, and a leading cause of death in US (over 300,000 deaths a year). Despite recent medical advances, the HF prognosis remains poor with over 50% mortality within 5 years of diagnosis. Currently, apart from heart transplantation, treatment options are largely palliative. There are no drugs approved for treatment of systolic heart failure. In critical ill patients with end-stage heart failure, positive inotropes like milrinone and dobutamine, which increase heart contractility, augment function of failing heart in the ICU setting. However, long-term administration of inotropes is curtailed by tachyphylaxis and increased risk of arrhythmias, heart failure progression and death.

The etiology of systolic heart failure, is multifactorial, involving complex interplay between genetic susceptibility and acquired insults, such as myocardial infarction, long-standing hypertension, cardiotoxins, or myocarditis. Disease progression involves maladaptive phenotypic alterations in myocardial structure and function, resulting from neurohormonal and cytokine activation. Despite the multitude of pathways leading to heart failure, cAMP regulation of PKA is emerging as a major regulator of cardiac contraction.

Calcium cycling, which drives the contractile mechanics of cardiomyocytes, is modulated by PKA phosphorylation of the ryanodine receptor, CREB, NCX1, KCNQ1, troponin I, and phospholamban (PLB) (an endogenous SERCA inhibitor). While short-term increases in cellular cAMP levels—either via stimulation of beta-adrenergic receptor or inhibition of phosphodiesterases (typically PDE3)—enhance cardiac function initially, chronic cAMP elevation results in tachyphylaxis and heart failure progression via adrenergic receptor desensitization and other maldaptive responses.

However, the present PDE4 inhibitors (e.g., EGM), can be used for the treatment of subjects with systolic heart failure. As described herein, Eggmanone increases fractional shortening (FS) and ejection fraction (EF) of heart without increasing heart rate. In comparison to the traditional inotropes, which increase total cAMP levels in the cardiomyocyte, the unique advantage of the present invention is that the EGM class of PDE4 inhibitors raise cAMP levels locally to wherever PDE4 is localized within specific subcellular compartments, but not globally. Hence, maladaptive responses to chronic stimulation, such as tachyphylaxis and heart failure progression, can be reduced or avoided.

Various treatments related to heart treatment can be implemented with the present compounds. In some embodiments the present compounds will comprise a pharmaceutical composition that can be administered to acutely improve cardiac function. This can be particularly beneficial with critically ill subjects with systolic heart failure (e.g, in ICU or inpatient setting). In other embodiments the present compounds can provide inotropic support following surgery (e.g., myocardial surgery), in critically ill subjects with inadequate cardiac output, regardless of etiology (i.e., cardiogenic shock, septic shock, hemorrhagic shock, etc.), and/or in pediatric subjects. In some embodiments the present compositions can be administered to improve or stabilize (i.e., treat) long-term cardiac function, to promote beneficial cardiac remodeling, to provide symptomatic relief and survival benefits in subjects with advanced systolic heart failure as a chronic therapy, and the like.

Additional Conditions of Interest

Additional conditions of interest include, but are not limited to, asthma, COPD, bronchitis and bronchiectasis, allergic rhinitis and sinusitis, rheumatoid arthritis, osteoarthritis, gout, eosinophil-related disorders, including chronic eosinophilic pneumonia, chronic interstitial lung disease, allergic granulomatous angiitis/Churg-Strauss syndrome, polyarteritis nodosa, atopic dermatitis, urticaria, conjunctivitis, uveitis, psoriasis, multiple sclerosis and other inflammatory autoimmune diseases, inflammatory bowel disease, including ulcerative colitis and Crohn's disease, septic shock, renal failure, cachexia and infection, liver injury, pulmonary hypertension, bone loss disease, CNS disorders: cognitive and memory defects in Parkinson's disease, Huntington's chorea, Wilson's disease, paralysis agitans and thalamic atrophies, arteriosclerotic dementia, improved learning in general, depression, ischemia-reperfusion injury in stroke, diabetes prevention, chronic lymphocytic leukemia, HIV-1 replication, prostate disease, pemphigus, pemphigoid, antiviral: HIV-1, HIV-2, HIV-3, cytomegalovirus, CMV, influenza, adenovirus, Herpes virus, yeast and fungal infections.

Conditions of interest include anti-viral applications, including applications related to enveloped RNA viruses, such as respiratory syncytial virus, and bronchiolitis (RSV is a leading cause of bronchiolitis), ebola virus, hepatitis C virus, Bovine Viral Diarrhea Virus, Dengue virus, west nile virus, yellow fever virus, measles virus, mumps virus.

Conditions of interest include improved learning in neurofibromatosis type 1 (http://www.ncbi.nlm.nih.gov/pubmed/25176649), Behcet's syndrome (https://www.rareconnect.org/en/community/behcet-s-syndrome/forum/topic/apremilast-a-novel-pde4-inhibitor), and psoriasis http://www.ncbi.nlm.nih.gov/pmc/articles/PMC3680635/, and psoriatic arthritis (http://www.ncbi.nlm.nih.gov/pubmed/22257911).

While the terms used herein are believed to be well understood by one of ordinary skill in the art, definitions are set forth to facilitate explanation of the presently-disclosed subject matter.

Unless defined otherwise, all technical and scientific terms used herein have the same meaning as commonly understood by one of ordinary skill in the art to which the presently-disclosed subject matter belongs. Although any methods, devices, and materials similar or equivalent to those described herein can be used in the practice or testing of the presently-disclosed subject matter, representative methods, devices, and materials are now described.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments±20%, in some embodiments±10%, in some embodiments±5%, in some embodiments 1%, in some embodiments±0.5%, and in some embodiments±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

The presently-disclosed subject matter is further illustrated by the following specific but non-limiting examples. The following examples may include compilations of data that are representative of data gathered at various times during the course of development and experimentation related to the present invention.

EXAMPLES

Example 1

Cyclic AMP (cAMP) is a ubiquitous secondary messenger which mediates diverse signals with extraordinary functional precision. Functional specificity is thought to involve compartmentalized signaling centers, or 'cAMP microdomains,' inside which cAMP levels are tightly controlled. By restricting cAMP changes to specific microdomains, a cell can manage multiple cAMP-dependent signals without undesired signal "leakage" between pathways. These cAMP microdomains arise from dynamic process of localized cAMP synthesis via adenyl cyclase (AC) and degradation via phosphodiesterases (PDEs). Consequently, a global loss of PDE activity results in the loss of signal specificity.

cAMP plays an important, evolutionarily conserved role in Hh regulation. In Drosophila, Hh activation of the Smoothened (Smo) transmembrane protein results in inhibition of cAMP production via Gαi, whereas the loss of PDE4 activity results in a Hh loss-of-function phenotype. Furthermore, PKA (cAMP-activated protein kinase) has a negative role on Hh activity. In vertebrates, where transient trafficking of the transcription factor Gli through the primary cilia is essential for Hh activation, PKA is localized to the basal body at the base of the cilium, and treatment with forskolin, an AC activator, disrupts the Gli trafficking to the cilia. However, whether the basal body might constitute a cAMP microdomain important for Hh regulation was not directly tested since forskolin causes a global PKA activation as well as non-PKA dependent pleiotropic effects.

Figure 1A:
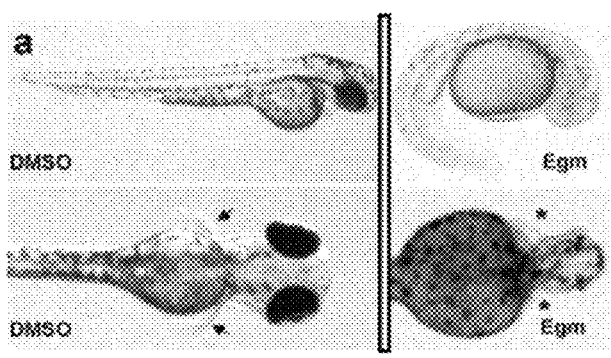
FIGS. 1a-1h include data and results of studies showing that Eggmanone inhibits Hedgehog signaling via inhibition of PDE4. Zebrafish embryos treated with 2 µM Eggmanone (Egm) starting at 4-hours post fertilization (hpf) exhibited range of phenotypes found in Hh pathway mutants, including ventral tail curvature, loss of pectoral fins (FIG. 1a), smaller eyes and (FIG. 1d) enlarged somites in place of normal chevron-shaped somites. Egm treatment abolished Hh-responsive ptch1 expression in adaxial cells at 12-hpf FIG. 1(b; arrow), in the pectoral fin bud at 48-hpf (FIG. 1c; arrow). Egm inhibited Sonic hedgehog (SHH)-responsive Gli-luciferase reporter activity (FIG. 1e) and Purmorphamine (Purm, 3 µM)-induced reporter activity FIG. 1(f) (n=4 for each condition, RLU, relative luciferase units, +/−standard error; P-value <0.0184 starting at 1 µM for I; P-value <0.0054 starting at 0.5 µM for J. Cyclopamine (Cyc) 5 uM).
Figure 1B:
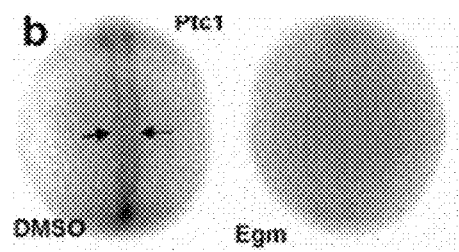
Figure 1C:
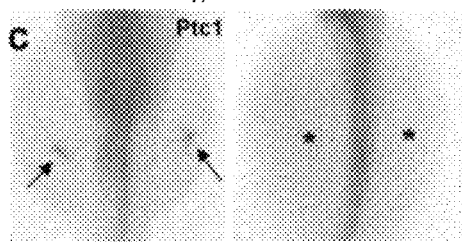
Figure 1D:
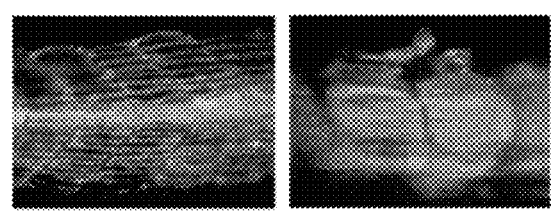
Figure 5A:
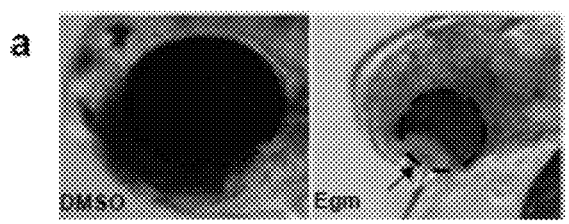
FIGS. 5a-5d include data and results of studies showing that Eggmanone does not recapitulate all hedgehog signaling defects. Zebrafish embryos treated with 2 µM Eggmanone (Egm) starting at 4-hours post fertilization (hpf) (FIG. 5a) smaller eyes, (FIG. 5b) defects in neurocranium chondrogenesis. Egm treatment abolished Hh-responsive ptch1 expression in somites at 24-hpf (FIG. 5c;*). Egm did not abolish ptch1 expression in myotome cells (FIG. 5c; arrow) and in ventral neural tube (FIG. 5c; arrowhead) nor abolish nkx2.2:eGFP expression (FIG. 5d; arrowhead)
Figure 5B:
Figure 5C:
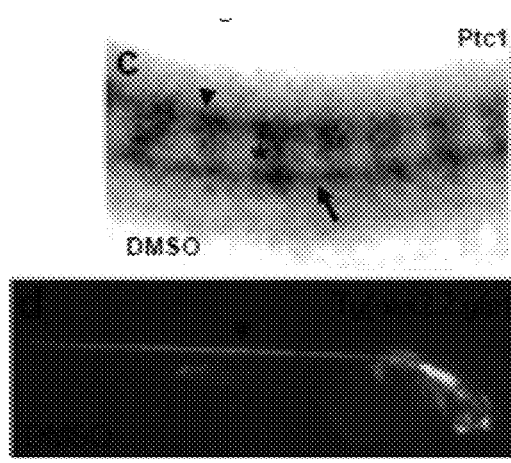
Figure 5D:
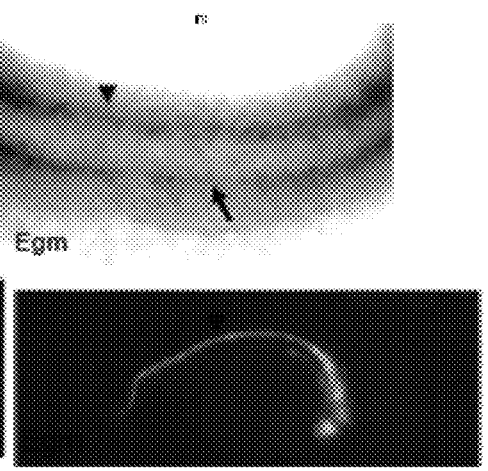

In a phenotypic screen for small molecule modulators of zebrafish pattern formation the present inventors identified a series of structurally related compounds, represented by the prototype named Eggmanone (3-(2-methylallyl)-2-((2-oxo-2-(thiophen-2-yl)ethyl)thio)-5,6,7,8-tetrahydrobenzo[4,5]thieno[2,3-d]pyrimidine-4(3H)-one) (FIG. 4-6), which caused a number of phenotypes resembling those of Hh-deficient mutant embryos; ventral tail curvature, absent pectoral fins, small eyes, loss of neurocranial chondrogenesis, and enlarged, rounded somites (FIG. 1a,d; FIG. 5a,b). Eggmanone abrogated the expression of the Hh target gene patched-1 (ptch1) in the bud stage adaxial cells, the pectoral fin fields, and the somites (FIG. 1b,c), but it did not eliminate ptch1 expression in the ventral neural tube or myotome cells immediately adjacent to the notochord (FIG. 5c). Consistent with the context-dependent inhibition of Hh signals in the embryo, the nkx2.2-expressing neurons in the ventral neural tube were not abolished in Eggmanone-treated embryos (FIG. 5d).

Figure 1E:
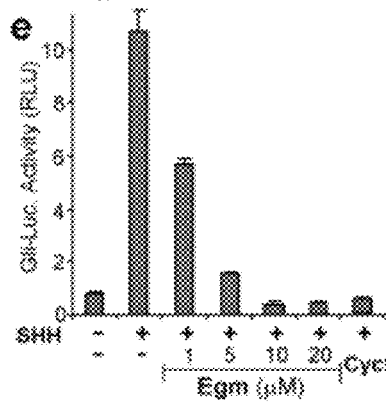
Figure 1F:
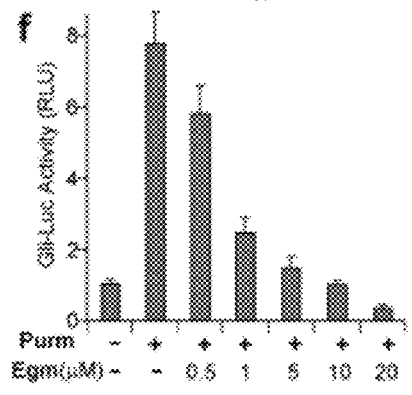
Figure 6:
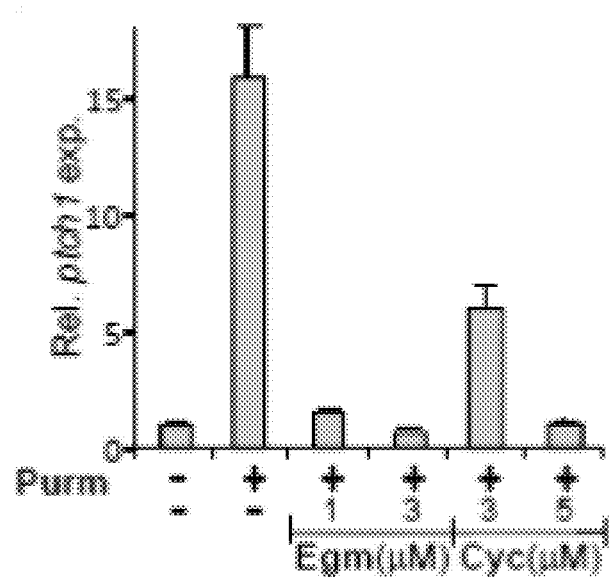
FIG. 6 includes data and results of studies showing that Eggmanone affects hedgehog signaling but does not affect BMP signaling. Eggmanone significantly inhibited ptch1 expression in response to purmorphamine in Nih3T3 fibroblasts.
Figure 7:
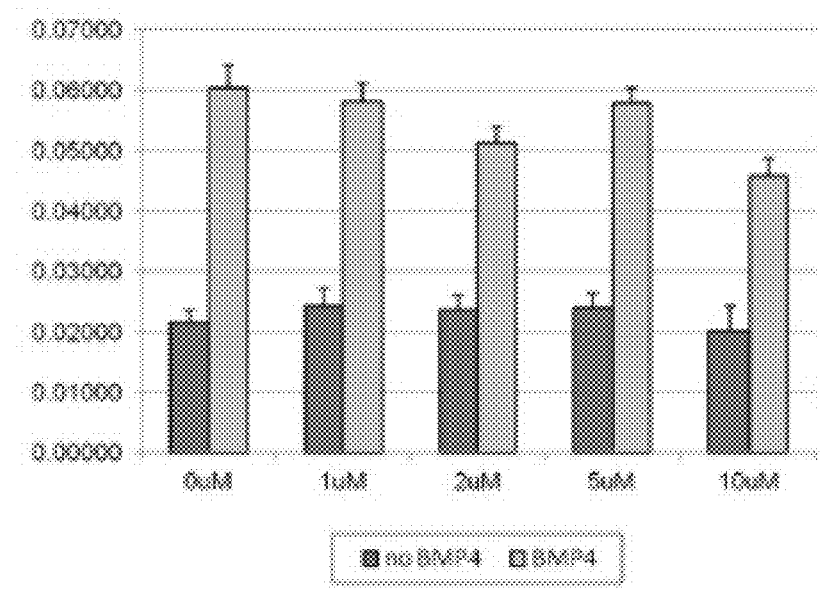
FIG. 7 includes data and results of studies showing that Eggmanone affects hedgehog signaling but does not affect BMP signaling. Eggmanone had no significant effects on BMP4-responsive reporter (BRE-luc) activity in C2C12BRA reporter cells[7]. BRE-luc (BMP responsive element driven luciferase) cells were stimulated with BMP4 ligand. Eggmanone had no agonist or antagonist activity.

In the mouse Hh reporter cell line Shh-Light2, Eggmanone inhibited Hh-inducible Gli-responsive luciferase (Gli-Luc) activity in a dose dependent manner, confirming that the molecular target is conserved in mammals (FIG. 1e). Eggmanone also blocked Gli-Luc reporter and ptch1 induction by purmorphamine, a Smo agonist, indicating that Eggmanone targeted Hh pathway at or downstream of Smo activation (FIG. 1f; FIG. 6). By contrast, Eggmanone did not affect BMP-responsive luciferase reporter activity, indicating that its Hh reporter inhibition was not due to nonspecific effects on luciferase activity (FIG. 7).

Figure 1G:
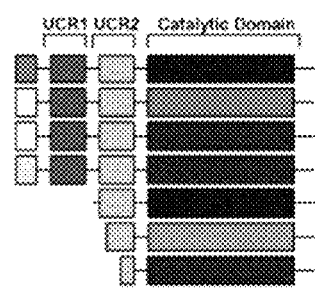
Figures 10A, 10B:
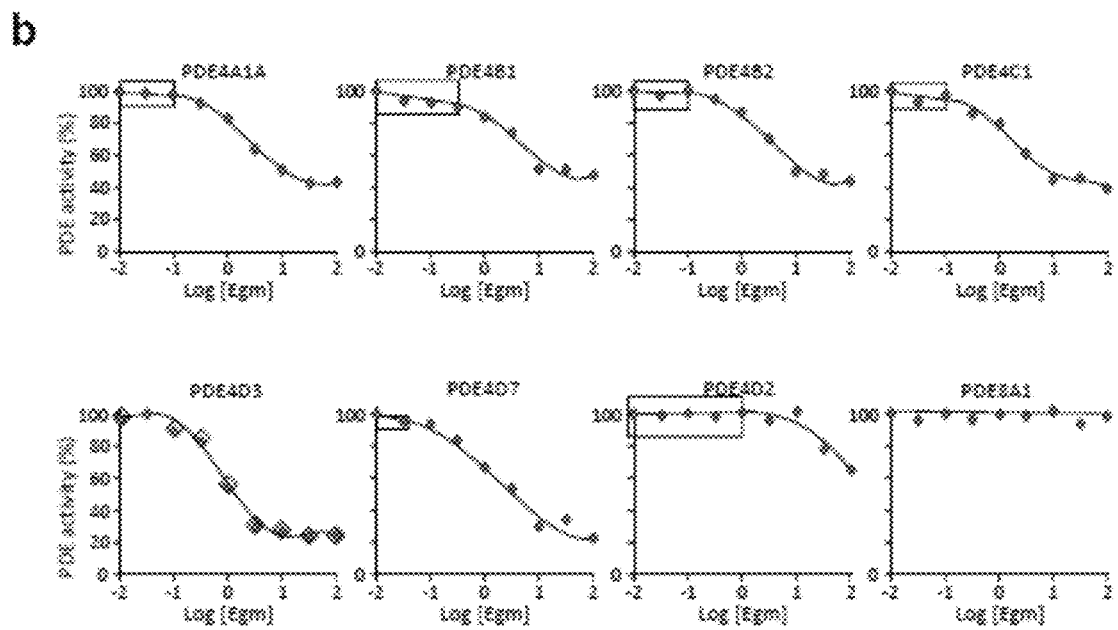
FIGS. 10a and 10b include data and results of studies showing Eggmanone's ability to inhibit different isoforms of PDE4.

To elucidate the mechanism of Hh inhibition by Eggmanone, the present inventors utilized the LASSO ("Ligand Activity by Surface Similarity Order") algorithm to virtually screen for potential targets. As this algorithm implicated PDE5 (FIGS. 9 and 10), the present inventors assayed Eggmanone for in vitro activity against eleven different PDE families and found that it significantly inhibited only the PDE4 family (FIG. 10a-b). Eggmanone significantly inhibited isoforms from each gene within the PDE4 (A-D) family (FIG. 1g), with an $IC_{50}$ (concentration causing 50% of maximal inhibition) range of 0.8-3 µM. Of the seven isoforms of PDE4s tested, only the super-short isoform PDE4D2 was not inhibited by Eggmanone. The naturally occurring N-terminal truncation found in PDE4D2 allowed us to infer that the first 33 residues of the UCR2 domain were essential for Eggmanone inhibition. Moreover, since the UCR2 domain is unique to the PDE4 family, this result also provided a molecular explanation for Eggmanone's selectivity toward PDE4 isoforms. Interestingly, even at high Eggmanone concentrations, the enzymatic activities of the PDE4s did not reach 0% (FIG. 7). Taken together, these results suggested that Eggmanone is a selective allosteric inhibitor of PDE4 that targets the UCR2 domain.

Figure 1H:
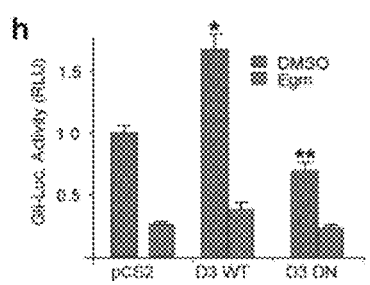

To rule out other potential targets, the present inventors tested Eggmanone against other pharmacologically relevant classes of biomolecules using a comprehensive panel of 442 kinases, 158 GPCRs and 21 phosphatases; remarkably, Eggmanone did not exhibit significant agonist or antagonist activity against any of them (Tables 4-6). To confirm the interaction between PDE4 and the Hh pathway in vertebrates, the long isoform PDE4D3 was transfected into Shh-Light2 reporter cells and was found to increase Hh signaling, which was abrogated in the presence of Eggmanone (FIG. 1h). Furthermore, a dominant negative construct consisting of a catalytically inactive PDE4D3 inhibited Hh signaling.

TABLE 4

| Kinase | Percent Control | Compound Concentration (nM) |
| --- | --- | --- |
| AAK1 | 100 | 10000 |
| ABL1(E255K)-phosphorylated | 85 | 10000 |
| ABL1(F317I)-nonphosphorylated | 100 | 10000 |
| ABL1(F317I)-phosphorylated | 85 | 10000 |
| ABL1(F317L)-nonphosphorylated | 98 | 10000 |
| ABL1(F317L)-phosphorylated | 100 | 10000 |
| ABL1(H396P)-nonphosphorylated | 100 | 10000 |
| ABL1(H396P)-phosphorylated | 96 | 10000 |
| ABL1(M351T)-phosphorylated | 100 | 10000 |
| ABL1(Q252H)-nonphosphorylated | 100 | 10000 |
| ABL1(Q252H)-phosphorylated | 100 | 10000 |
| ABL1(T315I)-nonphosphorylated | 73 | 10000 |
| ABL1(T315I)-phosphorylated | 80 | 10000 |
| ABL1(Y253F)-phosphorylated | 85 | 10000 |
| ABL1-nonphosphorylated | 100 | 10000 |
| ABL1-phosphorylated | 90 | 10000 |
| ABL2 | 95 | 10000 |
| ACVR1 | 100 | 10000 |
| ACVR1B | 100 | 10000 |
| ACVR2A | 99 | 10000 |
| ACVR2B | 100 | 10000 |
| ACVRL1 | 97 | 10000 |
| ADCK3 | 100 | 10000 |
| ADCK4 | 87 | 10000 |
| AKT1 | 92 | 10000 |
| AKT2 | 77 | 10000 |
| AKT3 | 100 | 10000 |
| ALK | 100 | 10000 |
| AMPK-alpha1 | 100 | 10000 |
| AMPK-alpha2 | 96 | 10000 |
| ANKK1 | 100 | 10000 |
| ARK5 | 94 | 10000 |
| ASK1 | 78 | 10000 |
| ASK2 | 95 | 10000 |
| AURKA | 95 | 10000 |
| AURKB | 100 | 10000 |
| AURKC | 100 | 10000 |
| AXL | 80 | 10000 |
| BIKE | 85 | 10000 |
| BLK | 85 | 10000 |
| BMPR1A | 100 | 10000 |
| BMPR1B | 99 | 10000 |
| BMPR2 | 99 | 10000 |
| BMX | 100 | 10000 |
| BRAF | 100 | 10000 |
| BRAF(V600E) | 100 | 10000 |
| BRK | 90 | 10000 |
| BRSK1 | 100 | 10000 |
| BRSK2 | 100 | 10000 |
| BTK | 100 | 10000 |
| CAMK1 | 84 | 10000 |
| CAMK1D | 99 | 10000 |
| CAMK1G | 100 | 10000 |
| CAMK2A | 100 | 10000 |
| CAMK2B | 96 | 10000 |
| CAMK2D | 100 | 10000 |
| CAMK2G | 99 | 10000 |
| CAMK4 | 91 | 10000 |
| CAMKK1 | 86 | 10000 |
| CAMKK2 | 100 | 10000 |
| CASK | 97 | 10000 |
| CDC2L1 | 90 | 10000 |
| CDC2L2 | 100 | 10000 |
| CDC2L5 | 87 | 10000 |
| CDK11 | 89 | 10000 |
| CDK2 | 100 | 10000 |
| CDK3 | 99 | 10000 |
| CDK4-cyclinD1 | 93 | 10000 |
| CDK4-cyclinD3 | 84 | 10000 |
| CDK5 | 85 | 10000 |
| CDK7 | 68 | 10000 |
| CDK8 | 100 | 10000 |
| CDK9 | 88 | 10000 |
| CDKL1 | 100 | 10000 |
| CDKL2 | 100 | 10000 |
| CDKL3 | 93 | 10000 |
| CDKL5 | 80 | 10000 |
| CHEK1 | 93 | 10000 |
| CHEK2 | 88 | 10000 |
| CIT | 99 | 10000 |
| CLK1 | 77 | 10000 |
| CLK2 | 82 | 10000 |
| CLK3 | 88 | 10000 |
| CLK4 | 95 | 10000 |
| CSF1R | 90 | 10000 |
| CSK | 100 | 10000 |
| CSNK1A1 | 83 | 10000 |
| CSNK1A1L | 91 | 10000 |
| CSNK1D | 100 | 10000 |
| CSNK1E | 85 | 10000 |
| CSNK1G1 | 100 | 10000 |
| CSNK1G2 | 100 | 10000 |
| CSNK1G3 | 94 | 10000 |
| CSNK2A1 | 100 | 10000 |
| CSNK2A2 | 100 | 10000 |
| CTK | 100 | 10000 |
| DAPK1 | 96 | 10000 |
| DAPK2 | 91 | 10000 |
| DAPK3 | 96 | 10000 |
| DCAMKL1 | 92 | 10000 |
| DCAMKL2 | 100 | 10000 |
| DCAMKL3 | 87 | 10000 |
| DDR1 | 99 | 10000 |
| DDR2 | 82 | 10000 |
| DLK | 63 | 10000 |
| DMPK | 100 | 10000 |
| DMPK2 | 100 | 10000 |
| DRAK1 | 80 | 10000 |

TABLE 4-continued

| Kinase | Percent Control | Compound Concentration (nM) |
|---|---|---|
| DRAK2 | 66 | 10000 |
| DYRK1A | 83 | 10000 |
| DYRK1B | 100 | 10000 |
| DYRK2 | 82 | 10000 |
| EGFR | 100 | 10000 |
| EGFR(E746-A750del) | 90 | 10000 |
| EGFR(G719C) | 100 | 10000 |
| EGFR(G719S) | 100 | 10000 |
| EGFR(L747-E749del, A750P) | 92 | 10000 |
| EGFR(L747-S752del, P753S) | 83 | 10000 |
| EGFR(L747-T751del, Sins) | 100 | 10000 |
| EGFR(L858R) | 89 | 10000 |
| EGFR(L858R, T790M) | 96 | 10000 |
| EGFR(L861Q) | 100 | 10000 |
| EGFR(S752-I759del) | 89 | 10000 |
| EGFR(T790M) | 80 | 10000 |
| EIF2AK1 | 100 | 10000 |
| EPHA1 | 88 | 10000 |
| EPHA2 | 100 | 10000 |
| EPHA3 | 74 | 10000 |
| EPHA4 | 100 | 10000 |
| EPHA5 | 87 | 10000 |
| EPHA6 | 100 | 10000 |
| EPHA7 | 100 | 10000 |
| EPHA8 | 100 | 10000 |
| EPHB1 | 91 | 10000 |
| EPHB2 | 81 | 10000 |
| EPHB3 | 100 | 10000 |
| EPHB4 | 100 | 10000 |
| EPHB6 | 57 | 10000 |
| ERBB2 | 75 | 10000 |
| ERBB3 | 99 | 10000 |
| ERBB4 | 95 | 10000 |
| ERK1 | 94 | 10000 |
| ERK2 | 72 | 10000 |
| ERK3 | 100 | 10000 |
| ERK4 | 100 | 10000 |
| ERK5 | 98 | 10000 |
| ERK8 | 86 | 10000 |
| ERN 1 | 85 | 10000 |
| FAK | 91 | 10000 |
| FER | 100 | 10000 |
| FES | 100 | 10000 |
| FGFR1 | 100 | 10000 |
| FGFR2 | 100 | 10000 |
| FGFR3 | 100 | 10000 |
| FGFR3(G697C) | 80 | 10000 |
| FGFR4 | 100 | 10000 |
| FGR | 99 | 10000 |
| FLT1 | 82 | 10000 |
| FLT3 | 65 | 10000 |
| FLT3(D835H) | 100 | 10000 |
| FLT3(D835Y) | 70 | 10000 |
| FLT3(ITD) | 77 | 10000 |
| FLT3(K663Q) | 88 | 10000 |
| FLT3(N841I) | 90 | 10000 |
| FLT3(R834Q) | 100 | 10000 |
| FLT4 | 88 | 10000 |
| FRK | 100 | 10000 |
| FYN | 100 | 10000 |
| GAK | 66 | 10000 |
| GCN2(Kin.Dom.2, S808G) | 100 | 10000 |
| GRK1 | 100 | 10000 |
| GRK4 | 88 | 10000 |
| GRK7 | 100 | 10000 |
| GSK3A | 93 | 10000 |
| GSK3B | 99 | 10000 |
| HCK | 82 | 10000 |
| HIPK1 | 84 | 10000 |
| HIPK2 | 89 | 10000 |
| HIPK3 | 70 | 10000 |
| HIPK4 | 91 | 10000 |
| HPK1 | 94 | 10000 |
| HUNK | 75 | 10000 |
| ICK | 88 | 10000 |
| IGF1R | 99 | 10000 |
| IKK-alpha | 91 | 10000 |
| IKK-beta | 100 | 10000 |
| IKK-epsilon | 100 | 10000 |
| INSR | 100 | 10000 |
| INSRR | 100 | 10000 |
| IRAK1 | 100 | 10000 |
| IRAK3 | 94 | 10000 |
| IRAK4 | 99 | 10000 |
| ITK | 81 | 10000 |
| JAK1(JH1domain-catalytic) | 100 | 10000 |
| JAK1(JH2domain-pseudokinase) | 100 | 10000 |
| JAK2(JH1domain-catalytic) | 100 | 10000 |
| JAK3(JH1domain-catalytic) | 97 | 10000 |
| JNK1 | 83 | 10000 |
| JNK2 | 96 | 10000 |
| JNK3 | 95 | 10000 |
| KIT | 89 | 10000 |
| KIT(A829P) | 94 | 10000 |
| KIT(D816H) | 99 | 10000 |
| KIT(D816V) | 91 | 10000 |
| KIT(L576P) | 100 | 10000 |
| KIT(V559D) | 98 | 10000 |
| KIT(V559D, T670I) | 96 | 10000 |
| KIT(V559D, V654A) | 85 | 10000 |
| LATS1 | 99 | 10000 |
| LATS2 | 79 | 10000 |
| LCK | 89 | 10000 |
| LIMK1 | 100 | 10000 |
| LIMK2 | 80 | 10000 |
| LKB1 | 87 | 10000 |
| LOK | 97 | 10000 |
| LRRK2 | 100 | 10000 |
| LRRK2(G2019S) | 100 | 10000 |
| LTK | 100 | 10000 |
| LYN | 92 | 10000 |
| LZK | 100 | 10000 |
| MAK | 81 | 10000 |
| MAP3K1 | 78 | 10000 |
| MAP3K15 | 100 | 10000 |
| MAP3K2 | 88 | 10000 |
| MAP3K3 | 81 | 10000 |
| MAP3K4 | 92 | 10000 |
| MAP4K2 | 79 | 10000 |
| MAP4K3 | 90 | 10000 |
| MAP4K4 | 100 | 10000 |
| MAP4K5 | 98 | 10000 |
| MAPKAPK2 | 76 | 10000 |
| MAPKAPK5 | 90 | 10000 |
| MARK1 | 100 | 10000 |
| MARK2 | 76 | 10000 |
| MARK3 | 86 | 10000 |
| MARK4 | 100 | 10000 |
| MAST1 | 72 | 10000 |
| MEK1 | 92 | 10000 |
| MEK2 | 96 | 10000 |
| MEK3 | 100 | 10000 |
| MEK4 | 100 | 10000 |
| MEK5 | 100 | 10000 |
| MEK6 | 94 | 10000 |
| MELK | 100 | 10000 |
| MERTK | 87 | 10000 |
| MET | 98 | 10000 |
| MET(M1250T) | 80 | 10000 |
| MET(Y1235D) | 88 | 10000 |
| MINK | 100 | 10000 |
| MKK7 | 100 | 10000 |
| MKNK1 | 100 | 10000 |
| MKNK2 | 100 | 10000 |
| MLCK | 93 | 10000 |
| MLK1 | 100 | 10000 |
| MLK2 | 100 | 10000 |
| MLK3 | 92 | 10000 |
| MRCKA | 88 | 10000 |
| MRCKB | 92 | 10000 |
| MST1 | 100 | 10000 |
| MST1R | 99 | 10000 |
| MST2 | 100 | 10000 |
| MST3 | 86 | 10000 |

TABLE 4-continued

| Kinase | Percent Control | Compound Concentration (nM) |
|---|---|---|
| MST4 | 98 | 10000 |
| MTOR | 100 | 10000 |
| MUSK | 79 | 10000 |
| MYLK | 85 | 10000 |
| MYLK2 | 100 | 10000 |
| MYLK4 | 81 | 10000 |
| MYO3A | 100 | 10000 |
| MYO3B | 91 | 10000 |
| NDR1 | 100 | 10000 |
| NDR2 | 100 | 10000 |
| NEK1 | 99 | 10000 |
| NEK11 | 94 | 10000 |
| NEK2 | 100 | 10000 |
| NEK3 | 87 | 10000 |
| NEK4 | 100 | 10000 |
| NEK5 | 87 | 10000 |
| NEK6 | 88 | 10000 |
| NEK7 | 88 | 10000 |
| NEK9 | 100 | 10000 |
| NIM1 | 100 | 10000 |
| NLK | 100 | 10000 |
| OSR1 | 95 | 10000 |
| p38-alpha | 100 | 10000 |
| p38-beta | 100 | 10000 |
| p38-delta | 86 | 10000 |
| p38-gamma | 100 | 10000 |
| PAK1 | 87 | 10000 |
| PAK2 | 83 | 10000 |
| PAK3 | 92 | 10000 |
| PAK4 | 98 | 10000 |
| PAK6 | 100 | 10000 |
| PAK7 | 85 | 10000 |
| PCTK1 | 79 | 10000 |
| PCTK2 | 100 | 10000 |
| PCTK3 | 96 | 10000 |
| PDGFRA | 98 | 10000 |
| PDGFRB | 87 | 10000 |
| PDPK1 | 99 | 10000 |
| PFCDPK1(*P. falciparum*) | 91 | 10000 |
| PFPK5(*P. falciparum*) | 80 | 10000 |
| PFTAIRE2 | 100 | 10000 |
| PFTK1 | 100 | 10000 |
| PHKG1 | 100 | 10000 |
| PHKG2 | 100 | 10000 |
| PIK3C2B | 100 | 10000 |
| PIK3C2G | 76 | 10000 |
| PIK3CA | 100 | 10000 |
| PIK3CA(C420R) | 100 | 10000 |
| PIK3CA(E542K) | 72 | 10000 |
| PIK3CA(E545A) | 95 | 10000 |
| PIK3CA(E545K) | 100 | 10000 |
| PIK3CA(H1047L) | 100 | 10000 |
| PIK3CA(H1047Y) | 67 | 10000 |
| PIK3CA(I800L) | 88 | 10000 |
| PIK3CA(M1043I) | 64 | 10000 |
| PIK3CA(Q546K) | 100 | 10000 |
| PIK3CB | 96 | 10000 |
| PIK3CD | 53 | 10000 |
| PIK3CG | 100 | 10000 |
| PIK4CB | 86 | 10000 |
| PIM1 | 86 | 10000 |
| PIM2 | 85 | 10000 |
| PIM3 | 71 | 10000 |
| PIP5K1A | 100 | 10000 |
| PIP5K1C | 97 | 10000 |
| PIP5K2B | 100 | 10000 |
| PIP5K2C | 100 | 10000 |
| PKAC-alpha | 80 | 10000 |
| PKAC-beta | 96 | 10000 |
| PKMYT1 | 82 | 10000 |
| PKN1 | 87 | 10000 |
| PKN2 | 99 | 10000 |
| PKNB(*M. tuberculosis*) | 90 | 10000 |
| PLK1 | 100 | 10000 |
| PLK2 | 100 | 10000 |
| PLK3 | 100 | 10000 |
| PLK4 | 83 | 10000 |
| PRKCD | 100 | 10000 |
| PRKCE | 87 | 10000 |
| PRKCH | 87 | 10000 |
| PRKCI | 87 | 10000 |
| PRKCQ | 87 | 10000 |
| PRKD1 | 79 | 10000 |
| PRKD2 | 86 | 10000 |
| PRKD3 | 99 | 10000 |
| PRKG1 | 100 | 10000 |
| PRKG2 | 96 | 10000 |
| PRKR | 91 | 10000 |
| PRKX | 86 | 10000 |
| PRP4 | 100 | 10000 |
| PYK2 | 96 | 10000 |
| QSK | 100 | 10000 |
| RAF1 | 89 | 10000 |
| RET | 96 | 10000 |
| RET(M918T) | 80 | 10000 |
| RET(V804L) | 78 | 10000 |
| RET(V804M) | 99 | 10000 |
| RIOK1 | 85 | 10000 |
| RIOK2 | 100 | 10000 |
| RIOK3 | 100 | 10000 |
| RIPK1 | 100 | 10000 |
| RIPK2 | 92 | 10000 |
| RIPK4 | 84 | 10000 |
| RIPK5 | 84 | 10000 |
| ROCK1 | 97 | 10000 |
| ROCK2 | 91 | 10000 |
| ROS1 | 90 | 10000 |
| RPS6KA4(Kin.Dom.1-N-terminal) | 100 | 10000 |
| RPS6KA4(Kin.Dom.2-C-terminal) | 79 | 10000 |
| RPS6KA5(Kin.Dom.1-N-terminal) | 100 | 10000 |
| RPS6KA5(Kin.Dom.2-C-terminal) | 90 | 10000 |
| RSK1(Kin.Dom.1-N-terminal) | 93 | 10000 |
| RSK1(Kin.Dom.2-C-terminal) | 92 | 10000 |
| RSK2(Kin.Dom.1-N-terminal) | 90 | 10000 |
| RSK3 (Kin.Dom.1-N-terminal) | 100 | 10000 |
| RSK3(Kin.Dom.2-C-terminal) | 87 | 10000 |
| RSK4(Kin.Dom.1-N-terminal) | 100 | 10000 |
| RSK4(Kin.Dom.2-C-terminal) | 55 | 10000 |
| S6K1 | 87 | 10000 |
| SBK1 | 100 | 10000 |
| SgK110 | 93 | 10000 |
| SGK3 | 51 | 10000 |
| SIK | 87 | 10000 |
| SIK2 | 100 | 10000 |
| SLK | 83 | 10000 |
| SNARK | 100 | 10000 |
| SNRK | 78 | 10000 |
| SRC | 85 | 10000 |
| SRMS | 90 | 10000 |
| SRPK1 | 76 | 10000 |
| SRPK2 | 100 | 10000 |
| SRPK3 | 100 | 10000 |
| STK16 | 100 | 10000 |
| STK33 | 71 | 10000 |
| STK35 | 91 | 10000 |
| STK36 | 94 | 10000 |
| STK39 | 64 | 10000 |
| SYK | 85 | 10000 |
| TAK1 | 80 | 10000 |
| TAOK1 | 87 | 10000 |
| TAOK2 | 92 | 10000 |
| TAOK3 | 85 | 10000 |
| TBK1 | 100 | 10000 |
| TEC | 77 | 10000 |
| TESK1 | 93 | 10000 |
| TGFBR1 | 86 | 10000 |
| TGFBR2 | 83 | 10000 |
| TIE1 | 100 | 10000 |
| TIE2 | 100 | 10000 |
| TLK1 | 86 | 10000 |
| TLK2 | 100 | 10000 |
| TNIK | 77 | 10000 |
| TNK1 | 100 | 10000 |
| TNK2 | 100 | 10000 |

TABLE 4-continued

| Kinase | Percent Control | Compound Concentration (nM) |
|---|---|---|
| TNNI3K | 100 | 10000 |
| TRKA | 100 | 10000 |
| TRKB | 80 | 10000 |
| TRKC | 74 | 10000 |
| TRPM6 | 86 | 10000 |
| TSSK1B | 82 | 10000 |
| TTK | 88 | 10000 |
| TXK | 94 | 10000 |
| TYK2(JH1domain-catalytic) | 83 | 10000 |
| TYK2(JH2domain-pseudokinase) | 100 | 10000 |
| TYRO3 | 100 | 10000 |
| ULK1 | 100 | 10000 |
| ULK2 | 100 | 10000 |
| ULK3 | 100 | 10000 |
| VEGFR2 | 89 | 10000 |
| VRK2 | 82 | 10000 |
| WEE1 | 97 | 10000 |
| WEE2 | 100 | 10000 |
| YANK1 | 92 | 10000 |
| YANK2 | 94 | 10000 |
| YANK3 | 94 | 10000 |
| YES | 100 | 10000 |
| YSK1 | 100 | 10000 |
| YSK4 | 100 | 10000 |
| ZAK | 73 | 10000 |
| ZAP70 | 63 | 10000 |

TABLE 5

Egmn913
Millipore-GPCR Panel

| GPCR | Agonist Data | Antagonist Data |
|---|---|---|
| 5-HT1A | −0.9 | −8.3 |
| 5-HT2A | −0.1 | 9.6 |
| 5-HT2B | 0.0 | 6.4 |
| 5-HT2C | 4.7 | −14.5 |
| 5-HT4B | 3.6 | −15.2 |
| 5-HT6 | −0.9 | −3.6 |
| A1 | 1.2 | 21.5 |
| A2B | 4.8 | 0.6 |
| A3 | −0.3 | 2.2 |
| ADRA1A | 2.8 | 4.9 |
| ADRA1B | 0.9 | 0.1 |
| ADRA1D | 0.4 | −11.2 |
| ADRA2A | 0.0 | −12.1 |
| ADRB1 | −0.9 | 4.0 |
| ADRB2 | 0.4 | −8.5 |
| ADRB3 | 1.2 | −2.2 |
| APJ | 1.1 | 0.9 |
| AT1 | −0.4 | −0.9 |
| BB1 | 0.2 | −3.4 |
| BB2 | −0.2 | 1.4 |
| BB3 | −1.2 | 3.7 |
| BDKR2 | −2.8 | 7.5 |
| BLT1 | 1.0 | −7.7 |
| C3aR | 0.0 | −0.8 |
| C5aR | 3.7 | −6.6 |
| CaS | 0.0 | −12.8 |
| CB1 | −0.3 | −16.7 |
| CB2 | −2.8 | 15.9 |
| CCK1 | 0.3 | 3.1 |
| CCK2 | −0.6 | 3.9 |
| CCR1 | −0.6 | −9.3 |
| CCR10 | −0.1 | −11.2 |
| CCR2B | 0.7 | −1.7 |
| CCR3 | 0.0 | 2.9 |
| CCR4 | −0.1 | 23.1 |
| CCR5 | −1.0 | 3.3 |
| CCR6 | 1.4 | −1.4 |
| CCR7 | 0.1 | −0.9 |
| CCR8 | 0.5 | 0.9 |
| CCR9 | 0.5 | 3.6 |
| CGRP1 | −0.2 | −12.8 |
| ChemR23 | −0.2 | −4.0 |
| CRF1 | 0.0 | −5.1 |
| CRF2 | 1.4 | −10.3 |
| CX3CR1 | −0.4 | 0.5 |
| CXCR1 | −0.7 | 1.7 |
| CXCR2 | 2.8 | −0.6 |
| CXCR3 | −0.1 | 1.1 |
| CXCR4 | 0.3 | 2.8 |
| CXCR5 | −0.4 | 4.0 |
| CXCR6 | 0.1 | −2.0 |
| CysLT1 | 1.0 | 2.2 |
| CysLT2 | −0.3 | −1.1 |
| D1 | −0.3 | −2.8 |
| D2 | 0.4 | 5.7 |
| D4 | 1.5 | −6.4 |
| D5 | 2.3 | −16.6 |
| DP | 0.0 | −4.6 |
| EP1 | 0.1 | −8.8 |
| EP2 | 0.1 | 0.1 |
| EP3 | 0.1 | −0.7 |
| EP4 | 0.0 | −2.1 |
| ETA | −0.3 | 3.4 |
| ETB | 5.7 | −11.8 |
| FP | 0.2 | 10.7 |
| FPR1 | −0.2 | 5.9 |
| FPR2 | −0.3 | 5.5 |
| GABAB1b | 0.4 | 12.8 |
| GAL1 | 2.4 | 0.7 |
| GAL2 | 0.2 | 10.8 |
| GCGR | 0.3 | −0.9 |
| Ghrelin | 0.1 | −14.6 |
| GIP | 0.7 | −0.6 |
| GLP-1 | 1.4 | 1.6 |
| GLP-2 | 1.4 | 5.3 |
| GnRH | −0.1 | 4.7 |
| GPR103 | −0.1 | −0.8 |
| GPR109A | 0.2 | −1.8 |
| GPR14 | 8.1 | 4.0 |
| GPR39 | −0.7 | 4.3 |
| GPR41 | 0.4 | −0.7 |
| GPR43 | 0.4 | 6.4 |
| GPR54 | 0.1 | −6.5 |
| GPR68 | −7.9 | 5.4 |
| GPR91 | 0.5 | −8.2 |
| GPR99 | 5.0 | −12.3 |
| H1 | 0.1 | −6.2 |
| H2 | 0.3 | −0.4 |
| H3 | −0.5 | −0.5 |
| IP1 | −0.1 | −9.9 |
| LPA1 | 0.2 | 4.5 |
| LPA3 | 0.5 | 3.7 |
| LPA5 | 0.0 | −14.6 |
| M1 | 1.4 | −1.8 |
| M2 | 0.0 | 1.4 |
| M3 | 0.2 | 4.3 |
| M4 | 0.1 | −2.9 |
| M5 | 0.1 | 0.9 |
| MC2 | 0.2 | −0.5 |
| MC4 | 0.0 | −3.6 |
| MC5 | −0.5 | 9.0 |
| MCHR1 | 0.1 | −6.3 |
| MCHR2 | 0.0 | −5.9 |
| mGlu2 | 0.1 | 7.6 |
| mGlu1 | 1.2 | −16.9 |
| Motilin | 0.6 | −4.6 |
| MrgD | −0.1 | −7.2 |
| MRGX1 | 0.4 | −8.0 |
| MRGX2 | −0.1 | 6.2 |
| NK1 | −2.2 | 1.4 |
| NK2 | 0.3 | −16.9 |
| NK3 | 0.2 | 2.3 |
| NMU1 | 2.2 | 13.2 |
| NMU2 | 0.5 | 0.0 |
| NOP | −0.1 | −0.7 |

TABLE 5-continued

Egmn913
Millipore-GPCR Panel

| GPCR | Agonist Data | Antagonist Data |
|---|---|---|
| NPBW1 | 0.0 | 5.1 |
| NTR1 | −0.1 | −5.4 |
| OPRD1 | 0.5 | 9.9 |
| OPRK1 | 3.8 | 2.2 |
| OPRM1 | −0.9 | 2.0 |
| OT | −0.3 | −3.7 |
| OX1 | 0.8 | 3.5 |
| OX2 | 0.4 | 0.1 |
| P2Y1 | 0.7 | −2.8 |
| P2Y11 | 0.4 | 7.4 |
| P2Y12 | −0.1 | −17.2 |
| P2Y2 | −0.2 | 18.2 |
| P2Y4 | 0.9 | 1.9 |
| PAC1 | 0.3 | 9.5 |
| PAF | 0.4 | −10.6 |
| PK1 | 0.1 | −0.6 |
| PK2 | 0.5 | 8.5 |
| PRP | −0.3 | −11.5 |
| PTH1 | 0.7 | −21.0 |
| PTH2 | 0.6 | −0.6 |
| S1P1 | −0.2 | −0.6 |
| S1P2 | 0.2 | 3.7 |
| S1P3 | 0.6 | −6.2 |
| S1P4 | 0.7 | −6.9 |
| SIP5 | 0.2 | 0.0 |
| Secretin | 1.0 | −3.9 |
| sst2 | 0.4 | −4.2 |
| sst3 | −0.1 | −6.5 |
| sst4 | −0.8 | 1.0 |
| sst5 | −0.6 | −2.8 |
| Thrombin-Activated PARs | 0.0 | −7.0 |
| TP | 0.5 | −6.0 |
| TRH | −0.1 | 12.1 |
| Trypsin-Activated PARs | −0.7 | 20.3 |
| TSH | 0.0 | 2.8 |
| V1A | 0.2 | −7.3 |
| V1B | −0.3 | 1.1 |
| V2 | 0.2 | 2.5 |
| VPAC1 | −0.1 | 7.3 |
| VPAC2 | 4.1 | 14.7 |
| XCR1 | 0.3 | 3.5 |
| Y2 | 2.8 | −10.2 |
| Y4 | −0.4 | −4.3 |

TABLE 6

| Phosphatase | Egmn913 @ 10 μM |
|---|---|
| CD45(h) | 91 |
| DUSP22(h) | 107 |
| HePTP(h) | 88 |
| LMPTP-A(h) | 97 |
| LMPTP-B (h) | 92 |
| MKP5(h) | 99 |
| PP1α(h) | 89 |
| PP2A(h) | 78 |
| PP5(h) | 99 |
| PTP MEG1(h) | 86 |
| PTP-MEG2(h) | 71 |
| PTP-1B(h) | 90 |
| PTPN22(h) | 92 |
| PTPβ(h) | 79 |
| RPTPμ(h) | 105 |
| SHP-1(h) | 96 |
| SHP-2(h) | 85 |
| TCPTP(h) | 98 |
| TMDP(h) | 99 |
| VHR(h) | 90 |
| YopH(y) | 98 |

Figure 2A:
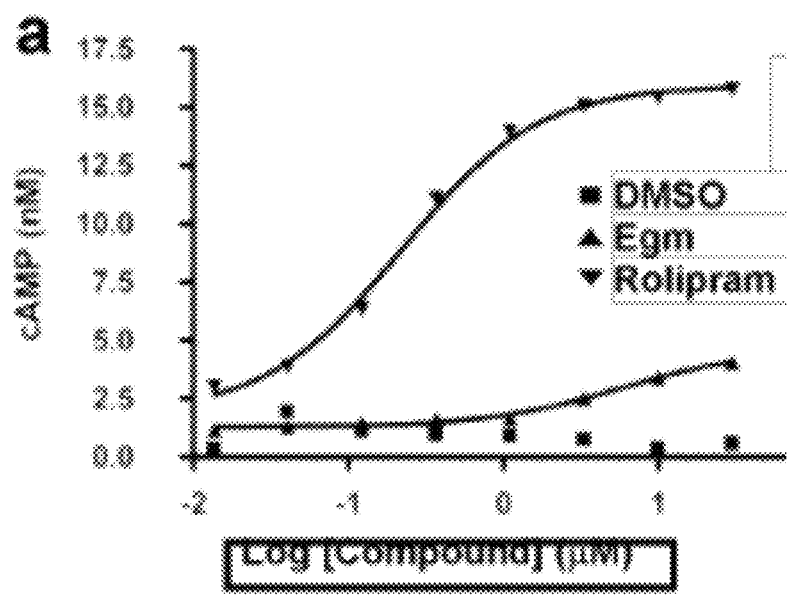
FIGS. 2a-2e include data and results of studies showing that Eggmanone causes local perturbations in cAMP levels resulting in PKA activation restricted to the basal bodies.
Figure 2B:
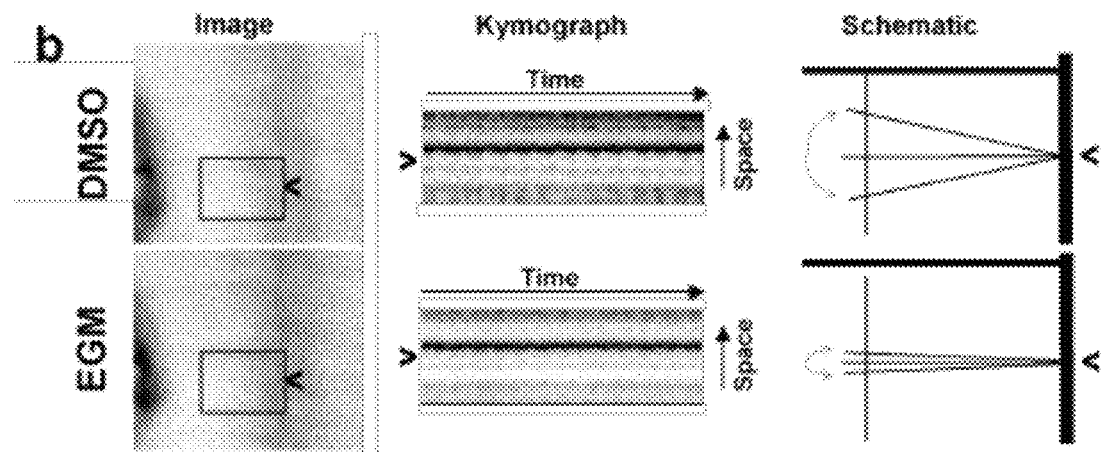

Surprisingly, Eggmanone did not significantly increase total cAMP levels in cells at the concentrations that abolish Hh signaling (FIG. 2a). Together with the fact that Eggmanone did not abolish neural tube patterning, which is relatively refractory to cilia disruption in zebrafish, this led us to consider a selective perturbation of local cAMP levels in a microdomain associated with the primary cilium. While there is no known technique to directly measure local cAMP levels within cilia, the frequency and the amplitude of beating cilia are modulated by cAMP levels. When zebrafish embryos were treated with 2 μM Eggmanone, the otic kino-cilia became markedly less motile (FIG. 2b). Since this concentration does not elicit a global cAMP change, this result suggests that Eggmanone selectively affects the local cAMP levels within a microdomain in or near the cilium.

Figure 2C:
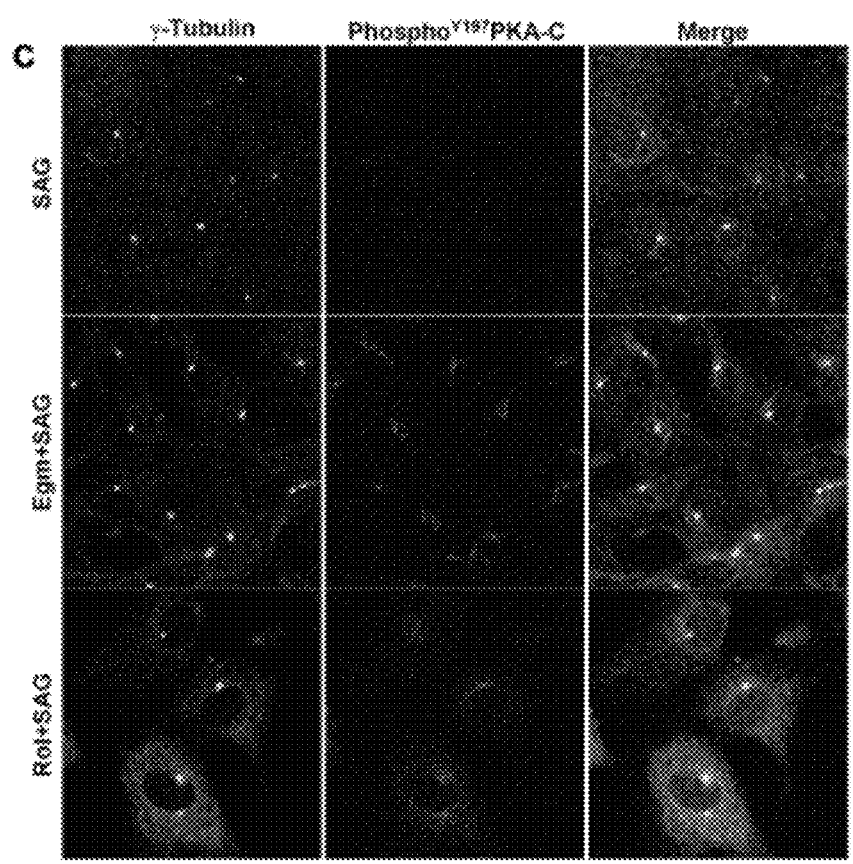
Figure 2D:
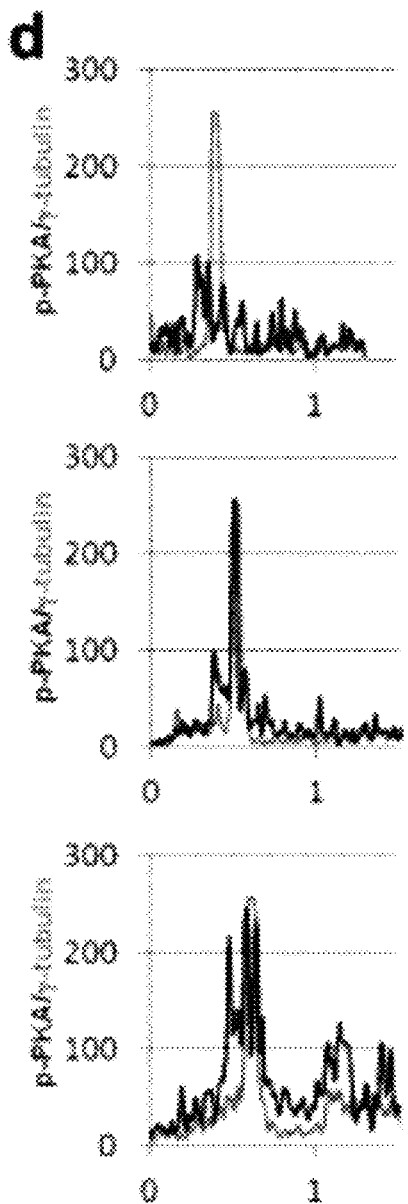
Figure 2E:
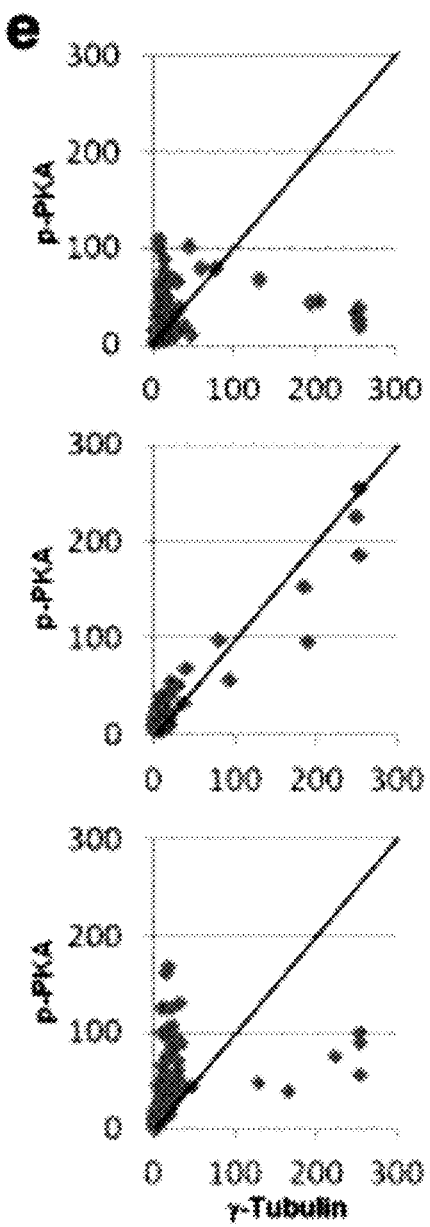
Figure 11A:
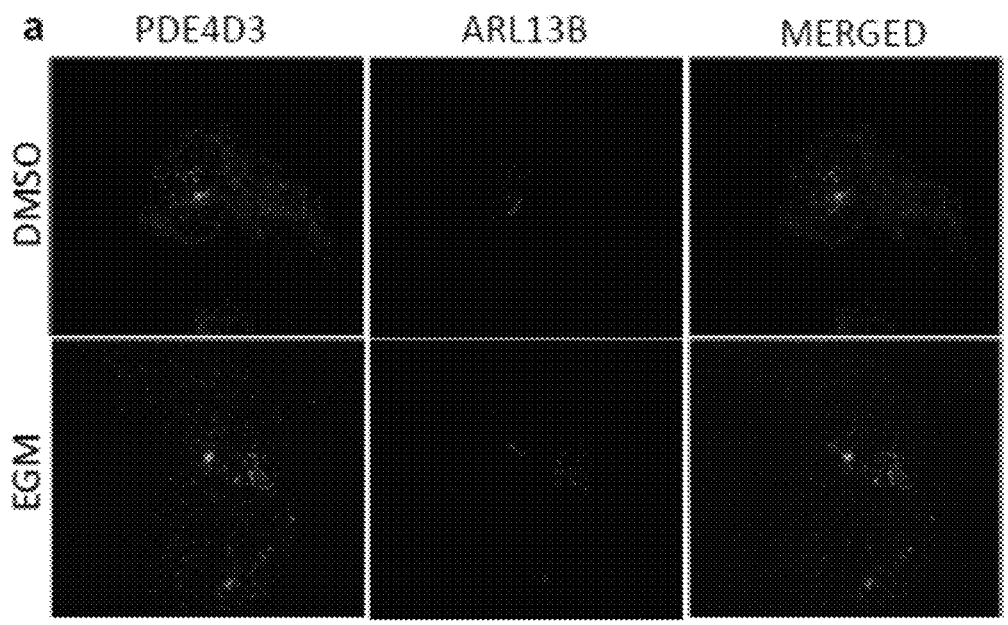
FIGS. 11a and 11b include data and results of studies showing that Eggmanone does not disrupt PDE4D3 localization to the peri-ciliary region at the base of the primary cilium.

A subset of PDE4 isoforms, notably PDE4D3, is localized to the centrosome, which also forms the basal body of the cilium and plays a central role in cilia biogenesis and function. Consistent with prior reports, the present inventors found that in NIH3T3 cells over-expressing a VSV-tagged PDE4D3, PDE4D3 co-localized to the base of the cilium (FIG. 11a). Eggmanone treatment did not disrupt PDE4D3 localization or physical association with AKAP450 (FIG. 11b), a scaffolding protein which anchors PKA to the cilium base. Interestingly, immunostaining for autophosphorylated, active form of the PKA catalytic subunit demonstrated that Eggmanone significantly increased the intensity of PKA activation almost exclusively at the basal body (FIG. 2c; FIG. 12a-f). This differs from a more diffuse increase in cytoplasmic phospho-PKA levels using the competitive PDE4 inhibitor rolipram (FIG. 2c-e) and from earlier findings in cerebellar granule neuron precursors using the cAMP analog dibutyril cAMP, which induced the dispersion of PKA from the centrosome and uniform PKA activation in the cell[3]. Taken together, the results indicated that Eggmanone selectively targets PDE4s localized to the basal body, leading to localized increases in cAMP levels and PKA activity. Moreover, because Eggmanone does not target the super-short PDE4D2, the most abundant PDE4 isoform present in the cytoplasm, the cAMP levels are largely unaffected outside the peri-ciliary microdomain.

Figure 3F:
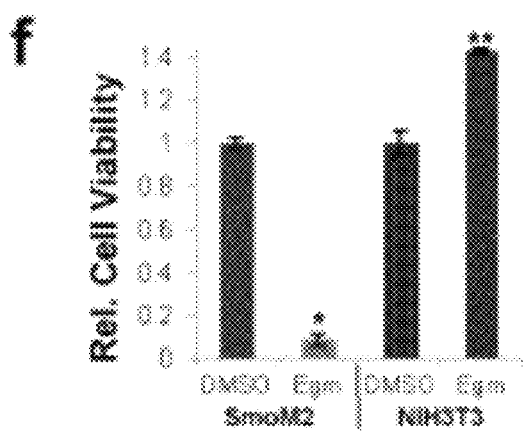
Figure 3G:
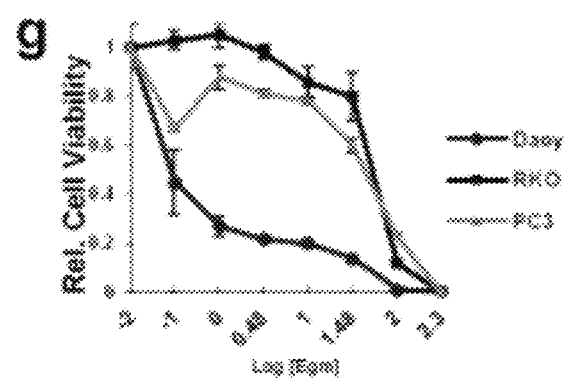
Figure 3H:
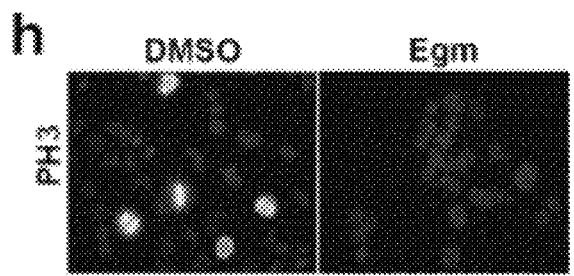
Figure 3I:
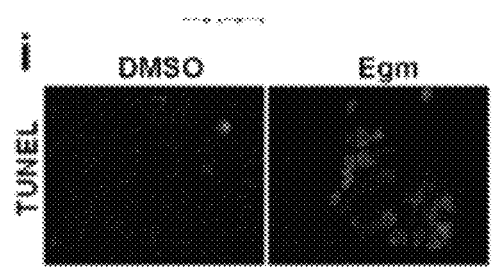

Eggmanone represents a unique class of selective small molecules to inhibit Hh signaling and a potentially new way to treat diseases caused by aberrant Hh activation. Eggmanone efficiently and selectively killed SmoM2-Light cells, which stably overexpress the constitutively active, oncogenic Smo mutant, which is resistant to cyclopamine (FIG. 3f), but not the parental NIH3T3 cells. Moreover, Eggmanone potently and preferentially reduced the viability of human medulloblastoma Daoy cells (FIG. 3g), which are known to be hedgehog and PDE4 dependent, by blocking proliferation and inducing apoptosis (FIG. 3h,i).

In vertebrate cells, forskolin prevents the ciliary localization of Gli and subsequent Gli-mediated transcription, but this may be mediated via a PKA-independent mechanism as Gli2 traffics to the cilia of PKA-null embryonic fibroblasts. Eggmanone did not prevent Gli2 localization to the primary cilium (FIG. 3a). Quantification of the intensity of Gli2 staining within the primary cilia revealed that significantly more Gli2 accumulated in Eggmanone-treated cilia than in controls (FIG. 3b). Moreover, Eggmanone blunted the nuclear accumulation of the full-length Gli2 (Gli2FL) induced by SAG, a Smo agonist, indicating that cAMP accumulation at basal body blocked Gli2 trafficking from the primary cilium to the nucleus (FIG. 3c-e).

Figure 13:
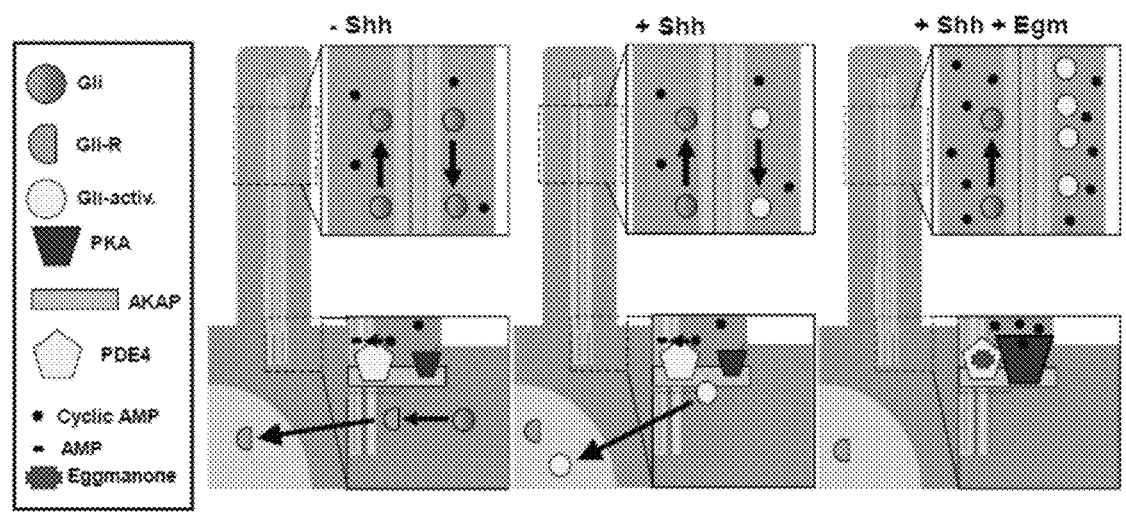
FIG. 13 depicts a model for Eggmanone mechanism of action. Left, in the absence of Hh ligand (SHH), Gli transiently enters and subsequently exits the primary cilia without getting activated. A proportion of Gli is proteolytically cleaved into the repressor form (Gli-R), which translocates to the nucleus to repress Hh target gene transcription. Middle, in the presence of Hh ligand (SHH), Gli becomes activated in the cilium by a still uncharacterized modification, then translocates to the nucleus as the full-length activator (Gli-activ.) to activate Hh target gene transcription. PDE4, which is localized to the basal body along with AKAP and PKA, functions as a "barrier" to isolate the primary cilium from the cAMP fluctuations occurring in the rest of the cell and serves to prevent aberrant PKA activation. Right, eggmanone (Egm) treatment selectively targets PDE4 isoforms localized to the basal body, leading to local elevations in the cAMP levels in the peri-ciliary microdomain and to local PKA activation. This in turn impedes Gli-activ. from translocating to the nucleus, resulting in down regulation of Hh signaling.

The precise roles of cAMP and PKA with respect to Hh regulation are not fully understood, but based on the findings and those of others, the present inventors propose the following model (FIG. 13): Hh activation requires the transport of Gli in and out of primary cilium, where it becomes activated. Eggmanone specifically targets the PDE4s localized to the basal body, resulting in locally elevated cAMP levels. This in turn prevents trafficking of activated Gli from the cilium to the nucleus via local PKA activation in the basal body. The present inventors postulate that the supramolecular complex consisting of PKA and PDE4 functions as a "cAMP barrier" to functionally isolate the peri-ciliary signal transduction events from cAMP fluctuations in the rest of the cell.

In summary, Eggmanone is an extraordinarily selective allosteric inhibitor of PDE4 whose effects on cAMP levels are spatially restricted to a cellular microdomain encompassing the basal body. The chemical genetic study underscores the importance of the basal body PDE4 activity and cAMP levels in Hh regulation. Considering there are over 29 PDE4 isoforms transcribed from 4 genes, it seems unlikely that traditional genetic and pharmacological approaches would have revealed these cell biological insights. The ability to selectively manipulate cAMP levels within a specific subcellular microdomain provides a new paradigm for molecular medicine.

Materials and Methods
Chemical Screen.

All zebrafish experiments were approved by Vanderbilt University Institutional Animal Care and Use Committee. Wild-type zebrafish of AB strain were maintained using standard protocols. Chemical screen for small molecules was performed as previously described. Briefly, pairs of zebrafish were mated, and fertilized eggs were arrayed in 96-well microtiter plates (5 embryos/well) containing 250 µl E3 water. At ~4-hpf, small molecule library from Vanderbilt High Throughput Screening Facility was added to each well to the final concentration of 5 µM. Embryos were incubated at 28.5° C. until 24 and 48-hpf, when they were examined for gross morphologic changes indicative of disruption in embryonic patterning. A total of ~30,000 compounds were screened.

Eggmanone Synthesis

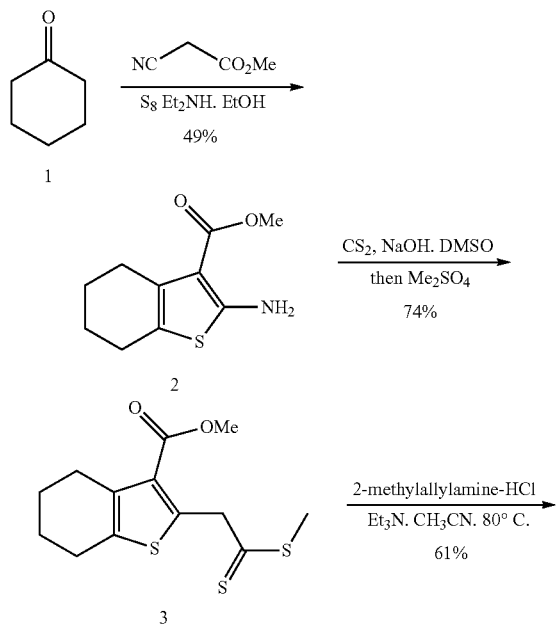

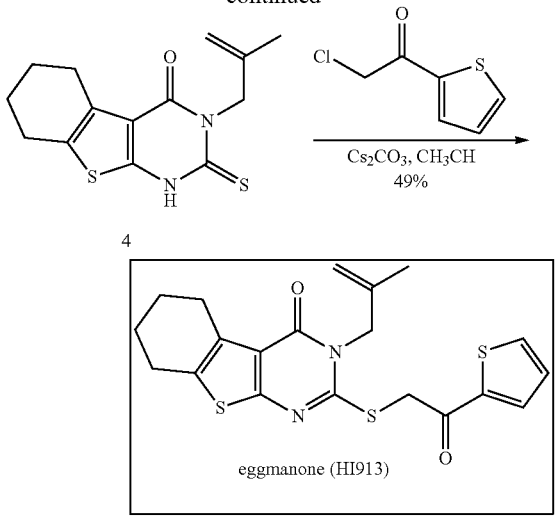

eggmanone (HI913)

Cyclohexanone was reacted with methyl cyanoacetate, $S_8$ and diethylamine in ethanol as previously reported to provide the 2-aminothiophene in 49% yield. Formation of the dithiocarbamate was effected with $C_2S$ and NaOH in DMSO followed by reaction with dimethylsulfate to give the methyl dithiocarbamate, as previously reported.

To a solution of 3 (1.00 g, 3.32 mmol, 1.0 eq) in $CH_3CN$ (2.2 mL) under argon atmosphere was added methylallylamine*HCl (446 mg, 4.15 mmol, 1.25 eq) then triethylamine (578 µL, 4.15 mmol, 1.25 eq) and the reaction was heated at 80° C. for 24 hours. The reaction mixture was diluted with $CH_2Cl_2$, washed with $H_2O$ (2×10 mL), and the combined aqueous layers were extracted with $CH_2Cl_2$ (2×10 mL). The combined organic layers were dried over $MgSO_4$, filtered and concentrated. The crude solid was recrystallized from $CH_3CN$ to provide 4 (591 mg, 2.02 mmol, 61%).

To a solution of 4 (50 mg, 0.171 mmol, 1.0 eq) in $CH_3CN$ (2.0 mL) was added 2-(chloroacetyl)thiophene (42 mg, 0.260 mmol, 1.5 eq) and $Cs_2CO_3$ (139 mg, 0.260 mmol, 1.5 eq) and the reaction was heated via microwave irradiation at 70° C. for 10 minutes. Addition of water caused precipitation of the desired product (30 mg, 0.0720 mmol, 42%). $^1H$ NMR (600 MHz, $CDCl_3$): δ 7.94 (dd, J=3.8, 1.0 Hz, 1H), 7.73 (dd, J=5.0, 1.0 Hz, 1H), 7.20 (dd, J=5.0, 3.9 Hz, 1H), 4.92 (s, 1H), 4.70 (s, 2H), 4.64 (s, 1H), 4.57 (s, 2H), 2.96 (t, J=6.0 Hz, 2H), 2.69 (t, J=6.0 Hz, 2H), 1.83 (s, 3H), 1.83 (m, 4H); LCMS, single peak, 1.42 min, m/e=416.8 [M+1].

Whole Mount Zebrafish In Situ Hybridization

In situ hybridization was performed as previously described. Zebrafish ptch1 probes were produced as previously described.

Whole Mount Immunofluorescence

Unless otherwise stated, manipulations were performed at RT. Embryos were fixed in 4% PFA at 4° C. overnight. Embryos were blocked with 1×PBS, 1% BSA, 1% Triton-X100, 0.1% DMSO for 2 hours. Embryos were incubated with primary antibodies diluted in block solution overnight at 4° C. Embryos were washed in 1×PBS with 1% Triton-X100 for 60 min. Embryos were incubated with secondary antibodies diluted in block solution for two hours. Primary antibodies specific against Myh1/2/4/6 (F-59) were obtained from Santa Cruz (1:50 dilution). Fluorescence immunocytochemistry was performed using anti-mouse secondary antibody Alexa 488 (1:500 dilution, Invitrogen).

Zebrafish Lines and Maintenance

Wild-type zebrafish lines of AB and TL; and transgenic line Tg(nkx2.2:egfp) were maintained using standard protocols.

Luciferase Reporter Assays

For Hh signaling assays, Shh-Light2 cells stably transfected with Gli-Luciferase reporter construct were used along with Shh-conditioned media, as previously described[7]. Alternatively, 3 μM purmorphamine or 20 nM Smoothened agonist (SAG) (Santa Cruz Biotechnology, Santa Cruz, Calif.) was used to induce Hh signaling. Reporter cells were seeded in 96-well plates and incubated overnight with the various concentrations of eggmanone and Shh-conditioned media. To assess the effects of overexpression of Gli-2, PDE4D3 and DN-PDE4D3 on Hh signaling, mammalian expression vectors containing these constructs were transfected into Shh-Light2 cells in 96-well plates using Fugene6 (Roche), according to manufacturer's instructions. The transfected or Shh-stimulated cells were incubated overnight with the various concentrations of compound. The cells were then lysed, and cell extracts were subjected to Steady-Glo luciferase assay (Promega) according to manufacturer's instructions. The results were normalized to cell titer, as determined using Cell Titer-Glo luminescence assay (Promega).

Immunocytochemistry

NIH3T3 cells were plated on Poly-D-Lysine-coated glass coverslips and were cultured at 37° C., 5% $CO_2$ in DMEM medium containing 10% fetal bovine serum until reaching 75% confluency. For one set of experiments, cells were then transfected with VSV-tagged PDE4D3 plasmid (gift from Miles Houslay, University of Glasgow, Scotland, UK) using Fugene6 transfection reagent (Roche, Indianapolis, Ind.) per manufacturer's protocol. Afterward, cell medium was replaced with DMEM/0.5% FBS containing either 5 μM eggmanone or DMSO and incubated overnight at 37° C., 5% $CO_2$. Cells were fixed in 4% PFA at room temperature for 10 minutes prior to permeabilization, blocking, and staining with primary antibodies against Arl13b (gift of Tamary Caspary, Emory University, Atlanta, Ga.) and VSV (AbCam, Cambridge, Mass.). Fluorescent immunocytochemistry was performed using species-specific, secondary antibodies (Jackson Immunoresearch, West Grove, Pa.). For additional immunocytochemistry experiment, cells were treated with 20 nM SAG in the presence or absence of 5 uM Eggmanone. After overnight incubation, cells were washed with PBS, fixed for 10 minutes in 4% PFA, permeabilized 20 minutes at −20C with cold methanol, blocked with PBS/1% BSA, and incubated with primary antibodies to phospho-PKA catalytic domain Thr197 (Cell Signaling, Danvers, Mass.) and then to Arl13b. An additional overnight blocking step using unconjugated rabbit IgG was required between primary antibody incubations since both antibodies were produced in rabbit. Fluorescent conjugated secondary antibodies were used for visualization. Data analysis was performed in part through the use of the VUMC Cell Imaging Shared Resource.

Quantitative Analysis of Gli and Phospho-PKA Intensity

Using ImageJ software (National Institutes of Health, developed by W. Rasband), a region of interest was created using the magic wand tool on Arl13b channel and transposed to the Gli2 channel, and integrated density was measured and reported as arbitrary units (a.u.). For phospho-PKA, using ImageJ, a line selection tool was used to select a line projected through the length of the primary cilia and an equal length beyond. The intensity values were potted and the cumulative florescence (area under the curve) was calculated for three cilia, blindly, for each treatment. These values for cilia and pericilia domain were analyzed by a two tailed students t-test. For correlation analysis, correlation coefficient for intensity of gamma-tubulin and phosphor-PKA were calculated and compared among treatments with students t-test.

Nuclear Fraction Western Blotting

Cells were fractionated using NE-PER Nuclear and Cytoplasmic extraction reagents (Thermo Scientific, Rockford, Ill.) per the manufacturer's protocol. For western blotting, goat anti-Gli2 (R & D Systems) and rabbit anti-Lamin-A/C (Cell Signaling Technology) antibodies were used as primary antibodies.

Co-Immunoprecipitation

NIH3T3 cells were transfected with VSV-tagged PDE4D3 plasmid (gift from Miles Houslay, University of Glasgow, Scotland, UK) using Fugene6 transfection reagent (Roche, Indianapolis, Ind.) per manufacturer's protocol. Afterward, cell medium was replaced with medium containing either 5 μM eggmanone or DMSO and incubated overnight. Cells were then lysed in CellLytic M Cell Lysis reagent supplemented with 1× Complete Mini Protease Inhibitor Cocktail (Roche). Cell lysate was incubated with mouse anti-AKAP450 antibody (Santa Cruz Biotechnology, Santa Cruz, Calif.) at 4'C overnight. Antibody-antigen complex was conjugated to Protein A/G agarose beads (Thermo Scientific) for 2 hours rocking at 4'C, followed by five cold 1×TBS washes. The beads were centrifuged, and bound protein was eluted in 1×LDS buffer (Invitrogen). Eluted protein was resolved in SDS-PAGE and transferred onto nitrocellulose membrane for Western blotting. Western blot analysis was performed using an anti-VSV antibody (AbCam, Cambridge, Mass.).

Video-Microscopy

For visualizing ciliary beating, live embryos (20 hpf) were removed from their chorion, mounted in SeaPlaque low-melting agarose (Biowhittaker Molecular Applications) (1.0% in embryo medium) in microwells of glass-bottom culture dishes (MatTek), and covered with embryo medium. Movies were acquired by using OPENLAB software (Improvision) at 55 frames per second with a 63×DIC objective on a Zeiss Axiovert 200 inverted fluorescence microscope equipped with a Retiga Exi Fast camera (Qimaging). Kymographs were obtained by drawing a line across a ciliary trajectory by using ImageJ software (National Institutes of Health, developed by W. Rasband) and Multiple-Kymograph plugin (developed by J. Rietdorf and A. Seitz).

RT-PCR

NIH3T3 cells were stimulated with 3 μM purmorphamine in the presence of eggmanone or DMSO for 24-hours. Cells were collected and RNA isolated with RNeasy kit (Qiagen, Valencia, Calif.). After subsequent cDNA amplification using Superscript III (Invitrogen, Carlsbad, Calif.), samples were quantified by comparing Q-PCR cycle thresholds (Ct) for gene expression normalized to GAPDH. The following TaqMan probe and primer sets (Applied Biosystems) were used: GAPDH (Mm99999915_g1), and Patch1 (Mm01306905_mi).

cAMP Assay

Shh-Light2 cells were seeded in a 96-well plate and incubated overnight. Varying concentrations of Rolipram or Eggmanone (0.013 uM-30 uM) or DMSO only were added to the cells in the absence of serum and incubated 30 minutes, at which time forskolin was added for a final concentration of 1 uM. After an additional 15 minutes, cells were washed with PBS and assayed for cAMP levels using EIA based chemiluminescence kit according to the manufacturer's protocol (Cell Signaling Technologies, Danvers, Mass.).

Target Profiling Assays for Kinases, GPCRs and Phosphatases

Profiling assays were not performed in-house. Compounds were shipped to the following companies for possible target identification: Kinase profiling assays were performed by DiscoverRx (San Diego, Calif.) using a phage display model; GPCR profiling assays were performed by Millipore (St. Louis, Mo.) using in cells expressing $G_{\alpha 15}$, a promiscuous G protein that enhances GPCR coupling to downstream $Ca^{2+}$ signaling pathways; phosphatase profiling assay was performed by Millipore (Dundee, UK).

PDE Assays

In vitro PDE profiling and dose-response assays were performed by BPS Biosciences (San Diego, Calif.). Kinetic Mechanism of inhibition studies were conducted by Millipore (St. Louis, Mo.). In brief, the PDE assay measures fluorescent polarization of FAM-AMP as FAM-cAMP is converted to FAM-AMP by PDE), the binding agent.

A series of dilutions of the test compound were prepared with 10% DMSO in assay buffer and 5 μl of the dilution was added to a 50 μl reaction so that the final concentration of DMSO is 1% in all of reactions. All of the PDE enzymatic reactions were conducted in duplicate at room temperature for 60 minutes in a 50 μl mixture containing PDE assay buffer (10 mM Tris-HCl, pH7.4, 10 mM MaCl2, 0.05% Tween 20), 100 nM FAM-cAMP, a PDE enzyme and a test compound.

After the enzymatic reaction, 100 μl of a binding solution (1:100 dilution of the binding agent, which contains the nano beads that recognize FAM-AMP, with the binding agent diluent) was added to each reaction and the reaction was performed at room temperature for 60 minutes. Fluorescence intensity was measured at an excitation of 485 nm and an emission of 528 nm using a Tecan Infinite M1000 microplate reader. Assays done by Millipore were conducted similarly with changes noted below:

|  | BPS | Millipore |
|---|---|---|
| PDE4D3 enzyme concentration used | 5.26 pM | 20 pM |
| Purity of PDE4D3 | 40% | >=75% |
| cAMP Substrate | 100 nM FAM-cAMP | 1.0 μM cAMP substrate |
| DMSO | 1% | 1% |

Cell Viability Assay

Cancer cell lines were seeded in 96 well tissue culture plate at a low density (10,000 cells per well) and treated with varying concentrations of Eggmanone. After 72 hr incubation, CellTiter-Blue Cell Viability Assay (Promega, Madison, Wis.) was then performed according to manufacturer's protocol. Absorbance was then measured in a Modulus Microplate reader (Promega, Madison, Wis.) at 590 nm and compared to cells treated with DMSO.

Example 2

Anti-Cancer Effect

Figure 14:
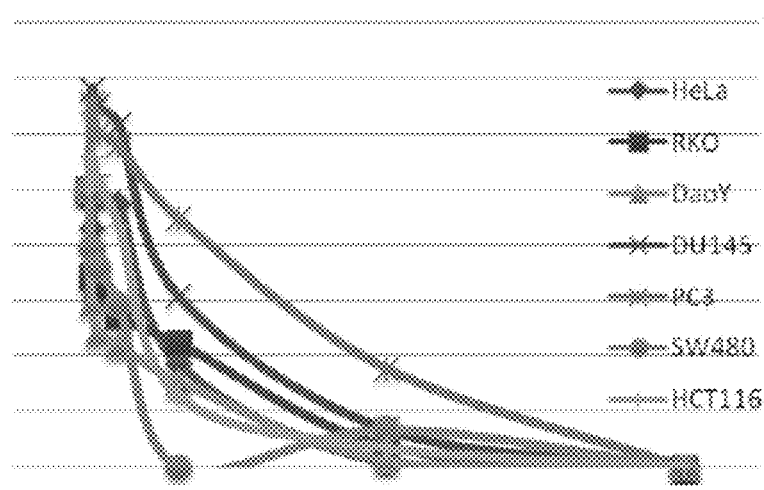
FIG. 14 is a graph showing anticancer effect of Eggmanone on various cancer cell lines.

Hedgehog signaling has been implicated in cancer formation and progression; therefore the present inventors assayed the effect of Eggmanone on various cancer lines. With reference to FIG. 14, the present inventors found that the prostate cancer cell line PC3 is affected, and the medulloblastoma cell line DAOY and colon cancer cell lines HCT116 and RKO are significantly inhibited.

It has been shown that Eggmanone has anti-proliferative effects in multiple cancer cell lines. There is growing literature that suggests that PDE4 would make an attractive target in a variety of cancers including brain, lung, and even chemo resistant colon cancers. In addition to anti proliferative effects inhibition of PDE4 has been linked to inhibition of VEGF (Vascular endothelial growth factor) which is essential for angiogenesis. As such Eggmanone could serve as an anti-tumor, anti-angiogenic, anti-metastatic, agent in the treatment of cancer. To this end, the present inventors assayed a series of clinically relevant cancer lines and assayed the anti-proliferative properties of a small cohort of eggmanone analogs. These gave a range of EC50s from 4 nM-8.4 uM.

Cancer cell lines were seeded in 96 well tissue culture plate at a low density and treated with varying concentrations of compounds identified in Table 7. After 72 hr incubation, CellTiter-Blue Cell Viability Assay (Promega, Madison, Wis.) was then performed according to manufacturer's protocol. Absorbance was then measured in a Modulus Microplate reader (Promega, Madison, Wis.) at 590 nm and compared to cells treated with DMSO.

TABLE 7

Cancer selectivity assays conducted across various tumor cell lines. Relative cell viability of various cancer cells following 72 hour treatment with increasing concentrations of eggmanone (n = 4 for each data point), ECSO represents concentration of example compounds that results in 50% reduction of viable cell count at 72 hours.

| Cancer Type | Cell Line Designation | Example comp'd, name & EC50 (uM) | Structure of example compound | Hh-Luciferase assay IC50 (uM) | PDE4D IC50 (uM) |
|---|---|---|---|---|---|
| Human Colorectal Adenocarcinoma | SW480 | 1KN7, 0.057 uM | 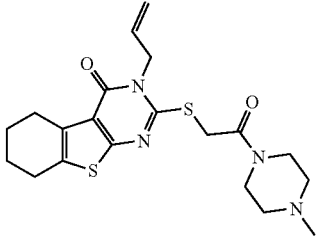 [SMILES: C=CCn1c(SCC(=O)N2CCN(C)CC2)nc2sc3c(c2c1=O)CCCC3] | 10 uM | 2.1 uM |

TABLE 7-continued

Cancer selectivity assays conducted across various tumor cell lines. Relative cell viability of various cancer cells following 72 hour treatment with increasing concentrations of eggmanone (n = 4 for each data point),␣EC50 represents concentration of example compounds that results in 50% reduction of viable cell count at 72 hours.

| Cancer Type | Cell Line Designation | Example comp'd, name & EC50 (uM) | Structure of example compound | Hh-Luciferase assay IC50 (uM) | PDE4D IC50 (uM) |
|---|---|---|---|---|---|
| Human Colorectal Carcinoma | HCT116 | 1KMF, 3.82 uM | 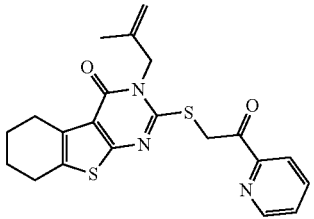 [SMILES: C=C(C)Cn1c(SCC(=O)c2ccccn2)nc2sc3c(c2c1=O)CCCC3] | 15 uM | 4.9 uM |
| Human Breast Adenocarcinoma | MDA-MB-231 | 1KLU, 2.05 uM | 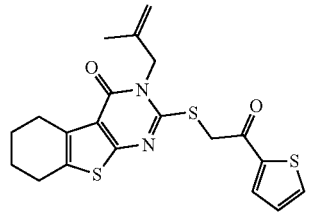 [SMILES: C=C(C)Cn1c(SCC(=O)c2cccs2)nc2sc3c(c2c1=O)CCCC3] | 1.5 uM | 0.89 uM |
| Mouse Melanoma | B16F11 | 1KLU, 2.05 uM | 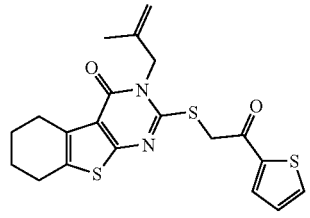 [SMILES: C=C(C)Cn1c(SCC(=O)c2cccs2)nc2sc3c(c2c1=O)CCCC3] | 1.5 uM | 0.89 uM |
| Human Prostate Adenocarcinoma | DU145 | 1KMF, 0.684 uM | 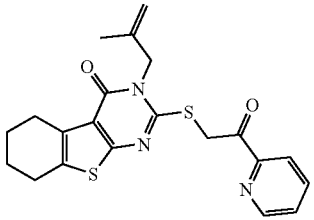 [SMILES: C=C(C)Cn1c(SCC(=O)c2ccccn2)nc2sc3c(c2c1=O)CCCC3] | 15 uM | 4.9 uM |
| Human Cerebellar Medulloblastoma | DaoY | 1KMG, 0.057 uM | 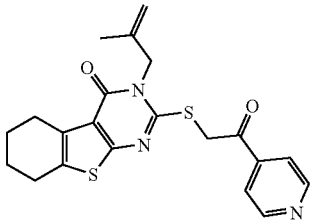 [SMILES: C=C(C)Cn1c(SCC(=O)c2ccncc2)nc2sc3c(c2c1=O)CCCC3] | 10 uM | 16 uM |
| Human Colon Carcinoma | RKO | 1KN7, 8.39 uM | 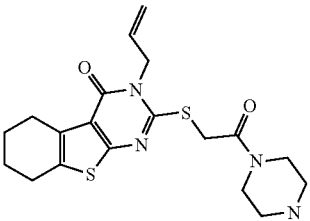 | 10 uM | 2.08 uM |

TABLE 7-continued

Cancer selectivity assays conducted across various tumor cell lines. Relative cell viability of various cancer cells following 72 hour treatment with increasing concentrations of eggmanone (n = 4 for each data point), EC50 represents concentration of example compounds that results in 50% reduction of viable cell count at 72 hours.

| Cancer Type | Cell Line Designation | Example comp'd, name & EC50 (uM) | Structure of example compound | Hh-Luciferase assay IC50 (uM) | PDE4D IC50 (uM) |
|---|---|---|---|---|---|
| Human Lung Carcinoma | RWGT2 | 1KLU, 6.87 uM | | 1.5 uM | 0.893 uM |
| Human Cervical Adenocarcinoma | HeLa | 1KMF, 9.2 uM | | 15 uM | 4.9 uM |
| Human Breast Adenocarcinoma | MCF7 | 1KY4, 0.483 uM | | No inhibition | 27 uM |

Example 3

Anti-Viral Effect

Figure 15:
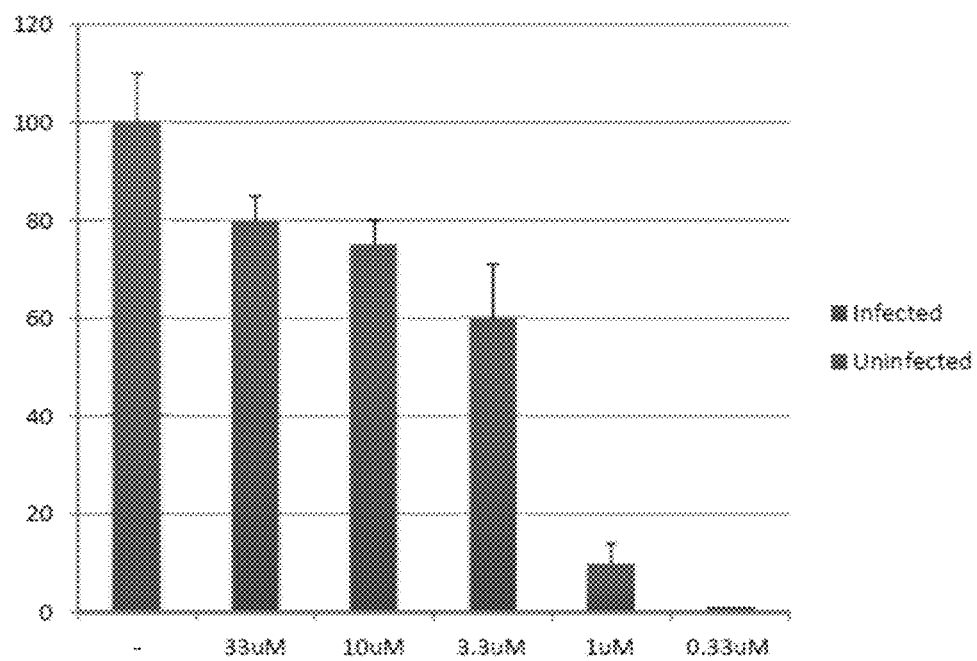
FIG. 15 includes results of a BVDV (Bovine Viral Diarrhea Virus, surrogate for Hepatitis C virus) CPE (cytotoxic effect) Assay with Eggmanone, where the compound was tested in half-log concentrations, and the data for the highest 3 concentrations is normalized to the respective DMSO concentrations.
Figure 16:
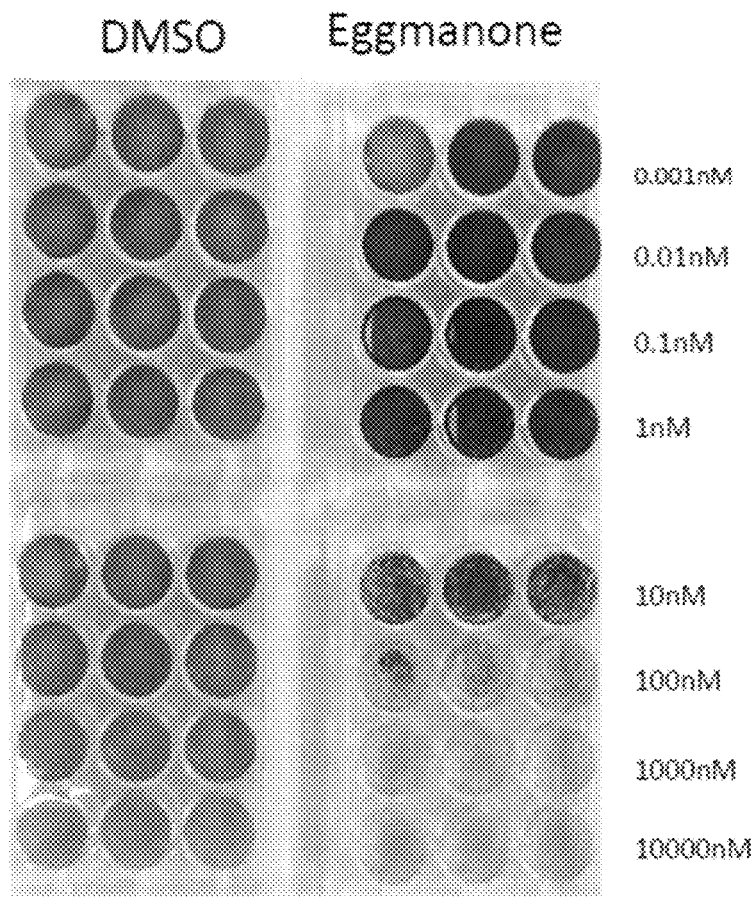
FIG. 16 includes the results of a plaque assay of respiratory syncytial virus (RSV), where 10 µM Eggmanone was added to cells 1 hour prior to the assay in serial 10 fold dilutions with each dilution performed in triplicate (shown), where the three columns to the left contained vehicle (DMSO) without drug, the three columns to the left are treated with drug, and dilutions are most concentrated in the uppermost wells and serially decrease through the rows.

PDE4 was found to be functionally up-regulated in human T-lymphotropic virus infected T-cells and may contribute to the virus-induced proliferation. Furthermore selective blocking of PDE4 activity inhibited IL-2R expression and thereby led to abolishing HIV-1 DNA nuclear import in memory T cells. Additionally there have been recent implications of PDE4 playing major important roles in the infection process of respiratory syncytial virus (RSV), Dengue, and cowpox. With reference to FIGS. 15 and 16, the present inventors have experimentally shown that Eggmanone has antiviral effects on, RSV, Influenza, Dengue, and BVDV.

Example 4

Hh Signaling Inhibition and PDE4 Inhibition of Various Compounds.

Hedgehog signaling inhibition and PDE4 inhibition of various compounds disclosed herein was assayed as described herein above. The following data, provided in Table 8, were obtained.

TABLE 8

| Structure | | Hh Inhibition Assay (EC50, μM) | PDE4 Inhibition Assay (IC50, μM) |
| --- | --- | --- | --- |
| [structure] | Formula (1) | 1.5 | 0.893 |
| [structure] | Formula (2) | Inactive | >100 |
| [structure] | Formula (3) | 3 | 1.27 |
| [structure] | Formula (4) | N/A | N/A |
| [structure] | Formula (5) | 2.5 | 1.2 |

TABLE 8-continued

| Structure | | Hh Inhibition Assay (EC50, μM) | PDE4 Inhibition Assay (IC50, μM) |
|---|---|---|---|
| 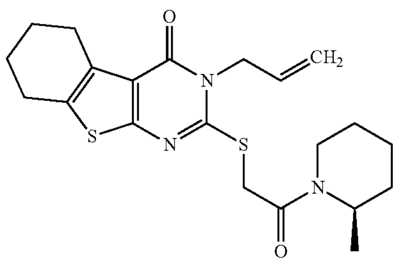 [SMILES: C=CCn1c(SCC(=O)N2CCCC[C@H]2C)nc2sc3c(c2c1=O)CCCC3] | Formula (6) | 5 | 7.6 |
| 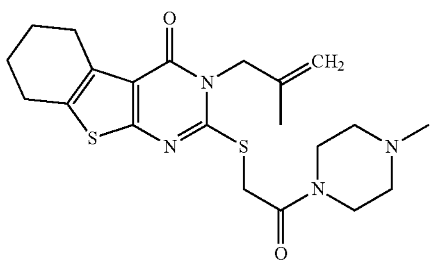 [SMILES: C=C(C)Cn1c(SCC(=O)N2CCN(C)CC2)nc2sc3c(c2c1=O)CCCC3] | Formula (7) | 20 (partial inhibition) | 8.5 |
| 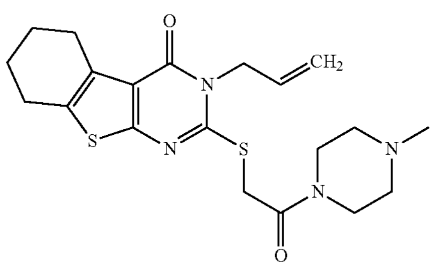 [SMILES: C=CCn1c(SCC(=O)N2CCN(C)CC2)nc2sc3c(c2c1=O)CCCC3] | Formula (8) | 10 | 2.08 |
| 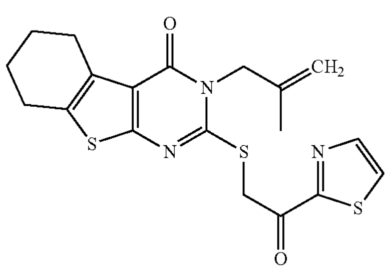 | Formula (9) | 7.5 | 6.4 |
| 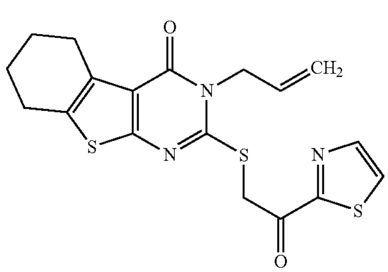 [SMILES: C=CCn1c(SCC(=O)c2nccs2)nc2sc3c(c2c1=O)CCCC3] | Formula (10) | Inactive | 27 |

TABLE 8-continued

| Structure | | Hh Inhibition Assay (EC50, μM) | PDE4 Inhibition Assay (IC50, μM) |
|---|---|---|---|
| (structure) | Formula (11) | 10 | 16 |
| (structure) | Formula (12) | 15 | 8.2 |
| (structure) | Formula (13) | 5-20 (partial inhibition) | 3.9 |
| (structure) | Formula (14) | Inactive | >100 |
| (structure) | Formula (15) | 15 | 23 |

TABLE 8-continued
| Structure | | Hh Inhibition Assay (EC50, μM) | PDE4 Inhibition Assay (IC50, μM) |
|---|---|---|---|
| 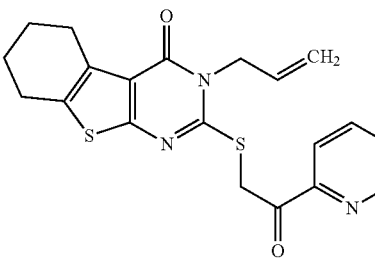 | Formula (16) | 20 | 25 |
| 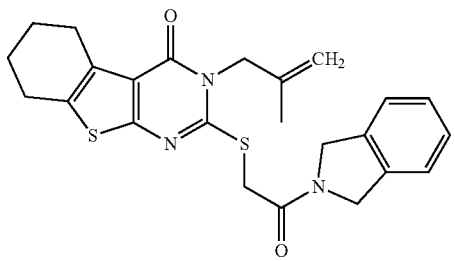 [SMILES: C=C(C)Cn1c(SCC(=O)N2Cc3ccccc3C2)nc2sc3c(c2c1=O)CCCC3] | Formula (17) | Inactive | 46 |
| 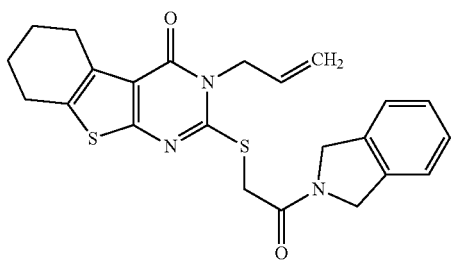 [SMILES: C=CCn1c(SCC(=O)N2Cc3ccccc3C2)nc2sc3c(c2c1=O)CCCC3] | Formula (18) | Inactive | >100 |
| 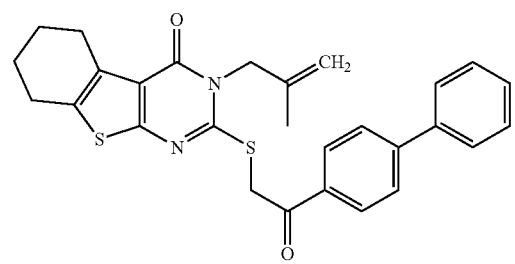 [SMILES: C=C(C)Cn1c(SCC(=O)c2ccc(-c3ccccc3)cc2)nc2sc3c(c2c1=O)CCCC3] | Formula (19) | Inactive | >100 |
| 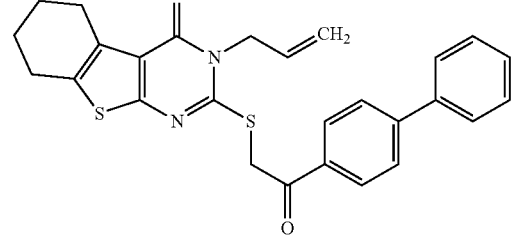 | Formula (20) | Inactive | N/A |

Example 5

General Synthesis of Methylallylamine Compounds

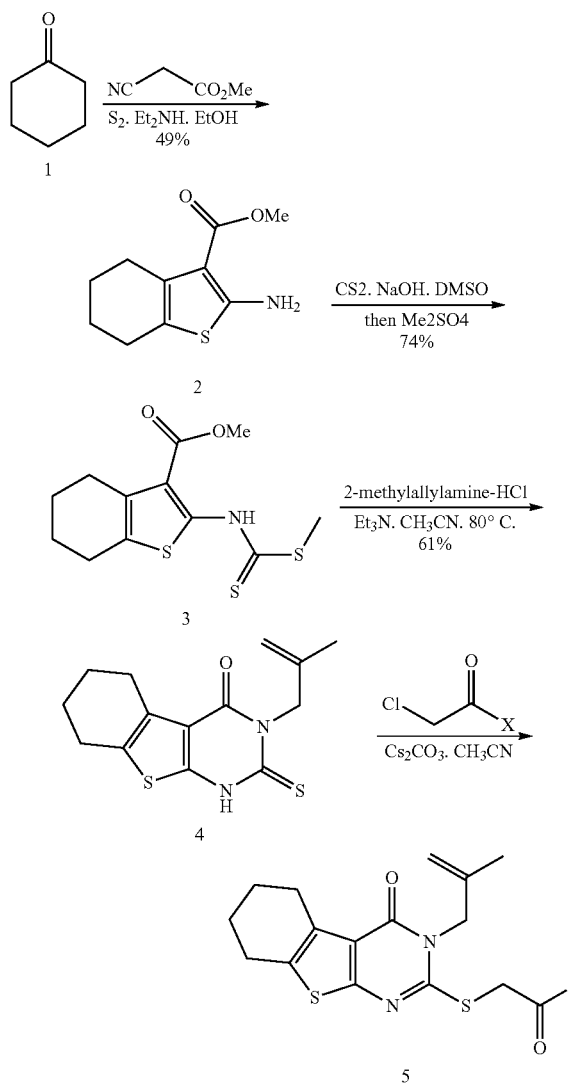

Cyclohexanone was reacted with methyl cyanoacetate, $S_8$ and diethylamine in ethanol as previously reported to provide the 2-aminothiophene in 49% yield.[1] Formation of the dithiocarbamate was effected with $C_2S$ and NaOH in DMSO followed by reaction with dimethylsulfate to give the methyl dithiocarbamate, as previously reported.[2,3] Treatment with methylallylamine·HCl effected cyclization to 4 in 61% yield. S-alkylation was performed with one of two methods, where X=aryl, heteroaryl, dialkylamine.

Method 1. To a solution of 4 (0.171 mmol, 1.0 eq) in $CH_3CN$ (2.0 mL) was added 2-(chloroacetyl)x(0.260 mmol, 1.5 eq) and $Cs_2CO_3$ (0.260 mmol, 1.5 eq) and the reaction was heated via microwave irradiation at 70° C. for 10 minutes. Addition of water caused precipitation of the desired product.

Method 2. To a solution of chloroacetyl chloride (0.26 mmol, 1.0 eq) in $CH_2Cl_2$ (1.5 mL) under argon atmosphere was added amine (0.26 mmol, 1.0 eq) and $Et_3N$ (0.31 mmol, 1.2 eq) and the reaction was stirred at RT for 3 hours. Solvent was removed in-vacuo. The crude product (0.260 mmol, 1.5 eq) was added as a solution in $CH_3CN$ (1.0 mL) to a solution of 4 (0.171 mmol, 1.0 eq) in $CH_3CN$ (1.0 mL). To the mixture was added $Cs_2CO_3$ (0.260 mmol, 1.5 eq) and the reaction was heated via microwave irradiation at 70° C. for 10 minutes. Addition of water caused precipitation of the desired product, which if necessary, was purified by flash column chromatography.

Example 6

General Synthesis of Allylamine Compounds

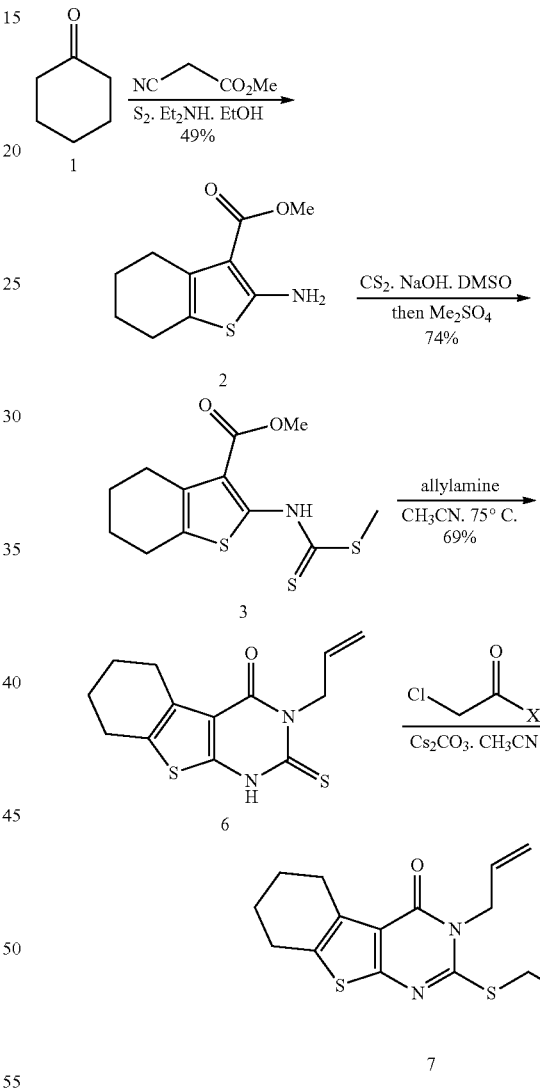

Cyclohexanone was reacted with methyl cyanoacetate, $S_8$ and diethylamine in ethanol as previously reported to provide the 2-aminothiophene in 49% yield.[1] Formation of the dithiocarbamate was effected with $C_2S$ and NaOH in DMSO followed by reaction with dimethylsulfate to give the methyl dithiocarbamate, as previously reported.[2,3] Treatment with allylamine effected cyclization to 4 in 61% yield. S-alkylation was performed with one of two methods, where X=aryl, heteroaryl, dialkylamine.

Method 1. To a solution of 4 (0.171 mmol, 1.0 eq) in $CH_3CN$ (2.0 mL) was added 2-(chloroacetyl)x(0.260 mmol, 1.5 eq) and Cs$_2$CO$_3$ (0.260 mmol, 1.5 eq) and the reaction was heated via microwave irradiation at 70° C. for 10 minutes. Addition of water caused precipitation of the desired product.

Method 2. To a solution of chloroacetyl chloride (0.26 mmol, 1.0 eq) in CH$_2$Cl$_2$ (1.5 mL) under argon atmosphere was added amine (0.26 mmol, 1.0 eq) and Et$_3$N (0.31 mmol, 1.2 eq) and the reaction was stirred at RT for 3 hours. Solvent was removed in-vacuo. The crude product (0.260 mmol, 1.5 eq) was added as a solution in CH$_3$CN (1.0 mL) to a solution of 4 (0.171 mmol, 1.0 eq) in CH$_3$CN (1.0 mL). To the mixture was added Cs$_2$CO$_3$ (0.260 mmol, 1.5 eq) and the reaction was heated via microwave irradiation at 70° C. for 10 minutes. Addition of water caused precipitation of the desired product, which if necessary, was purified by flash column chromatography.

Example 7

This Examples describes further procedures conducted to synthesize and characterize Eggmanone. Unless stated otherwise, the methods utilized in this Example are the same as the methods described in Example 1. Thus, to avoid undue repetition, the methods described in Example 1 are not restated in this Example.

A phenotypic screen for small molecule modulators of zebrafish pattern formation identified a series of structurally related compounds, represented by the prototype named eggmanone (3-(2-methylallyl)-2-((2-oxo-2-(thiophen-2-yl)ethyl)thio)-5,6,7,8-tetrahydrobenzo[4,5]thieno[2,3-d]pyrimidine-4(3H)-one). NMR spectra analysis of eggmanone. $^1$H NMR (600 MHz, CDCl$_3$): δ 7.94 (dd, J=3.8, 1.0 Hz, 1H), 7.73 (dd, J=5.0, 1.0 Hz, 1H), 7.20 (dd, J=5.0, 3.9 Hz, 1H), 4.92 (s, 1H), 4.70 (s, 2H), 4.64 (s, 1H), 4.57 (s, 2H), 2.96 (t, J=6.0 Hz, 2H), 2.69 (t, J=6.0 Hz, 2H), 1.83 (s, 3H), 1.83 (m, 4H); LCMS, single peak, 1.42 min, m/e=416.8 [M+1]. This compound caused a number of phenotypes resembling those of Hh-deficient mutant embryos: ventral tail curvature, absent pectoral fins, small eyes, loss of neurocranial chondrogenesis, impaired slow muscle formation, and enlarged, rounded somites (FIG. 17*a, b*; FIG. 5*a-c*). Eggmanone (EGM) abrogated the expression of the Hh target gene patched-1 (ptch1) in the bud-stage adaxial cells, pectoral fin fields, and the somites (FIG. 17*c, d*). However, eggmanone did not eliminate ptch1 expression in the ventral neural tube or myotome cells adjacent to the notochord (FIG. 5*d*). Moreover, nkx2.2-expressing neurons in the ventral neural tube were not abolished in eggmanone-treated embryos, indicating that Hh inhibition was context-dependent (FIG. 5*e*). Since the zebrafish ventral neural tube patterning is relatively insensitive to ciliary dysfunction, these selective effects of eggmanone suggest a mechanism of action that is cilia dependent.

In the mouse Hh reporter cell line Shh-Light2, eggmanone inhibited Hh-inducible Gli-responsive luciferase (Gli-Luc) activity in a dose dependent manner, confirming that the molecular target is conserved in mammals (FIG. 17*e*). Eggmanone also blocked Gli-Luc reporter and ptch1 induction by purmorphamine, a Smo agonist, indicating that eggmanone targeted the Hh pathway at or downstream of Smo activation (FIG. 17*f,g*). By contrast, eggmanone did not affect BMP-responsive luciferase reporter activity, indicating that Hh reporter inhibition was not due to nonspecific effects on luciferase activity (FIG. 17*h*). Additionally, eggmanone did not block Gli-Luc reporter activity in cells transiently overexpressing Gli2 (FIG. 17*i*), thus ruling out indirect, non-Hh related effects downstream of Gli function.

To identify the molecular target of eggmanone, we utilized the LASSO ("Ligand Activity by Surface Similarity Order") algorithm to virtually screen for potential targets. This algorithm implicated cGMP-specific PDE5 (FIG. 8), presumably based on the similarity of the eggmanone's core structure to guanine (FIG. 9). We assayed eggmanone for in vitro activity against eleven different PDE family members and found, surprisingly, that it significantly inhibited only the cAMP specific PDE4 family (FIG. 18). Eggmanone significantly inhibited isoforms from each gene within the PDE4 (A-D) family (FIG. 18*b, c*), with an IC$_{50}$ (concentration causing 50% of maximal inhibition) range of 0.80-3.75 µM. The enzymatic activities of specific PDE4 isoforms did not reach 0% even at high eggmanone concentrations (FIG. 18*c*). Eggmanone had minimal effect (<10% inhibition at 50 µM) on PDE1A1, PDE5A1, PDE6C, PDE7A1, PDE8A1, PDE9A1, and PDE10A2, and the IC50s for PDE2A, PDE3A and PDE11A4 were well above 50 µM (FIG. 18*a, b*), indicating that EGM is highly selective for the PDE4 family. Based on these measurements, eggmanone is at least 60-fold more potent against PDE4D3 than any of the tested PDE not belonging to the PDE4 family.

Figure 19:
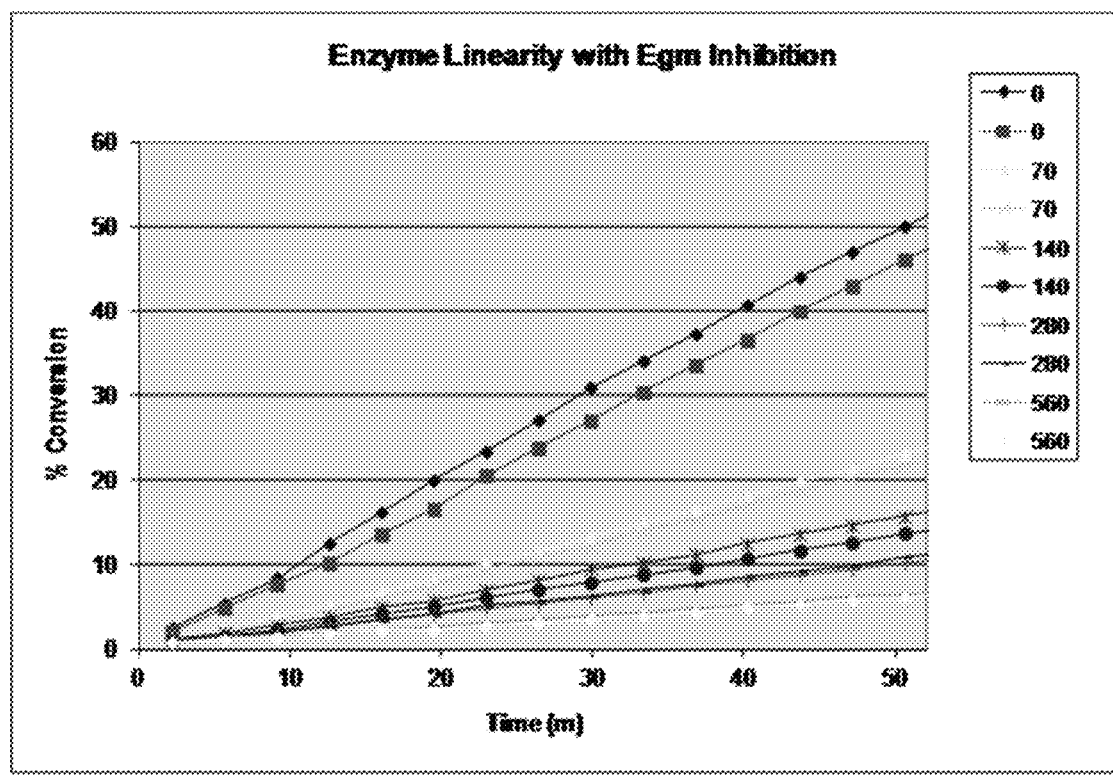
FIG. 19 includes a chart of a PDE 4D3 enzyme linearity study showing that inhibition of PDE4 with Egm occurs in a linear manner.
Figure 20:
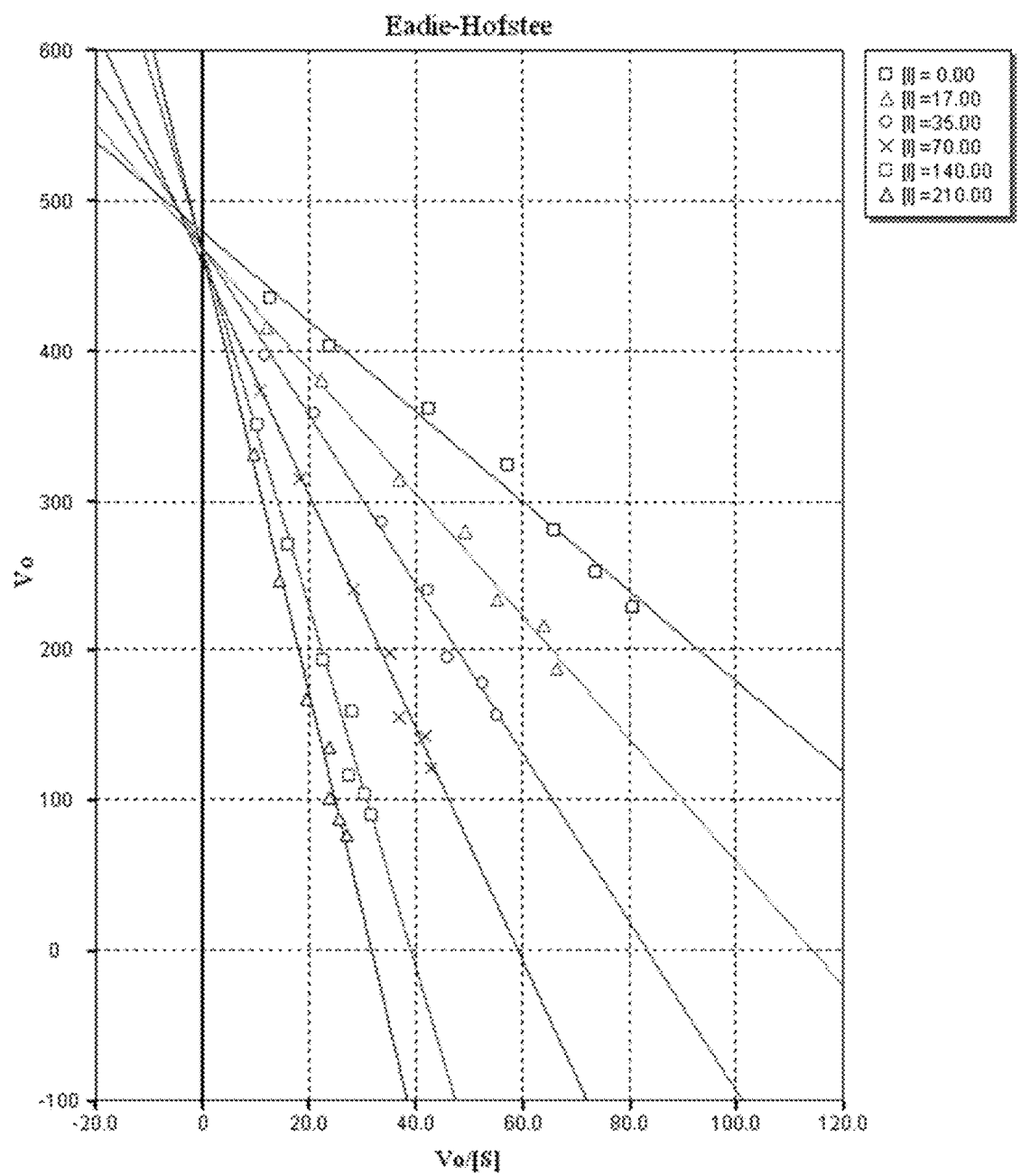
FIG. 20 includes a Eadie Hofstee plot showing that Egm acts in a competitive manner.
Figure 21:
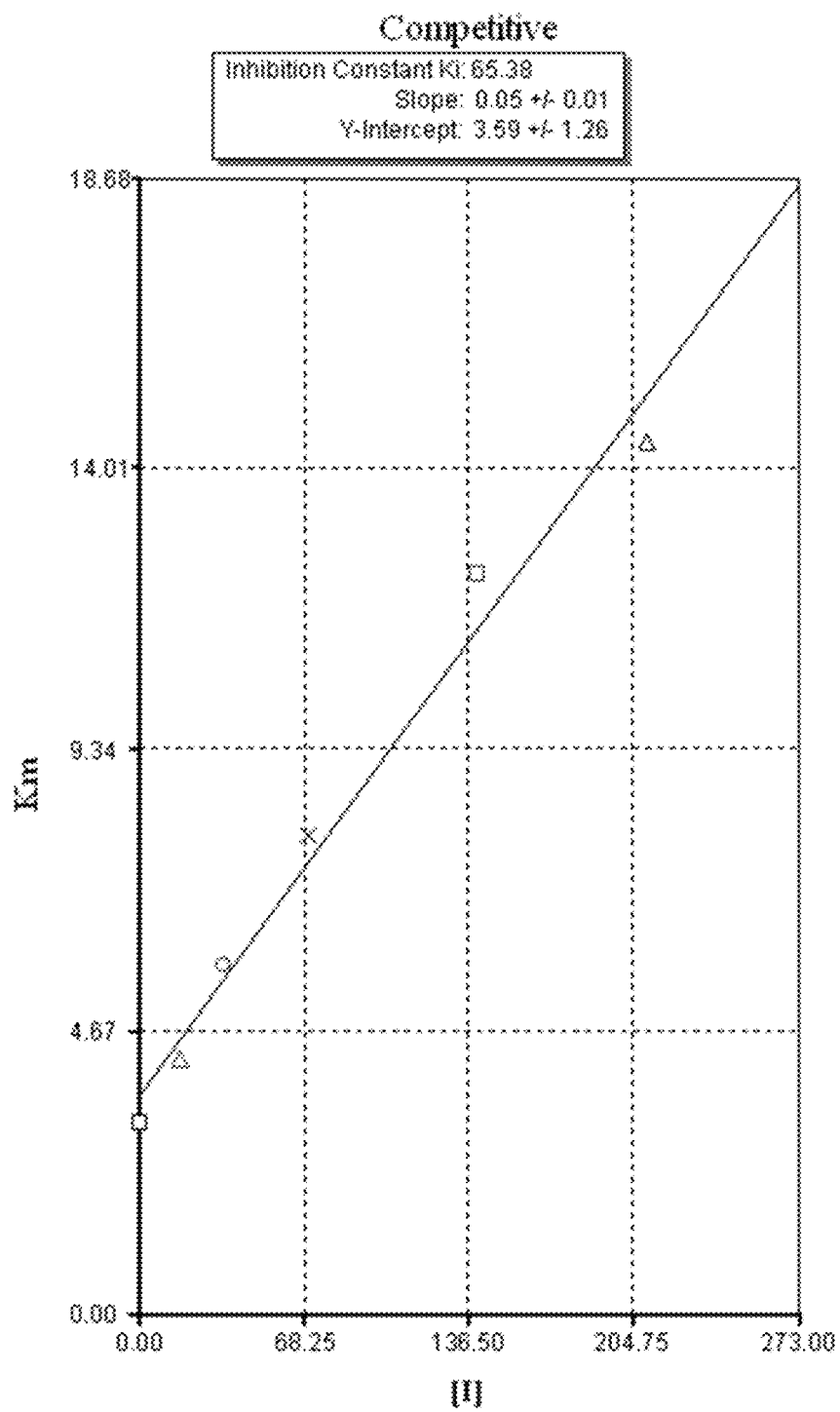
FIG. 21 includes a graph showing Km versus Egm concentration, wherein the linear relationship suggests that Egm acts in a competitive manner.

The PDE4 gene family consists of 4 genes (PDE4A, B, C, D), each containing upstream conserved regions, UCR1 (55 A.A) and UCR2 (78 A.A) that are unique to the PDE4 family. Of the seven isoforms of PDE4s tested, only the super-short isoform PDE4D2, which contains a truncated UCR2 domain, was not inhibited by eggmanone (FIG. 18*b*). Since the UCR2 domain is unique to all of the PDE4 family, this result provides a molecular explanation for eggmanone's selectivity toward PDE4 isoforms, and suggested that eggmanone might interact with an allosteric site on the UCR2 domain. To ascertain the mode of inhibition, kinetic studies were undertaken using purified PDE4D3, and the results were plotted in the double reciprocal Lineweaver-Burk plot (FIG. 18*d*; FIGS. 19-21). Eggmanone exhibited a competitive mode of inhibition on PDE4D3. As discussed below, the results indicate that eggmanone is a selective PDE4 inhibitor with a unique mechanism of action that interacts with both the catalytic and the UCR2 domains.

Figure 22B:
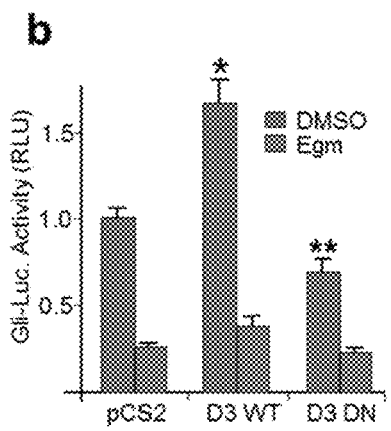
Figure 23A:
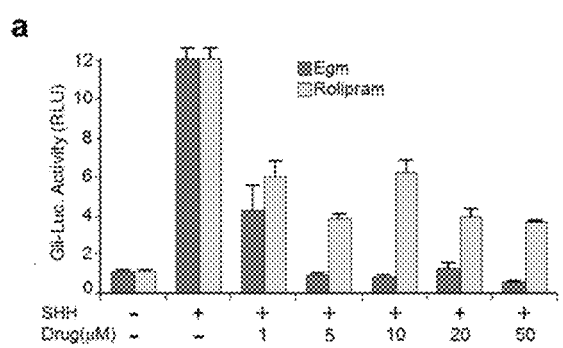
FIGS. 23a and 23b includes graphs showing the effects of known PDE4 inhibitors rolipram and D159153 on Hedgehog signaling.
Figure 23B:
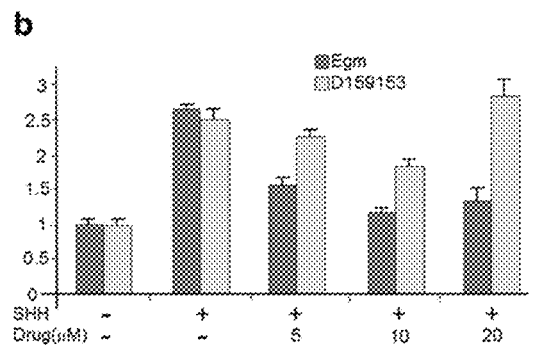

To rule out other potential targets, eggmanone was tested against other pharmacologically relevant classes of biomolecules using a comprehensive panel of 442 kinases, 158 GPCRs and 21 phosphatases; remarkably, eggmanone exhibited no significant inhibition (>10 µM) against any of these targets (Tables 4-6). Additionally, we conducted a small-scale structure activity relationship (SAR) study of eggmanone analogs. Of 12 analogs tested in both Hh-reporter assay and in vitro PDE4 assay, we found a strong correlation between each analog's ability to inhibit PDE4 and its ability to block Hh (FIG. 22*a*). Consistent with the idea that PDE4 antagonism was responsible for Hh signal inhibition, we found that Rolipram, a structurally unrelated competitive PDE4 inhibitor, could block Hh signaling as well (FIG. 23). Interestingly, even though Rolipram is a far more potent PDE4 inhibitor than eggmanone in vitro[29], Rolipram's effect on Hh signaling was incomplete even at high concentrations. Furthermore, to confirm the interaction between PDE4 and the Hh pathway in vertebrates, the long isoform PDE4D3 was transfected into Shh-Light2 reporter cells and was found to increase Hh signaling, which was abrogated by the presence of eggmanone (FIG. 22*b*). Finally, a dominant negative construct consisting of a catalytically inactive PDE4D3 inhibited Hh signaling (FIG. 22*b*). Taken together, these results indicate the pharmacological inhibition of PDE4 activity is central to Hh inhibition by eggmanone and its analogs.

Although eggmanone and its analogs block the hydrolytic activity of PDE4 in purified enzyme assays (FIG. 18), eggmanone surprisingly did not increase total cAMP levels in cells at the concentrations that abolish Hh signaling (FIG. 24a). By contrast, rolipram elicited robust cAMP accumulation and the allosteric PDE4 inhibitor D159153 elicited moderate cAMP accumulation (FIG. 24a). These observations, together with the fact that eggmanone did not abolish neural tube patterning, led us to consider whether eggmanone only increases local cAMP levels in or near the cilium. While there is no known technique to directly visualize local cAMP levels within cilium, the frequency and the amplitude of beating cilium are modulated by cAMP levels. When zebrafish embryos were treated with 2 μM eggmanone, the otic kinocilium became markedly less motile (FIG. 24b). Since this concentration does not elicit a global cAMP change, this result suggests that eggmanone selectively modulates the cAMP levels localized within a microdomain associated with the cilium.

Figure 11B:
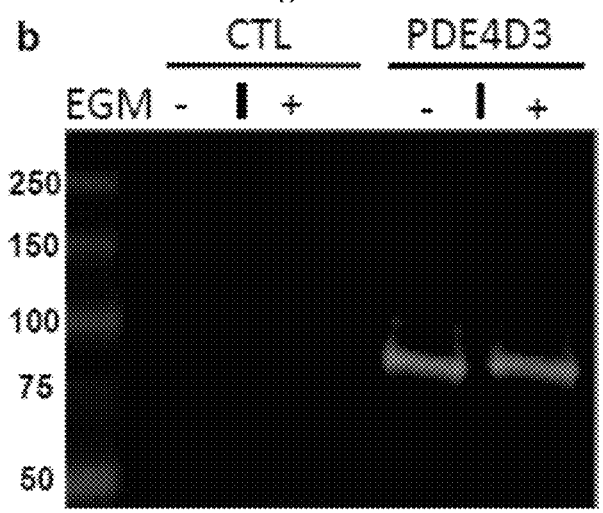

Without being bound by theory or mechanism, the centrosome, which also forms the basal body of the primary cilium and plays a central role in cilium biogenesis and function, was the cAMP microdomain targeted by eggmanone. Consistent with prior reports, in NIH3T3 cells over-expressing a VSV-tagged PDE4D3, PDE4D3 co-localized to the base of the cilium in physical association with AKAP450, a scaffolding protein which also anchors PKA to the basal body (FIG. 11). Eggmanone treatment did not disrupt PDE4D3 localization or physical association with AKAP450 (FIG. 11b). These results support the notion that eggmanone promotes local cAMP accumulation by specifically inhibiting the PDE4s, such as PDE4D3, which are localized to the basal body.

To visualize changes in cAMP concentrations in individual cells and cellular regions, we utilized two distinct FRET (fluorescence resonance energy transfer)-based cAMP sensors: the Epac-FRET sensor (mTurquoiseΔ-Epac (CD, ΔDEP)-cp173 Venus-Venus)[35], which detects cytosolic cAMP concentration and the PKA-based cAMP sensor (PKAC-YFP and PKARII-CFP combination), which has been used to document changes in local cAMP levels in the centrosome and basal body. In accordance with the cell lysate data, we found by using the Epac-FRET sensor that rolipram treatment (2 μM) significantly increased the FRET signal throughout the cell (FIG. 4c). By contrast, eggmanone treatment (2 μM) had no effect on the cytosolic FRET signal (FIG. 24c). Using the PKA-based cAMP sensor we found that eggmanone treatment (2 μM) increased cAMP levels only at discrete regions, presumably corresponding to the centrosome/basal body, without affecting cAMP levels elsewhere in the cell (FIG. 24d).

Since PKA is a critical downstream mediator activated by cAMP, we next examined the spatial distribution of PKA activation following eggmanone treatment. Immunostaining for the autophosphorylated active form of the PKA catalytic subunit demonstrated that eggmanone significantly increased the intensity of PKA activation almost exclusively in the basal body, which was marked with the γ-tubulin antibody (FIGS. 2, 12, and 25-26). This differed dramatically from a more diffuse increase in phospho-PKA staining following treatment with the competitive PDE4 inhibitor rolipram, the allosteric inhibitor D159153[30] (FIG. 26), and the cAMP analog dibutyril cAMP, which induced the dispersion of PKA from the centrosome and more uniform PKA activation in the cell (FIG. 26). Thus, eggmanone is functionally unique in its ability to increase cAMP levels and PKA activation precisely in the basal body.

Figure 27F:
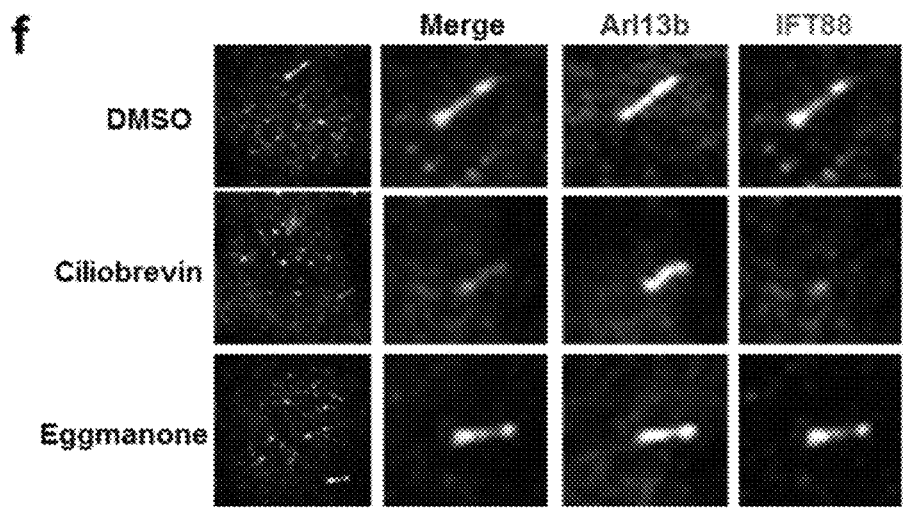

In vertebrate cells, forskolin antagonizes Hh signaling by preventing ciliary localization of Gli and subsequent Gli-mediated transcription[15]. While this effect was attributed to PKA activation, it may be mediated via a PKA-independent mechanism as forskolin blocked ciliary translocation of Gli2 in PKA-null embryonic fibroblasts. By contrast, eggmanone did not prevent Gli2 localization to the primary cilium (FIG. 27a). In fact, quantification of the intensity of Gli2 staining within the primary cilium revealed that more Gli2 accumulated in eggmanone-treated cilium than in controls (FIG. 27b). Importantly, eggmanone blunted the nuclear accumulation of the full-length Gli2 (Gli2FL) induced by SAG, a Smo agonist, indicating that cAMP accumulation at the basal body blocked Gli2 trafficking from the primary cilium to the nucleus (FIGS. 27c-e).

To investigate whether the disruption of the cilium-to-nucleus trafficking of Gli2 by eggmanone was due to a general defect in the retrograde transport within the primary cilium, we compared the effect of the cytoplasmic dynein motor inhibitor ciliobrevin D with the effect of eggmanone on the intraflagellar transport protein 88 (IFT88) trafficking[19]. Unlike ciliobrevin D, which severely disrupted the IFT88 localization in the cilium and is known to disrupt cilium morphology, eggmanone had no effect on IFT88 localization or cilium morphology (FIG. 27c). Thus, the effects of eggmanone on Gli2 trafficking is specific, rather than an indirect consequence of a global defect in ciliary transport machinery.

Eggmanone represents a novel class of selective small molecules that inhibit Hh signaling and is a potentially new way to treat diseases caused by aberrant Hh activation[37]. Eggmanone efficiently and selectively killed SmoM2-Light cells, which stably overexpress the constitutively active, oncogenic Smo mutant, and are resistant to the Smo antagonist cyclopamine (FIG. 3f). Eggmanone had no effect on parental NIH3T3 cells. Moreover, eggmanone potently and preferentially reduced the viability of hedgehog and PDE4 dependent human medulloblastoma Daoy cells (FIG. 3g) by blocking proliferation and inducing apoptosis (FIG. 3h, i).

Based on the findings, it is proposed that (FIG. 13): Hh activation requires trafficking of Gli through the primary cilium, where Gli becomes activated. Eggmanone targets PDE4s localized to the basal body, preventing the normal clearance of cAMP resulting in elevated cAMP levels at or near the cilium base. This in turn leads to the local activation of PKA in the basal body, where it prevents trafficking of Gli activator from the cilium to the nucleus. We postulate that the basal body, which contains the supramolecular complex comprised of both the mediator PKA and the negative regulator PDE4, functions as a "cAMP barrier" and a "signaling rheostat": as a barrier, the basal body functionally isolates periciliary signal transduction events from cAMP fluctuations in the rest of the cell[33], and as a rheostat, the basal body sets the threshold cAMP levels required for transduction or suppression of upstream signals emanating from the primary cilium. Eggmanone, by selectively raising the cAMP levels in the basal body, resets the "rheostat" to turn off Hh signaling.

PDE4 possesses a flexible structure, in which the UCR2 domain folds across the catalytic pocket, in essence to form a "cap" which modulates access to and binding efficiency in the catalytic pocket[48]. Interestingly, the UCR2-capped and uncapped states appear to be mediated by the phosphorylation status mediated by PKA, with phosphorylation by PKA favoring the uncapped (fully open) state, promoting cAMP degradation and conferring a negative feedback regulation on the PKA activity. While rolipram's affinity for the catalytic pocket is independent of the UCR2-uncapped or capped states, eggmanone may exhibit a tighter affinity in the UCR2-capped state, abrogating negative feedback regulation of PKA.

PDE4 also exists as a multimeric complex with the potential for both intramolecular and intermolecular capping and that association with scaffold proteins promote the monomeric conformation. Since eggmanone causes cAMP accumulation only at the basal body, to which various PDE4 isoforms are found in associations with scaffold proteins, we propose that eggmanone is an unusual conditional PDE4 inhibitor whose in vivo activity is dependent on enzyme confirmations conferred by subcellular localization.

Example 8

This Example describes procedures conducted to evaluate the effectiveness of the present compounds and composition for treating heart failure and the like.

Figure 28:
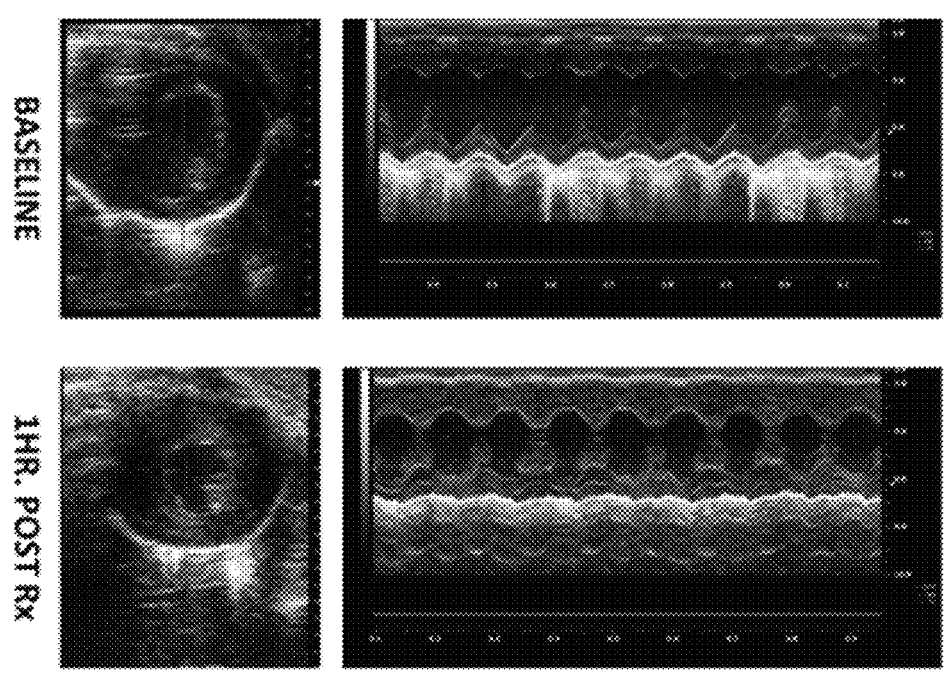
FIG. 28 includes an echocardiogram of a mouse after having been administered 20 mg/kg Egm via an intraperitoneal injection.
Figure 29:
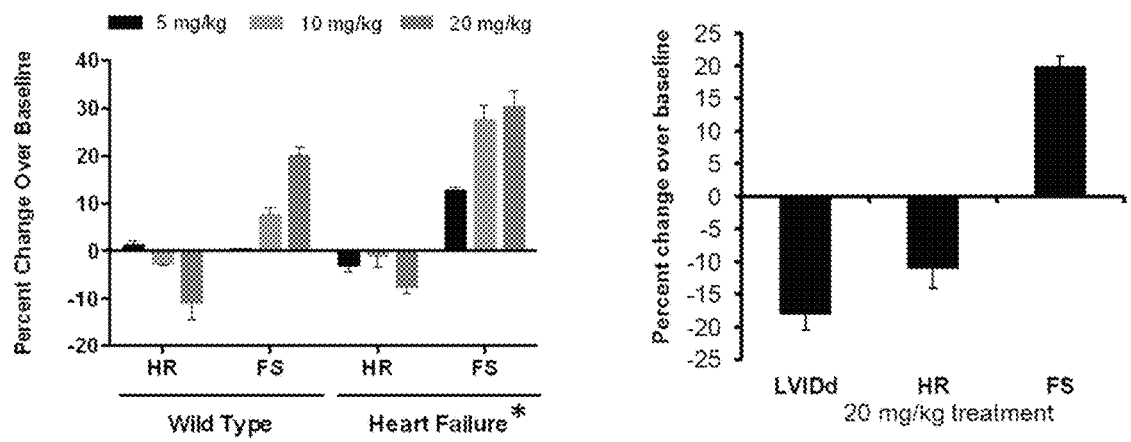
FIG. 29 includes data of the effects on the heart of a mouse after having been administered levels of from 5 mg/kg to 20 mg/kg Egm via an intraperitoneal injection. It includes data that, in both healthy wild type mice and mice with heart failure, EGM increases fractional shortening (FS) and decreases end-diastolic left ventricular internal dimension (LVIDd) without increasing heart rate.

As shown below (FIGS. 28 and 29), ionotropic effects are seen within 30 minutes of eggmanone administration to a mouse (20 mg/kg IP injection). The ionotropic effects to Eggmanone treatment were observed in the absence of a chronotropic response (FIG. 28). This compound also does not increase the heart rate in mice, and mice treated with EGM exhibited no significant side effects and returned back to baseline heart function within 24 hrs of treatment (FIG. 29). Mechanistically compound EGM targets the hydrolase PDE4. In Human adult myocardium, PDE4 localizes strictly to the z-bands.

In fibroblasts, PDE4 localized to the subcellular organelle called the centrosome (FIG. 30). The addition of EGM to fibroblasts caused a spatially restricted activation of PKA around the centrosome without raising total cellular cAMP content (FIG. 31). Likewise, allosteric inhibition of PDE4 in the heart lead to localized activation of PKA around the Z-disc without raising total cellular cAMP content.

To observe whether the effects of eggmanone administration are cardiomyocyte specific or due to off target effects, the contractility of individual mouse cardiomyocytes and the tone of ascending/descending aorta was observed. In mouse cardiomyocytes, Egm caused a 50% increase in contractility over vehicle control (FIG. 32). The substantial increase in contractility with EGM (10 μM) was not associated with alterations in calcium handling in isolated mouse cardiomyocytes (FIG. 33). EGM also increased contractile function in human induced pluripotent stem cell derived cardiomyocytes (hiPSC-CMs) indicating that EMG will increase contractility in human myocytes (FIG. 34).

For myography, to test the vascular tone for presense of downstream or off target effects, mouse aorta was mounted and cannulated on a closed system. A physiological buffer (with respect to pH, $CO_2$, and temperature) was circulated through the vessel. Drugs or compounds known to cause vessel constriction (e.g., KCl) or dilation were added to buffer, and the vessel was observed for change in diameter (FIG. 35). After pre-constriction, Egm administration had no effect on the vessel. However, Rolipram caused the vessel to dilate (FIGS. 35 and 36). These data illustrate that Egm may be acting directly on cardiomyocytes to cause left ventricular constriction rather than acting upon the vascularature leading to a pre-load effect.

Thus, allosteric PDE4 inhibitors can be used to cause localized activation of PKA without increasing total cAMP content, and the use of a novel class of PDE4 inhibitors with unique mechanism of action to increase cardiac inotropy without chronotropy. Moreover, as this approach does not involve increase in total cAMP content and global PKA activation, the proposed invention of the use of allosteric PDE4 inhibitors for heart failure will increase cardiac output without tachycardia, and without concern for tachyphylaxis and heart failure progression upon chronic administration.

Example 9

Compounds in Tables 9A and 9B were generated according to schemes set forth herein, in the specification.

Hh $EC_{50}$ Gli-Luc refers to treatment of stably transfected NIH-3T3 cells incorporating a Gli promoter-driven firefly luciferase and constitutively active renilla luciferase with multiple concentrations of inhibitor compound from a 10 mM DMSO stock solution and estimation of half-maximal effective inhibitory concentration.

ZF refers to wild-type embryonic zebrafish phenotypic assay involving dosing n=~10 embryos in E3 egg water with compound from either a stock of 1 mM or 10 mM in DMSO at 5 hours post-fertilization and observing at 24, 48, and 72 hours post-fertilization. The 50% maximal effective concentration was determined by the concentration of compound at which embryos exhibited the identical phenotype compared to eggmanone-treated embryos.

Hh % Inh. refers to assaying C3H10T½ cells for reduction in SAG-induced (100 nM) Gli1 expression caused by inhibitors after 24 hours at either 10 μM, 1 μM, or five concentrations to determine $EC_{50}$. Compounds are dosed from 10 mM DMSO stock solutions, and mRNA is isolated after 24 hours of compound treatment. mRNA is reverse transcribed to produce cDNA which is quantified by quantitative polymerase chain reaction (qPCR) in triplicate and levels are normalized to GAPDH levels. Data is presented as percent inhibition compared to positive control (SAG).

TM3 Gli Luciferase, C3H10T$_{1/2}$ qPCR, Gli1 mRNA; Sufu Null (Ptc), PDE4D3, and PDE4D2 data is included for compounds where analyzed. Methods utilized are according to the methods and procedures discussed herein, in the specification.

TABLE 9A

| Structure | Ref. |
|---|---|
| (structure) | EGM |
| (structure) | KYK-1-76 |
| (structure) | 1KXQ |

TABLE 9A-continued
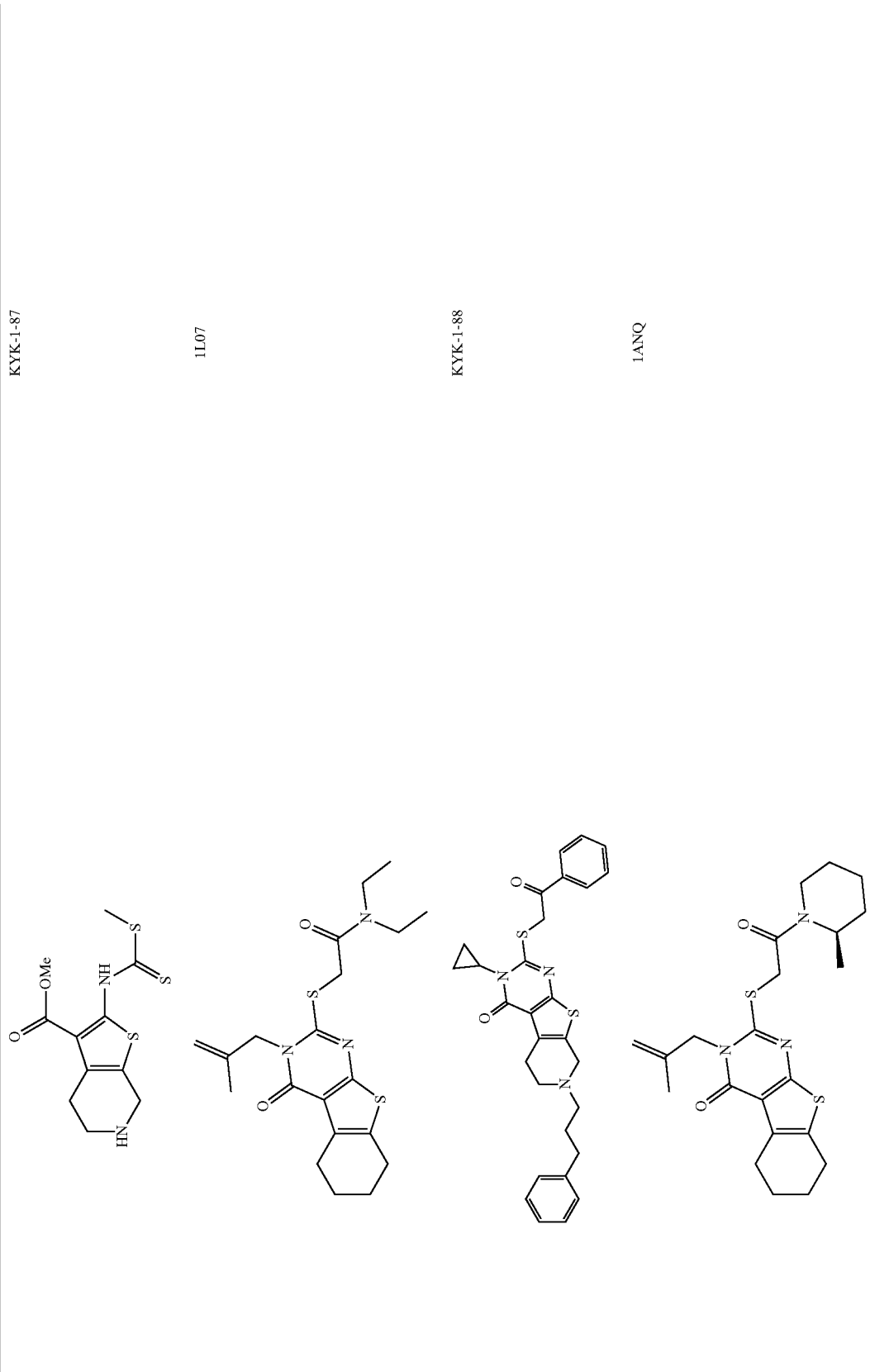
KYK-1-87
1L07
KYK-1-88
1ANQ

TABLE 9A-continued
KYK-1-96
1KMT
KYK-1-99
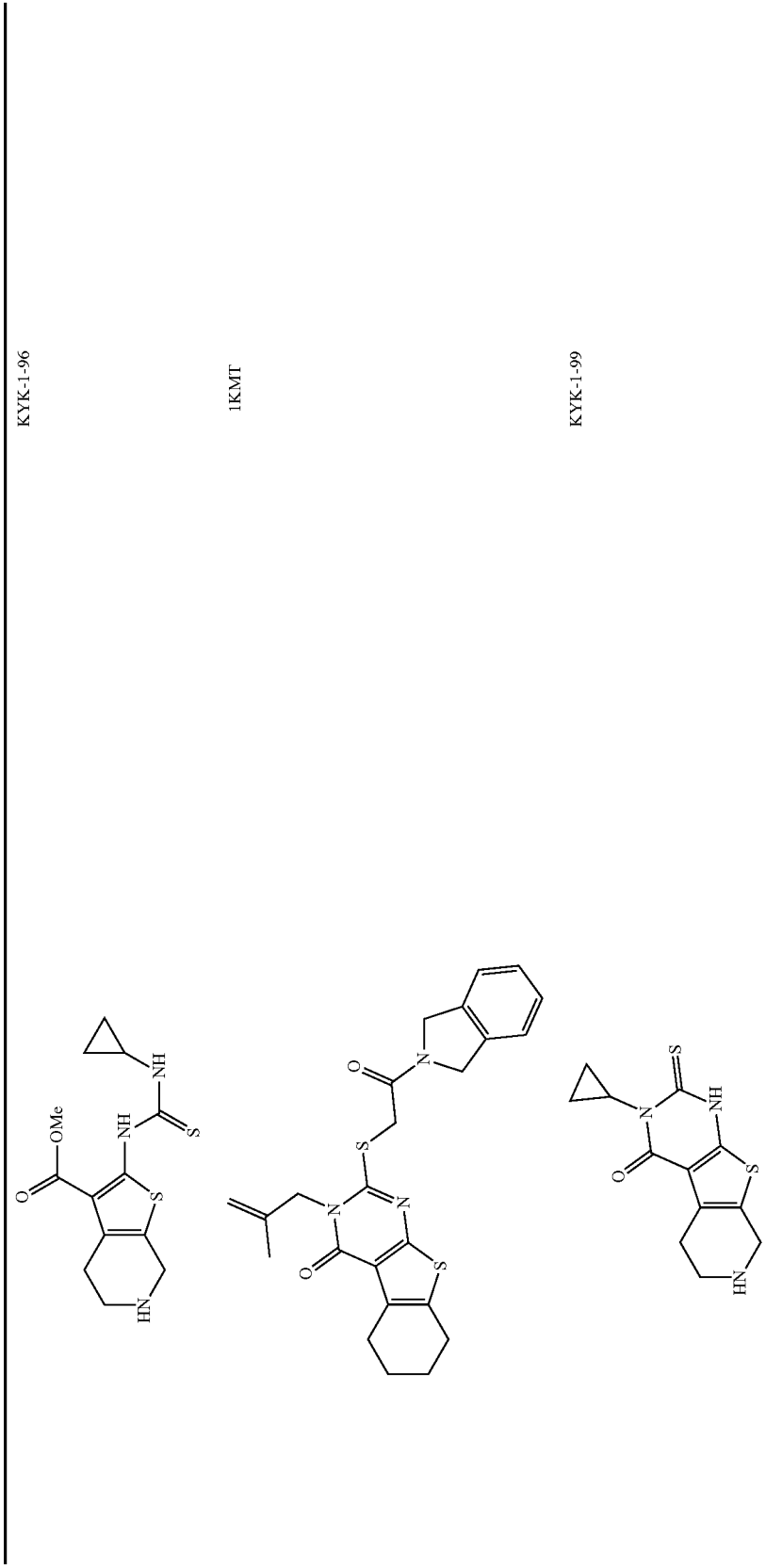

TABLE 9A-continued
KK-14-093-1
KYK-1-100
KK-14-094-1
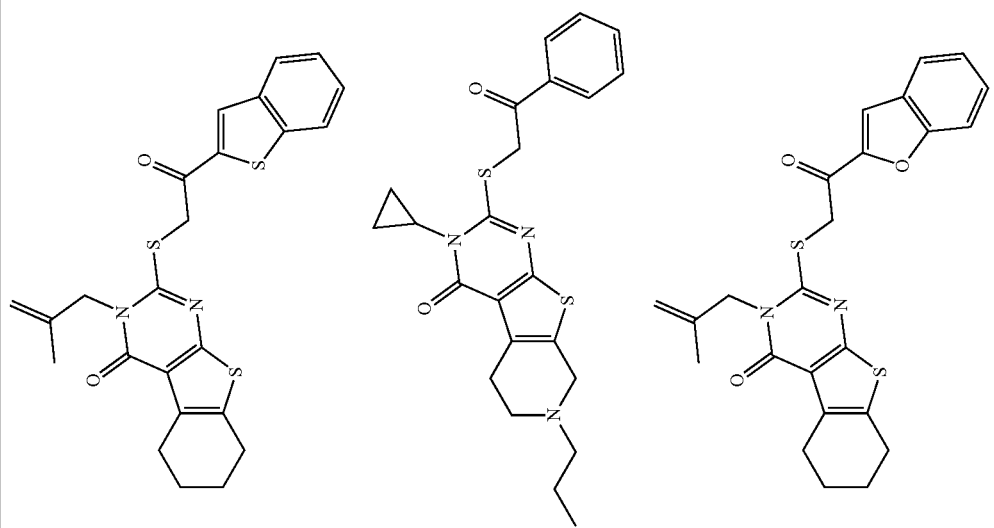

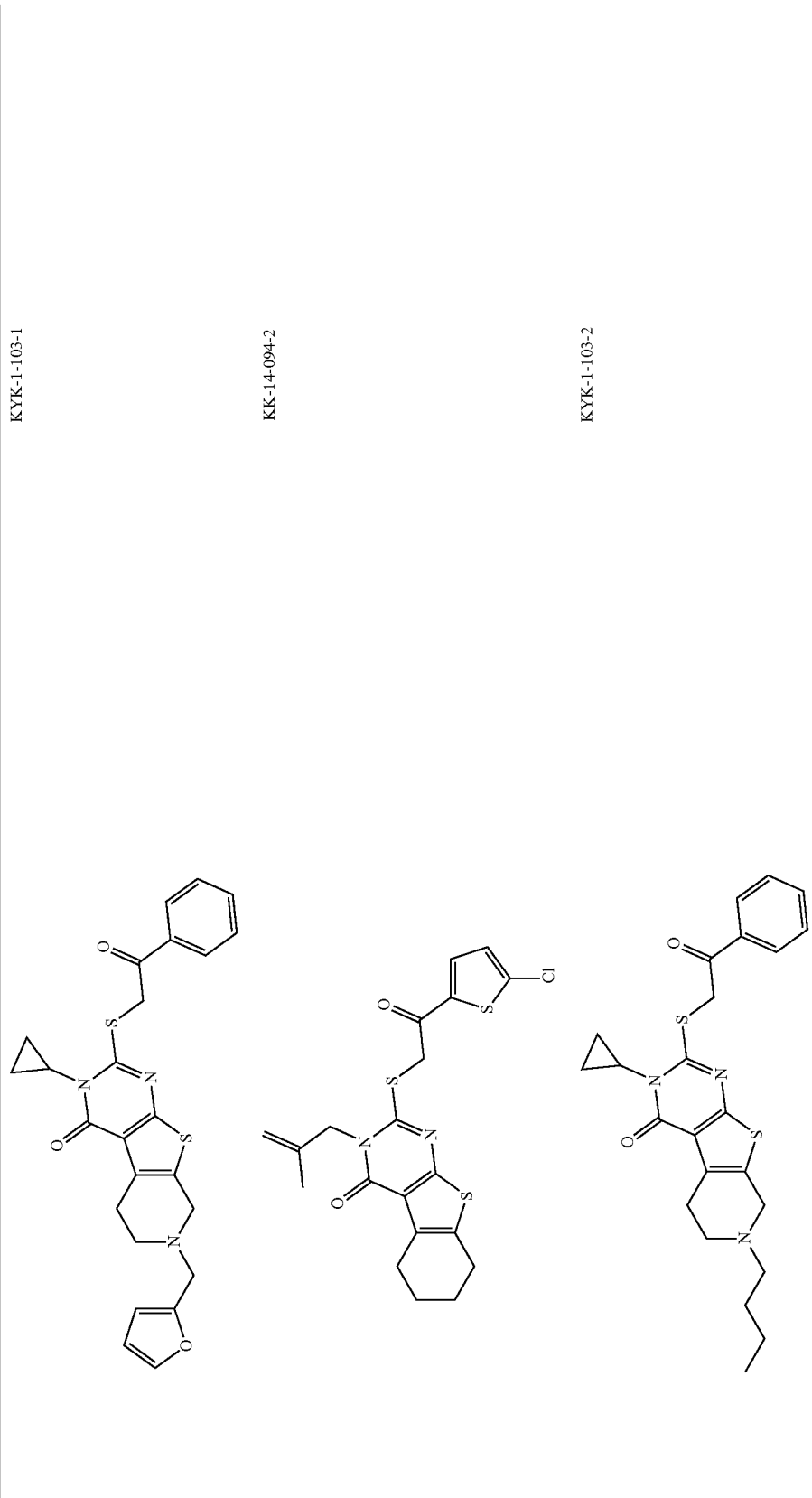

TABLE 9A-continued
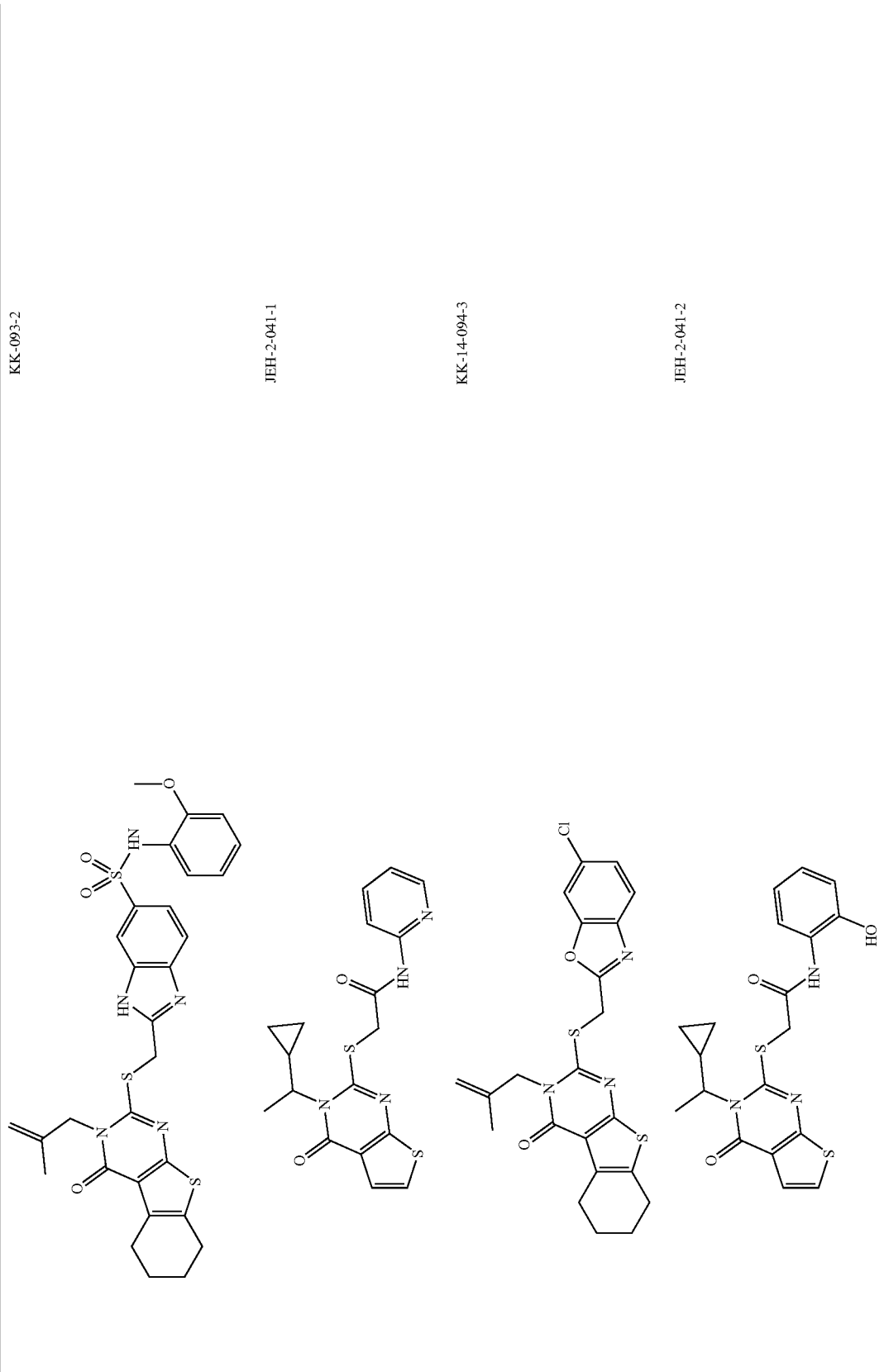
KK-093-2
JEH-2-041-1
KK-14-094-3
JEH-2-041-2

TABLE 9A-continued
KK-14-096-1
JEH-2-048
KK-14-096-2
JEH-2-053-1
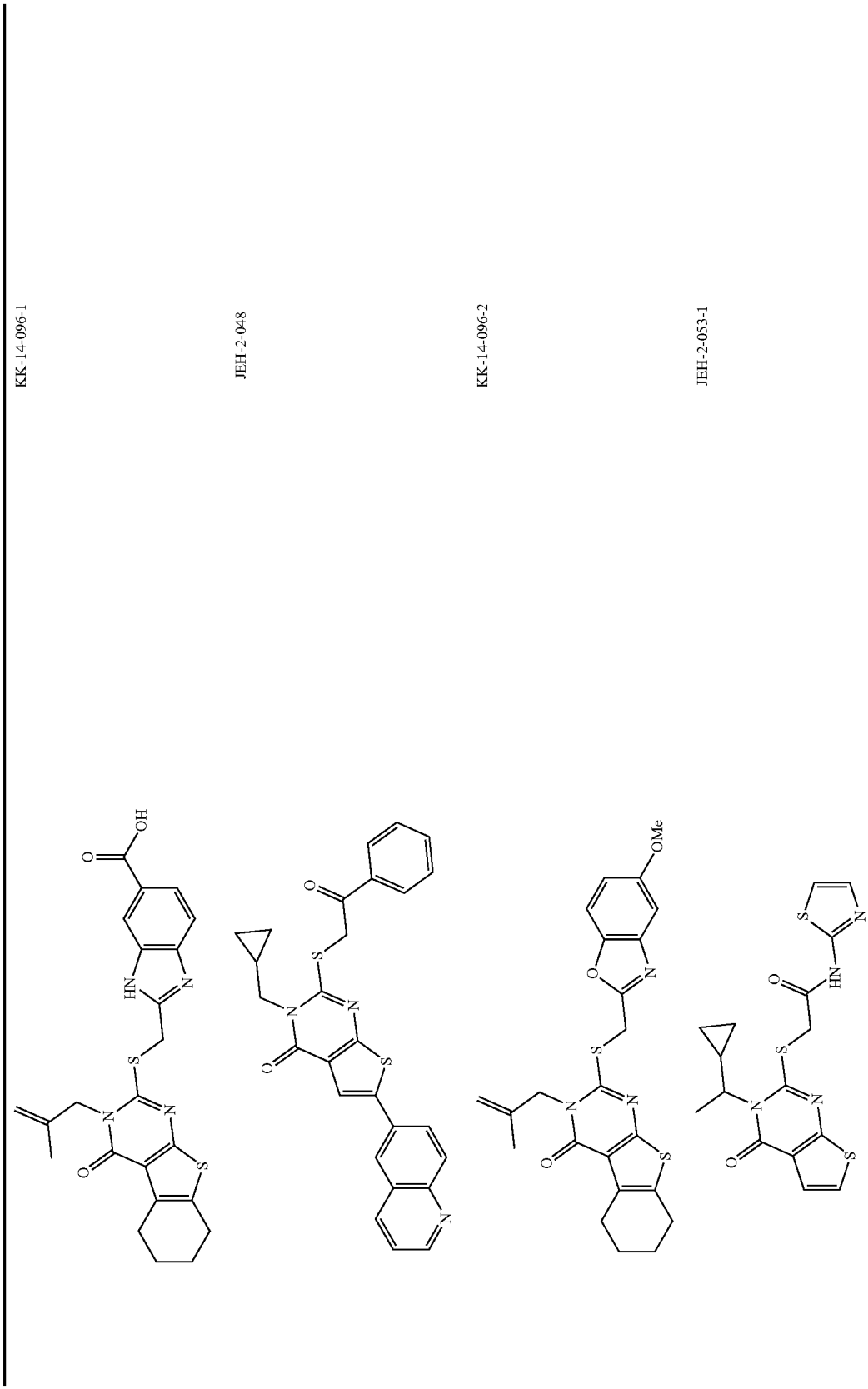

TABLE 9A-continued
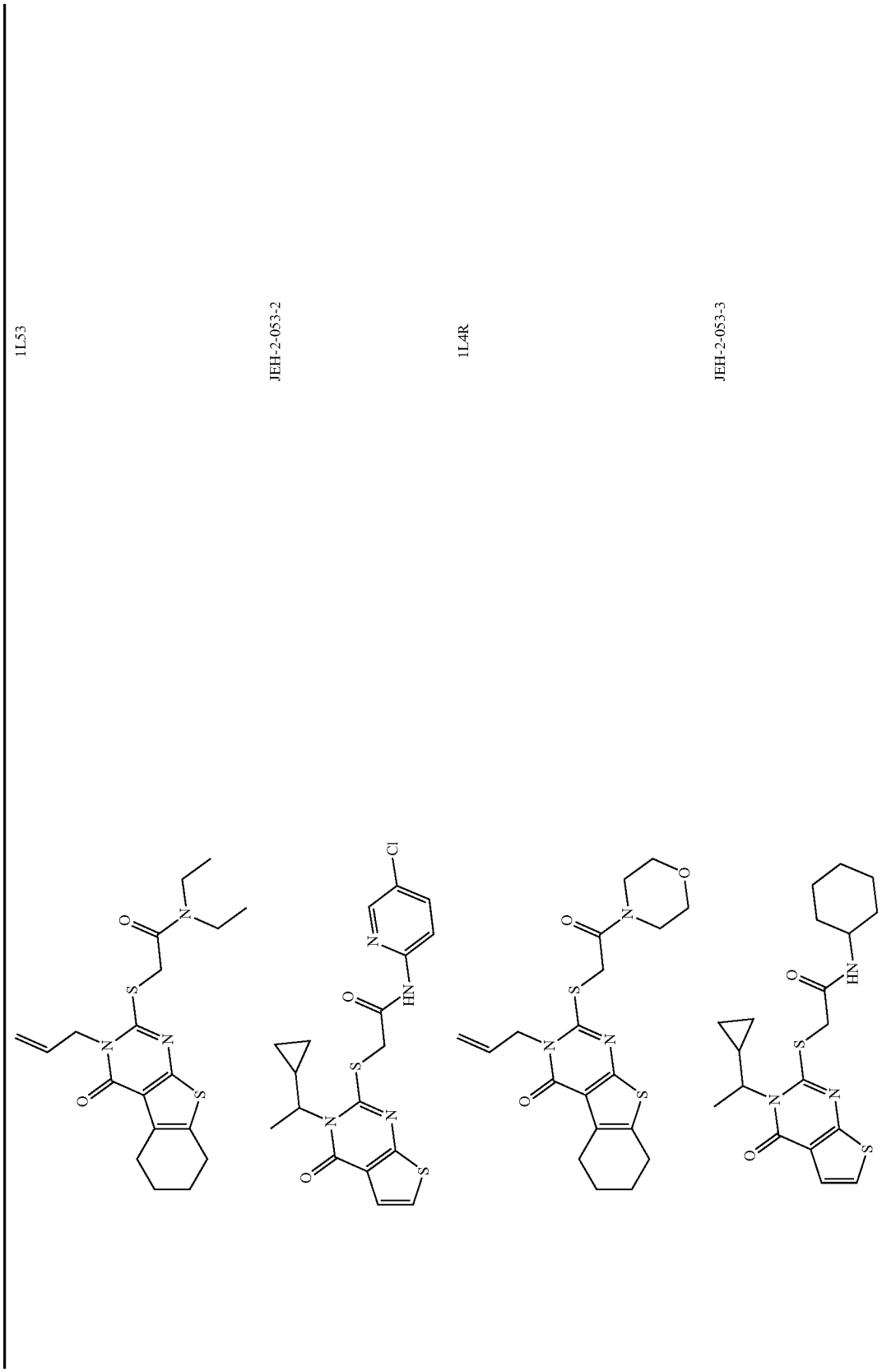
1L53
JEH-2-053-2
1L4R
JEH-2-053-3

TABLE 9A-continued
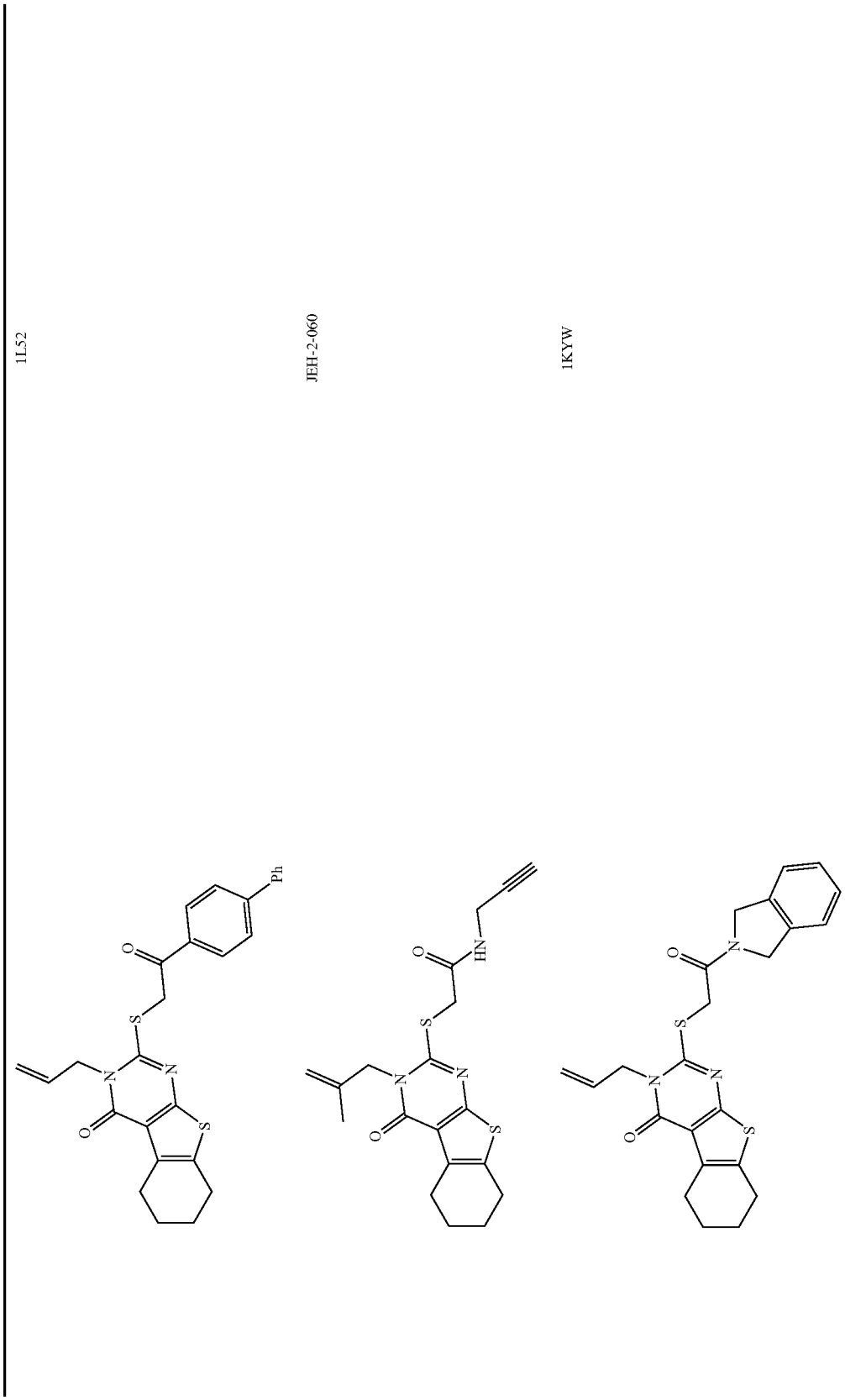
1L52
JEH-2-060
1KYW

TABLE 9A-continued
JEH-2-069-2  1KY4  JEH-2-088  1KMR
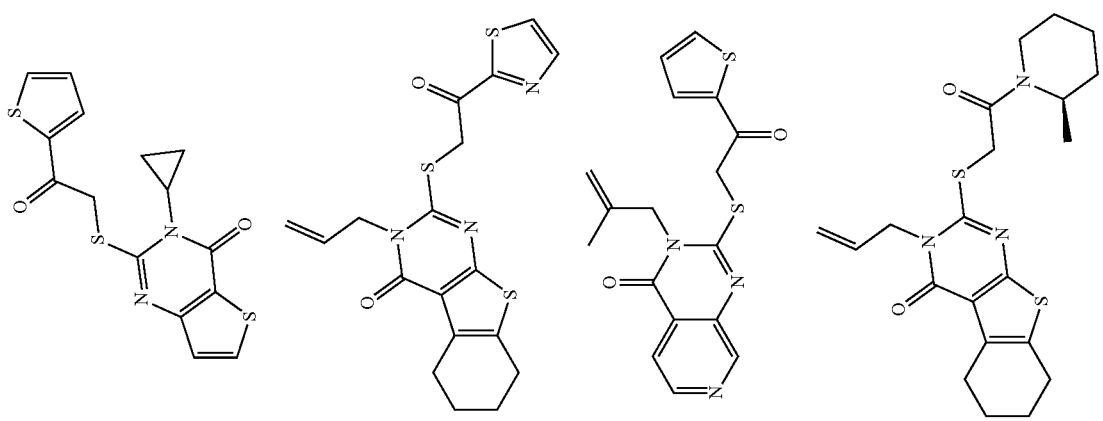

TABLE 9A-continued
| JEH-2-103-1 | 1KMH | JEH-2-103-2 |
|---|---|---|
| 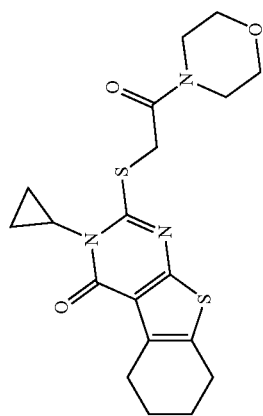 | 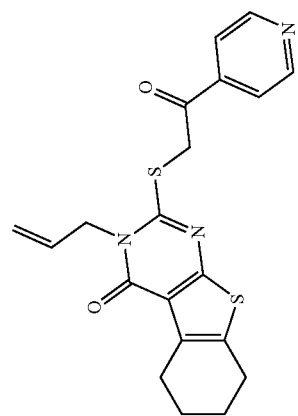 | 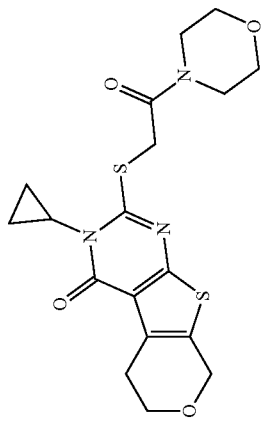 |

TABLE 9A-continued
1KN7    JEH-2-103-3    1KL1
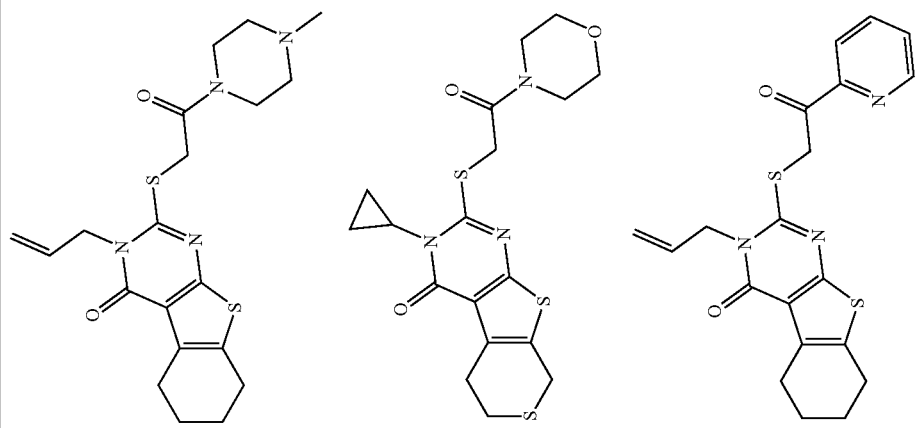

TABLE 9A-continued
JEH-2-105
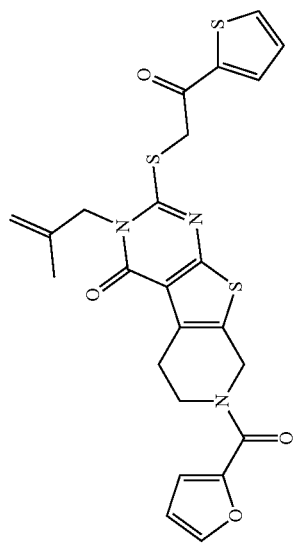
JEH-1-034
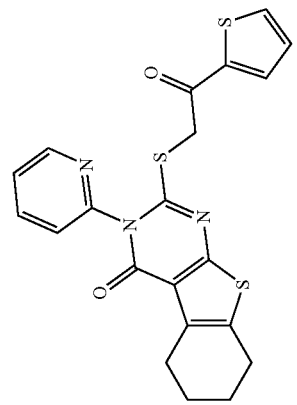
JEH-2-120-1
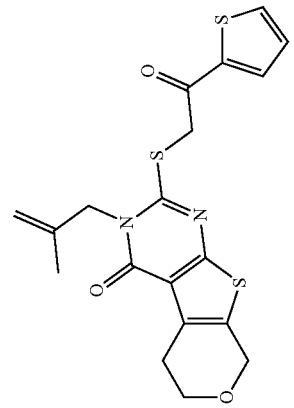

TABLE 9A-continued
| JEH-1-050-1 | JEH-2-120-2 | JEH-1-050-2 |
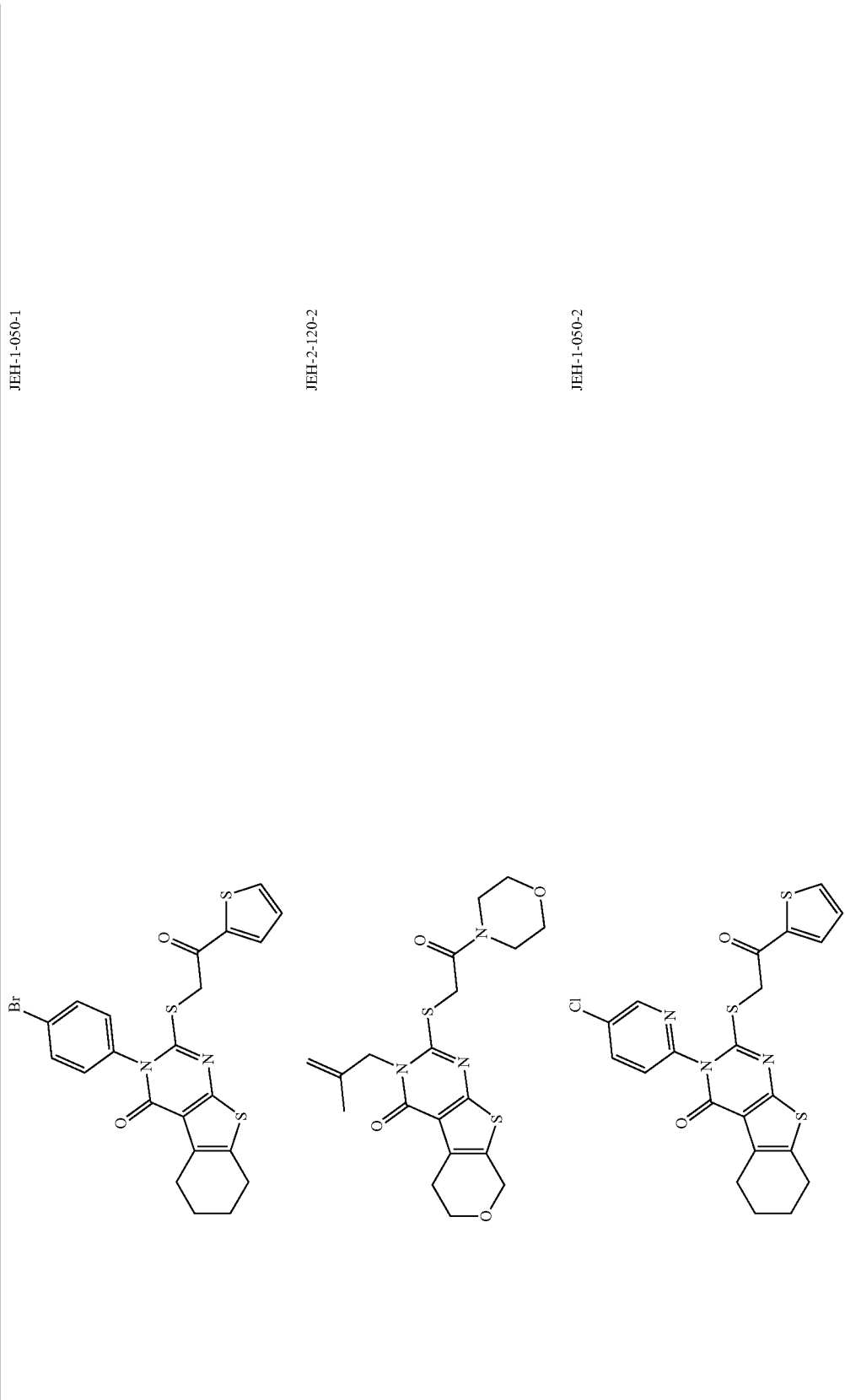

TABLE 9A-continued
| | |
|---|---|
| JEH-2-120-3 | |
| JEH-1-054 | |
| JEH-2-157 | |
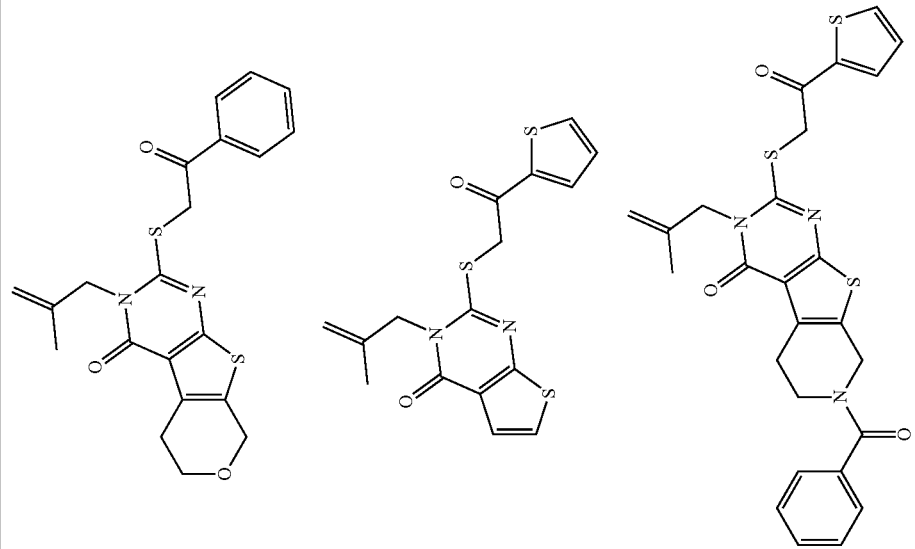

TABLE 9A-continued
JEH-1-064
JEH-3-031
JEH-1-065-1
JEH-3-038-2
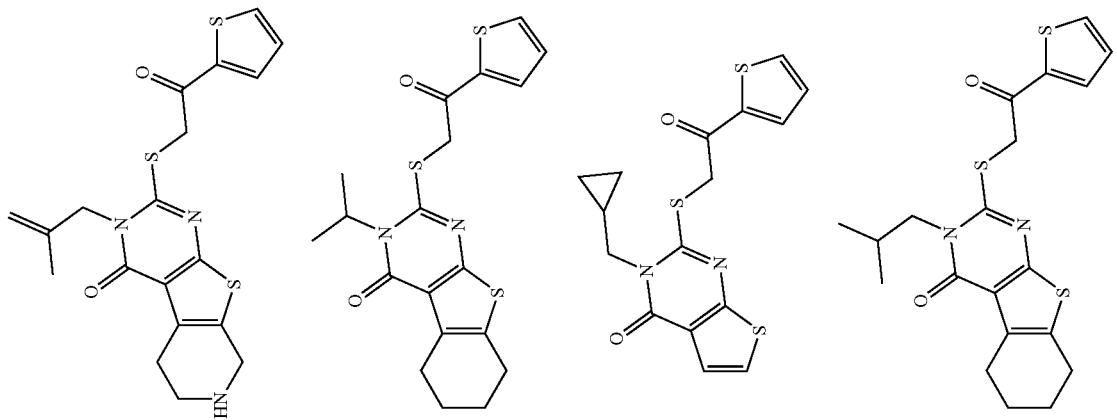

TABLE 9A-continued
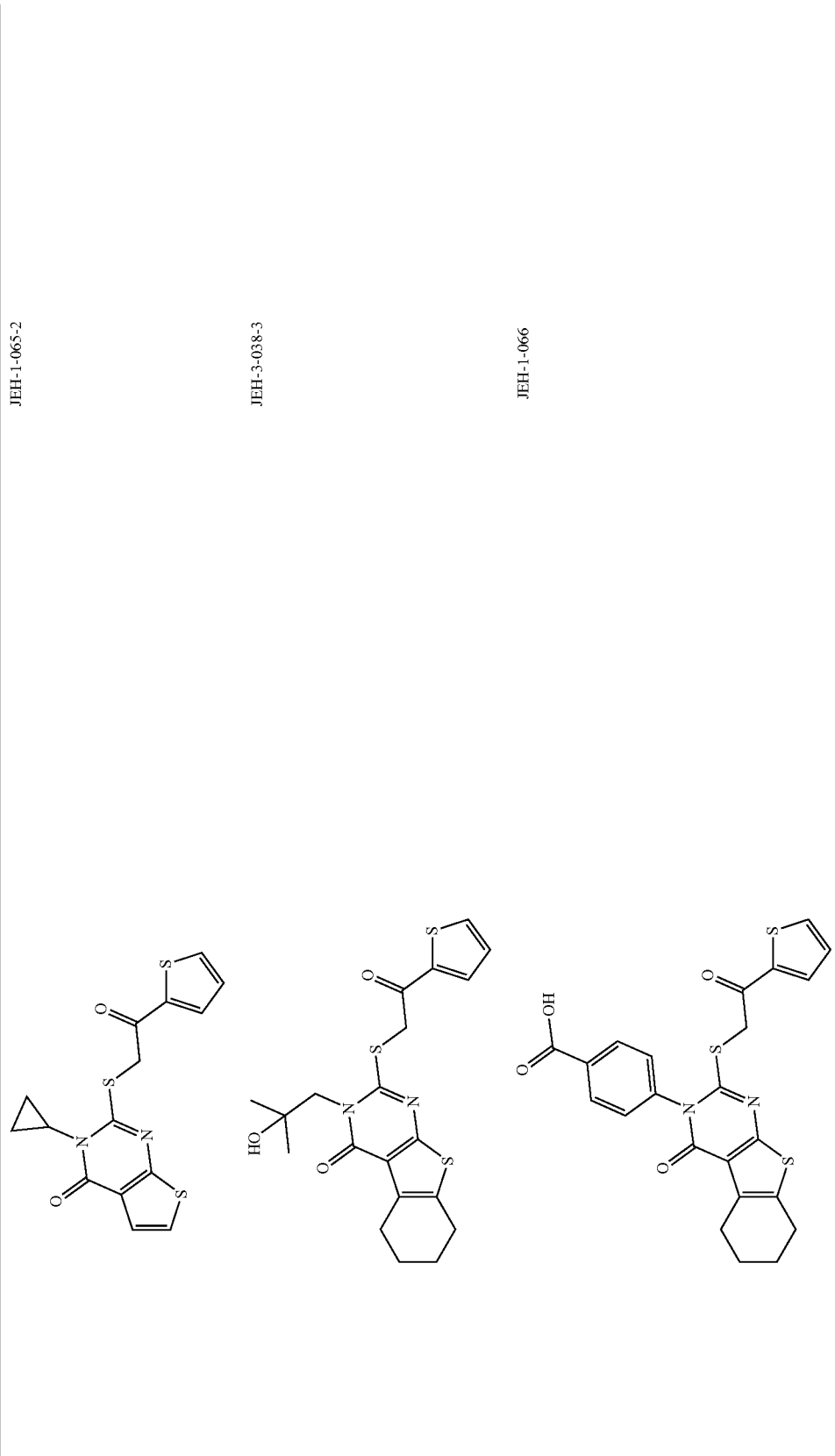
JEH-1-065-2
JEH-3-038-3
JEH-1-066

TABLE 9A-continued
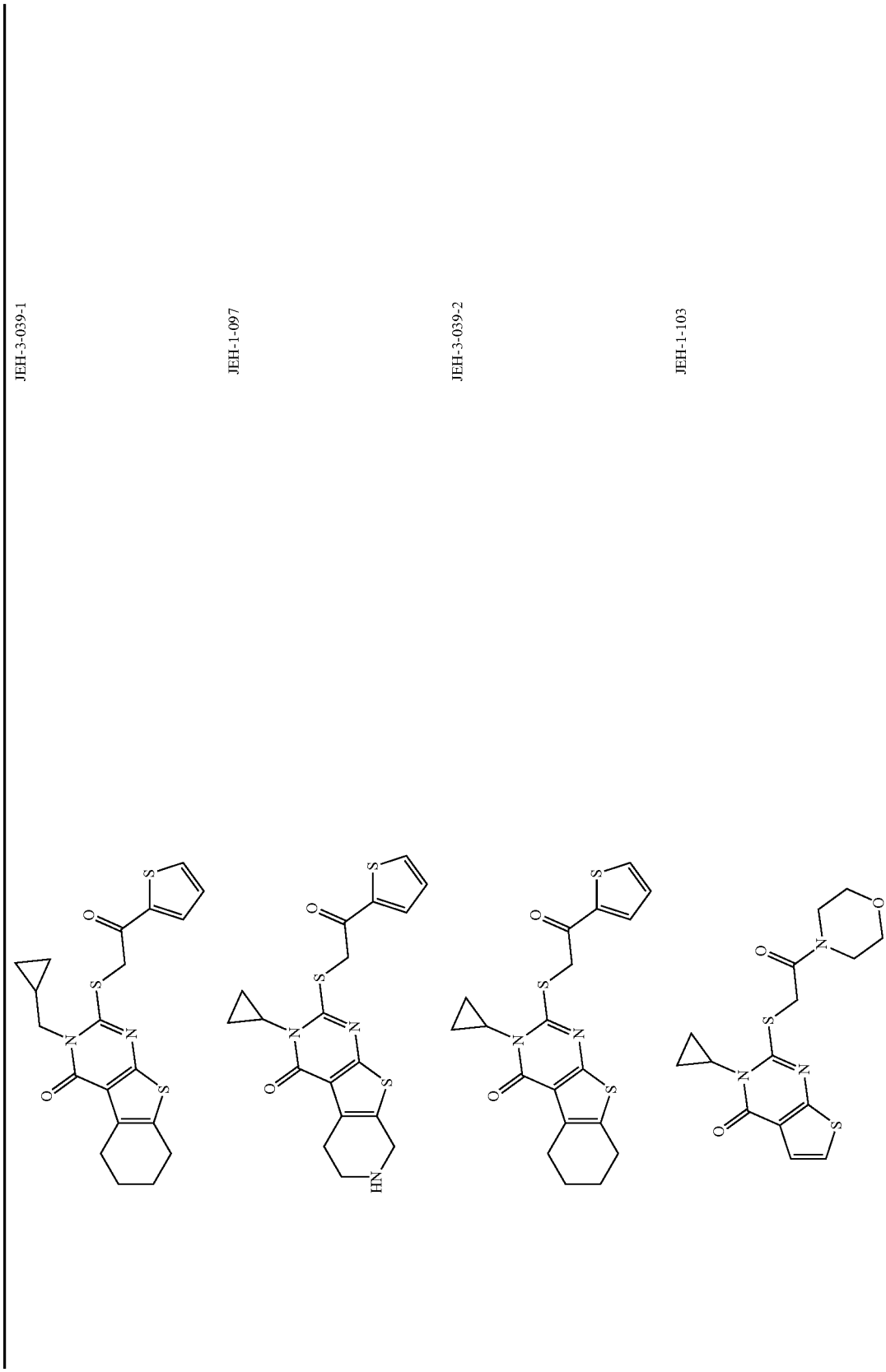
JEH-3-039-1
JEH-1-097
JEH-3-039-2
JEH-1-103

TABLE 9A-continued
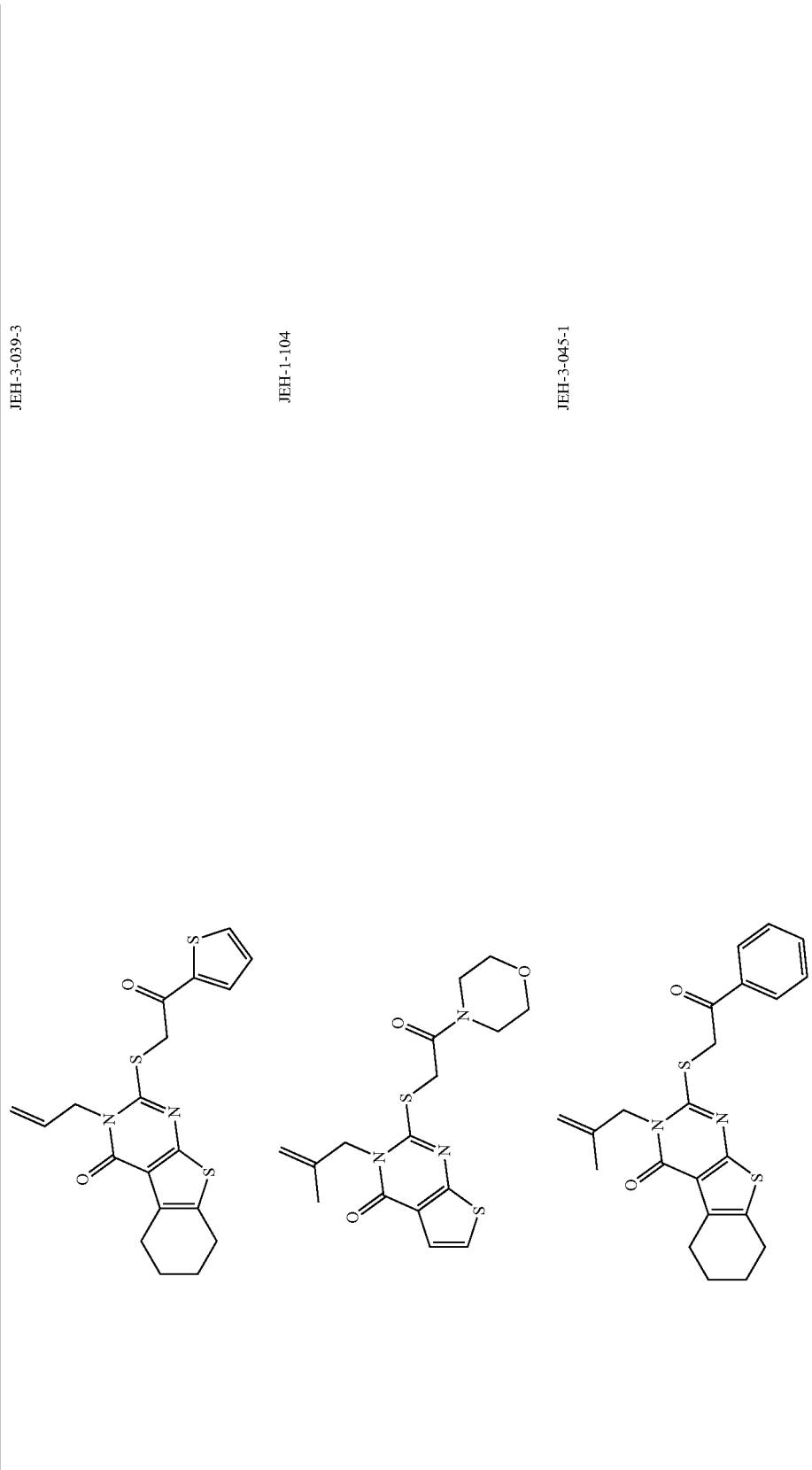
JEH-3-039-3
JEH-1-104
JEH-3-045-1

TABLE 9A-continued
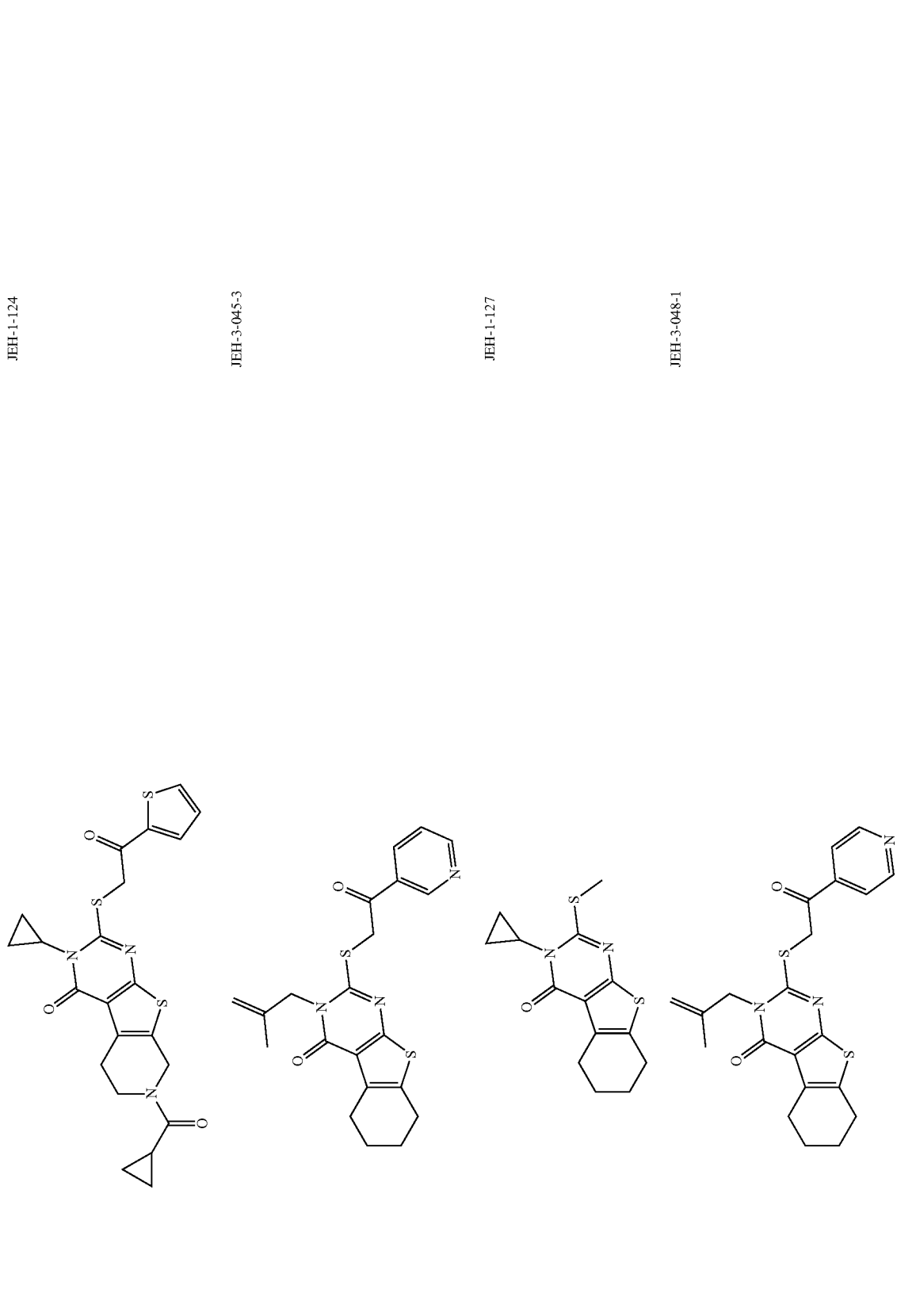
JEH-1-124
JEH-3-045-3
JEH-1-127
JEH-3-048-1

TABLE 9A-continued
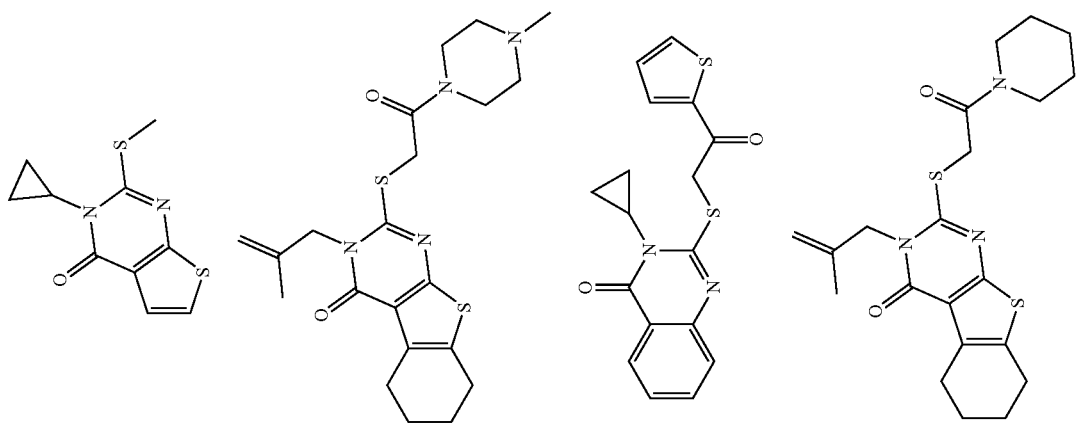
JEH-1-131-2
JEH-3-048-2
JEH-1-134
JEH-3-048-3

TABLE 9A-continued
| | |
|---|---|
| JEH-1-137 | |
| JEH-3-056-1 | |
| JEH-1-146-1 | |
| JEH-3-056-2 | |
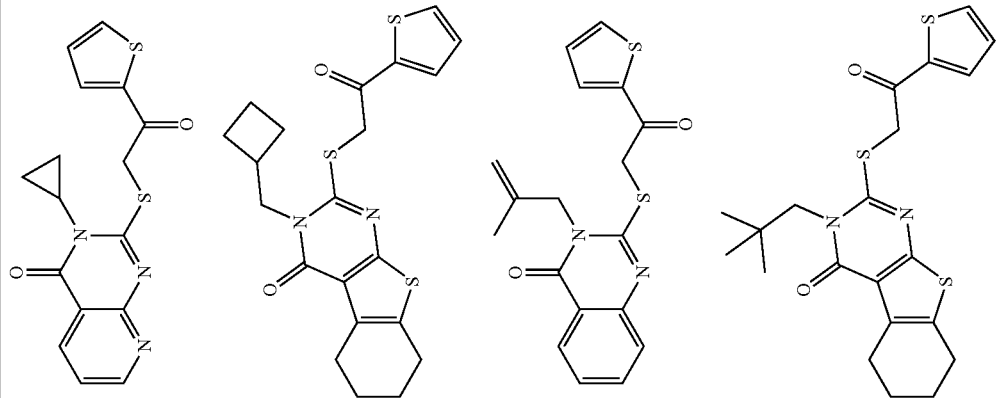

TABLE 9A-continued
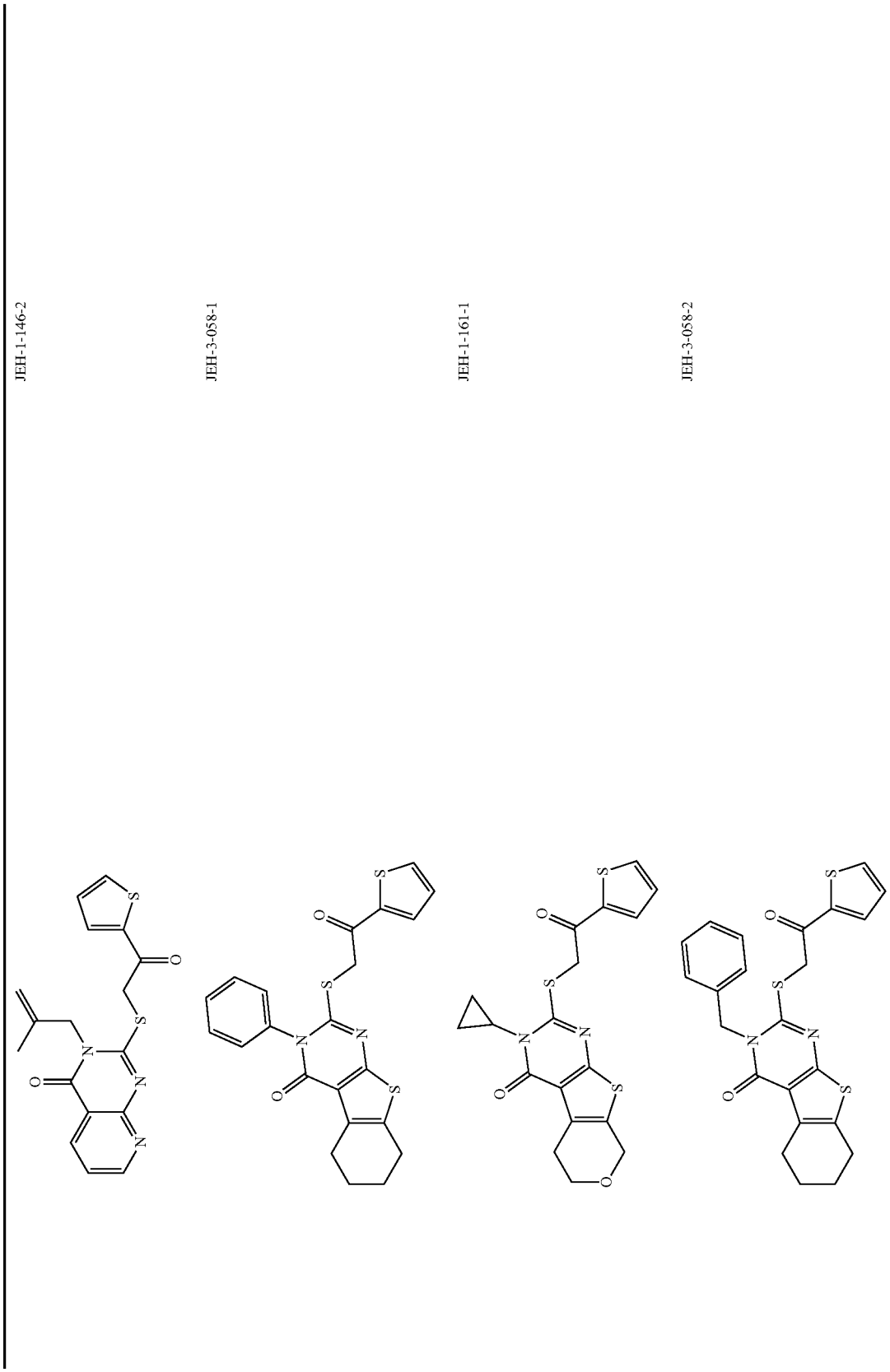
JEH-1-146-2
JEH-3-058-1
JEH-1-161-1
JEH-3-058-2

TABLE 9A-continued
| | |
|---|---|
| 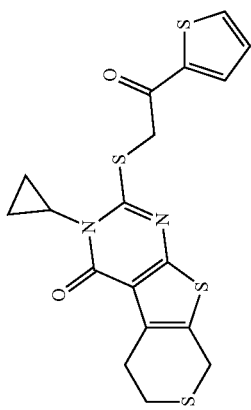 | JEH-1-161-2 |
| 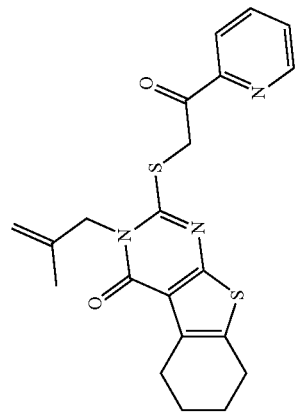 | JEH-3-063 |
| 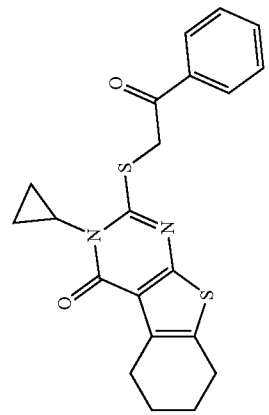 | JEH-1-163-1 |

TABLE 9A-continued
| | |
|---|---|
| JEH-3-069-1 | 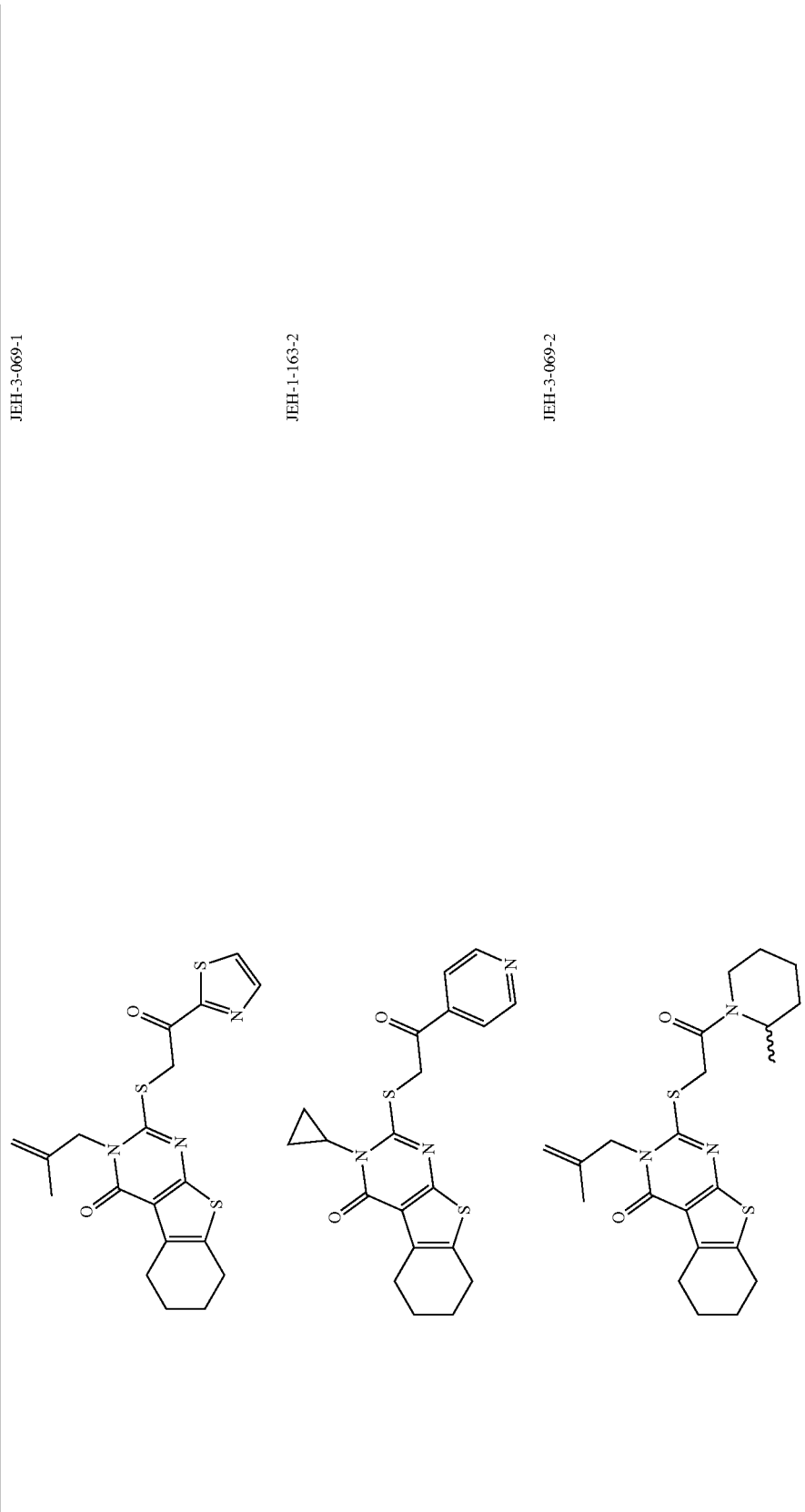 |
| JEH-1-163-2 | |
| JEH-3-069-2 | |

TABLE 9A-continued
| | |
|---|---|
| JEH-1-172 | |
| JEH-3-077 | |
| JEH-1-190-1 | |
| JEH-3-079 | |
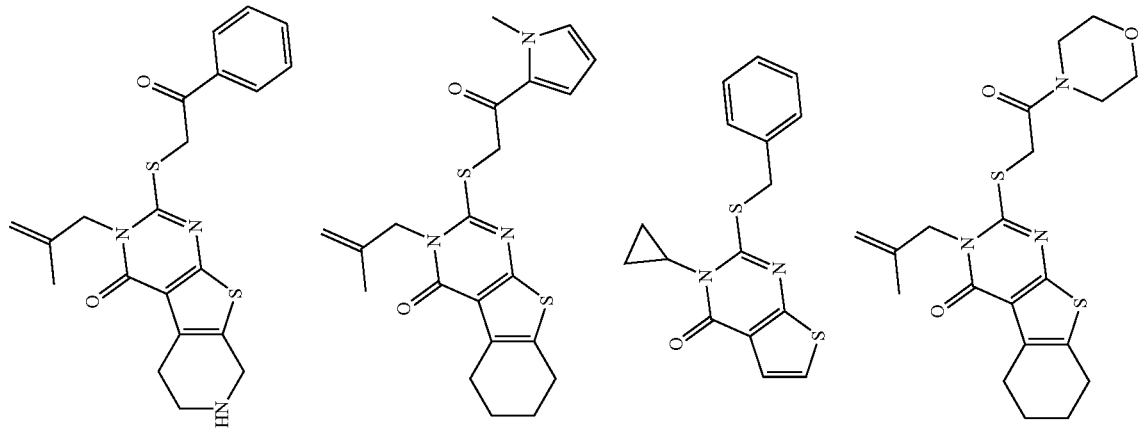

TABLE 9A-continued
| | | | |
|---|---|---|---|
| JEH-1-190-2 | JEH-3-087-1 | JEH-1-190-3 | JEH-3-087-2 |
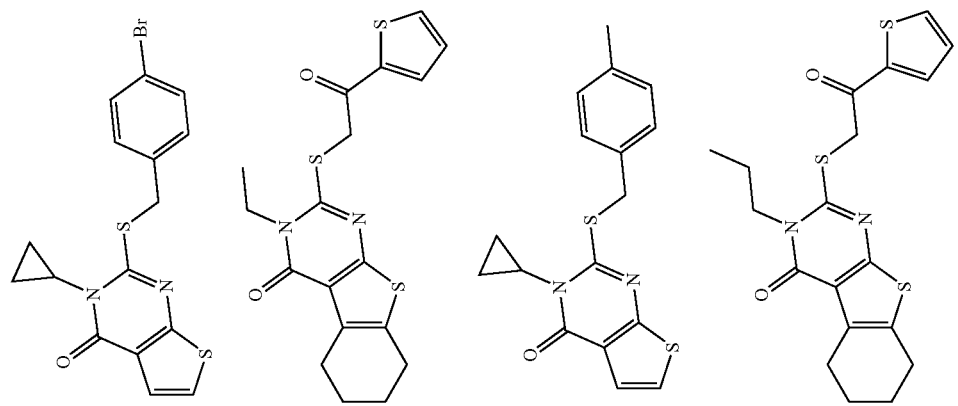

TABLE 9A-continued
| | |
|---|---|
| JEH-2-003 | 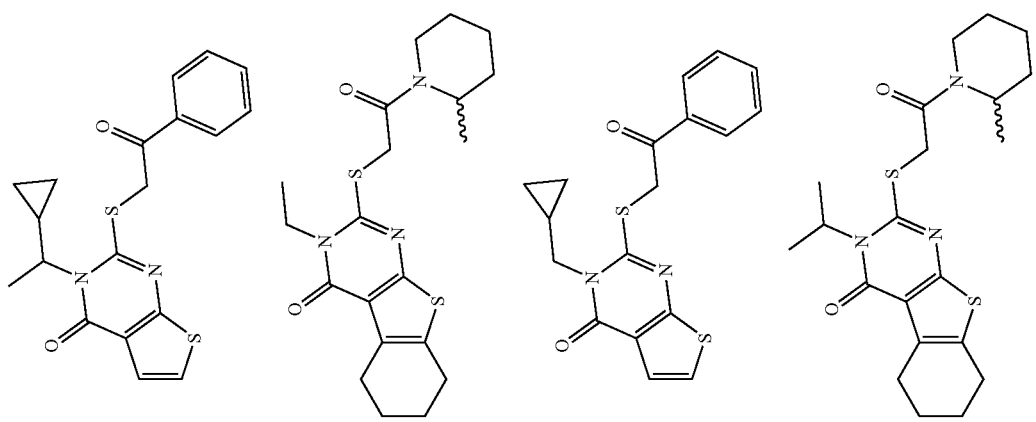 |
| JEH-3-104-1 | |
| JEH-2-007-1 | |
| JEH-3-104-2 | |

TABLE 9A-continued
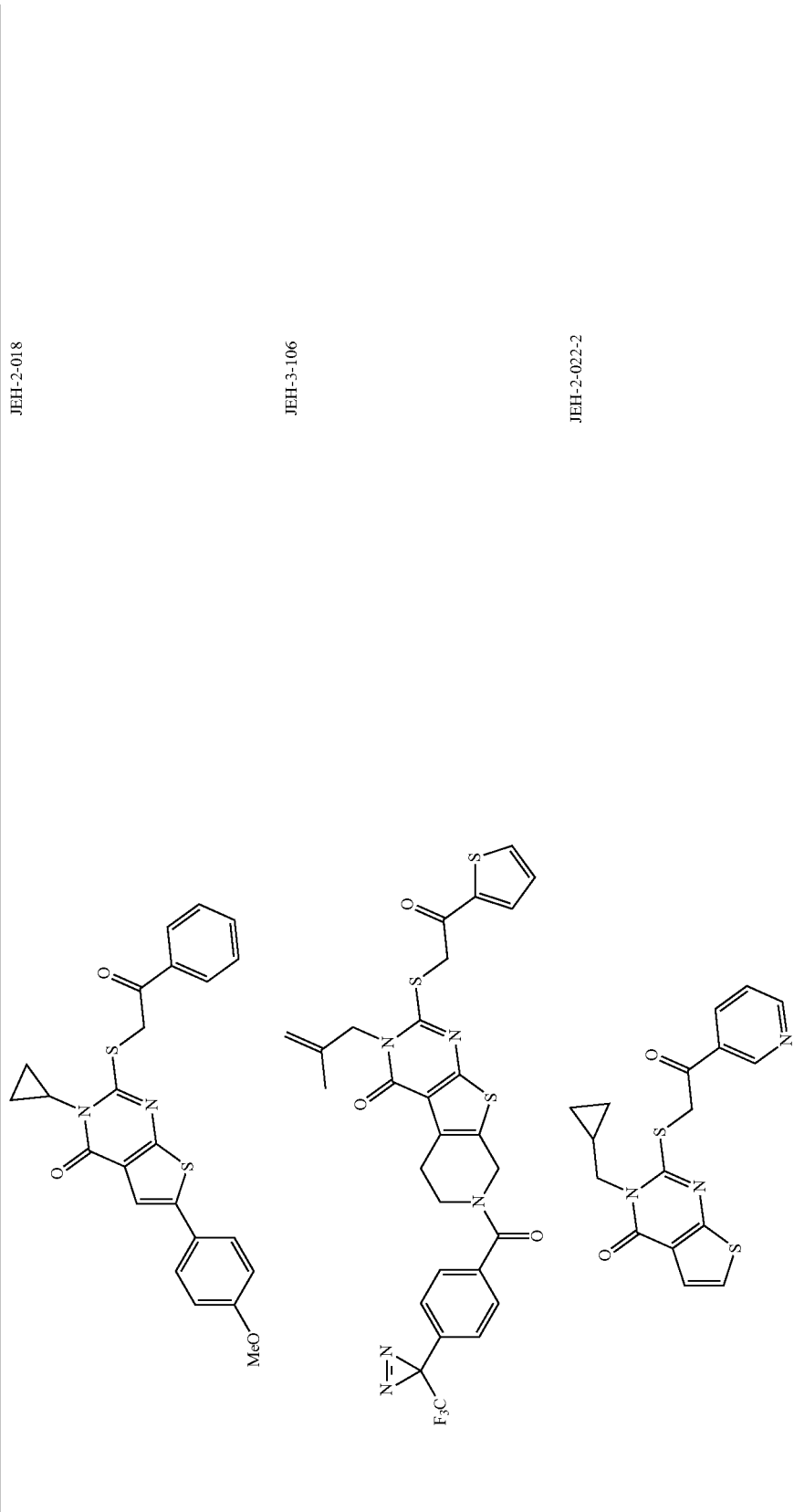
JEH-2-018
JEH-3-106
JEH-2-022-2

TABLE 9A-continued
JEH-3-111
JEH-2-026
JEH-3-120-1
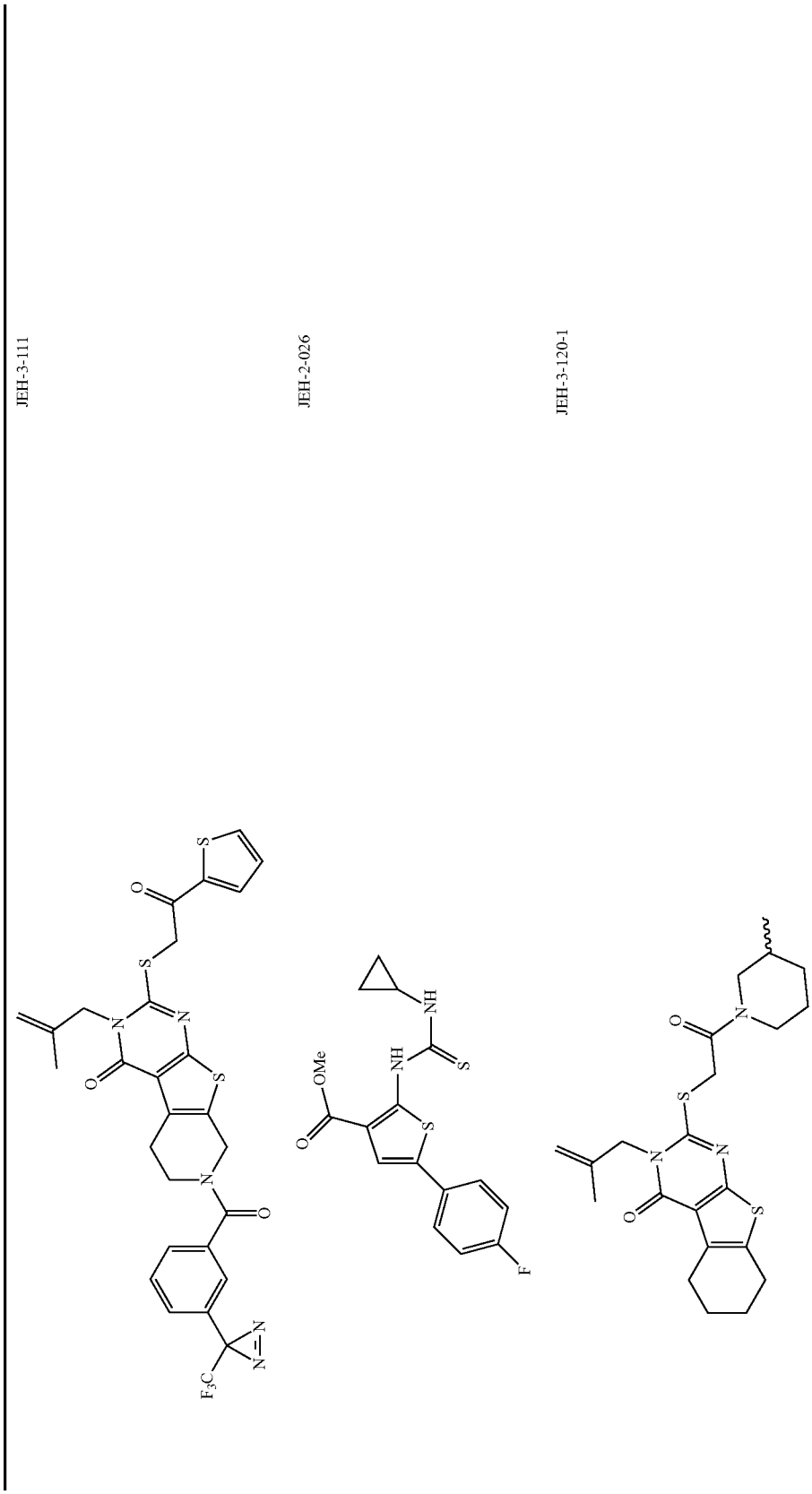

TABLE 9A-continued
| | |
|---|---|
| JEH-2-034 | 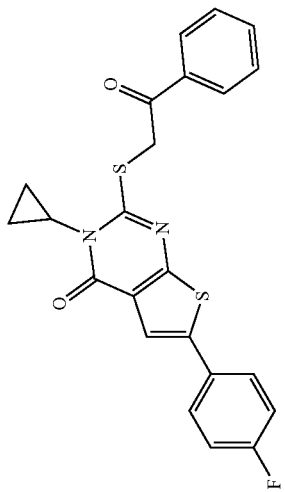 |
| JEH-3-120-2 | 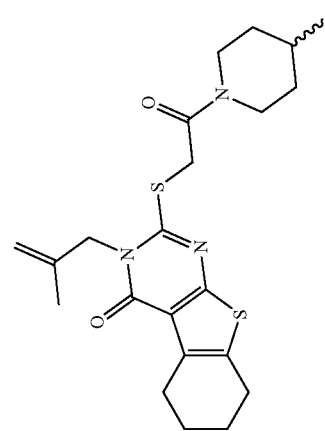 |
| KYK-1-54 | 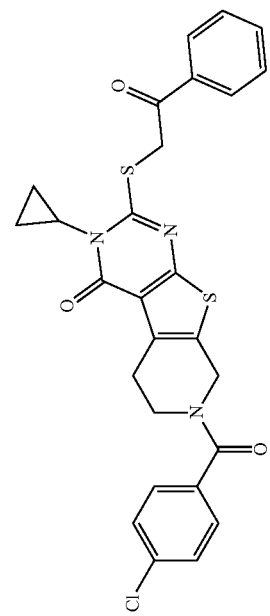 |

TABLE 9A-continued
| | |
|---|---|
| JEH-3-125 | 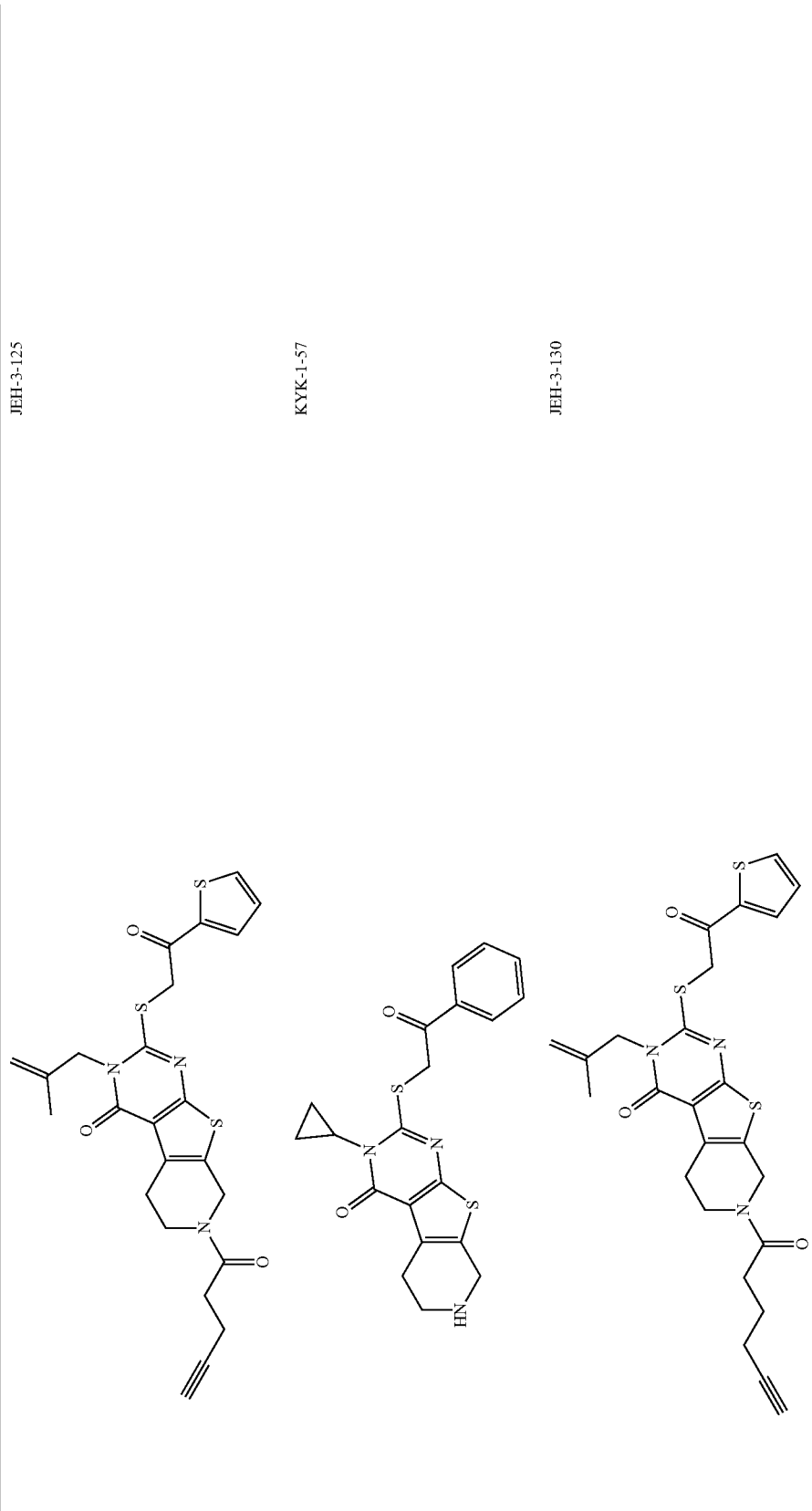 |
| KYK-1-57 | |
| JEH-3-130 | |

TABLE 9A-continued
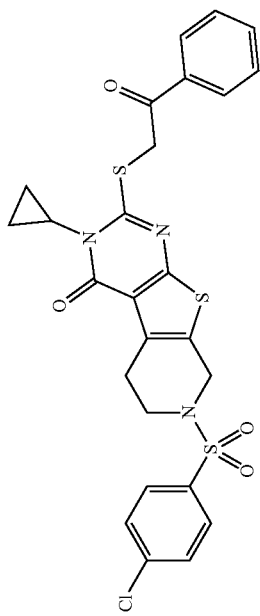 KYK-1-58
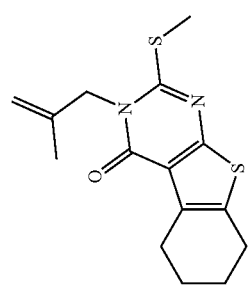 JEH-3-146
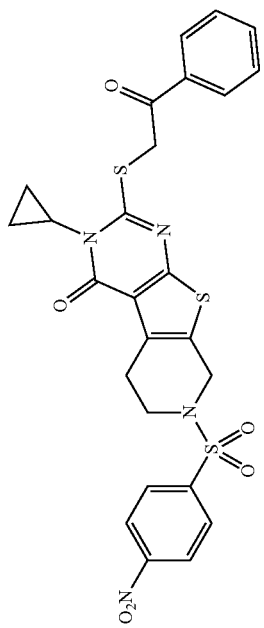 KYK-1-61
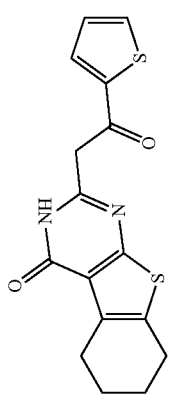 JEH-3-159

TABLE 9A-continued
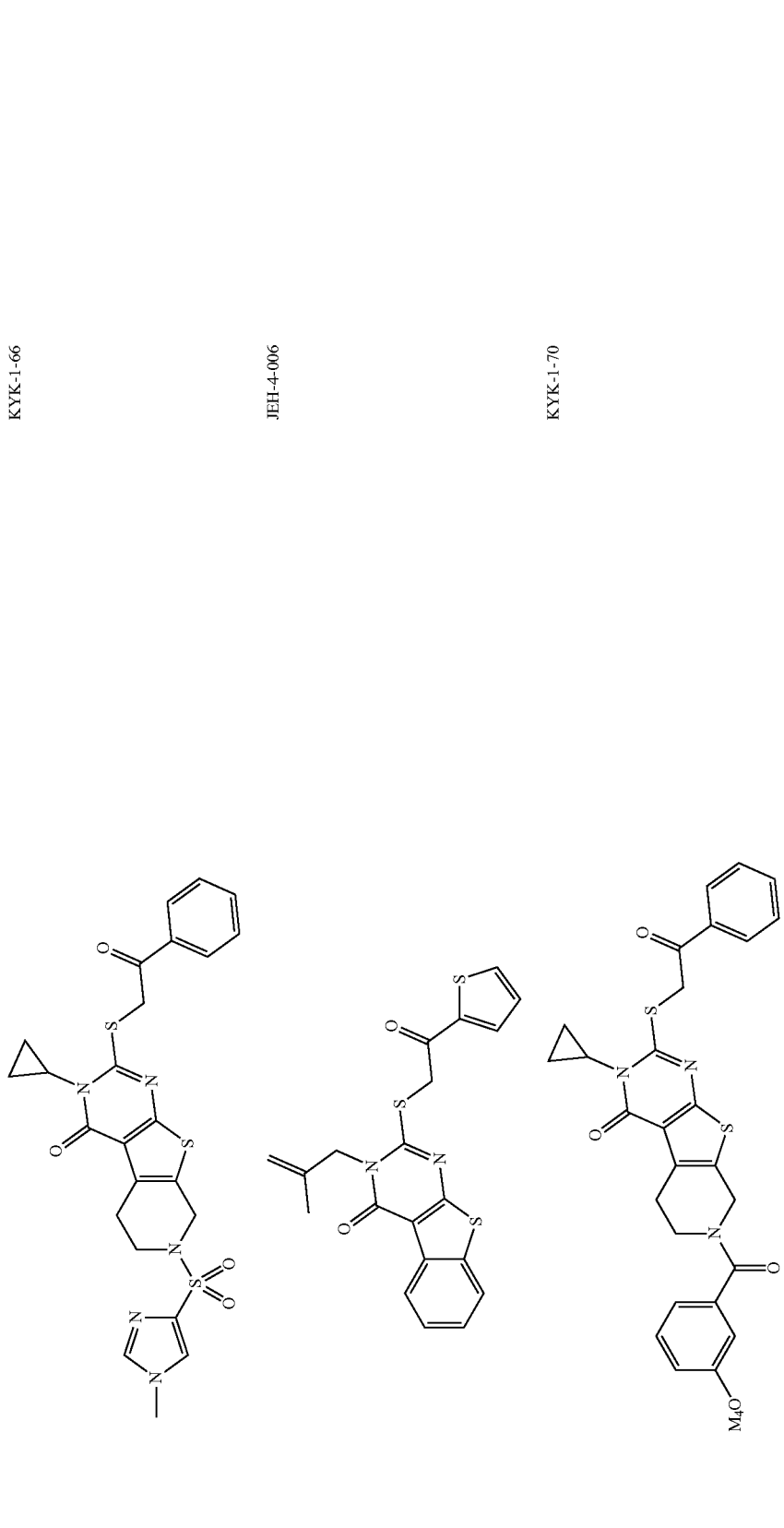
KYK-1-66
JEH-4-006
KYK-1-70

TABLE 9A-continued
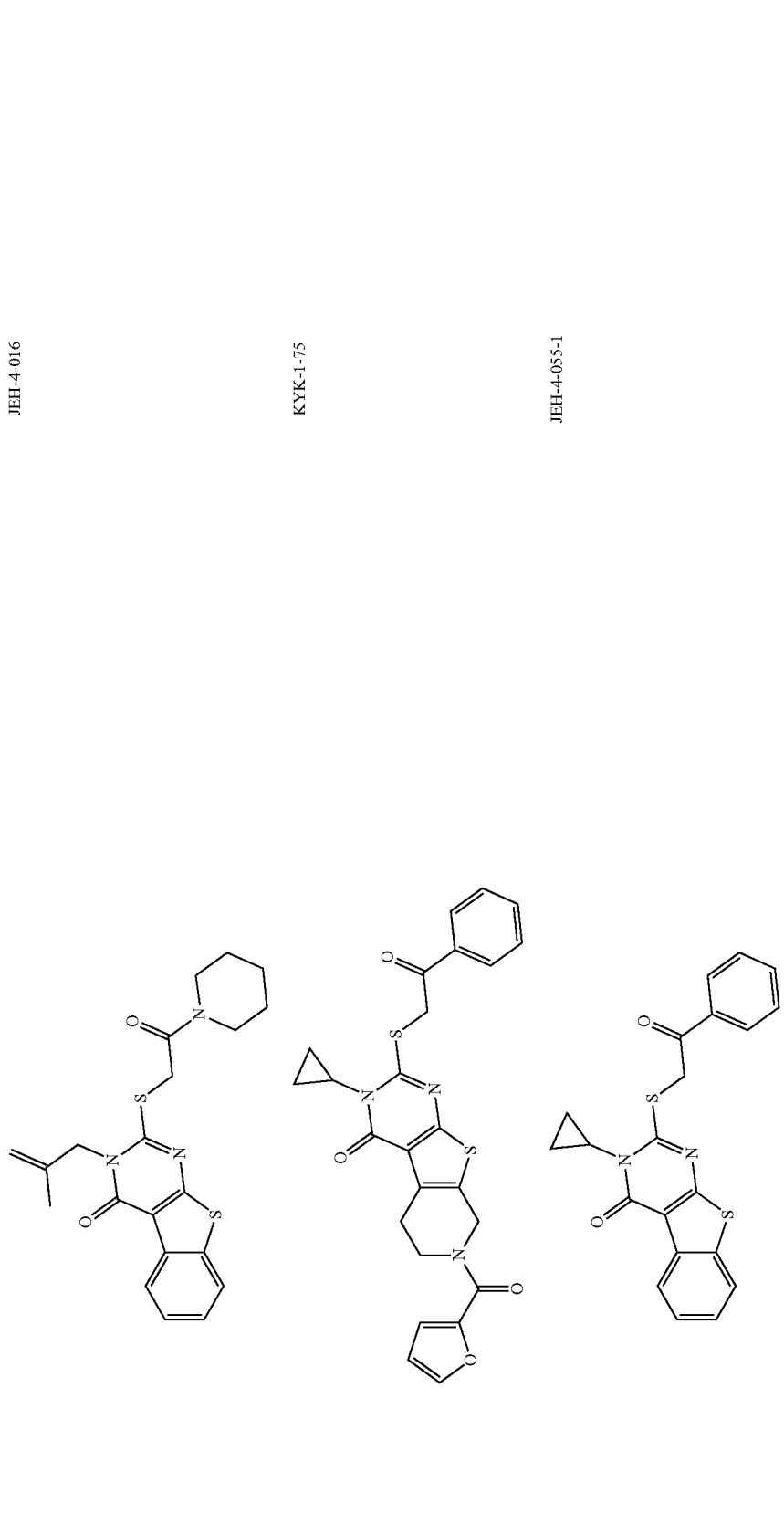
JEH-4-016
KYK-1-75
JEH-4-055-1

TABLE 9A-continued
| | |
|---|---|
| JEH-4-421 | |
| JEH-4-055-2 | |
| JEH-4-135 | |
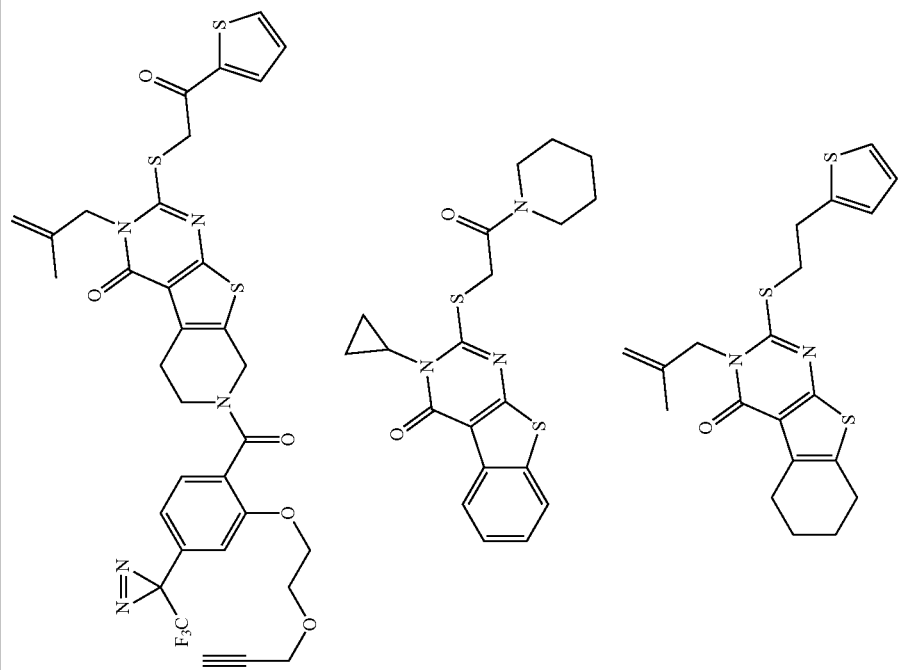

TABLE 9A-continued
JEH-4-110
JEH-4-136
JEH-4-143
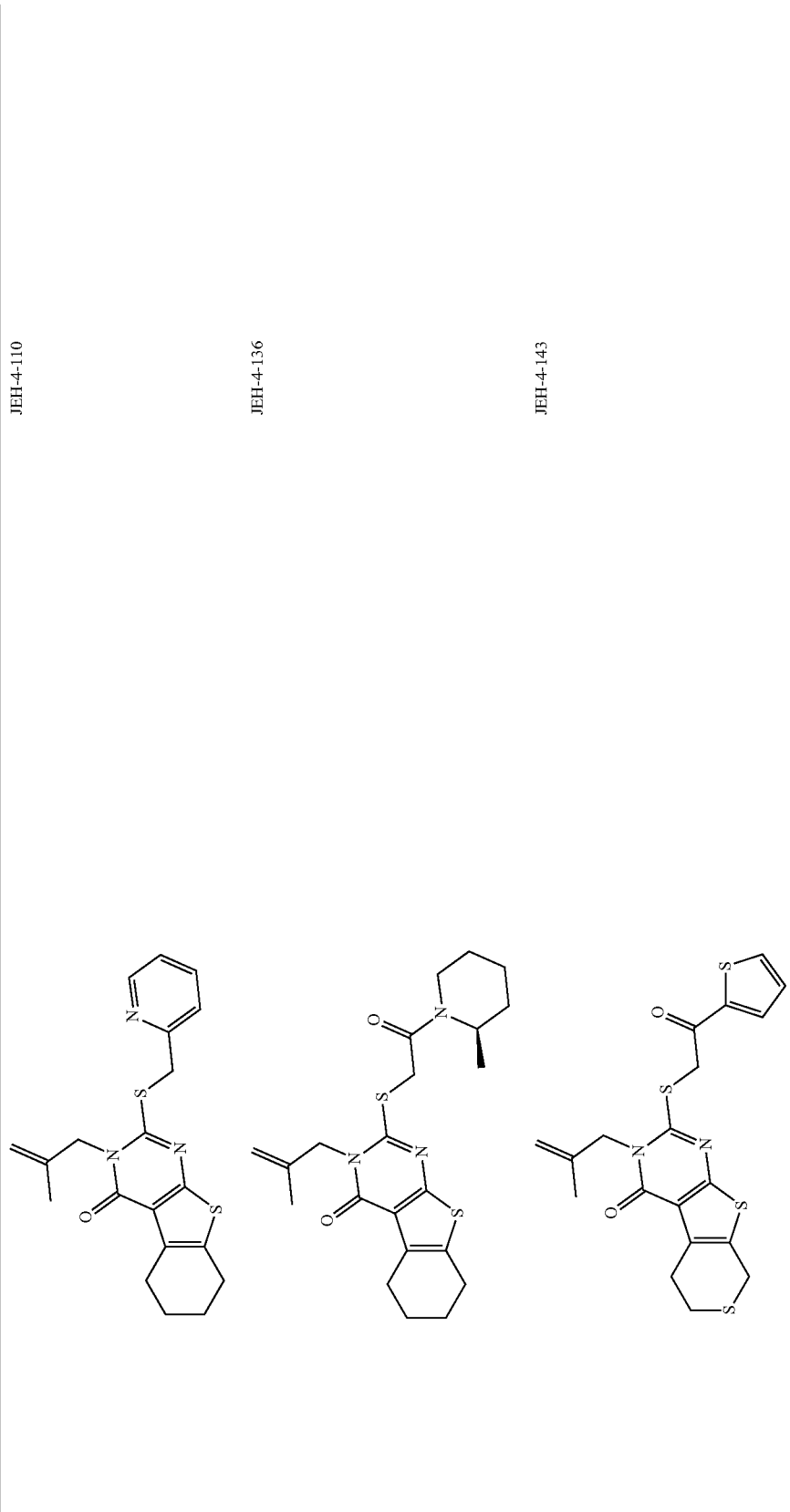

TABLE 9A-continued
| JEH-4-137 | 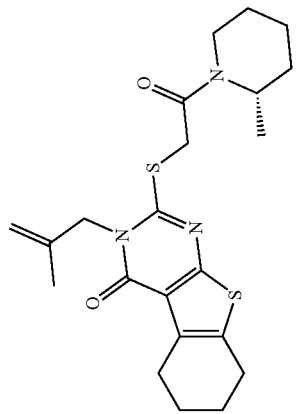 |
| JEH-4-145 | 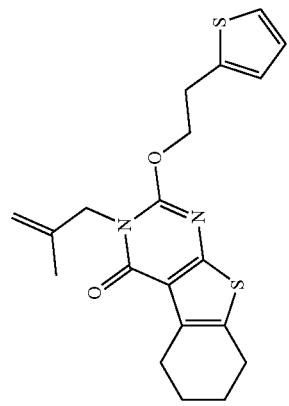 |
| JEH-5-052 | 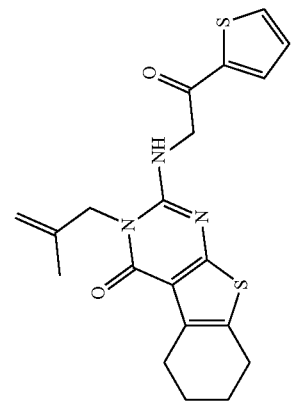 |

TABLE 9A-continued
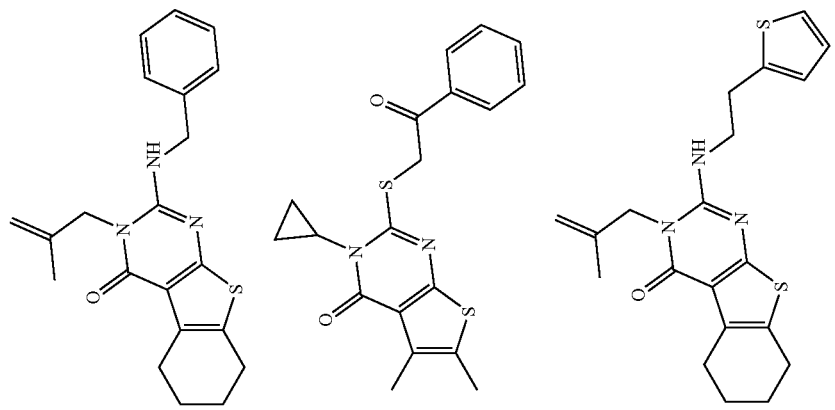
| Ref | Alt. Ref. | MW | LCMS [M + H] |
|---|---|---|---|
| | | | |
| EGM | 1KLU, EHF1, HI913 | 416.572 | 416.6, 100.0% |
| 1KXQ | | 486.648 | |
| 1L07 | | 405.575 | |
| 1ANQ | | 431.613 | |
| 1KMT | | 451.603 | 452.0, 100.0% |
| KK-14-093-1 | | 466.632 | |
| KK-14-094-1 | | 450.571 | |
| KK-14-094-2 | | 451.014 | |
JEH-4-146
JEH-5-087
JEH-4-155

TABLE 9A-continued

| | | | |
|---|---|---|---|
| KK-093-2 | | | |
| KK-14-094-3 | | | |
| KK-14-096-1 | | | |
| KK-14-096-2 | | | |
| 1L53 | | 391.548 | |
| KYK-1-99 | | 279.050 | |
| KYK-1-100 | | 439.140 | 440.1, 100.0% |
| KYK-1-103-1 | | 477.120 | 478.0, 91.1% |
| KYK-1-103-2 | | 453.150 | 454.1, 97.0% |
| JEH-2-041-1 | | 386.488 | 387.0, 100.0% |
| JEH-2-041-2 | | 401.499 | 402.0, 94.4% |
| JEH-2-048 | | 483.604 | 484.0, 90.3% |
| JEH-2-053-1 | | 392.510 | |
| JEH-2-053-2 | | 420.930 | 421.0, 97.8% |
| JEH-2-053-3 | | 391.548 | 392.1, 100.0% |
| JEH-2-060 | | 387.516 | 388.1, 95.4% |
| JEH-2-069-2 | | 348.453 | 349.0, 100.0% |
| JEH-2-088 | | 357.446 | 358.1, 96.3% |
| 1L4R | | 405.531 | |
| 1L52 | | 472.621 | |
| 1KYW | | 437.576 | |
| 1KY4 | | 403.533 | |
| 1KMR | | 417.586 | |
| 1KMH | | 397.511 | |
| 1KN7 | | 418.574 | |
| 1KL1 | H1321 | 397.511 | |
| JEH-1-034 | | 439.574 | 440.0, 99.2% |
| JEH-1-050-1 | | 517.482 | 518.8, 96.8% |
| JEH-1-050-2 | | 474.019 | 473.9, 100.0% |
| JEH-1-054 | | 362.490 | 363.0, 100.0% |
| JEH-1-064 | | 417.568 | 418.0, 100.0% |
| JEH-1-065-1 | | 362.490 | 363.0, 98.8% |
| JEH-1-065-2 | | 348.463 | 349.0, 100.0% |
| JEH-1-066 | | 482.595 | 482.9, 97.1% |
| JEH-1-097 | | 403.541 | 403.6, 100.0% |
| JEH-1-103 | | 351.444 | 352.1, 100.0% |
| JEH-1-104 | | 365.470 | 366.1, 95.3% |
| JEH-1-124 | | 471.615 | 472.0, 100.0% |
| JEH-1-127 | | 292.42 | 293.1, 100.0% |
| JEH-1-131-2 | | 238.323 | 239.0, 89.0% |
| JEH-1-134 | | 342.435 | 343.0, 99.1% |
| JEH-1-137 | | 343.423 | 344.1, 100.0% |
| JEH-1-146-1 | | 356.462 | 357.0, 100.0% |
| JEH-1-146-2 | | 357.450 | 358.1, 100.0% |
| JEH-1-161-1 | | 404.526 | 405.0, 100.0% |
| JEH-1-161-2 | | 420.592 | 420.9, 100.0% |
| JEH-1-163-1 | | 396.526 | 397.1, 96.8% |
| JEH-1-163-2 | | 397.514 | |
| JEH-1-172 | | 411.540 | 412.0, 100.0% |
| JEH-1-190-1 | | 314.425 | 315.1, 100.0% |
| JEH-1-190-2 | | 393.321 | 394.9, 97.0% |
| JEH-1-190-3 | | 328.452 | 329.1, 100.0% |
| JEH-2-003 | | 370.488 | 371.1, 100.0% |

TABLE 9A-continued

| | | | |
|---|---|---|---|
| JEH-2-007-1 | | 356.462 | 357.0, 100.0% |
| JEH-2-018 | | 448.557 | 449.0, 95.6% |
| JEH-2-022-2 | | 357.450 | 358.1, 100.0% |
| JEH-2-026 | | 350.431 | 351.1, 96.9% |
| JEH-2-034 | | 436.519 | 437.0, 92.2% |
| KYK-1-54 | | 535.060 | 536.0, 92.2% |
| KYK-1-57 | | 397.514 | 398.1, 100.0% |
| KYK-1-58 | | 571.050 | 571.9, 100.0% |
| KYK-1-61 | | 582.664 | 582.9, 90.8% |
| KYK-1-66 | | 541.090 | 542.0, 100.0% |
| KYK-1-70 | | 531.13 | 532.0, 90.9% |
| KYK-1-75 | | 491.10 | 492.0, 100.0% |
| KYK-1-76 | | 411.11 | 412.1, 100.0% |
| KYK-1-87 | | 284.070 | |
| KYK-1-88 | | 515.170 | 516.1, 100.0% |
| KYK-1-96 | | 311.080 | |
| JEH-2-103-1 | | 405.531 | 406.0, 100.0% |
| JEH-2-103-2 | | 407.503 | 408.0, 100.0% |
| JEH-2-103-3 | | 423.564 | 424.0, 100.0% |
| JEH-2-105 | | 511.629 | 511.9, 90.9% |
| JEH-2-120-1 | | 418.544 | 419.0, 100.0% |
| JEH-2-120-2 | | 421.530 | 422.1, 100.0% |
| JEH-2-120-3 | | 412.522 | 413.1, 100.0% |
| JEH-2-157 | | 521.668 | |
| JEH-3-031 | | 404.561 | 405.0, 100.0% |
| JEH-3-038-2 | | 418.588 | 419.0, 100.0% |
| JEH-3-038-3 | | 434.587 | 435.0, 100.0% |
| JEH-3-039-1 | JEH-1-007 | 416.580 | 417.0, 100.0% |
| JEH-3-039-2 | JEH-1-028 | 402.553 | 403.0, 100.0% |
| JEH-3-039-3 | 1L4Q, H1037 | 402.545 | 403.0, 100.0% |
| JEH-3-045-1 | H1573 | 410.55 | 411.1, 100.0% |
| JEH-3-045-1 | | 411.538 | 412.1, 100.0% |
| JEH-3-048-1 | 1KMG | 411.538 | 412.0, 90.0% |
| JEH-3-048-2 | 1L9B | 432.601 | 433.1, 100.0% |
| JEH-3-048-3 | | 417.586 | 418.1, 100.0% |
| JEH-3-056-1 | JEH-1-009 | 430.607 | 431.2, 100.0% |
| JEH-3-056-2 | | 432.615 | 433.2, 100.0% |
| JEH-3-058-1 | H1647 | 438.578 | 439.0, 100.0% |
| JEH-3-058-2 | | 452.605 | 452.9, 100.0% |
| JEH-3-063 | 1KMF | 411.538 | 412.0, 100.0% |
| JEH-3-069-1 | 1KLF | 417.560 | 418.0, 100.0% |
| JEH-3-069-2 | | 431.613 | 432.1, 100.0% |
| JEH-3-077 | | 413.554 | 414.1, 100.0% |
| JEH-3-079 | 1KY9, H1321, EGM001 | 419.558 | 420.0, 100.0% |
| JEH-3-087-1 | | 390.534 | 391.0, 100.0% |
| JEH-3-087-2 | | 404.561 | 405.0, 100.0% |
| JEH-3-104-1 | | 405.575 | |
| JEH-3-104-2 | | 419.602 | |
| JEH-3-106 | | 629.691 | |
| JEH-3-111 | | 629.691 | |
| JEH-3-120-1 | | 431.613 | 432.1, 100.0% |
| JEH-3-120-2 | | 431.613 | 432.1, 100.0% |

TABLE 9A-continued

| Ref. | | | | | | | | | 
|---|---|---|---|---|---|---|---|---|
| JEH-3-125 | | | | 497.646 | | | 498.0, 100.0% | |
| JEH-3-130 | | | | 511.673 | | | 511.9, 100.0% | |
| JEH-3-146 | | | | 306.442 | | | 307.1, 100.0% | |
| JEH-3-159 | | | | 330.42 | | | 331.0, 100.0% | |
| JEH-4-006 | | | | 412.54 | | | 413.0, 100.0% | |
| JEH-4-016 | | | | 413.554 | | | 414.1, 100.0% | |
| JEH-4-055-1 | | | | 392.491 | | | 393.0, 100.0% | |
| JEH-4-055-2 | | | | 399.527 | | | 400.0, 100.0% | |
| JEH-4-110 | | | | 383.528 | | | 384.0, 100.0% | |
| JEH-4-121 | | | | 727.792 | | | | |
| JEH-4-135 | | | | 402.589 | | | 403.0, 100.0% | |
| JEH-4-136 | | | | 431.613 | | | 432.0, 100.0% | |
| JEH-4-137 | | | | 431.613 | | | 432.1, 100.0% | |
| JEH-4-143 | | | | 434.605 | | | 435.0, 100.0% | |
| JEH-4-145 | | | | 386.528 | | | 387.1, 100.0% | |
| JEH-4-146 | | | | 365.495 | | | 366.3, 100.0% | |
| JEH-4-155 | | | | 385.544 | | | 386.2, 100.0% | |
| JEH-5-052 | | | | 399.53 | | | | |
| JEH-5-087 | | | | 370.485 | | | 371.1, 100.0% | |

| Ref. | Shh Light2 Luc EC50 (µM) | TM3 G8 Luciferase | | | C3H10T1/2 qPCR, Gh1 mRNA | | | Sufu Null (Ptc) % Inh., 10 µM | ZF Phenotype EC100 (µM) | PDE4D3 IC50 | PDE4D2 IC50 |
|---|---|---|---|---|---|---|---|---|---|---|---|
| | | % Inh., 0.5 pM | % Inh., 2 pM | EC 50 | % Inh., 1 pM | % Inh., 10 pM | EC50 | | | | |
| EGM | | 6.51% | 69.85% | 1.35 | 53.3% | 92.7% | 1.41 | 65.6% | | 1.1 | 1.3 |
| 1KXQ | >20 | 20.4% | 33.3% | | | | | | | >100 | >100 |
| 1L07 | | 17.4% | 30.9% | | | | | | | | |
| 1ANQ | | 27.4% | 38.4% | | | | | | | 1.7 | 1.2 |
| 1KMT | >20 | 23.8% | 56.0% | | | | | | | 30 | 46 |
| KK-14-093-1 | | 17.8% | 44.0% | | | | | | >50 | | |
| KK-14-094-1 | | 10.7% | 34.3% | | | | | | >50 | | |
| KK-14-094-2 | | 3.7% | 36.9% | | | | | | >50 | | |
| KK-093-2 | | | | | | | | | >50 | | |
| KK-14-094-3 | | 9.4% | 23.3% | | | | | | >50 | | |
| KK-14-096-1 | | 21.2% | 39.7% | | | | | | >50 | | |
| KK-14-096-2 | | 0.3% | 19.8% | | | | | | | | |
| 1L53 | | 50.6% | 89.2% | 2.82 | | | | | | >100 | >100 |
| 1L4R | | | | | | | | | | | |
| 1L52 | | | | | | | | | | | |
| 1KYW | | 27.9% | 37.2% | | | | | | | >100 | >100 |
| 1KY4 | >20 | 20.8% | 34.7% | | | | | | | 27 | 13 |
| 1KMR | | 12.4% | 39.9% | | | | | | | 11 | 7.6 |
| 1KMH | | 19.0% | 35.0% | | | | | | | 8.2 | 5 |
| 1KN7 | 5-10 | 7.5% | 35.4% | | | | | | | 1.8 | 1.7 |
| 1KL1 | | 26.1% | 50.8% | | | | | | | 62 | 25 |
| JEH-1-034 | | 10.3% | 37.5% | | | | | | 1 | | |
| JEH-1-050-1 | | 3.2% | 47.6% | | | | | | >50 | | |

TABLE 9A-continued

| | | | | | | | |
|---|---|---|---|---|---|---|---|
| JEH-1-050-2 | -1.3% | 49.9% | | | | 25 | 6.4 |
| JEH-1-054 | 14.8% | 40.7% | 1.10 | 19.6% | 50.4% | >50 | |
| JEH-1-064 | 17.9% | 41.7% | 7.06 | | 64.1% | >50 | |
| JEH-1-065-1 | 10.2% | 37.6% | | | | 5 | |
| JEH-1-065-2 | -1.3% | 67.4% | 1.09 | | | 10 | |
| JEH-1-066 | 6.9% | 32.5% | | | | >50 | |
| JEH-1-097 | 0.0% | 25.3% | | | | >50 | |
| JEH-1-103 | 3.8% | 35.1% | | | | >50 | |
| JEH-1-104 | 5.0% | 15.8% | | | | >50 | |
| JEH-1-124 | 5.9% | 40.7% | | | | >50 | |
| JEH-1-127 | -29.8% | 25.8% | | | | >50 | |
| JEH-1-131-2 | -3.5% | 27.7% | | | | 1 | |
| JEH-1-134 | 14.7% | 56.0% | 0.713 | | | 1 | |
| JEH-1-137 | 9.5% | 52.4% | 3.32 | | | 10 | |
| JEH-1-146-1 | -5.0% | 46.1% | >50 | | 68.9% | >50 | |
| JEH-1-146-2 | 14.8% | 42.1% | 11.2 | | 28.7% | | |
| JEH-1-161-1 | 10.4% | 46.5% | 19.1 | | | 0.5 | |
| JEH-1-161-2 | 25.8% | 75.3% | 9.55 | | | 1 | |
| JEH-1-163-1 | 57.4% | 92.0% | 1.96 | | 41.9% | 0.81 | |
| JEH-1-163-2 | 43.8% | 70.4% | 3.79 | | | >50 | |
| JEH-1-172 | 12.6% | 21.9% | | | | 50 | |
| JEH-1-190-1 | -6.9% | 33.8% | | | | 50 | |
| JEH-1-190-2 | 12.5% | 37.9% | | | | >50 | |
| JEH-1-190-3 | 37.5% | 61.4% | 5.01 | | | 30 | |
| JEH-2-003 | 15.8% | 45.5% | | | | 10 | |
| JEH-2-007-1 | -10.1% | 48.6% | | | | | |
| JEH-2-018 | -42.5% | -12.9% | | | | 25 | |
| JEH-2-022-2 | 17.0% | 59.5% | 3.16 | | | 25 | |
| JEH-2-026 | -73.1% | -16.0% | | | | >50 | |
| JEH-2-034 | 11.9% | 17.4% | | | | >50 | |
| KYK-1-54 | 6.6% | 29.3% | | | | >50 | |
| KYK-1-57 | 6.3% | 49.2% | 8.55 | | | >50 | |
| KYK-1-58 | -6.3% | 18.9% | | | | >50 | |
| KYK-1-61 | -12.4% | 11.5% | | | | >50 | |
| KYK-1-66 | 15.9% | 47.5% | | | | >50 | |
| KYK-1-70 | 9.3% | 22.2% | | | | >50 | |
| KYK-1-75 | 25.5% | 44.3% | 3.59 | | | >50 | |
| KYK-1-76 | 19.0% | 54.5% | 5.13 | | | >50 | |
| KYK-1-87 | 1.6% | 25.6% | | | | >50 | |
| KYK-1-88 | 10.7% | 46.9% | | | | >50 | |
| KYK-1-96 | 9.4% | 21.1% | | | | >50 | |
| KYK-1-99 | 12.2% | 30.0% | | | | >50 | |
| KYK-1-100 | 36.1% | 70.0% | 4.67 | | | >50 | |
| KYK-1-103-1 | -18.9% | 18.9% | | | | >50 | |
| KYK-1-103-2 | 11.6% | 51.9% | | | | 20 | |
| JEH-2-041-1 | -11.0% | 29.2% | | | | 30 | |
| JEH-2-041-2 | 9.6% | 26.3% | | | | | |

TABLE 9A-continued

| | | | | | | | | | | |
|---|---|---|---|---|---|---|---|---|---|---|
| JEH-2-048 | | 27.0% | 44.3% | | | | | | | |
| JEH-2-053-1 | | 17.7% | 29.2% | | | | | | | |
| JEH-2-053-2 | | -10.1% | 28.1% | | | | | | | |
| JEH-2-053-3 | | 10.8% | 34.6% | | | | | | N/A | |
| JEH-2-060 | | 10.0% | 36.7% | | | | | | N/A | |
| JEH-2-069-2 | | 28.3% | 52.0% | 1.11 | | | | | N/A | | |
| JEH-2-088 | | 15.8% | 40.5% | 14.1 | | 24.2% | | | 30 | | |
| JEH-2-103-1 | | 20.5% | 35.2% | | | | | | 48 | | |
| JEH-2-103-2 | | -5.5% | 30.9% | | | | | | | | |
| JEH-2-103-3 | | 12.8% | 37.5% | | | | | | | | |
| JEH-2-105 | | 15.1% | 35.4% | 30.2 | | 54.9% | | | | | |
| JEH-2-120-1 | | 15.2% | 40.1% | | | 82.9% | | | | | |
| JEH-2-120-2 | | -1.3% | 29.7% | | | | | | | | |
| JEH-2-120-3 | | -2.6% | 37.5% | | | | | | | | |
| JEH-2-157 | | 20.1% | 33.5% | | | | | | | | |
| JEH-3-031 | | 11.9% | 48.0% | | 11.7% | 100.8% | | | | | |
| JEH-3-038-2 | | 15.5% | 32.6% | | 27.8% | 102.0% | | | | 1 | >100 |
| JEH-3-038-3 | | -39.5% | -13.0% | | 24.4% | 14.8% | | | | >100 | 14 |
| JEH-3-039-1 | | 21.8% | 46.8% | 2.96 | -3.3% | 81.6% | | | | >100 | 16 |
| JEH-3-039-2 | | 82.4% | 93.6% | 0.476 | 49.3% | 89.1% | 0.593 | 80.4% | 0.1 | 18 | 5.6 |
| JEH-3-039-3 | | 51.2% | 84.0% | 3.02 | 64.9% | 66.5% | 0.809 | 38.1% | | 24 | |
| JEH-3-045-1 | | -11.2% | 56.2% | 8.49 | 58.1% | 95.4% | | 47.6% | | 8.3 | |
| JEH-3-045-3 | | 20.3% | 42.3% | 10.5 | | 43.6% | | | | | |
| JEH-3-048-1 | | 17.1% | 36.0% | 19.0 | | 28.7% | | | | | |
| JEH-3-048-2 | | 21.5% | 33.1% | 17.8 | | 36.9% | | | | | |
| JEH-3-048-3 | | 21.5% | 40.5% | 6.31 | 33.8% | 98.6% | | -13.7% | 1 | | |
| JEH-3-056-1 | | 24.2% | 40.4% | 7.08 | 14.7% | 67.2% | | | | | |
| JEH-3-056-2 | | -17.6% | 28.0% | | 13.1% | 84.8% | | | | | 45 |
| JEH-3-058-1 | | 28.1% | 51.8% | 12.6 | 12.0% | 85.3% | | | | 14 | 4.9 |
| JEH-3-058-2 | | 27.8% | 41.8% | | | 18.3% | | | | 23 | 6.4 |
| JEH-3-063 | 10-20 | 18.9% | 40.4% | 39.8 | | 35.4% | | | | 15 | |
| JEH-3-069-1 | 10-20 | -15.7% | 27.3% | 32.5 | | 42.8% | | | | | |
| JEH-3-069-2 | | 1.5% | 31.3% | 2.50 | 38.6% | 97.6% | 2.74 | 77.6% | | | 3.2 |
| JEH-3-069-3 | | 25.4% | 46.9% | | 47.1% | 89.1% | 1.13 | 52.1% | | | |
| JEH-3-077 | | 24.8% | 43.5% | 18.2 | 25.1% | 50.8% | | | | | |
| JEH-3-079 | | 42.1% | 84.7% | 12.0 | 39.5% | 96.1% | 1.37 | 21.6% | | 4.1 | |
| JEH-3-087-1 | | 39.2% | 69.3% | 1.58 | 64.2% | 100.6% | 0.789 | 12.1% | | | |
| JEH-3-087-2 | | | | | | | | | | | |
| JEH-3-104-1 | | | | | | | | | | | |
| JEH-3-104-2 | | | | | | | | | | | |
| JEH-3-106 | | | | | | | | | | | |
| JEH-3-111 | | 14.2% | 22.3% | | 28.7% | 106.1% | | | | | |
| JEH-3-120-1 | | 8.1% | 29.1% | | 36.9% | 95.2% | | | | | |
| JEH-3-120-2 | | | | | | | | | | | |
| JEH-3-125 | | | | | | | | | | | |
| JEH-3-130 | | | | | | | | | | | |
| JEH-3-146 | | 5.4% | 26.0% | 23.9 | 48.4% | 83.9% | | | | | |
| JEH-3-159 | | 21.4% | 31.8% | >50 | 14.3% | 79.3% | 4.30 | | | >100 | |
| JEH-4-006 | | -7.8% | 28.9% | | | | | | | | |

TABLE 9A-continued

| | | |
|---|---|---|
| JEH-4-016 | 14.2% | 33.8% |
| JEH-4-055-1 | 14.3% | 38.8% |
| JEH-4-055-2 | 19.7% | 37.9% |
| JEH-4-110 | 0.0% | 43.4% |
| JEH-4-121 | 70.6% | 82.8% |
| JEH-4-135 | 21.2% | 35.7% |
| JEH-4-136 | 3.7% | 44.3% |
| JEH-4-137 | -0.8% | 25.5% |
| JEH-4-143 | 8.6% | 40.5% |
| JEH-4-145 | 0.4% | 12.1% |
| JEH-4-146 | 6.5% | 28.2% |
| JEH-4-155 | | | 
| JEH-5-052 | | |
| JEH-5-087 | | |

(additional column values: 16.6, 6.03, 5.50, 2.51, 25.0, 31.6)

TABLE 9B

| Structure | Reference |
|---|---|
| (structure) | HI0863 |
| (structure) | HI113 |
| (structure) | HI682 |
| (structure) | HI352 |
| (structure) | HI011 |
| (structure) | HI864 |
| (structure) | HI612 |
| (structure) | HI499 |
| (structure) | HI798 |
| (structure) | HI931 |
| (structure) | HI918 |
| (structure) | HI277 |

TABLE 9B-continued

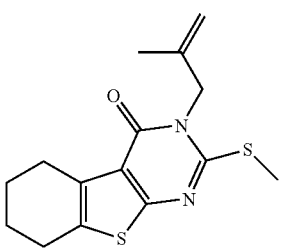 [SMILES: C=C(C)Cn1c(SC)nc2sc3c(c2c1=O)CCCC3]
HI272

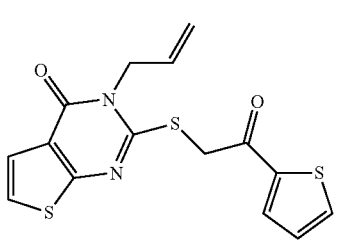 [SMILES: C=CCn1c(SCC(=O)c2cccs2)nc2sccc2c1=O]
HI110

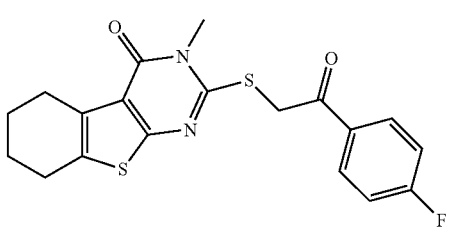 [SMILES: Cn1c(SCC(=O)c2ccc(F)cc2)nc2sc3c(c2c1=O)CCCC3]
HI302

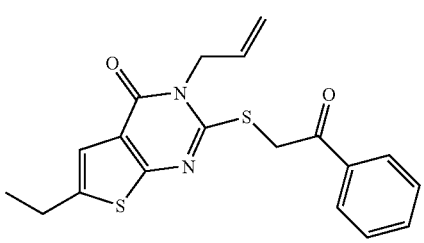 [SMILES: C=CCn1c(SCC(=O)c2ccccc2)nc2sc(CC)cc2c1=O]
HI630

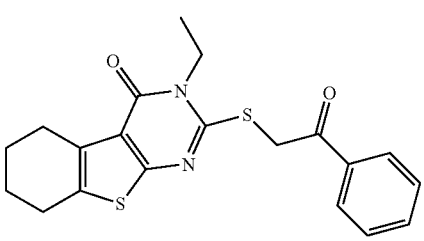 [SMILES: CCn1c(SCC(=O)c2ccccc2)nc2sc3c(c2c1=O)CCCC3]
HI925

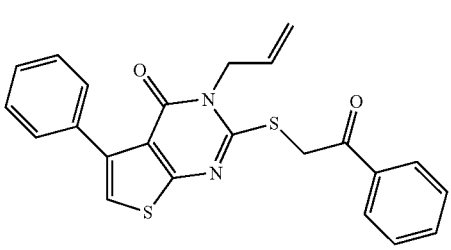 [SMILES: C=CCn1c(SCC(=O)c2ccccc2)nc2scc(-c3ccccc3)c2c1=O]
HI696

TABLE 9B-continued

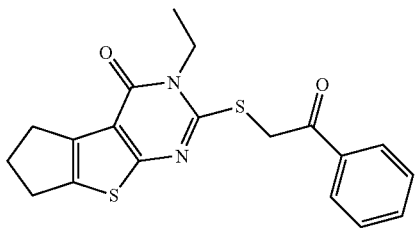 [SMILES: CCn1c(SCC(=O)c2ccccc2)nc2sc3c(c2c1=O)CCC3]
HI598

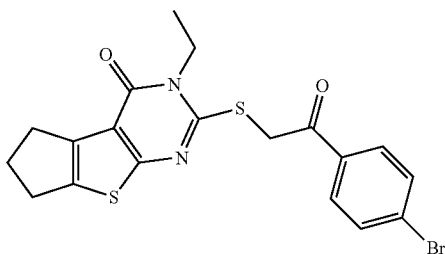 [SMILES: CCn1c(SCC(=O)c2ccc(Br)cc2)nc2sc3c(c2c1=O)CCC3]
HI2863

| Physical Data | | Shh Light2 Luc | PDE4D3 | PDE4D2 |
|---|---|---|---|---|
| Reference | MW | EC50 (µM) | IC50 | IC50 |
| HI0863 | 428.54 | 2.44 | N.D. | |
| HI682 | 414.513 | >10 | N.D. | |
| HI011 | 396.523 | 1.8 to 5 (variable) | N.D. | |
| HI612 | 410.55 | >10 | N.D. | |
| HI798 | 426.549 | >10 | >100 | |
| HI918 | 336.424 | >10 | N.D. | |
| HI272 | 292.415 | >10 | N.D. | |
| HI302 | 388.475 | >10 | N.D. | |
| HI925 | 384.512 | N.D. | N.D. | |
| HI598 | 370.485 | >10 | N.D. | |
| HI2863 | 449.381 | >10 | N.D. | |
| HI113 | 404.927 | >20 | 4.1 | |
| HI352 | 398.539 | >10 | 20 | |
| HI864 | 358.474 | >10 | N.D. | |
| HI499 | 410.949 | 4.6 to 9.5 | N.D. | |
| HI931 | 388.475 | N.D. | N.D. | |
| HI277 | 356.458 | >10 | N.D. | |
| HI110 | 348.453 | N.D. | N.D. | |
| HI630 | 370.485 | >10 | 6 | |
| HI696 | 418.529 | <1 | 14 | 7.4 |

Example 10

General Synthesis of Thienopyrimidine Compounds

Thienopyrimidines with general structure 1 were synthesized in approximately 5 steps from commercially available starting materials. $R_1$ and $R_2$ most commonly exist as a fused cyclohexyl ring.

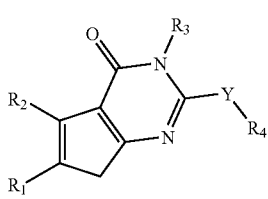

1

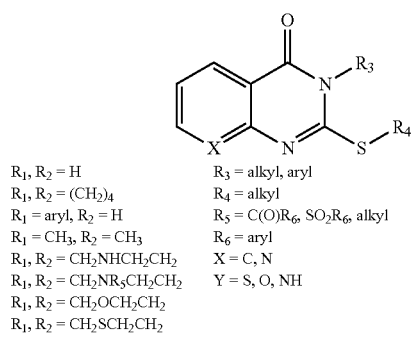

R$_1$, R$_2$ = H
R$_1$, R$_2$ = (CH$_2$)$_4$
R$_1$ = aryl, R$_2$ = H
R$_1$ = CH$_3$, R$_2$ = CH$_3$
R$_1$, R$_2$ = CH$_2$NHCH$_2$CH$_2$
R$_1$, R$_2$ = CH$_2$NR$_5$CH$_2$CH$_2$
R$_1$, R$_2$ = CH$_2$OCH$_2$CH$_2$
R$_1$, R$_2$ = CH$_2$SCH$_2$CH$_2$ R$_3$ = alkyl, aryl
R$_4$ = alkyl
R$_5$ = C(O)R$_6$, SO$_2$R$_6$, alkyl
R$_6$ = aryl
X = C, N
Y = S, O, NH General synthetic scheme for 1 where R$_1$=R$_2$=cyclohexyl, Boc-piperidine, or Y=O, S.
Where Y=O, S, the R3-NCS procedure was utilized.

General Synthesis of 1.

In Scheme 1, where Y=NBoc, the Boc group was removed with trifluoroacetic acid in DCM. The secondary amine was functionalized through either reaction with a sulfonyl chloride in the presence of base, through amide formation with the R$_6$-carboxylic acid, or through reductive amination with the R$_8$-aldehyde.

Where R$_1$=R$_2$=H, scheme 2 was utilized, and Scheme 1 was followed upon formation of the 2-aminothiophene shown in Scheme 2, through the route employing dithiourea synthesis and amine substitution.

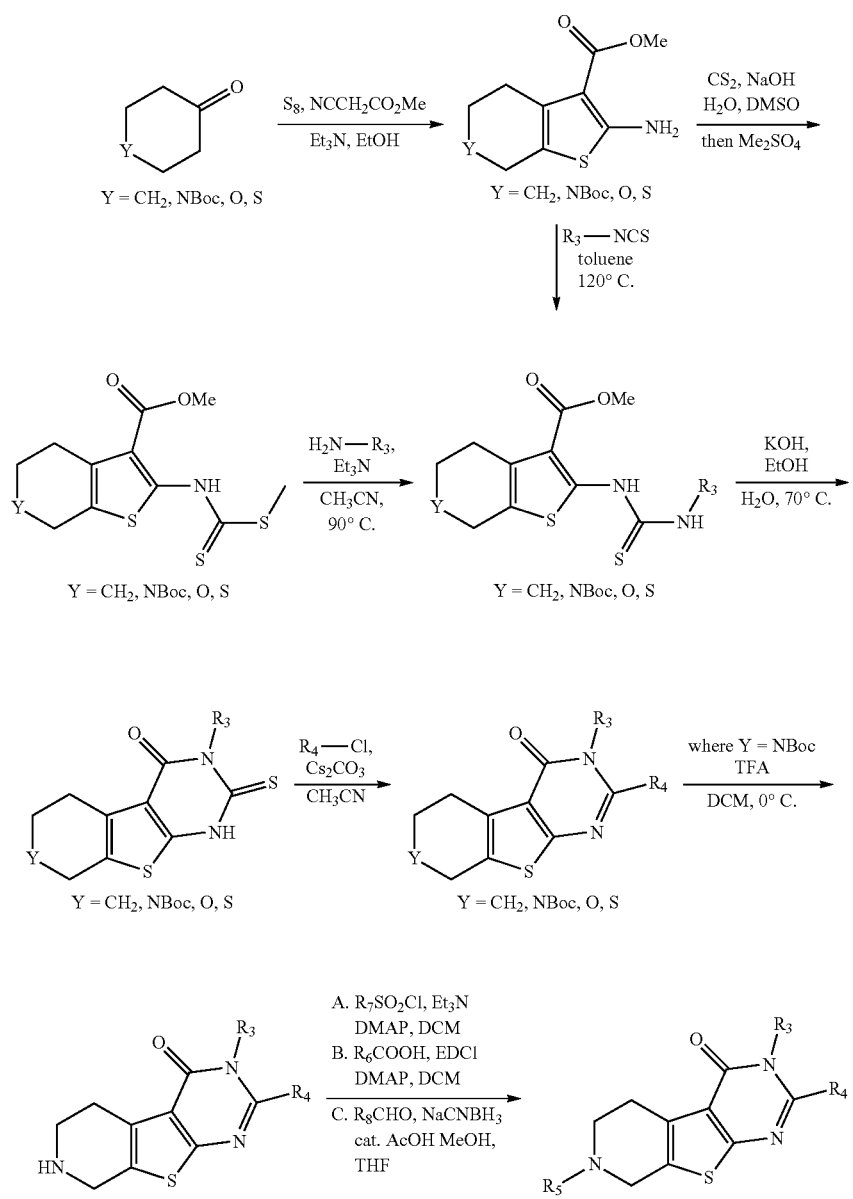

Scheme 2.

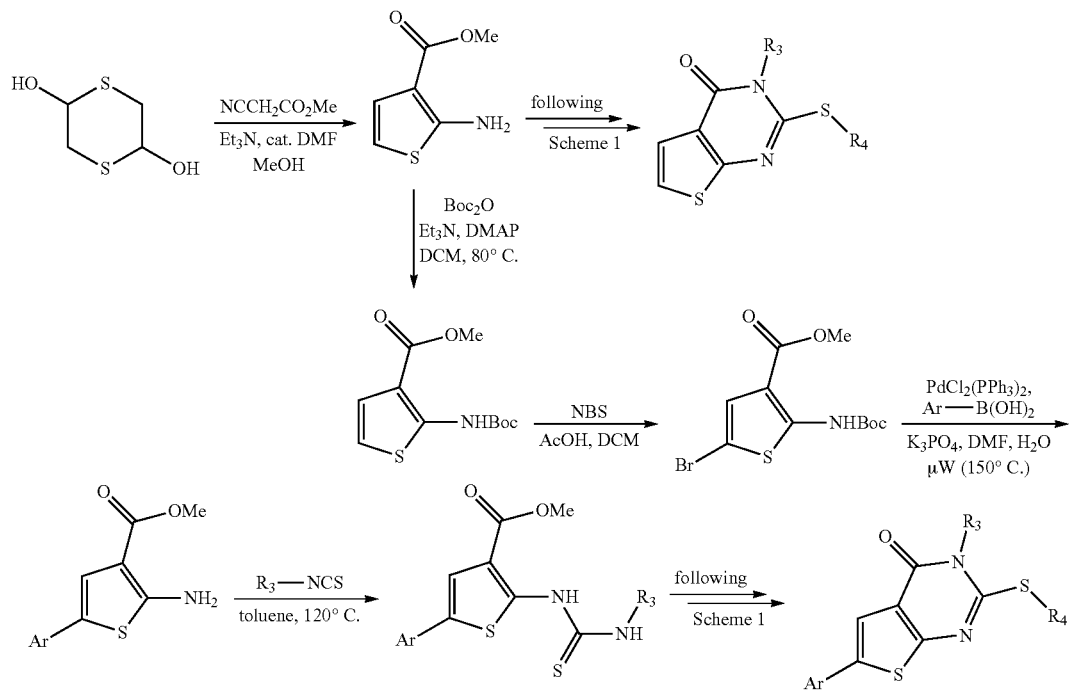

General synthesis of 1 where $R_1 = R_2 = H$ or $R_1 = Ar$, $R_2 = H$.

Where $R_1=Ar$, $R_2=H$, Scheme 2 was followed, involving mono-Boc protection of the 2-aminothiophene, 2-position bromination and Suzuki cross coupling during which Boc group deprotection also occurred. All examples of $R_1=Ar$ employed $R_3$-NCS formation of the $R_3$-thiourea, and Scheme 1 was followed for the remainder of the synthesis.

Synthesis of 2 followed the general scheme 3. In each case, reaction with the isothiocyanate directly formed the cyclic thiourea.

$R_3$ derived from either the free amine through cyclization with the dithiourea of Scheme 1 or from the isothiocyanate through direct reaction with the 2-aminothiophene.

$R_4$ derived from S-alkylation of the cyclic thiourea with primary alkyl halides. Where $R_4$ derives from a 2-haloacetyl starting material, the starting material was purchased from commercial suppliers. Where $R_4$ derives from a substituted 2-haloacetamide, the 2-haloacetamide was synthesized from 2-chloroacetyl chloride and either a primary or secondary amine.

Compound 3-159 was synthesized as shown in Scheme 4 from the 2-aminocyclohexylthiophene by reacting with the cyanoacetate with 4 M HCl in dioxane. No other compounds were synthesized using this method.

Scheme 3.

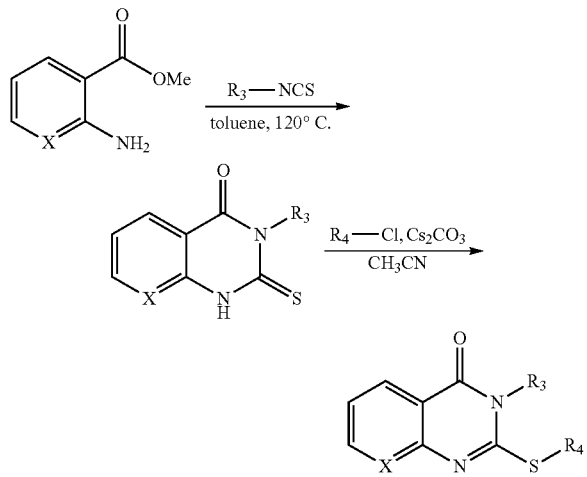

General synthesis of 2 where $X = C, N$.

Scheme 4. Cyclization of to provide 3-159.

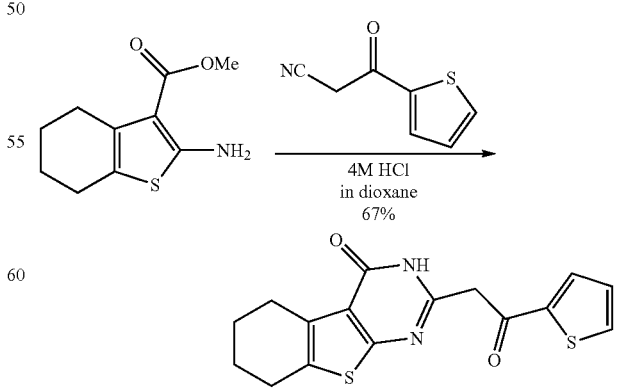

3-159

Benzothiophenes were synthesized following Scheme 5 and upon aromatization and deprotection, were elaborated according to Scheme 1.

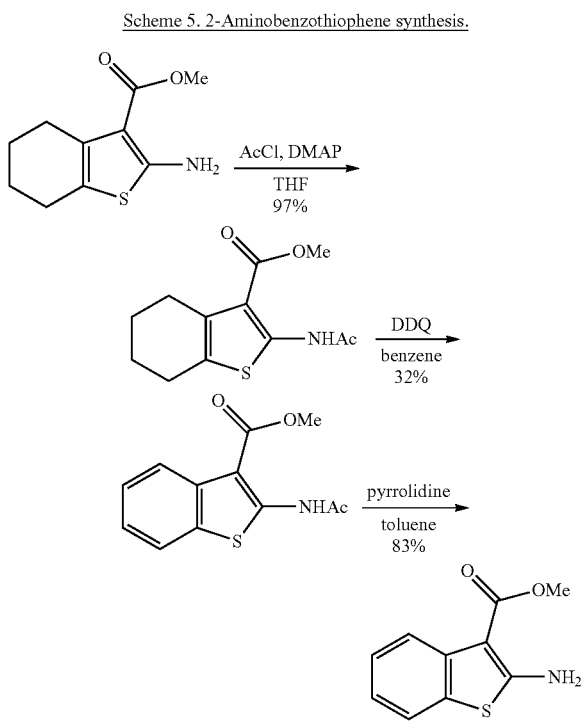

Substitutions for the thiopyrin anidinone S-linkage were performed by nucleophilic substitution with the requisite chloropyrimidinone to provide O-linked and N-linked analogs as shown in Scheme 6. Conditions slightly varied depending on the nature of the X group.

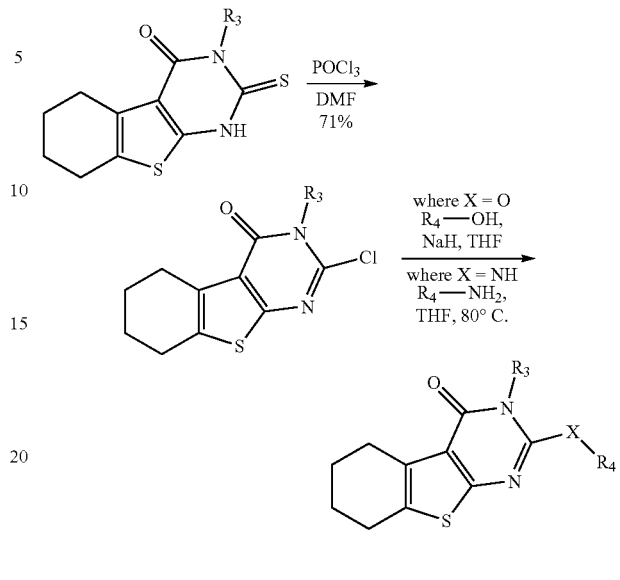

Example 11

Chemical characterization and biological data are included for representative compounds in the specification.

Example 11

It is anticipated that compounds disclosed herein could serve as an anti-tumor, anti-angiogenic, anti-metastatic, agent in the treatment of cancer. To this end, a series of clinically relevant cancer lines were assayed and the cell-killing $EC_{50}$s for compounds according to the subject matter disclosed herein are provided in Table 10.

TABLE 10

| Structure | Ref. |
|---|---|
| 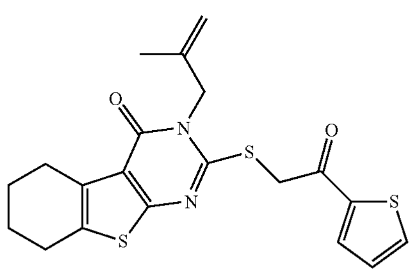 [SMILES: C=C(C)Cn1c(SCC(=O)c2cccs2)nc2sc3c(c2c1=O)CCCC3] | EGM |
| 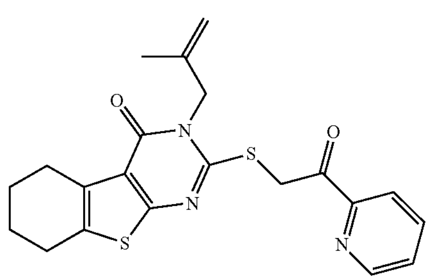 [SMILES: C=C(C)Cn1c(SCC(=O)c2ccccn2)nc2sc3c(c2c1=O)CCCC3] | JEH-3-063 |

TABLE 10-continued
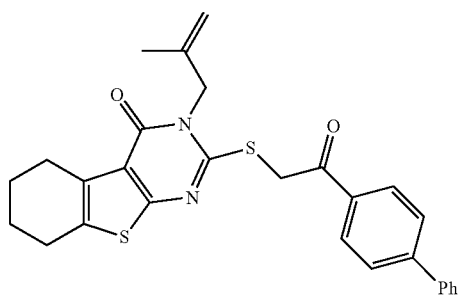 [SMILES: C=C(C)Cn1c(SCC(=O)c2ccc(-c3ccccc3)cc2)nc2sc3c(c2c1=O)CCCC3] 1KXQ
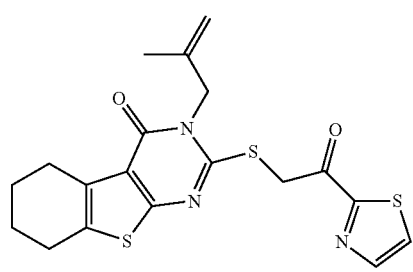 [SMILES: C=C(C)Cn1c(SCC(=O)c2nccs2)nc2sc3c(c2c1=O)CCCC3] JEH-3-069-1
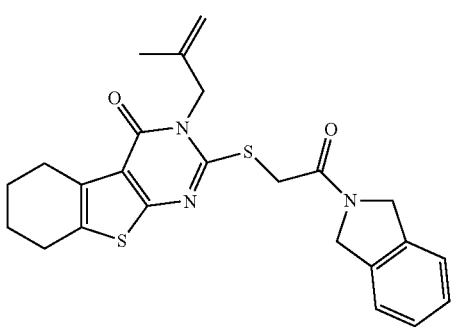 [SMILES: C=C(C)Cn1c(SCC(=O)N2Cc3ccccc3C2)nc2sc3c(c2c1=O)CCCC3] 1KMT
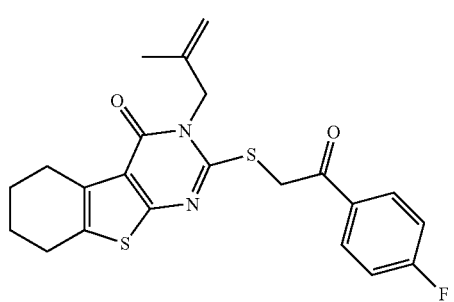 [SMILES: C=C(C)Cn1c(SCC(=O)c2ccc(F)cc2)nc2sc3c(c2c1=O)CCCC3] HI0863
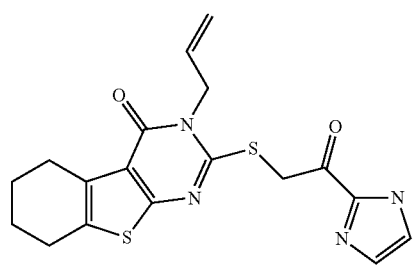 1KY4

TABLE 10-continued
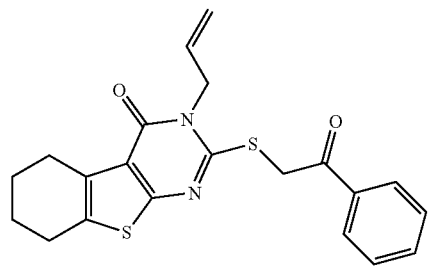 [SMILES: C=CCn1c(SCC(=O)c2ccccc2)nc2sc3c(c2c1=O)CCCC3]
HI011
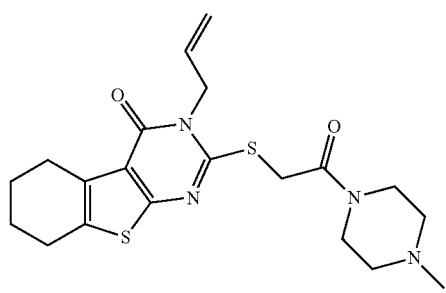 [SMILES: C=CCn1c(SCC(=O)N2CCN(C)CC2)nc2sc3c(c2c1=O)CCCC3]
1KN7
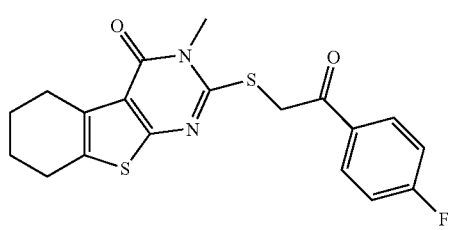 [SMILES: Cn1c(SCC(=O)c2ccc(F)cc2)nc2sc3c(c2c1=O)CCCC3]
HI302
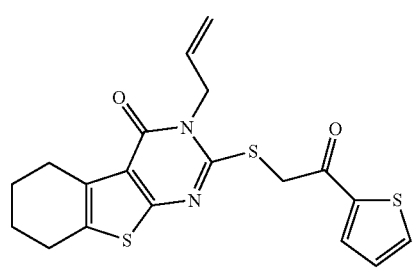 [SMILES: C=CCn1c(SCC(=O)c2cccs2)nc2sc3c(c2c1=O)CCCC3]
JEH-3-039-3
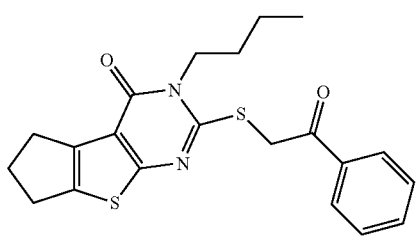 [SMILES: CCCCn1c(SCC(=O)c2ccccc2)nc2sc3c(c2c1=O)CCC3]
HI352
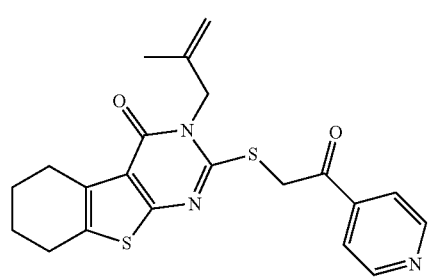 [SMILES: C=C(C)Cn1c(SCC(=O)c2ccncc2)nc2sc3c(c2c1=O)CCCC3]
JEH-3-048-1

TABLE 10-continued
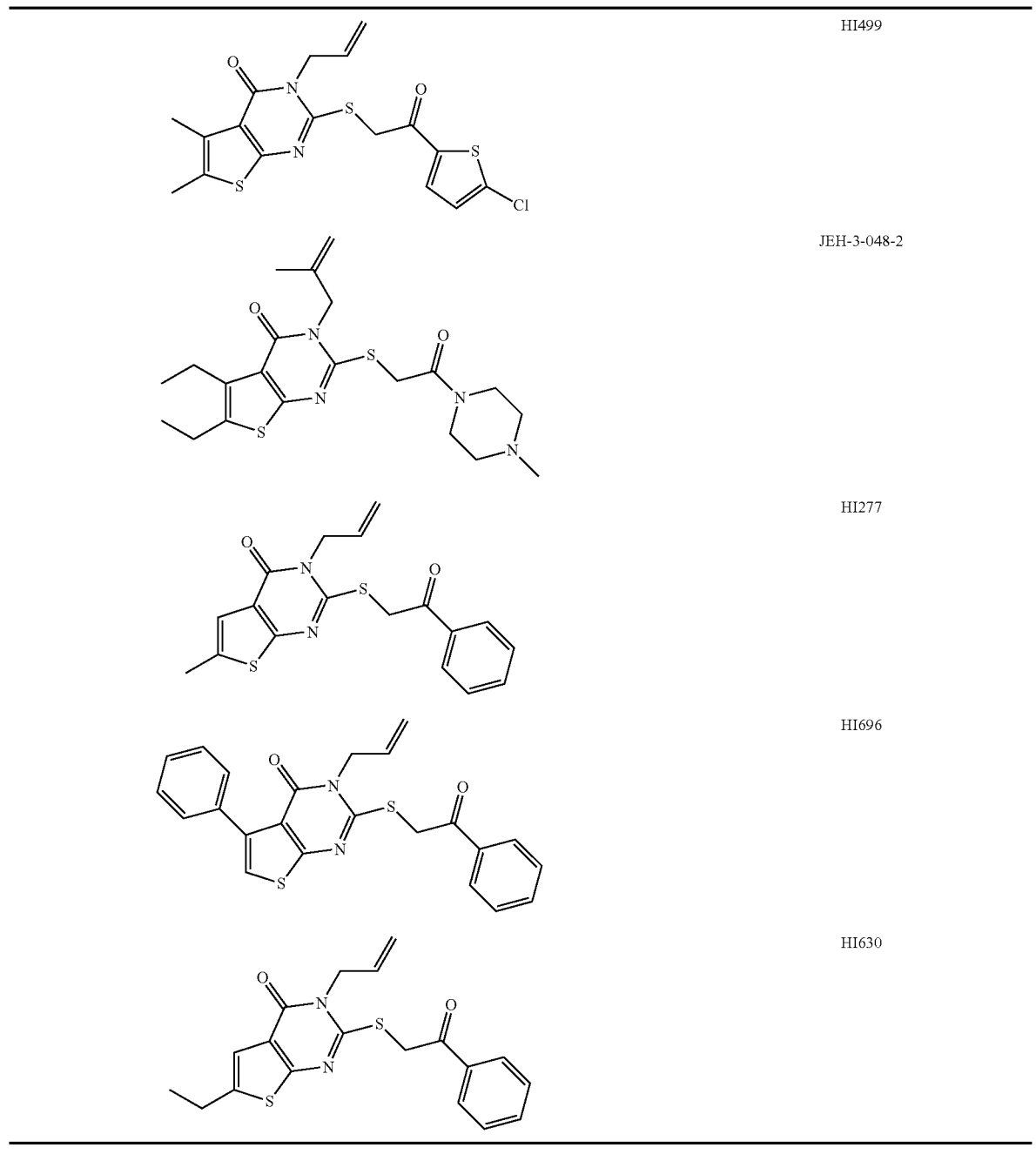
| | HI499 |
| | JEH-3-048-2 |
| | HI277 |
| | HI696 |
| | HI630 |
| Physical Data |||
| --- | --- | --- |
| Ref. | Alt. Ref. | LCMS [M + H] |
| EGM | 1KLU, EHF1, HI913 | 416.6, 100.0% |
| 1KXQ | | |
| 1KMT | | 452.0, 100.0% |
| 1KY4 | | |
| 1KN7 | | |
| JEH-3-039-3 | 1L4Q, HI037 | 403.0, 100.0% |
| JEH-3-048-1 | 1KMG | 412.0, 90.0% |
| JEH-3-048-2 | 1L9B | 433.1, 100.0% |
| JEH-3-063 | 1KMF | 412.0, 100.0% |
| JEH-3-069-1 | 1KLF | 418.0, 100.0% |
| HI0863 | | |
| HI011 | | |
| HI302 | | |
| HI352 | | |

TABLE 10-continued

HI499
HI277
HI630
HI696

| | CELL KILLING EC50 (µM), human cancer cells unless specified otherwise | | | | | |
|---|---|---|---|---|---|---|
| Ref. | Colon SW480 | Prostate PCx3 | Colon HTC116 | Breast MDA-231 | Melanoma B16F10 | Prostate DU145 |
| EGM | 0.534 | 77.19 | 11.43 | 2.053 | 2.223 | 41.92 |
| 1KXQ | 43.99 | 41.07 | 12.02 | >100 | 28.68 | 0.029 |
| 1KMT | 4.89 | 73.97 | 89.24 | 68.28 | 61.69 | 32.4 |
| 1KY4 | 12.18 | 78.74 | .0828 | 9.98 | 6.24 | N.D. |
| 1KN7 | 0.0574 | 45.73 | 21.33 | 10.31 | 25.78 | 91.44 |
| JEH-3-039-3 | 3.63 | 50.1 | 54.53 | 1.74 | 3.69 | 71.03 |
| JEH-3-048-1 | 1.87 | 81.25 | 87.86 | 6.82 | 14.19 | 100.44 |
| JEH-3-048-2 | 4.68 | 105.2 | 66.36 | 17.3 | 25.34 | 40.27 |
| JEH-3-063 | 8.05 | 100 | 3.82 | 4.46 | 2.29 | 0.684 |
| JEH-3-069-1 | 6.92 | 69.68 | 22.9 | 13.96 | 16.06 | 47.5 |
| HI0863 | 5.4 | 47.7 | 0.078 | 3.12 | 4.46 | 2.38 |
| HI011 | 24.5 | 85 | 10 | 1.6 | 9.1 | 0.004 |
| HI302 | 3.3 | >100 | 21.9 | 18.7 | 16 | 0.078 |
| HI352 | 0.287 | 0.03 | 74.7 | 84.5 | 108.9 | 98.1 |
| HI499 | 0.69 | 202 | 28.1 | >100 | 46 | 48.8 |
| HI277 | 0.03 | >100 | 135.7 | 186.2 | >100 | 180.1 |
| HI630 | 182.2 | >100 | N.D. | 23.1 | N.D. | >100 |
| HI696 | 2.6 | >100 | 3.2 | 1.2 | 0.0066 | >100 |

| | CELL KILLING EC50 (µM), human cancer cells unless specified otherwise | | | | | |
|---|---|---|---|---|---|---|
| Ref. | Medulloblastoma DaoY | Colon RKO | Lung Squam, NSCLC RWGT2 | Cervix HeLa | Breast MCF7 | Lung H82 |
| EGM | 31.53 | 54.28 | 6.869 | 12.43 | UnCh | UnCh |
| 1KXQ | 46.79 | UnCh | 80.85 | 12.25 | UnCh | UnCh |
| 1KMT | 58.22 | 75.63 | 51.11 | 49.72 | 1.08 | UnCh |
| 1KY4 | 115.67 | 33.24 | 156.72 | 24.79 | 0.4828 | UnCh |
| 1KN7 | 58.57 | 8.39 | 28.36 | 27.47 | UnCh | UnCh |
| JEH-3-039-3 | 34.02 | 306.5 | 5.07 | 36.94 | UnCh | UnCh |
| JEH-3-048-1 | 0.0574 | 52.88 | 40.17 | 23.64 | UnCh | UnCh |
| JEH-3-048-2 | 44.9 | 29.25 | 59.5 | 78.6 | 74.56 | UnCh |
| JEH-3-063 | 15.33 | 7.18 | 23.72 | 9.18 | UnCh | UnCh |
| JEH-3-069-1 | 26.89 | 38.27 | 27.6 | 100 | UnCh | UnCh |
| HI0863 | 39.8 | 42.8 | 38.8 | 12.2 | >100 | >100 |
| HI011 | 110.8 | >100 | 2.96 | >100 | >100 | >100 |
| HI302 | 26.6 | 0.0096 | 22.9 | 20.22 | >100 | >100 |
| HI352 | 100 | 100 | 73.8 | 114.4 | >100 | >100 |
| HI499 | 176.8 | 35.7 | 45.8 | 440.8 | 2.67 | >100 |
| HI277 | 246.6 | >100 | 30.5 | 5.11 | >100 | >100 |
| HI630 | >100 | 100 | 44.4 | >100 | >100 | >100 |
| HI696 | 2.95 | >100 | 64.9 | 3.75 | >100 | >100 |

Example 12

PDE4 as a Target for RSV

The small molecule PDE4 inhibitors of the presently disclosed subject matter are actively anti-viral in viral CPE (cytopathic effect) assays versus RSV (respiratory syncytial virus), Dengue (1 experiment), and BVDV (bovine viral diarrhea virus, surrogate for human hepatitis C virus). Of note, PDE4 inhibitors are now approved for COPD, for which RSV may be an exacerbating factor).

As a Treatment for Hepatitis C Virus:

Provided in FIG. 37 are the results from BVDV (Bovine Viral Diarrhea Virus, surrogate for Hepatitis C virus) CPE (cytotoxic effect) testing done. The assay was repeated with H1913 (a PDE4B and PDE4D inhibitor). Hi913 (our prototypic PDE4 inhibitor) was tested in half-log concentrations ranging from 100 µM to 0.33 µM. As the stock solution of H1913 was 10 mM, this meant that the final DMSO concentrations for the highest Hi913 concentrations were 1%, 0.33%, and 0.1%. The normal final DMSO concentrations used is 0.1%, so additional DMSO controls of 1% and 0.33% were included. The Hi913 data for the highest 3 concentrations is normalized to the respective DMSO concentrations. Note that at 3.3 to 10 µM, our PDE4 inhibitor blocked cytopathic effects of BVDV by ~60 and ~75%, respectively. The outlier effects at 100 µM are probably due to cytotoxicity at the high drug concentration.

Anti-RSV Effects of PDE4 Inhibitor

RSV is an enveloped single (−) stranded RNA virus, which is the most common cause of severe respiratory illness in children, responsible for majority (70%) of bronchiolitis. RSV infection is the most common cause of hospitalization in USA of young children up to the first year of life. Globally, there are 33 million new cases of RSV each year, responsible for deaths of 66,000 to 199,000 children each year. In addition, elderly over 65-years old and immunocompromised individuals are at increased risk for severe respiratory disease from RSV. In the elderly, symptomatic respiratory illness due to RSV is associated with high morbidity and mortality (11.9%), responsible for 10,000 deaths each year in US alone. Currently, there is no targeted therapy against RSV and treatment remains supportive.

In Table 11, the results of CPE assays following infection of human epidermoid cancer cells (HEp-2) with RSV. Even at 10,000 higher viral titers, our compound achieved complete inhibition at 10 µM. At 1 and 3 µM, the compound achieved over 98% reduction. The exemplary compound alone caused no apparent cytotoxicity at these concentrations.

TABLE 11

| Study | Dilution | Relative RSV titer | Ave Plaque # (each represent 3 independent experiments) | Plaques per normalized viral titer | % CPE relative to DMSO |
|---|---|---|---|---|---|
| DMSO | 100000 | 1 | 10666667 | 1.07E+07 | 100.00 |
| HI 1 uM | 10000 | 10 | 1733333 | 1.73E+05 | 1.62 |
| HI 3 uM | 10000 | 10 | 1933333 | 1.93E+05 | 1.81 |
| HI 10 uM | 1 | 100000 | 0 | 0.00E+00 | 0.00 |
| 2014 Study | | | | | |
| DMSO | 100000 | 1 | 11333333 | 1.13E+07 | 100.00 |
| Negative control | 100000 | 1 | 14000000 | 1.40E+07 | 123.53 |
| HI 10 uM | 1 | 100000 | 0 | 0.00E+00 | 0.00 |

Example 13

An unbiased zebrafish in vivo chemical genetic screen for small molecule developmental patterning modulators identified EGM1, which phenocopied the loss of Hh zebrafish mutant. In vitro, EGM1 inhibited Hh target gene transcription downstream of SMo and functioned epistatic to the Gli transcription factor regulator Suppressor of Fused (SuFu), as provided in FIG. 39. The SAR and hit to lead efforts, as presented in FIGS. 40 and 41 and target identification campaign, are positioned to identify an improved downstream of Smo probe of Hh signaling. Initial appendage and core scaffold SAR indicated narrow parameters for potency improvement while focusing on optimization of solubility properties and elimination of metabolic liabilities. However, a series of cyclopropanes exhibited up to three-fold $EC_{50}$ reduction and slight solubility optimization. These compounds can serve as intermediates toward identification of a downstream Smo Hh inhibitor, which will be useful for treatment of non-Gorlin syndrome oncogenic mutations and Smo inhibitor resistance.

Example 14

Based on the discovery of eggmanone (EGM1) from a high content screen for small molecule modulators of developmental patterning in embryonic zebrafish and its recapitulation of the Hh-null phenotype, EGM1 was confirmed to inhibit Hh signaling in cell-based assays, functioning downstream of Smo and the negative regulator Sufu but upstream of Gli TFs. This downstream inhibition was linked to inhibition of phosphodiesterase 4 (PDE4) via protein kinase A (PKA) activation, leading to Gli phosphorylation and resultant Gli processing. Conceptual modulation of Hh transcriptional activity at signaling nodes downstream of Smo has gained favor for subverting clinical resistance, with Gli antagonism (GANT-61) and bromodomain inhibition emerging as two approaches. In addition to studies with EGM1, mounting evidence has linked PDE4 to Hh signaling and tumorigenesis. Therefore, viewed EGM1 was viewed as a starting point for in vitro probe development toward an optimized downstream of Sufu Hh inhibitor; however, EGM1's limited aqueous solubility and modest potency required improvement. Several EGM1 analogs with improved activity are provided below in Table 12A.

TABLE 12A

EGM1 analogs with improved Hh activity and cLogP.

| Structure | Reference | Alternate Ref. | MW | cLogP | LCMS [M + H] |
|---|---|---|---|---|---|
| 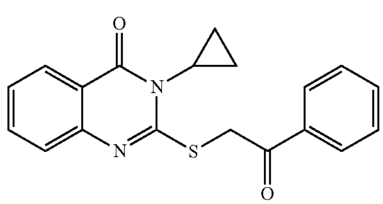 [SMILES: O=C(CSc1nc2ccccc2c(=O)n1C1CC1)c1ccccc1] | JEH-5-123-1 | | 336.409 | 3.48 | 337.1, 100.0% |
| 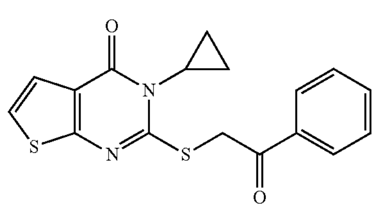 [SMILES: O=C(CSc1nc2sccc2c(=O)n1C1CC1)c1ccccc1] | JEH-5-124-1 | | 342.431 | 3.24 | 343.0, 100.0% |

TABLE 12A-continued

EGM1 analogs with improved Hh activity and cLogP.

| Structure | Reference | Alternate Ref. | MW | cLogP | LCMS [M + H] |
|---|---|---|---|---|---|
| | JEH-5-156 | | 344.45 | 2.91 | 345.1, 100.0% |
| | JEH-5-187 | | 325.39 | 2.50 | 326.0, 100.0% |
| | JEH-5-189 | | 326.37 | 2.70 | 327.0, 100.0% |
| | JEH-6-001 | | 358.47 | 3.49 | 359.0, 100.0% |

Initially, three points of modification of EGM11 were targeted: incorporation of polar atoms in the cyclohexyl ring, substitution of the methylallyl functionality, and replacement of the pendant thiophene. In linear fashion starting with cyclohexanone and derivatives (5a-d), the tricyclic ring system was fashioned from left to right starting with a Gewald reaction to provide the 2-aminothiophene 6. In most cases, formation of the dithiourea 7 was followed by two-step cyclization with primary amines to yield the cyclic thiourea 8; however, on smaller scales, direct formation of thioureas with isothiocyanates and subsequent cyclization also arrived at 8. S-alkylation under mild conditions installed alkyl ketones to provide EGM1 analogs 9a-n and tetrahydropyran and tetrahydrothiopyran analogs 9o and 9p. In the case of Y=NBoc, further Boc deprotection gave piperidine 10a.

Scheme 1.

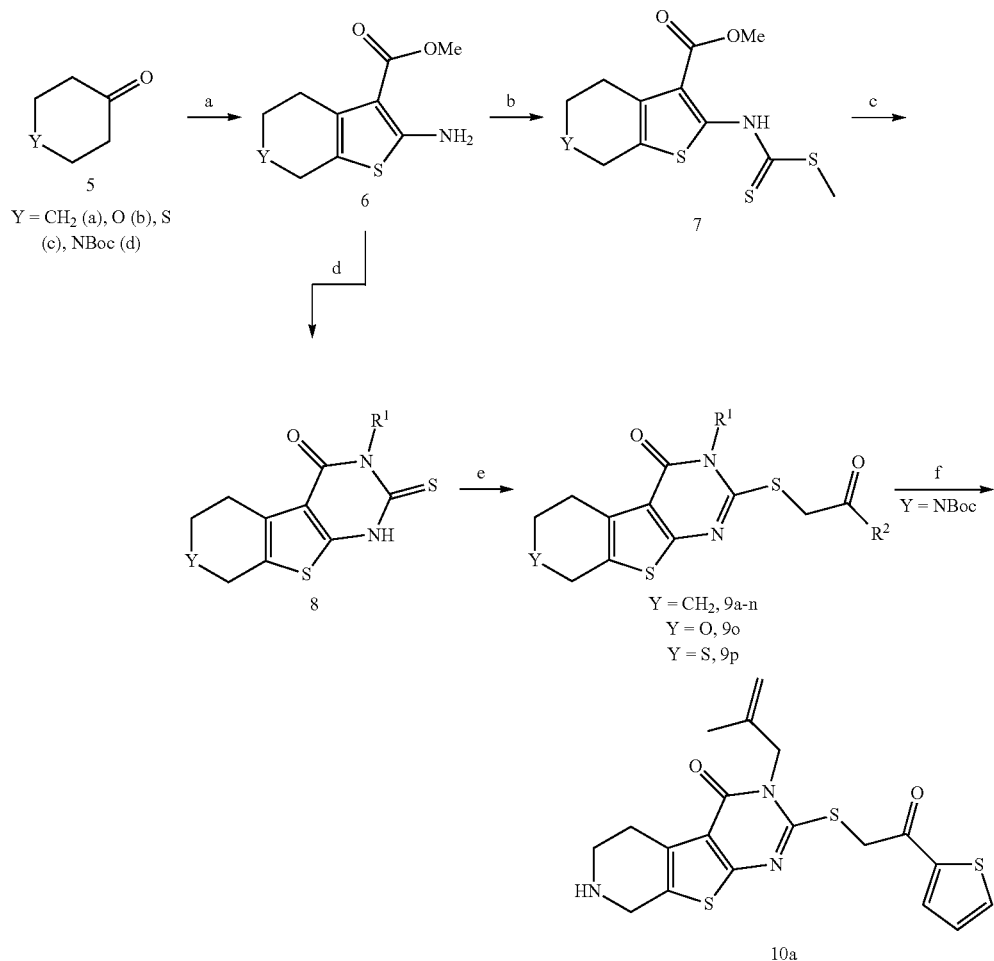

Reagents and conditions: (a) S₈, NCCH₂CO₂Me, Et₃N, EtOH, rt, 16 h, 49-80%; (b) CS₂, NaOH, DMSO, H₂O, rt, 1 h then Me₂SO₄, rt, 3 h, 72-93%; (c) R¹NH₂, Et₃N, CH₃CN, 90° C., 16 h; KOH, EtOH, H₂O, 70° C., 4 h, 17-72%, two steps; (d) R¹NCS, PhMe, 115° C., 72 h; KOH, EtOH, H₂O, 70° C., 4 h, 16-80%, two steps; (e) XCH₂C(O)R², Cs₂CO₃, CH₃CN, rt, 3 h, 9-88%; (f) TFA, CH₂Cl₂, 0-25° C., 3 h, 27%. X = Cl, Br.

When choosing the primary assay for analog evaluation, consideration was given to two factors: cellular reduction of Hh target gene Gli1 transcription is directly linked to in vivo control of tumor growth; and micromolar potency of the marketed PDE4 inhibitor Roflumilast for Hh signaling inhibition (data not shown) indicated partial contribution of PDE4 to EGM1's observed Hh inhibition. Therefore, we prioritized phenotypic analog evaluation in the Gli-responsive luciferase reporter line TM3-Gli-Luc stimulated with 20 nM Smo agonist (SAG) while concurrently monitoring non-specific cellular toxicity. Additionally, lipophilic efficiency (LipE), a concurrent readout of a compound's potency (pEC50) and lipophilicity (cLogP) derived by subtracting the latter from the former, was utilized to optimize solubility properties (Table 12B), allowing for straightforward tracking of compounds with improvements in both parameters. Marketed Smo antagonists Vismodegib and Sonidegib displayed expected potency, while the $EC_{50}$ of the Gli antagonist GANT-61 was slightly higher than the reported ~5 μM $EC_{50}$ in the Shh-LIGHT2 reporter line. Pleased with the response of known Hh inhibitors, we profiled EGM1 and noted a benchmark $EC_{50}$ for EGM1 of 1.34 μM and a corresponding LipE of 0.73. Given that the low-nanomolar $EC_{50s}$ of 1 and 2 support LipEs of 4.33 and 3.02 respectively, we targeted a LipE for optimized EGM1 analogs of >2 deriving from an $EC_{50}$ of <1 μM ($pEC_{50}$>6). Replacement of the methylallyl group with small alkyl and cycloalkyl substituents revealed broad tolerance and a resulting improvement of LipE to 1.40 with cyclopropyl analog 9b, driven by cLogP reduction. Phenyl analog 9f indicated steric disfavoring of large substituents. In marked contrast to the favorable structure activity relationships (SAR) of the R¹ functionality, substitution of the R² thiophene in EGM1 showed little tolerance for alternate (hetero) aromatic and cycloalkyl amides with major potency losses across the series (9g-n). Only 2-methylpiperidine 9m displayed an acceptable reduction in potency (~2-fold); however, an $LD_{50}$ of 16.7 μM precluded further investigation. Therefore, bioisosteric replacement of the thiophene group for a phenyl ring was seen as a prudent strategy going forward despite the modest potency of 9g. Finally, analogs 9o, 9p, and 10a indicated disfavored incorporation of polar atoms into the western cyclohexyl ring.

TABLE 12B
Initial EGM1 SAR with constant thienopyrimidinone core.
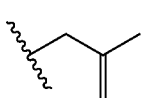 [SMILES: *CC(=C)C]
| Entry | Y | R¹ | R² | TM3-Gli-Luc EC$_{50}$ (μM)$^a$ | TM3-Gli-Luc LD$_{50}$ (μM)$^a$ | LipE$^b$ |
|---|---|---|---|---|---|---|
| 1 | — | — | — | 0.013 ± 0.004 | >50 | 4.33 |
| 2 | — | — | — | 0.0012 ± 0.0002 | >50 | 3.02 |
| 3 | CH | 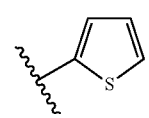 [SMILES: *c1cccs1] | 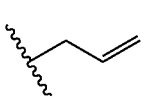 [SMILES: *CC=C] | 1.34 ± 0.002 | >50 | 0.73 |
| 4 | — | — | — | 9.27 ± 1.8 | >50 | 1.34 |
| 9a | CH$_2$ | 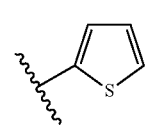 [SMILES: *c1cccs1] | 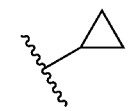 [SMILES: *C1CC1] | 2.36 ± 0.12 | >50 | 1.03 |
| 9b | CH$_2$ | 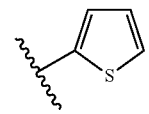 [SMILES: *c1cccs1] | 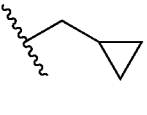 [SMILES: *CC1CC1] | 1.89 ± 0.75 | >50 | 1.40 |
| 9c | CH$_2$ | 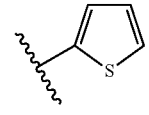 [SMILES: *c1cccs1] | 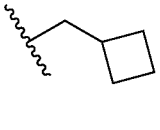 [SMILES: *CC1CCC1] | 2.07 ± 0.87 | >50 | 0.86 |
| 9d | CH$_2$ | 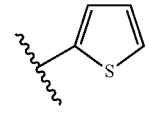 [SMILES: *c1cccs1] | 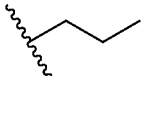 [SMILES: *CCC] | 1.99 ± 1.1 | 45.6 ± 5.2 | 0.70 |
| 9e | CH$_2$ | 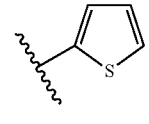 [SMILES: *c1cccs1] | 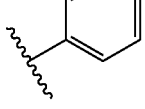 | 1.30 ± 0.18 | >50 | 1.06 |
| 9f | CH$_2$ | 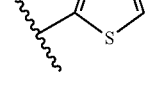 | 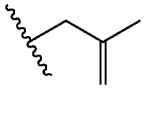 | 8.25 ± 0.14 | >50 | −0.15 |
| 9g | CH$_2$ | 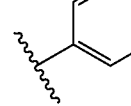 | 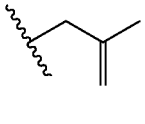 | 5.70 ± 2.1 | >50 | −0.01 |
| 9h | CH$_2$ | 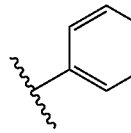 | | 19.8 ± 1.0 | >50 | 0.74 |

TABLE 12B-continued

Initial EGM1 SAR with constant thienopyrimidinone core.

| Entry | Y | R¹ | R² | TM3-Gli-Luc EC$_{50}$ (μM)[a] | TM3-Gli-Luc LD$_{50}$ (μM)[a] | LipE[b] |
|---|---|---|---|---|---|---|
| 9i | CH$_2$ | isobutenyl | 3-pyridyl | 11.1 ± 0.59 | 35.4 ± 1.1 | 0.94 |
| 9j | CH$_2$ | isobutenyl | 2-pyridyl | >20 | >50 | — |
| 9k | CH$_2$ | isobutenyl | 2-thiazolyl | >20 | >50 | — |
| 9l | CH$_2$ | isobutenyl | piperidinyl | 10.7 ± 1.4 | 24.6 ± 2.7 | 0.61 |
| 9m | CH$_2$ | isobutenyl | 2-methylpiperidinyl | 2.32 ± 0.73 | 16.7 ± 0.25 | 0.94 |
| 9n | CH$_2$ | isobutenyl | morpholinyl | >20 | >50 | — |
| 9o | O | isobutenyl | 2-thienyl | >20 | >50 | — |
| 9p | S | isobutenyl | 2-thienyl | 4.57 ± 1.8 | >50 | 0.67 |

TABLE 12B-continued

Initial EGM1 SAR with constant thienopyrimidinone core.

| Entry | Y | R[1] | R[2] | TM3-Gli-Luc EC$_{50}$ (μM)[a] | TM3-Gli-Luc LD$_{50}$ (μM)[a] | LipE[b] |
|---|---|---|---|---|---|---|
| 10a | NH | (isobutenyl) | (thiophene) | 6.40 ± 0.33 | 20.1 ± 1.2 | 1.45 | aValues represent mean ± standard error of the mean for at least two independent experiments performed in triplicate.
[b]Calculated as pEC$_{50}$ - cLogP, determined by Molinspiration Cheminformatics.

Having established SAR for the most readily modifiable groups of EGM1, replacements were explored for the cyclohexylthiophene core, which was postulated could ameliorate inherent EGM1 solubility limitations. Therefore, the Scheme 1 synthetic route was intercepted with α-aminoarylesters, including benzothiophene 11 derived from three step conversion of 2-aminocyclohexylthiophene 6a by a protection, oxidation, and deprotection strategy (Scheme 2). Benzothiophene 11 and readily available methyl anthranilate were converted to EGM1-like structures following Scheme 1 steps b-e, providing analogs 12 and 14a-c.

Scheme 2.

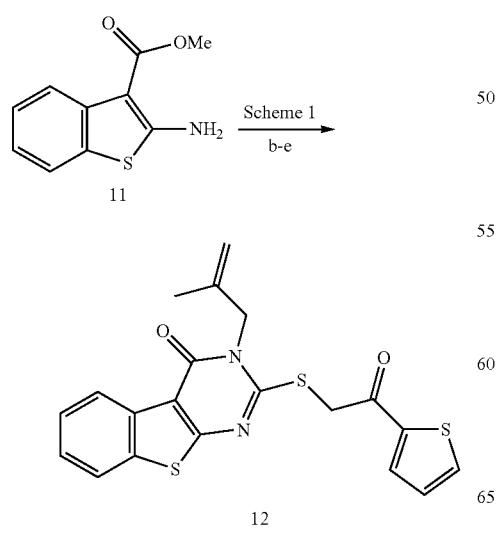

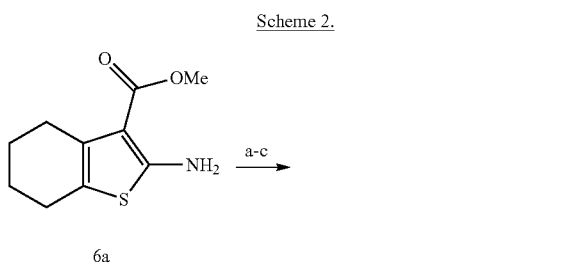

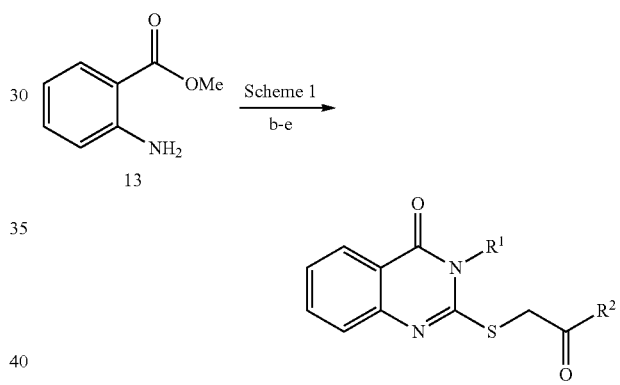

Reagents and conditions: (a) AcCl, DMAP, THF, rt, 2 h, 82%; (b) DDQ, PhH, 85° C., 5 d, 34%; (c) pyrrolidine, PhMe, 100° C., 18 h, 87%.

Similar to analogs 14a-c, in which we removed the cyclohexyl ring, arrival at the terminal thiophene core commenced by a modified Gewald reaction with 1,4-dithiane-2,5-diol (15, Scheme 3). As in Scheme 1, conversion to dithiourea 17 was followed by two-step cyclization with primary amines to yield cyclic thioureas 18 which were S-alkylated to provide EGM1 analogs 19a-c. In light of biological activity presented in Table 13, the role of the linker was further explored with 20a and 20b in which secondary and tertiary alcohols were formed from ketone 19c by either reduction with NaBH4 or Grignard addition with MeMgCl. Additionally, chloropyrimidinone 21 provided the necessary electrophilic center to investigate thioether modifications as the ether 22a or secondary amine 22b.

Scheme 3.

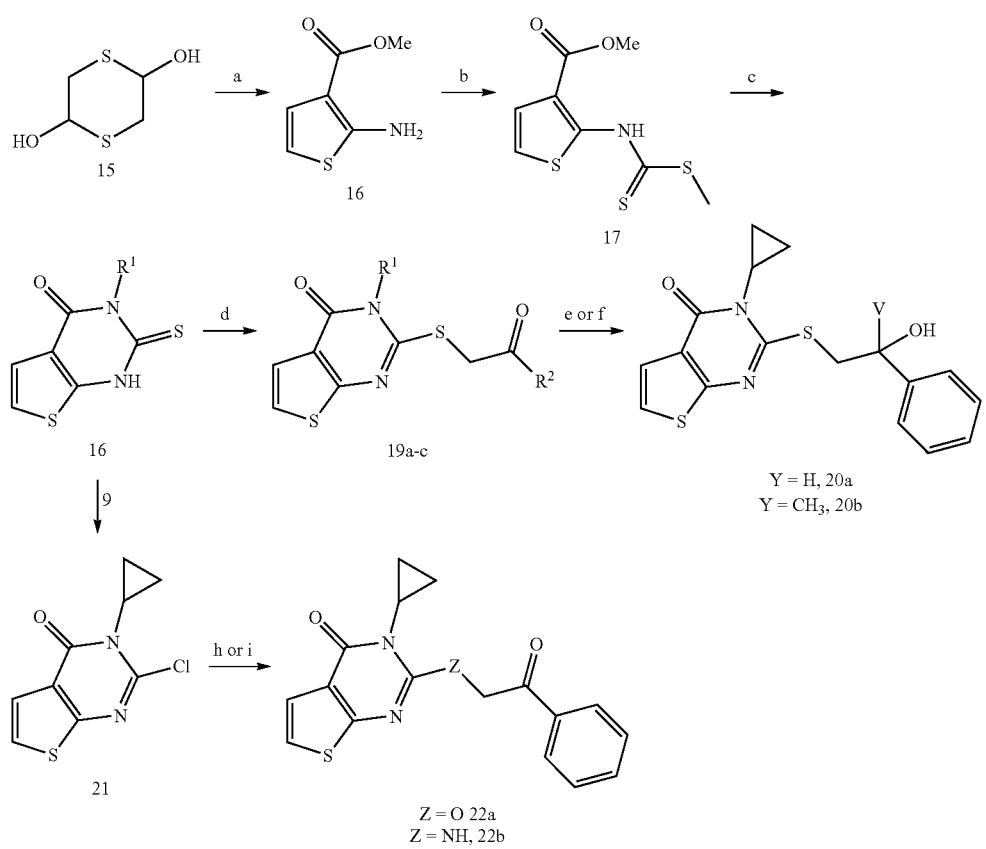

Reagents and conditions: (a) NCCH2CO2Me, Et3N, MeOH, DMF, 50° C. via µW, 3 min, 83%; (b) CS2, NaOH, DMSO, H2O, rt, 1 h then Me2SO4, rt, 3 h, 74%; (c) R[1]NH2, Et3N, CH3CN, 90° C., 16 h; KOH, EtOH, H2O, 70° C., 4 h, 11-84%, two steps; (d) XCH2C(O)R[2], Cs2CO3, CH3CN, rt, 3 h, 21-71%; (e) NaBH4, THF, EtOH, 0-25° C., 2 h, 66%; (f) MeMgCl, THF, 0° C., 1 h, 19%; (g) POCl3, DMF, 0-55° C., 72 h, 30%; (h) PhC(O)CH2OH, NaH, THF, rt, 0.5 h, then 21, 65° C., 18 h, 1%; (i) PhC(O)CH2NH2·HCl, DIPEA, i-PrOH, rt 0.5 h, then 21, 100° C., 18 h, 8%. X = Cl, Br.

The benzothiophene analog of EGM11 12 displayed a complete loss of Hh inhibitory activity, likely due to disfavored conformational and/or aromatic effects compared to EGM1, and its physical properties precluded any further investigation of this scaffold (Table 13). Benzopyrimidinone 14a similarly disappointed in its complete loss of activity; however, it was surprising to see that slight modifications to the eastern functionalities with 14b and 14c could more than return activity, yielding the first analogs with potency improvements over EGM1 and satisfying increases in LipE to above two. Even more promising was the thienopyrimidinone series 19a-c, which met initial qualifications of a quality in vitro Hh probe, where 19c displayed exceptional potency and solubility with no non-specific cellular toxicity. Thus at this juncture, 19c constituted the candidate in vitro Hh probe.

TABLE 13

EGM1 analogs with core modifications.

| Entry | X | R[1] | R[2] | TM3-Gli-Luc EC$_{50}$ (µM)[a] | TM3-Gli-Luc LD$_{50}$ (µM)[a] | LipE[b] |
|---|---|---|---|---|---|---|
| 12 | benzothiophene | isobutenyl | thiophene | >20 | >50 | — |

TABLE 13-continued

EGM1 analogs with core modifications.

| Entry | X | R¹ | R² | TM3-Gli-Luc EC$_{50}$ (µM)[a] | TM3-Gli-Luc LD$_{50}$ (µM)[a] | LipE[b] |
|---|---|---|---|---|---|---|
| 14a | benzene | isobutenyl | thiophene | >20 | >50 | — |
| 14b | benzene | cyclopropyl | thiophene | 0.685 ± 0.02 | >50 | 2.78 |
| 14c | benzene | cyclopropyl | phenyl | 1.16 ± 0.39 | >50 | 2.46 |
| 19a | thiophene | isobutenyl | thiophene | 0.931 ± 0.11 | >50 | 2.06 |
| 19b | thiophene | cyclopropyl | thiophene | 0.933 ± 0.10 | >50 | 2.89 |
| 19c | thiophene | cyclopropyl | phenyl | 0.082 ± 0.01 | >50 | 3.84 |

[a]Values represent mean ± standard error of the mean for at least two independent experiments performed in triplicate.
[b]Calculated as pEC50 - cLogP, determined by Molinspiration Cheminformatics.

The final SAR investigations focused on analog 19c and the heretofore unexplored role of the thioether and attached linker. Thus, secondary and tertiary alcohols 20a and 20b respectively indicated preference for the benzylic ketone moiety but showed only modest potency reductions, with 20a still having a desirable probe profile with <500 nM potency and a LipE of 3.41. In contrast, the thioether proved essential to biological activity, with ether and secondary amine analogs 22a and 22b respectively showing complete loss of inhibition.

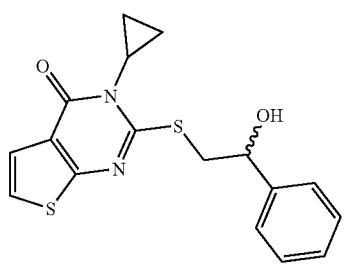

20a

EC$_{30}$: 0.481 ± 0.12 µM
LD$_{50}$: >50 µM
LipE: 3.41

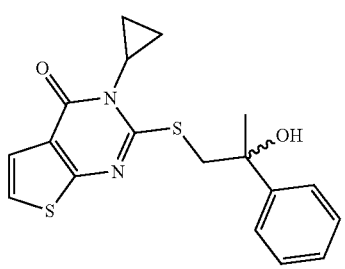

EC$_{60}$: 0.948 ± 0.02 μM
LD$_{50}$: >50 μM
LipE: 2.53

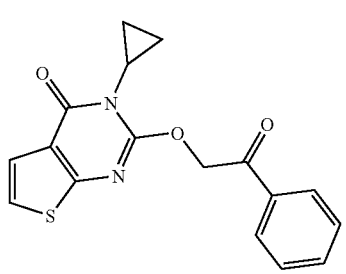

EC$_{60}$: > 20 μM
LD$_{50}$: >50 μM

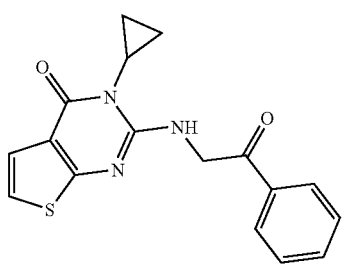

EC$_{60}$: > 20 μM
LD$_{50}$: >50 μM

SAR of the linker functionality of 19c.

In light of EGM1's ability to halt Hh transcriptional activity at a node downstream of the negative regulator Sufu, and thus also downstream of Smo, we sought to confirm mode of action retention with our most promising analogs. Therefore, we employed Sufu−/− mouse embryonic fibroblasts (MEF) that display constitutively active transcription of Hh target genes Gli1 and Ptch1 and monitored the ability of our optimized analogs to repress signaling via quantitative reverse transcription-PCR (qRT-PCR). Smo antagonists are expected to have no effect on the constitutively active signaling, and Sonidegib, tested at 0.1 μM (~100-fold its EC$_{50}$), failed to inhibit transcription of both genes (Table 14). In contrast, the Gli antagonist GANT-61 and EGM1 both showed significant reductions in transcription of Gli1 and Ptch1, with approximately 50% inhibition at 10 μM. We then evaluated improved analogs from multiple structural classes including those from Table 1 with cyclohexylthiophene cores as well as from Table 13 with structurally distinct core modifications. Strikingly, while EGM1 analogs retaining the cyclohexyl-thiophene core (9b, 9e, 9g, 9m) showed a general ability to inhibit transcriptional activity in the Sufu−/− cell line consistent with EGM1's mechanism of action, more potent TM3-Gli-Luc inhibitors lacking the western cyclohexyl ring (14b, 19b, 19c, 20a) indicated a mechanistic drift, observed as a lack of Sufu−/− transcriptional inhibition. Specifically, 14b, the most consistently potent inhibitor among the non-cyclohexylthiophene group, showed 10% reduction of Gli1 and Ptch1 mRNA transcripts at 10 μM; however, with a TM3-Gli-Luc $_{EC50}$ of 0.685 μM, these results indicate that 14b and structurally related non-cyclohexyl analogs function at a node upstream of Sufu.

TABLE 14

Summary of optimized analogs and mechanistic profiling.

| Entry | TM3-Gli-Luc EC$_{50}$ (μM) | LipE | Sufu$^{-/-}$ % Inh. Gli1 mRNA$^{a,b}$ | Sufu$^{-/-}$ % Inh. Ptch1 mRNA$^{a,b}$ | PDE4D IC$_{50}$ (μM)$^a$ |
|---|---|---|---|---|---|
| 2 | 0.0012 ± 0.0002 | 3.02 | 5.8 ± 4.0 | −0.2 ± 2.1 | — |
| 3 | 1.34 ± 0.002 | 0.73 | 46.5 ± 5.1 | 32.2 ± 1.9 | 0.380 ± 0.02 |
| 4 | 9.27 ± 1.8 | 1.34 | 43.8 ± 5.2 | 52.8 ± 2.7 | — |
| 9b | 1.89 ± 0.75 | 1.40 | 26.8 ± 8.4 | 26.5 ± 1.1 | N/D |
| 9e | 1.30 ± 0.18 | 1.06 | 44.9 ± 5.1 | 39.9 ± 6.6 | 0.486 ± 0.001 |
| 9g | 5.70 ± 2.1 | −0.01 | 64.8 ± 0.65 | 60.4 ± 1.9 | 0.965 ± 0.10 |
| 9m | 2.32 ± 0.73 | 0.94 | 35.0 ± 2.1 | 49.2 ± 1.8 | N/D |
| 14b | 0.685 ± 0.02 | 2.78 | 10.3 ± 4.8 | 9.9 ± 5.6 | N/D |
| 19b | 0.933 ± 0.10 | 2.89 | 5.5 ± 4.4 | −3.3 ± 2.2 | N/D |
| 19c | 0.082 ± 0.01 | 3.84 | 13.6 ± 2.6 | −0.3 ± 4.5 | 3.10 ± 0.48 |
| 20a | 0.481 ± 0.12 | 3.41 | 3.2 ± 2.2 | −4.8 ± 3.3 | 6.07 ± 1.5 |

$^a$Values represent mean ± standard error of the mean for at least two independent experiments performed in triplicate normalized to DMSO.
$^b$Compounds tested at 10 μM, except Sonidegib tested at 0.1 μM.
N/D = not determined.

Discussion

The examples include disclosure of identifying Eggmanone (EGM1) from a small molecule screening campaign for disrupters of developmental pattern formation in the embryonic zebrafish. Also disclosed are additional structures related to the in vivo phenotypic screening hit eggmanone. EGM1 was determined to exert its developmental perturbation through inhibition of the Hedgehog (Hh) signaling pathway in cell-based assays and was confirmed to function at a node downstream of the most commonly targeted Hh receptor Smoothened. Specifically, EGM1 inhibited the stable Gli1-based reporter cell line TM3GliLuc and transcription of Gli1 in the Hh-responsive cell line C3H10T½ as monitored by quantitative RT-PCR. EGM1 was shown to not bind to the cyclopamine binding site of Smo as evidenced by its inability to displace a fluorescent analog of cylopamine from its binding site on Smo. EGM1 reduced the transcriptional activity of the downstream Hh target gene Gli1 in the Sufu−/− cell line which displays constitutive activation due to the loss of the signaling repressor Sufu. Finally, EGM1 could not overcome constitutive activation of signaling by overexpression of the Gli1 protein, thus indicating that EGM1 functioned between Sufu and Gli to effect Hh signaling inhibition.

Based on this cellular profile and the potential clinical value of a downstream of Smo Hh inhibitor, analogs of EGM1 were identified with improved cellular potency and aqueous solubility. From a high content in vivo screen for modulators of developmental patterning in embryonic zebrafish, eggmanone (EGM1) was identified as a Hedgehog (Hh) signaling inhibitor functioning downstream of Smoothened. Phenotypic optimization studies for in vitro probe development utilizing a Gli transcription-linked stable luciferase reporter cell line identified EGM1 analogs with improved potency and aqueous solubility. Mechanistic profiling of optimized analogs indicated two distinct scaffold clusters: PDE4 inhibitors able to inhibit downstream of Sufu, and PDE4-independent Hh inhibitors functioning between Smo and Sufu. Each class represents valuable in vitro probes for elucidating the complex mechanisms of Hh regulation. Multiple factors may be responsible for the divergence of EGM1 analogs' efficacy in the Sufu$^{-/-}$ cell line; therefore, we profiled select analogs were profiled in a set of assays devised to illuminate their mechanistic underpinnings. First, the contribution of PDE4 was revisited as a potential explanation for the observed mechanistic drift. Against the consensus PDE4D sequence, EGM1 displayed an $IC_{50}$ of 0.380 µM, slightly less potent than previously reported but likely due to minor isoform variation. Related cyclohexylthiophene analogs 9e and 9g tracked well with EGM1's $IC_{50}$:$EC_{50}$ ratio; however, interestingly the potent Hh inhibitors 19c and 20a showed only modest ICs against PDE4D. These results indicate that the ability of cyclohexylthiophene analogs to function downstream of Sufu is dependent on their ability to inhibit PDE4, and that the observed mechanistic drift of non-cyclohexylthiophene analogs results from a decreased ability to inhibit PDE4.

Next, considering the mechanistic drift of robotnikinin analogs to Smo antagonists, we evaluated 14b, 19b, 19c, and 20a in a competition assay for the Smo cyclopamine (Cyc) binding site to determine if the Hh potency of non-cyclohexylthiophene analogs could be explained by Smo antagonism (FIG. 44). Thus, HEK-293T cells overexpressing Smo were concurrently treated with 5 nM BODIPY-Cyc and molecules of interest. The potent Smo antagonist KAAD-Cyc completely displaced BODIPY-Cyc at 200 nM, and EGM1, as previously reported, showed no ability to compete for Smo binding. At the indicated concentrations (10- to 20-fold their $EC_{50s}$), non-cyclohexylthiophene analogs 14b, 19b, 19c, and 20a failed to compete for the Smo binding site, indicating that their functional target lay in between Smo and Sufu. Finally, EGM1 and analogs from Table 14 do not inhibit luciferase, as tested in a BMP-responsive element stable reporter cell line (data not shown).

Phenotypic screening and subsequent development allows for relevant clinical mechanism-driven discovery and optimization as well as novel target elucidation for improved targeted therapy strategies. Using this phenotypic optimization strategy, we have identified small molecule Hh inhibitors based on the EGM1 scaffold. As EGM1 functions downstream of the most targeted node within the pathway which is also commonly associated with clinical resistance, we expected analogs to retain this activity. Removal of the western-most cyclohexyl ring provided analogs with significant TM3-Gli-Luc potency and solubility improvements, with 19c constituting our most promising compound. This analog series displayed an inability to inhibit constitutively active signaling at or downstream of Sufu, in contrast to EGM1 and cyclohexylthiophene analogs, which was correlated with reduced PDE4 inhibition; however, these compounds do not antagonize Smo. Additionally, cyclohexylthiophene analogs 9b and 9e, which retain the ability to inhibit both PDE4 and Hh signaling downstream of Sufu, constitute EGM1 analogs with improved aqueous solubility.

In summary, our results indicate that non-cyclohexylthiophene analogs inhibit Hh signaling via a PDE4-independent mechanism which functions in between Smo and Sufu, whereas cyclohexylthiophene analogs inhibit Hh signaling via a PDE4-dependent mechanism downstream of Sufu. It is thus notable that this PDE4-independent activity leading to significant improvements in Hh inhibition potency would have not been discovered using a target-based optimization approach. Without being bound by theory, it is likely that the parent compound EGM1 and cyclohexylthiophene analogs display dual PDE4-dependent and PDE4-independent mechanisms of action rather than that non-cyclohexylthiophene analogs gained a new functionality not present in EGM1. Compounds from both series are valuable in vitro probes, as neither compete for Smo binding, and thus will be further utilized to elucidate the complex mechanisms of Hh signal regulation toward future targeted Hh therapeutics.

Experimental Procedures

Chemistry

General Procedures:

Non-aqueous reactions were performed under an argon atmosphere in flame-dried glassware unless stated otherwise. Stainless steel syringes or cannula were used to transfer air- and moisture-sensitive liquids. Reaction temperatures were controlled using a thermocouple thermometer and analog hotplate stirrer. Reactions were conducted at room temperature (RT, approximately 23° C.) unless noted otherwise. Analytical thin layer chromatography was performed on E. Merck pre-coated silica gel 60 F254 plates and visualized using UV light. Flash column chromatography was conducted as described by Still et al.[1] using indicated solvents and Dynamic Adsorbents silica gel 60 (230-240 mesh). Yields are reported as isolated amount for spectroscopically pure compounds.

Materials:

Reagents were purchased at the highest commercial quality and used without further purification unless stated otherwise. Dichloromethane ($CH_2Cl_2$) was dried by passing commercially available solvent through activated alumina columns (MBraun MB-SPS solvent system). Tetrahydrofuran (THF) was purified by distillation from sodium metal with benzophenone indicator. When necessary, solvents were further dried over activated 4 Å molecular sieves under an atmosphere of argon overnight.

Instrumentation:

$^1$H NMR spectra were recorded on Bruker 400 or 600 MHz spectrometers and are reported relative to deuterated solvent signals ($CDCl_3$: 7.26; DMSO: 2.50). Data for $^1$H NMR spectra are reported as follows: chemical shift (δ ppm), multiplicity (s=singlet, d=doublet, t=triplet, q=quartet, p=pentet, sept.=septet, m=multiplet, br=broad), coupling constants (Hz), and integration. $^{13}$C NMR spectra were recorded at 100 or 150 MHz and are reported relative to deuterated solvent signals ($CDCl_3$: 77.0; DMSO: 39.5). LC-MS data was recorded on an Agilent Technologies 1200 Series LC instrument coupled to an Agilent Technologies 6130 Quadrupole MS with a 1 minute gradient on an AccuCore C18 2.6 µm 2.1×30 mm column, and UV traces were obtained at 215 and 254 nm. Reversed phase HPLC purification was performed on a Gilson HPLC system using a Gemini-NX Su C18 110 Å 50×21.20 mm column with $CH_3CN$ and $H_2O$ (containing 0.1% TFA). Microwave reactions were performed using a Biotage Initiator 2.0 microwave reactor.

Synthetic Procedures

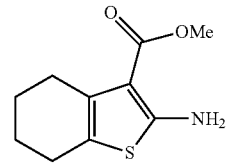

6a

To EtOH (37.5 mL) in an open flask was added S₈ (4.68 g, 150 mmol, 1.0 eq.), cyclohexanone (23.3 mL, 225 mmol, 1.5 eq.), methyl cyanoacetate (13.3. mL, 150 mmol, 1.0 eq.), and Et₃N (10.4 mL, 75 mmol, 0.5 eq.), and the reaction was stirred at rt overnight. The flask was cooled to 0° C. with no stirring for 5 h followed by collection of the precipitate by filtration. The solid was washed with ice cold EtOH then dried at rt overnight to yield 6a as an off-white solid (22.1 g, 105 mmol, 70%): $^1$H NMR (400 MHz, CDCl₃): δ 5.96 (br. s, 2H), 3.78 (s, 3H), 2.68 (ddd, J=8.2, 6.3, 2.1 Hz, 2H), 2.48 (ddd, J=7.7, 5.8, 1.8 Hz, 2H), 1.81-1.68 (m, 4H); $^{13}$C NMR (100 MHz, CDCl₃): δ 166.4, 161.8, 132.3, 117.5, 105.5, 50.5, 26.8, 24.4, 23.2, 22.7; LC-MS (ESI): m/z calcd. for C₁₀H₁₄NO₂S [M+H]⁺ 212.1, found 212.1.

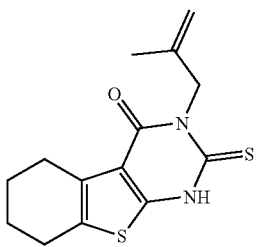

8a

To 6a (9.00 g, 42.6 mmol, 1.0 eq.) in DMSO (85.2 mL) was added simultaneously CS₂ (3.34 mL, 55.4 mmol, 1.3 eq.) and a solution of NaOH (1.70 g, 42.6 mmol, 1.0 eq.) in H₂O (2.55 mL) via syringe pump over 30 min at rt. The reaction was stirred for an additional 30 min at rt followed by addition of Me₂SO₄ (4.04 mL, 42.6 mmol, 1.0 eq.). To the thick slurry was added DMSO (10 mL) and the reaction was stirred at rt for 3 h, added to ice water (100 mL), and the solid was collected by filtration. Product was recrystallized from EtOH to yield 7a as a yellow solid (9.54 g, 31.6 mmol, 74%). $^1$H NMR (400 MHz, CDCl₃): δ 3.90 (s, 3H), 2.79-2.75 (m, 2H), 2.69 (s, 3H), 2.67-2.60 (m, 2H), 1.85-1.73 (m, 4H); $^{13}$C NMR (100 MHz, CDCl₃): δ 192.5, 167.5, 149.6, 130.8, 126.4, 113.3, 51.7, 26.2, 24.3, 22.9, 22.7, 18.4. LC-MS (ESI): m/z calcd. for C₁₂H₁₆NO₂S₃[M+H]⁺ 302.0, found 302.1.

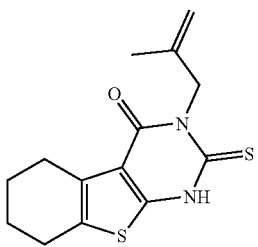

8a

To two 20 mL microwave pressure vials was each added 7a (2.50 g, 8.30 mmol, 1.0 eq.), CH₃CN (8.30 mL), and the vials were sealed. Through the septa was added methylallylamine (0.950 mL, 10.4 mmol, 1.25 eq.) and Et₃N (2.31 mL, 16.6 mmol, 2.0 eq.), and the reactions were heated at 90° C. overnight. The reactions were allowed to reach rt, diluted with EtOAc (20 mL), combined, then added to saturated NH₄Cl (50 mL) and extracted 3×25 mL with EtOAc. The combined organic layers were dried with MgSO₄, filtered, and concentrated to yield crude 8a (3.00 g, 62%) as a yellow solid which was used without further purification except recrystallized from CH₃CN for characterization purposes: $^1$H NMR (400 MHz, CDCl₃): δ 5.02 (s, 2H), 4.86 (s, 1H), 4.62 (s, 1H), 2.91 (dd, J=6.0, 6.0 Hz, 2H), 2.67 (dd, J=6.0, 5.8 Hz, 2H), 2.18 (s, 1H), 1.90-1.74 (m, 4H), 1.85 (s, 3H); $^{13}$C NMR (100 MHz, CDCl₃): δ 174.1, 156.5, 148.0, 138.4, 132.3, 129.3, 116.9, 109.7, 50.8, 25.1, 24.6, 22.8, 21.8, 20.8; LC-MS (ESI): m/z calcd. for C₁₄H₁₇N₂OS₂ [M+H]⁺ 293.1, found 293.1.

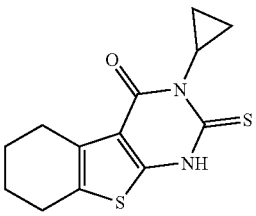

8b

To a 20 mL microwave pressure vial was added 7a (2.50 g, 8.29 mmol, 1.0 eq.), CH₃CN (8.29 mL), and the vial was sealed. Through the septum was added cyclopropylamine (718 µL, 10.4 mmol, 1.25 eq.) and Et₃N (2.31 mL, 16.6 mmol, 2.0 eq.) and the reaction was heated at 90° C. overnight. At rt, the reaction was diluted with EtOAc (25 mL), added to saturated NH₄Cl (50 mL), and extracted 3×25 mL with EtOAc. The combined organic layers were dried with MgSO₄, filtered, and concentrated to provide a crude mixture of cyclized and uncyclized thioureas (821 mg). The mixture was dissolved in 70% EtOH (13.2 mL) then added KOH (297 mg, 5.29 mmol, 2.0 eq.), and the reaction was heated at 70° C. for 1.5 h. At rt, 1 N HCl was added slowly until a precipitate formed which was collected by filtration to yield 8b as a white solid (387 mg, 1.39 mmol, 17%). $^1$H NMR (600 MHz, DMSO-d₆): δ 2.78-2.73 (m, 2H), 2.70 (tt, J=7.0, 4.1 Hz, 1H), 2.65-2.60 (m, 2H), 1.79-1.73 (m, 2H), 1.73-1.67 (m, 2H), 1.16-1.11 (m, 2H), 0.77-0.72 (m, 2H); $^{13}$C NMR (150 MHz, DMSO-d₆): δ 175.6, 157.9, 148.5, 130.9, 127.9, 116.1, 29.4, 24.9, 23.9, 22.4, 21.6, 11.8; LC-MS (ESI): m/z calcd. for C₁₃H₁₅N₂OS₂ [M+H]⁺ 279.1, found 279.1.

To a 2 mL microwave pressure vial was added 7a (500 mg, 1.66 mmol, 1.0 eq.), CH₃CN (1.66 mL), and the vial was sealed. Through the septum was added propylamine (170 µL, 2.07 mmol, 1.25 eq.) and Et₃N (462 µL, 3.32 mmol, 2.0 eq.) and the reaction was heated at 90° C. overnight. At rt, the reaction was diluted with EtOAc (10 mL), added to saturated NH₄Cl (20 mL), and extracted 3×15 mL with EtOAc. The combined organic layers were dried with MgSO₄, filtered, and concentrated to yield crude 8c (194 mg, 42%) which was used without further purification except recrystallized from CH₃CN for characterization purposes: $^1$H NMR (600 MHz, DMSO-d₆): δ 4.31-4.22 (m, 2H), 2.81-2.74 (m, 2H), 2.68-2.61 (m, 2H), 1.80-1.74 (m, 2H), 1.74-1.69 (m, 2H), 1.69-1.61 (m, 2H), 0.88 (dd, J=7.5, 7.4 Hz, 3H); $^{13}$C NMR (150 MHz, DMSO-d₆): δ 173.3, 156.4, 130.9, 128.4, 115.6, 46.7, 40.1, 24.9, 23.9, 22.4, 21.5, 19.5, 11.1; LC-MS (ESI): m/z calcd. for C₁₃H₁₇N₂OS₂ [M+H]⁺ 281.1, found 281.1.

General Procedure for S-Alkylation

To a 1 dram vial was added 8 (1.0 eq.), CH₃CN (0.2 M), alkyl halide (1.3 eq.), and Cs₂CO₃ (1.5 eq.), and following brief sonication to homogenize the slurry, the reaction was stirred at rt for 4 h. To the slurry was added cold water, and in the event of product precipitation, the precipitate was collected by filtration and washed with ice water and cold CH₃CN. In the absence of precipitation, the mixture was added to saturated NH₄Cl and extracted 3× with CH₂Cl₂. The combined organic layers were dried with MgSO₄, filtered, and concentrated. Products were recrystallized from CH₃CN.

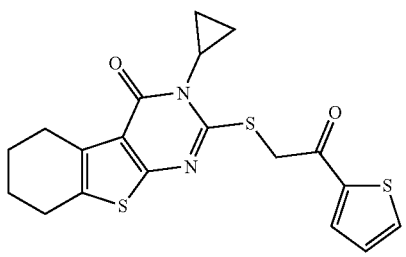

9b

9b: cyclic thiourea=8b; alkyl halide=2-(2-bromoacetyl)thiophene, (55%). ¹H NMR (400 MHz, CDCl₃): δ 7.95 (dd, J=3.9, 1.1 Hz, 1H), 7.72 (dd, J=4.9, 1.1 Hz, 1H), 7.20 (dd, J=4.9, 3.9 Hz, 1H), 4.53 (s, 2H), 2.97-2.88 (m, 2H), 2.82 (tt, J=7.0, 4.1 Hz, 1H), 2.71-2.62 (m, 2H), 1.88-1.73 (m, 4H), 1.37-1.28 (m, 2H), 1.09-1.03 (m, 2H); ¹³C NMR (100 MHz, CDCl₃): δ 186.8, 160.7, 159.4, 157.7, 143.0, 134.4, 132.9, 131.5, 131.4, 128.2, 119.2, 39.4, 26.6, 25.4, 25.0, 22.9, 22.2, 11.0; LC-MS (ESI): m/z calcd. for $C_{19}H_{19}N_2O_2S_3$ [M+H]⁺ 403.1, found 403.0.

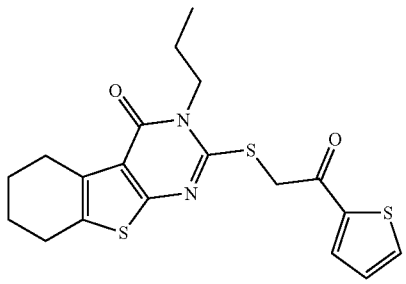

9e

9e: cyclic thiourea=8c; alkyl halide=2-(2-bromoacetyl)thiophene, (33%). ¹H NMR (600 MHz, CDCl₃): δ 7.95 (dd, J=3.9, 1.1 Hz, 1H), 7.72 (dd, J=5.0, 1.1 Hz, 1H), 7.20 (dd, J=4.9, 3.9 Hz, 1H), 4.58 (s, 2H), 4.05 (ddd, J=9.8, 8.0, 6.2 Hz, 2H), 2.98-2.91 (mn, 2H), 2.71-2.64 (mn, 2H), 1.87-1.76 (m, 6H), 1.01 (t, J=7.4 Hz, 3H); ¹³C NMR (150 MHz, CDCl₃): δ 186.4, 161.3, 158.2, 154.5, 142.8, 134.5, 133.0, 131.6, 131.3, 128.3, 118.9, 46.0, 39.3, 25.4, 25.1, 22.9, 22.2, 21.4, 11.3; LC-MS (ESI): m/z calcd. for $C_{19}H_{21}N_2O_2S_3$[M+H]⁺ 405.1, found 405.0.

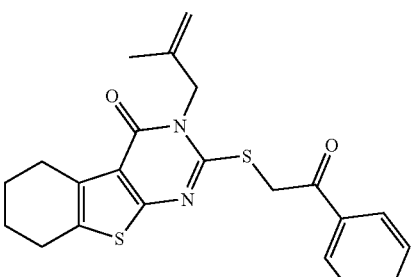

9g

9g: cyclic thiourea=8a; alkyl halide=2-chloroacetophenone, (55%). ¹H NMR (400 MHz, CDCl₃): δ 8.09-8.01 (mn, 2H), 7.66-7.59 (m, 1H), 7.56-7.47 (m, 2H), 4.92 (s, 1H), 4.71 (s, 2H), 4.67 (s, 2H), 4.64 (s, 1H), 3.00-2.91 (m, 2H), 2.72-2.64 (m, 2H), 1.89-1.74 (m, 4H), 1.83 (s, 3H); ¹³C NMR (100 MHz, CDCl₃): δ 193.5, 161.5, 158.0, 155.4, 138.3, 136.2, 133.6, 131.7, 131.5, 128.7, 128.5, 118.7, 111.0, 48.5, 39.8, 25.4, 25.1, 22.9, 22.2, 20.3; LC-MS (ESI): m/z calcd. for $C_{22}H_{23}N_2O_2S_2$[M+H]⁺ 411.1, found 411.1.

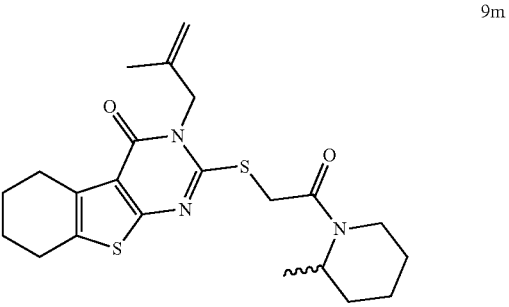 [SMILES: C=C(C)Cn1c(SCC(=O)N2CCCCC2C)nc2sc3c(c2c1=O)CCCC3]

9m

9m: cyclic thiourea=8a; alkyl halide=2-chloro-1-(2-methylpiperidin-1-yl)ethan-1-one, (30%); ~2:1 conformational mixture: ¹H NMR (600 MHz, CDCl₃): δ 4.95-4.42 (m, 5H), 4.38-3.75 (m, 3H), 3.33-2.69 (m, 5H), 1.91-1.84 (m, 2H), 1.84-1.79 (m, 5H), 1.79-1.72 (m, 1H), 1.72-1.60 (m, 4H), 1.59-1.47 (m, 1H), 1.37-1.11 (m, 3H); ¹³C NMR (* denotes minor conformation peaks, 150 MHz, CDCl₃): δ 165.3, 161.8, 158.1, 156.3, 138.3, 131.6, 131.4, 118.7, 110.9, 49.1*, 48.3, 44.6*, 41.5*, 37.0*, 36.6*, 36.3*, 30.8*, 29.7*, 26.3*, 25.5, 25.4, 25.1, 22.9, 22.2, 20.4, 18.6, 16.9*, 15.5*; LC-MS (ESI): m/z calcd. for $C_{22}H_{30}N_3O_2S_2$ [M+H]⁺ 432.2, found 432.1.

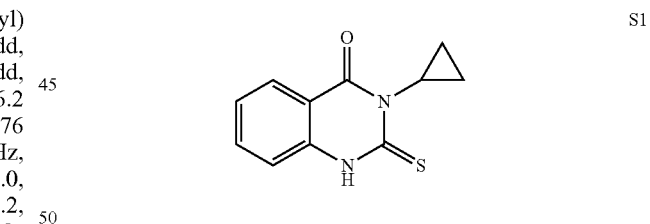

S1

To a 5 mL microwave pressure vial was added methyl anthranilate (129 μL, 1.00 mmol, 1.0 eq.) and PhCH₃ (1.00 mL), and the vial was capped and placed under an atmosphere of argon. Through the septum was added cyclopropylisothiocyanate (94 μL, 1.00 mmol, 1.0 eq.), and the reaction was heated at 115° C. for 72 h. At rt, the precipitate was collected by filtration and washed with cold PhCH₃ to yield crude S1 (189 mg, 87%) which was used without further purification except recrystallized from CH₃CN for characterization purposes: ¹H NMR (600 MHz, DMSO-d₆): δ 7.92 (d, J=7.6 Hz, 1H), 7.69 (td, J=8.1, 1.0 Hz, 1H), 7.34 (d, J=8.4 Hz, 1H), 7.29 (dd, J=7.6, 7.4 Hz, 1H), 2.81 (tt, J=7.0, 4.0 Hz, 1H), 1.19-1.12 (m, 2H), 0.83-0.77 (m, 2H); ¹³C NMR (150 MHz, DMSO-d₆): δ 177.1, 160.7, 139.3, 135.0, 127.1, 124.0, 116.3, 115.3, 29.6, 11.6; LC-MS (ESI): m/z calcd. for $C_{11}H_{11}N_2OS$ [M+H]⁺ 219.1, found 219.1.

14b

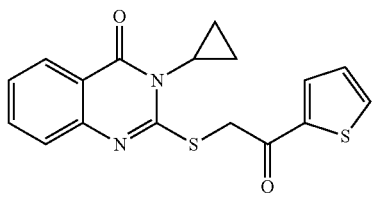

Following General Procedure for S-Alkylation, 14b: cyclic thiourea=S1; alkyl halide=2-(2-chloroacetyl)thiophene, (47%). $^1$H NMR (600 MHz, CDCl$_3$): δ 8.14 (dd, J=7.9, 1.3 Hz, 1H), 8.00 (dd, J=3.9, 0.9 Hz, 1H), 7.74 (dd, J=4.9, 1.0 Hz, 1H), 7.55 (td, J=8.4, 1.5 Hz, 1H), 7.31 (td, J=8.0, 0.9 Hz, 1H), 7.22 (dd, J=4.9, 3.8 Hz, 1H), 7.11 (d, J=8.2 Hz, 1H), 4.58 (s, 2H), 2.93 (tt, J=6.9, 4.0 Hz, 1H), 1.38-1.32 (m, 2H), 1.12-1.07 (m, 2H); $^{13}$C NMR (150 MHz, CDCl$_3$): δ 186.7, 162.5, 158.0, 146.7, 143.2, 134.3, 134.1, 132.7, 128.2, 126.8, 125.8, 125.4, 119.8, 39.3, 26.8, 11.0; LC-MS (ESI): m/z calcd. for C$_{17}$H$_{15}$N$_2$O$_2$S$_2$ [M+H]$^+$ 343.1, found 343.1.

16

To two 20 mL microwave pressure vials was each added 1,4-dithiane-2,5-diol (2.0 g, 13.1 mmol, 1.0 eq.) and MeOH (10.5 mL), and the vials were sealed. Through the septa was added methylcyanoacetate (2.32 mL, 26.3 mmol, 2.0 eq.), Et$_3$N (1.28 mL, 9.20 mmol, 0.7 eq.), and DMF (3 drops), and the reactions were heated via microwave irradiation at 50° C. for 3 min. At rt, the precipitates were combined and collected by filtration and washed with cold MeOH to provide 16 as a white solid (3.88 g, 24.7 mmol, 94%): $^1$H NMR (600 MHz, CDCl$_3$): δ 6.96 (d, J=5.7 Hz, 1H), 6.18 (d, J=5.8 Hz, 1H), 3.81 (s, 3H); $^{13}$C NMR (150 MHz, CDCl$_3$): δ 165.8, 162.7, 125.8, 107.0, 106.9, 51.0; LC-MS (ESI): m/z calcd. for C$_6$H$_8$NO$_2$S [M+H]$^+$ 158.0, found 158.2.

17

To 16 (3.88 g, 24.7 mmol, 1.0 eq.) in DMSO (24.7 mL) at rt was added simultaneously CS$_2$ (1.94 mL, 32.1 mmol, 1.3 eq.) and a solution of NaOH (987 mg, 24.7 mmol, 1.0 eq.) in H$_2$O (1.48 mL) via syringe pump over 30 min at rt. The reaction was stirred for an additional 40 min at rt followed by addition of Me$_2$SO$_4$ (2.34 mL, 24.7 mmol, 1.0 eq). The reaction was stirred at rt for 2 h, added to ice water (100 mL), and the solid was collected by filtration and washed with ice water to yield 17 as an orange solid (5.09 g, 20.6 mmol, 83%): $^1$H NMR (600 MHz, CDCl$_3$): δ 7.25 (d, J=5.8 Hz, 1H), 6.72 (dd, J=5.8, 0.4 Hz, 1H), 3.92 (s, 3H), 2.72 (s, 3H); $^{13}$C NMR (150 MHz, CDCl$_3$): δ 193.7, 166.4, 150.9, 123.5, 115.2, 114.4, 52.0, 18.6; LC-MS (ESI): m/z calcd. for C$_8$H$_{10}$NO$_2$S$_3$ [M+H]$^+$ 248.0, found 247.9.

18b

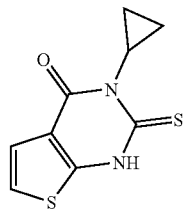

To a 20 mL microwave pressure vial was added 17 (1.00 g, 4.04 mmol, 1.0 eq.) and the vial was sealed and placed under an atmosphere of argon. Through the septum was added CH$_3$CN (4.04 mL), cyclopropylamine (350 μL, 5.05 mmol, 1.25 eq.), and Et$_3$N (1.13 mL, 8.09 mmol, 2.0 eq.), and the reaction was heated at 90° C. overnight. At rt, the reaction was diluted with EtOAc (10 mL), added to saturated NH$_4$Cl (25 mL), and extracted 3×15 mL with EtOAc. The combined organic layers were dried with MgSO$_4$, filtered and concentrated to provide a crude mixture of cyclized and uncyclized thioureas. The mixture was dissolved in 70% EtOH (20.2 mL) then added KOH (454 mg, 8.09 mmol, 2.0 eq.), and the reaction was heated at 75° C. for 3 h. At rt, 1 N HCl was added slowly until a precipitate formed which was collected by filtration to yield 18b as a white solid (518 mg, 2.31 mmol, 57%): $^1$H NMR (600 MHz, DMSO-d$_6$): δ 7.23 (d, J=5.5 Hz, 1H), 7.19 (d, J=5.4 Hz, 1H), 2.78-2.71 (m, 1H), 1.19-1.12 (m, 2H), 0.82-0.76 (m, 2H); $^{13}$C NMR (150 MHz, DMSO-d$_6$): δ 176.3, 157.7, 150.2, 122.2, 119.6, 118.4, 29.6, 11.7; LC-MS (ESI): m/z calcd. for C$_9$H9N$_2$OS$_2$ [M+H]$^+$ 225.0, found 225.0.

19b

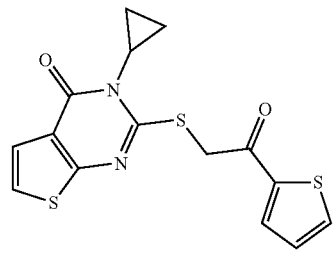

Following General Procedure for S-Alkylation, 19b: cyclic thiourea=18b; alkyl halide=2-(2-chloroacetyl)thiophene, (47%). $^1$H NMR (600 MHz, CDCl$_3$): δ 7.95 (dd, J=3.8, 1.0 Hz, 1H), 7.73 (dd, J=5.0, 1.0 Hz, 1H), 7.33 (d, J=5.8 Hz, 1H), 7.21 (dd, J=4.9, 3.8 Hz, 1H), 6.99 (d, J=5.8 Hz, 1H), 4.56 (s, 2H), 2.88 (tt, J=7.1, 4.1 Hz, 1H), 1.39-1.33 (m, 2H), 1.12-1.07 (m, 2H); $^{13}$C NMR (150 MHz, CDCl$_3$): δ 186.6, 162.3, 159.2, 159.1, 142.9, 134.5, 132.9, 128.3, 122.2, 121.2, 121.1, 39.6, 26.8, 11.1; LC-MS (ESI): m/z calcd. for C$_{15}$H$_{13}$N$_2$O$_2$S$_3$ [M+H]$^+$ 349.0, found 349.0.

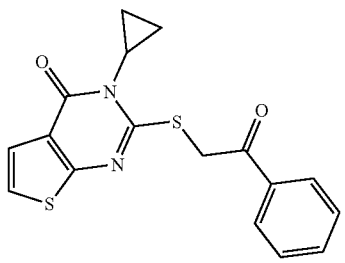

19c

Following General Procedure for S-Alkylation, 19c: cyclic thiourea=18b; 2-chloroacetophenone, (44%). $^1$H NMR (600 MHz, CDCl$_3$): δ 8.08 (d, J=7.5 Hz, 2H), 7.64 (t, J=7.4 Hz, 1H), 7.54 (dd, J=7.8, 7.7 Hz, 2H), 7.33 (d, J=5.8 Hz, 1H), 6.99 (d, J=5.8 Hz, 1H), 4.66 (s, 2H), 2.89 (tt, J=7.0, 4.1 Hz, 1H), 1.37 (dd, J=14.0, 7.0 Hz, 2H), 1.11 (dd, J=10.3, 7.7 Hz, 2H); $^{13}$C NMR (150 MHz, CDCl$_3$): δ 193.8, 162.3, 159.4, 159.1, 136.3, 133.6, 128.8, 128.5, 122.2, 121.2, 121.1, 39.8, 26.9, 11.1; LC-MS (ESI): m/z calcd. for C$_{17}$H$_{15}$N$_2$O$_2$S$_2$ [M+H]$^+$ 343.1, found 343.0.

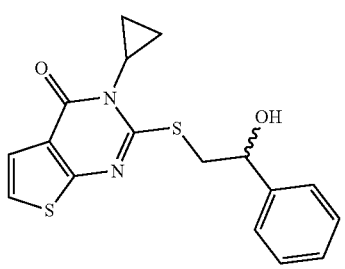

20a

To 19c (50 mg, 0.146 mmol, 1.0 eq.) in THF/EtOH (1:1, 730 µL) at 0° C. was added NaBH$_4$ (8.3 mg, 0.219 mmol, 1.5 eq.) and the reaction was stirred at rt for 2 h. The reaction was diluted with CH$_2$Cl$_2$ (5 mL), added to saturated NH$_4$Cl, and extracted 3×5 mL) with CH$_2$Cl$_2$. The combined organics were dried with MgSO$_4$, filtered, and concentrated. Flash column chromatography with a gradient of 20-50% EtOAc/hexanes provided 20a as an orange solid (33 mg, 0.0958 mmol, 66%); $^1$H NMR (600 MHz, CDCl$_3$): δ 7.47 (d, J=7.3 Hz, 2H), 7.40 (dd, J=7.8, 7.5 Hz, 2H), 7.37 (d, J=5.7 Hz, 1H), 7.32 (dd, J=7.4, 7.3 Hz, 1H), 7.07 (d, J=5.7 Hz, 1H), 5.11 (dd, J=8.4, 3.1 Hz, 1H), 3.69 (dd, J=14.4, 3.2 Hz, 1H), 3.42 (dd, J=14.4, 8.5 Hz, 1H), 2.82 (tt, J=6.9, 4.2 Hz, 1H), 2.49 (br. s, 1H), 1.38-1.29 (m, 2H), 1.10-1.01 (m, 2H); $^{13}$C NMR (150 MHz, CDCl$_3$): δ 162.2, 161.4, 159.1, 142.8, 128.6, 128.0, 125.8, 122.3, 121.3, 121.2, 73.4, 41.3, 27.0, 11.3, 11.2; LC-MS (ESI): m/z calcd. for C$_{17}$H17N$_2$O$_2$S$_2$ [M+H]$^+$ 345.1, found 345.1.

Biology

Cell Lines and Reagents:

TM3-Gli-Luc cells were maintained on sterile 0.1% gelatin (from porcine skin, Type A, prepared in MilliQ water, autoclaved, then sterile-filtered) in 1:1 Dulbecco's Modified Eagle Medium (DMEM)/F12 supplemented with 5% horse serum, 2.5% fetal bovine serum (FBS), and 15 mM HEPES, hereafter referred to as TM3 Culture Medium. For small molecule evaluation, TM3-Gli-Luc cells were assayed on 0.1% gelatin in DMEM/F12 supplemented with 2.5% FBS and 15 mM HEPES, hereafter referred to as TM3Luc Medium. Sufu$^{-/-}$ cells were maintained in DMEM supplemented with 4.5 g/L D-glucose, L-glutamine, 25 mM HEPES, and 10% FBS, hereafter referred to as D10 FBS. For small molecule evaluation, Sufu$^{-/-}$ cells were assayed in DMEM supplemented with 4.5 g/L D-glucose, L-glutamine, 25 mM HEPES, and 0.5% FBS, hereafter referred to as D0.5 FBS. All cells were cultured at 37° C. with a 5% CO$_2$ atmosphere.

GDC-0449, LDE225, and GANT-61 were purchased from Selleck Chemicals (Houston, Tex., USA). SAG was purchased from Cayman Chemical (Ann Arbor, Mich., USA). All small molecules were dissolved in molecular biology-grade DMSO to 10 mM and stored in glass vials at 4° C., except SAG which was dissolved to 2.5 mM in DMSO. Negative controls utilized equi-volume amounts of DMSO as compared to compound treated conditions unless stated otherwise.

TM3-Gli-Luc Cell Treatment with Small Molecules for Luciferase and Cell Viability Assays:

On the day of cell plating, 96-well plates were coated with 50 µL/well of sterile 0.1% gelatin for 5 minutes then aspirated and replaced with 50 µL/well of TM3 Culture Medium. TM3-Gli-Luc cells were seeded at a density of 5,000 cells/well in TM3 Culture Medium and incubated for 24 hours. A master mix of 20 nM SAG in TM3Luc Medium was prepared, and small molecule solutions were prepared by adding the desired amount of compound from 10 mM DMSO stock to TM3Luc Medium containing 20 nM SAG. Negative control was prepared by adding an equi-volume amount of DMSO as compared to small molecule treated conditions to TM3Luc Medium not containing SAG. Cell plating medium was aspirated and replaced with 100 µL/well of prepared small molecule-containing media, and plates were incubated for 48 hours before proceeding to luciferase activity and cell viability reading.

Luciferase Activity and Cell Viability Measurement:

TM3Luc Medium from compound treated plates was aspirated and replaced with 82 µL/well of Glo Lysis Buffer (Promega, Madison, Wis., USA), and plates were shaken at 300 rpm and room temperature for 12 minutes. Lysate was split between two white 96-well plates, 45 µL/well and 25 µL/well for luciferase reading and cell viability respectively. For luciferase activity monitoring, 45 µL/well of Steady Glo (Promega, Madison, Wis., USA) was added to 45 µL/well of cell lysate, incubated at room temperature for 5 minutes, then luminescence was measured on a Turner Biosystems Modulus Microplate Reader (Sunnyvale, Calif., USA) with an integration time of 0.5 seconds. For cell viability measurement, 25 µL/well of Cell Titer Glo (Promega, Madison, Wis., USA) (prepared by 1:10 dilution with Glo Lysis Buffer) was added to 25 µL/well of cell lysate, incubated at room temperature for 5 minutes, then luminescence was measured as above.

Luciferase Activity Data Analysis:

Luciferase activity data (Steady Glo) was divided by corresponding cell viability data (Cell Titer Glo) to arrive at a live cell number-normalized luciferase activity reading. The average of negative control data (DMSO treated) was subtracted from all wells, and percent activity was calculated by dividing all wells by the positive control (SAG treated) average. EC$_{50}$s were determined using GraphPad Prism 6 (GraphPad Software, La Jolla, Calif., USA) using a nonlinear regression variable slope (four parameter or normalized response) model of percent pathway activity data including positive control as 100% and represent each concentration tested in triplicate. At least two independent assays tested on separate days were averaged to provide EC$_{50}$±standard error of the mean.

Cell Viability Data Analysis:

All raw data was divided by the average of positive control cell titer data to arrive at percent cells remaining compared to positive control. $LD_{50}$s were determined using GraphPad Prism 6 (GraphPad Software, La Jolla, Calif., USA) using a nonlinear regression variable slope (log inhibitor vs. normalized response) model of percent cells remaining including positive control as 100% and represent each concentration tested in triplicate. At least two independent assays tested on separate days were averaged to provide $LD_{50}$±standard error of the mean.

Sufu$^{-/-}$ Cell Treatment with Small Molecules for RNA Isolation:

Sufu$^{-/-}$ cells were seeded into 12-well plates at a density of 100,000 cells/well in D10 FBS and incubated for 24 hours. Small molecule solutions were prepared by adding the desired amount of compound from 10 mM DMSO stock to D0.5 FBS. Negative control was prepared by adding an equi-volume amount of DMSO to D0.5 FBS as compared to small molecule treated conditions. Cell plating medium was aspirated and replaced with 1 mL of prepared small molecule-containing media, and plates were incubated for 24 hours before proceeding to RNA isolation.

Total RNA Isolation:

Cells were washed 1× with 1× phosphate-buffered saline (PBS) then RNA was isolated using the Qiagen RNeasy Mini Kit (Qiagen, Germantown, Md., USA) according to the manufacturer's protocol, eluting RNA from the spin column with 30 µL of RNase-free water. RNA was placed on ice and immediately subjected to reverse transcription. Remaining RNA was stored at −80° C.

Reverse Transcription PCR:

Reverse transcription polymerase chain reaction (RT-PCR) was performed with the Applied Biosystems High Capacity cDNA Reverse Transcription Kit (ThermoFisher Scientific, Waltham, Mass., USA) using an Eppendorf MasterCycler. Each 20 µL reaction contained 0.5 µg of total RNA, 2 µL of 10×RT Buffer, 0.8 µL of 25×dNTP Mix (100 mM), 2 µL of 10×RT Random Primers, 1 µL of MultiScribe® Reverse Transcriptase (50 U/µL), 1 µL of Recombinant RNasin® Ribonuclease Inhibitor (40 U/µL) (Promega, Madison, Wis., USA), and nuclease-free water. Reverse transcription was performed with the following program: 25° C. for 10 minutes, 37° C. for 120 minutes, and 85° C. for 5 minutes. The cDNA was subjected to quantitative real-time PCR (Q-PCR) or stored at −20° C.

Quantitative Real-Time PCR for Hh Pathway Transcripts:

Quantitative real-time PCR was performed on an Applied Biosystems 7900 HT Fast Real Time PCR System in 384-well format. Each cDNA sample was assayed in triplicate with both probe of interest and control probe. Master mixes for each probe were prepared corresponding to 10 µL of Applied Biosystems TaqMan Universal PCR Master Mix (ThermoFisher Scientific, Waltham, Mass., USA), 1 µL of primer, and nuclease-free water corresponding to a volume providing 20 µL reactions when loading an average of 50 ng of cDNA. Quantitative real-time PCR was run with the following thermal cycling protocol: 50° C. for 2 min., 95° C. for 10 min., and 40 cycles of 95° C. for 15 seconds, 60° C. for 1 min., then fluorescence reading. The following FAM probes were purchased from Life Technologies (Carlsbad, Calif., USA): mouse GAPDH, Mm99999915_g1; mouse Gli1, Mm00494646_g1; mouse Ptch1, Mm01306905_m1.

Q-PCR Data Analysis:

Quantitative real-time PCR data for Hh signaling inhibition was quantitated using the ΔΔCt method. Control probe values were subtracted from probe of interest values to arrive at the ΔCt value. The ΔCt value was transformed by $2^{-\Delta Ct}$ to arrive at the ΔΔCt value. All ΔΔCt values were divided by the average negative control ΔΔCt value to provide percent Hh signaling activity. Percent inhibition values were derived by calculating the inverse of percent activity. Data is reported as mean±standard error of the mean (SEM), representing at least two biological replicates, each quantitated in triplicate.

Example 15

The effects of EGM treatment on RSV in vivo were explored. RSV strains were propagated and titrated in HEp-2 cells, as previously described. Mice were housed in microisolator cages under specific pathogen-free conditions. For infection, mice were anesthetized with a ketamine/xylazine solution and inoculated by means of intranasal delivery of equal units plaque-forming units (PFU) of RSV. Animals were separated into Control (DMSO) receiving 3× daily intraperitoneal (IP) injections of 20 uL Dimethyl sulphoxide and Treatment (EGM) receiving 3× daily IP injections of 20 ul 50 mM Eggmanone stock (for final 20 mg/kg). (FIG. 45(a)). Animals were then monitored for body weight and then sacrificed at day 4 and day 6 for lung harvest plaque assay. Lung homogenates were generated and were used to inoculate a monolayer of HEp-2 cells. The infected monolayers were incubated in semi-solid methyl cellulose media for several days to allow formation of plaques. Because semi-solid media prevents spread of the virus (otherwise seen in liquid media), infection of cells is localized and virus released from an infected cell can infect only cells in the immediate surrounding of the originally-infected one thus producing a plaque. The plaques were visualized against background of healthy cells stained with crystal violet stain. One plaque corresponds to one plaque-forming unit of RSV and total number of plaques reflects amount of infectious virions present in the original lung sample. As shown in FIG. 45, normalized body weight after administration with EGM was slightly lower than that with control (FIG. 45(b)), with significantly reduced viral titer at day 3 after treatment with EGM versus control (FIG. 45(c)).

Throughout this document, various references are mentioned. All such references are incorporated herein by reference, including the references set forth in the following list:

REFERENCES 1. van Eeden, F. J., et al., Genetic analysis of fin formation in the zebra fish, *Danio rerio*. Development, 1996. 123: p. 255-62.
2. Taipale, J., et al., Effects of oncogenic mutations in Smoothened and Patched can be reversed by cyclopamine. Nature, 2000. 406(6799): p. 1005-9.
3. Cooper, M. K., et al., Teratogen-mediated inhibition of target tissue response to Shh signaling. Science, 1998. 280(5369): p. 1603-7.
4. Incardona, J. P., et al., The teratogenic Veratrum alkaloid cyclopamine inhibits sonic Hedgehog signal transduction. Development, 1998. 125(18): p. 3553-62.
5. Lawson, N. D., A. M. Vogel, and B. M. Weinstein, sonic Hedgehog and vascular endothelial growth factor act upstream of the Notch pathway during arterial endothelial differentiation. Dev Cell, 2002. 3(1): p. 127-36.
6. Chen, W., S. Burgess, and N. Hopkins, Analysis of the zebrafish smoothened mutant reveals conserved and divergent functions of Hedgehog activity. Development, 2001. 128(12): p. 2385-96.

7. Gering, J., et al., Taking a patient safety approach to an integration of two hospitals. Jt Comm J Qual Patient Saf, 2005. 31(5): p. 258-66.
8. Sasaki, H., et al., A binding site for Gli proteins is essential for HNF-3beta floor plate enhancer activity in transgenics and can respond to Shh in vitro. Development, 1997. 124(7): p. 1313-22.
9. Wu, X, et al., A small molecule with osteogenesis-inducing activity in multipotent mesenchymal progenitor cells. J Am Chem Soc, 2002. 124(49): p. 14520-1.
10. Sinha, S. and J. K. Chen, Purmorphamine activates the Hedgehog pathway by targeting Smoothened. Nat Chem Biol, 2006. 2(1): p. 29-30.
11. Gering, M. and R. Patient, Hedgehog signaling is required for adult blood stem cell formation in zebrafish embryos. Dev Cell, 2005. 8(3): p. 389-400.
12. Xie, J., et al., Activating Smoothened mutations in sporadic basal-cell carcinoma. Nature, 1998. 391(6662): p. 90-2.
13. Ingham, P. W. and A. P. McMahon, Hedgehog signaling in animal development: paradigms and principles. Genes Dev, 2001. 15(23): p. 3059-87.
14. Chiang, C., et al., Cyclopia and defective axial patterning in mice lacking Sonic Hedgehog gene function. Nature, 1996. 383(6599): p. 407-13.
15. Fietz, M. J., et al., The Hedgehog gene family in Drosophila and vertebrate development. Dev Suppl, 1994: p. 43-51.
16. Nusslein-Volhard, C. and E. Wieschaus, Mutations affecting segment number and polarity in Drosophila. Nature, 1980. 287(5785): p. 795-801.
17. McMahon, A. P., P. W. Ingham, and C. J. Tabin, Developmental roles and clinical significance of Hedgehog signaling. Curr Top Dev Biol, 2003. 53: p. 1-114.
18. Chiang, C., et al., Essential role for Sonic Hedgehog during hair follicle morphogenesis. Dev Biol, 1999. 205 (1): p. 1-9.
19. Pasca di Magliano, M. and M. Hebrok, Hedgehog signalling in cancer formation and maintenance. Nat Rev Cancer, 2003. 3(12): p. 903-11.
20. Kasper, M., et al., GLI transcription factors: mediators of oncogenic Hedgehog signalling. Eur J Cancer, 2006. 42(4): p. 437-45.
21. Gailani, M. R. and A. E. Bale, Developmental genes and cancer: role of patched in basal cell carcinoma of the skin. J Natl Cancer Inst, 1997. 89(15): p. 1103-9.
22. Stecca, B. and A. Ruiz i Altaba, Brain as a paradigm of organ growth: Hedgehog-Gli signaling in neural stem cells and brain tumors. J Neurobiol, 2005. 64(4): p. 476-90.
23. Thayer, S. P., et al., Hedgehog is an early and late mediator of pancreatic cancer tumorigenesis. Nature, 2003. 425(6960): p. 851-6.
24. Watkins, D. N., et al., Hedgehog signalling within airway epithelial progenitors and in small-cell lung cancer. Nature, 2003. 422(6929): p. 313-7.
25. Peacock, C. D., et al., Hedgehog signaling maintains a tumor stem cell compartment in multiple myeloma. Proc Natl Acad Sci USA, 2007. 104(10): p. 4048-53.
26. Stecca, B., et al., Melanomas require HEDGEHOG-GLI signaling regulated by interactions between GLI1 and the RAS-MEK/AKT pathways. Proc Natl Acad Sci USA, 2007. 104(14): p. 5895-900.
27. Karhadkar, S. S., et al., Hedgehog signalling in prostate regeneration, neoplasia and metastasis. Nature, 2004. 431(7009): p. 707-12.
28. Berman, D. M., et al., Widespread requirement for Hedgehog ligand stimulation in growth of digestive tract tumours. Nature, 2003. 425(6960): p. 846-51.
29. Yauch, R. L., et al., A paracrine requirement for Hedgehog signalling in cancer. Nature, 2008.
30. Clement, V., et al., HEDGEHOG-GLI1 signaling regulates human glioma growth, cancer stem cell self-renewal, and tumorigenicity. Curr Biol, 2007. 17(2): p. 165-72.
31. Beachy, P. A., S. S. Karhadkar, and D. M. Berman, Tissue repair and stem cell renewal in carcinogenesis. Nature, 2004. 432(7015): p. 324-31.
32. Frank-Kamenetsky, M., et al., Small-molecule modulators of Hedgehog signaling: identification and characterization of Smoothened agonists and antagonists. 1 Biol, 2002. 1(2): p. 10.
33. Hosoya, T., et al., Naturally occurring small-molecule inhibitors of Hedgehog/GLI-mediated transcription. Chembiochem, 2008. 9(7): p. 1082-92.
34. Chen, J. K., et al., Small molecule modulation of Smoothened activity. Proc Natl Acad Sci USA, 2002. 99(22): p. 14071-6.
35. Williams, J. A., et al., Identification of a small molecule inhibitor of the Hedgehog signaling pathway: effects on basal cell carcinoma-like lesions. Proc Natl Acad Sci USA, 2003. 100(8): p. 4616-21.
36. Rahnama, F., et al., Inhibition of GLI1 gene activation by Patched1. Biochem 1, 2006. 394(Pt 1): p. 19-26.
37. Berman, D. M., et al., Medulloblastoma growth inhibition by Hedgehog pathway blockade. Science, 2002. 297(5586): p. 1559-61.
38. Hahn, H., et al., Mutations of the human homolog of Drosophila patched in the nevoid basal cell carcinoma syndrome. Cell, 1996. 85(6): p. 841-51.
39. Gailani, M. R., et al., The role of the human homologue of Drosophila patched in sporadic basal cell carcinomas. Nat Genet, 1996. 14(1): p. 78-81.
40. Johnson, R. L., et al., Human homolog of patched, a candidate gene for the basal cell nevus syndrome. Science, 1996. 272(5268): p. 1668-71.
41. Sanchez, P., et al., Inhibition of prostate cancer proliferation by interference with SONIC HEDGEHOG-GLI1 signaling. Proc Natl Acad Sci USA, 2004. 101(34): p. 12561-6.
42. Feldmann, G., et al., Blockade of Hedgehog signaling inhibits pancreatic cancer invasion and metastases: a new paradigm for combination therapy in solid cancers. Cancer Res, 2007. 67(5): p. 2187-96.
43. Jones, S., et al., Core Signaling Pathways in Human Pancreatic Cancers Revealed by Global Genomic Analyses. Science, 2008.
44. Parsons, D. W., et al., An Integrated Genomic Analysis of Human Glioblastoma Multiforme. Science, 2008.
45. Gudjonsson, J. E., et al., Lack of Evidence for Activation of the Hedgehog Pathway in Psoriasis. J Invest Dermatol, 2008.
46. McFerren, M.A., Useful plants of dermatology. VIII. The false hellebore (Veratrum califomicum). J Am Acad Dermatol, 2006. 54(4): p. 7 18-20.
47. Surace, E. M., et al., Inhibition of ocular neovascularization by Hedgehog blockade. Mol Ther, 2006. 13(3): p. 573-9.
48. Gaspard, N., et al., An intrinsic mechanism of corticogenesis from embryonic stem cells. Nature, 2008.
49. Wichterle, H., et al., Directed differentiation of embryonic stem cells into motor neurons. Cell, 2002.110(3): p. 385-97.

50. Taipale, J. and P. A. Beachy, The Hedgehog and Wnt signalling pathways in cancer. Nature, 2001. 411 (6835): p. 349-54.
51. Pola, R., et al., The morphogen Sonic Hedgehog is an indirect angiogenic agent upregulating two families of angiogenic growth factors. Nat Med, 2001. 7(6): p. 706-11.
52. Noveen A, Jiang T X, Chuong C M. cAMP, an activator of protein kinase A, suppresses the expression of sonic hedgehog. Biochem Biophys Res Commun. 1996 Feb. 6; 219(1):180-5.
53. Seldon P M, Barnes P J, Meja K, Giembycz M A. Suppression of lipopolysaccharide-induced tumor necrosis factor-alpha generation from human peripheral blood monocytes by inhibitors of phosphodiesterase 4: interaction with stimulants of adenylyl cyclase. Mol Pharmacol. 1995 October; 48(4):747-57
54. Jimenez J L, Punzón C, Navarro J, Mufioz-Femandez M A, Fresno M. Phosphodiesterase 4 inhibitors prevent cytokine secretion by T lymphocytes by inhibiting nuclear factor-kappaB and nuclear factor of activated T cells activation. J Pharmacol Exp Ther. 2001 November; 299 (2):753-9.
55. Marko D, Romanakis K, Zankl H, Ftlrstenberger G, Steinbauer B, Eisenbrand G. Induction of apoptosis by an inhibitor of cAMP-specific PDE in malignant murine carcinoma cells overexpressing PDE activity in comparison to their nonmalignant counterparts. Cell Biochem Biophys. 1998; 28(2-3):75-101.
56. Favot L, Keravis T, Lugnier C. Modulation of VEGF-induced endothelial cell cycle protein expression through cyclic AMP hydrolysis by PDE2 and PDE4. Thromb Haemost. 2004 September; 92(3):634-45.
57. Nikulina E, Tidwell J L, Dai H N, Bregman B S, Filbin M T. The phosphodiesterase inhibitor rolipram delivered after a spinal cord lesion promotes axonal regeneration and functional recovery. Proc Natl Acad Sci USA. 2004 Jun. 8; 101(23):8786-90.
58. Barad M, Bourtchouladze R, Winder D G, Golan H, Kandel E. Rolipram, a type IV-specific phosphodiesterase inhibitor, facilitates the establishment of long-lasting long-term potentiation and improves memory. Proc Natl Acad Sci USA. 1998 Dec. 8; 95(25): 15020-5.
59. Hulley P, Hartikka J, Lilbbert H. Cyclic AMP promotes the survival of dopaminergic neurons in vitro and protects them from the toxic effects of MPP+. J Neural Transm Suppl. 1995; 46:217-28.
60. Zhang H T, Zhao Y, Huang Y, Dorairaj N R, Chandler L J, O'Donnell J M. Inhibition of the phosphodiesterase 4 (PDE4) enzyme reverses memory deficits produced by infusion of the MEK inhibitor U0126 into the CA1 subregion of the rat hippocampus. Neuropsychopharmacology. 2004 August; 29(8): 1432-9.
61. Baillie, G. S. Compartmentalized signalling: spatial regulation of cAMP by the action of compartmentalized phosphodiesterases. FEBS J. 276, 1790-1799 (2009).
62. Collier, L. S., Suyama, K., Anderson, J. H. & Scott, M. P. Drosophila Costal1 mutations are alleles of protein kinase A that modulate hedgehog signaling. Genetics 167, 783-796 (2004).
63. Barzi, M., Berenguer, J., Menendez, A., Alvarez-Rodriguez, R. & Pons, S. Sonic-hedgehog-mediated proliferation requires the localization of PKA to the cilium base. J. Cell. Sci. 123, 62-69 (2010).
64. Jiang, J. & Struhl, G. Protein kinase A and hedgehog signaling in Drosophila limb development. Cell 80, 563-572 (1995).
65. Ogden, S. K. et al. G protein Galphai functions immediately downstream of Smoothened in Hedgehog signalling. Nature 456, 967-970 (2008).
66. Wen, X. et al. Kinetics of hedgehog-dependent full-length Gli3 accumulation in primary cilia and subsequent degradation. Mol. Cell. Biol. 30, 1910-1922 (2010).
67. Tukachinsky, H., Lopez, L. V. & Salic, A. A mechanism for vertebrate Hedgehog signaling: recruitment to cilia and dissociation of SuFu-Gli protein complexes. J. Cell Biol. 191, 415-428 (2010).
68. Tuson, M., He, M. & Anderson, K. V. Protein kinase A acts at the basal body of the primary cilium to prevent Gli2 activation and ventralization of the mouse neural tube. Development 138, 4921-4930 (2011).
69. Barresi, M. J., Stickney, H. L. & Devoto, S. H. The zebrafish slow-muscle-omitted gene product is required for Hedgehog signal transduction and the development of slow muscle identity. Development 127, 2189-2199 (2000).
70. van Eeden, F. J. et al. Genetic analysis of fin formation in the zebrafish, Danio rerio. Development 123, 255-262 (1996).
71. van Eeden, F. J. et al. Mutations affecting somite formation and patterning in the zebrafish, Danio rerio. Development 123, 153-164 (1996).
72. Wada, N. et al. Hedgehog signaling is required for cranial neural crest morphogenesis and chondrogenesis at the midline in the zebrafish skull. Development 132, 3977-3988 (2005).
73. Schwend, T., Loucks, E. J. & Ahlgren, S. C. Visualization of Gli activity in craniofacial tissues of hedgehog-pathway reporter transgenic zebrafish. PLoS ONE 5, e14396 (2010).
74. Reid, D., Sadjad, B. S., Zsoldos, Z. & Simon, A. LASSO-ligand activity by surface similarity order: a new tool for ligand based virtual screening. J. Comput. Aided Mol. Des. 22, 479-487 (2008).
75. Huang, P. & Schier, A. F. Dampened Hedgehog signaling but normal Wnt signaling in zebrafish without cilia. Development 136, 3089-3098 (2009).
76. Huitorel, P. From cilia and flagella to intracellular motility and back again: a review of a few aspects of microtubule-based motility. Biol. Cell 63, 249-258 (1988).
77. McCahill, A. et al. In resting COS 1 cells a dominant negative approach shows that specific, anchored PDE4 cAMP phosphodiesterase isoforms gate the activation, by basal cyclic AMP production, of AKAP-tethered protein kinase A type II located in the centrosomal region. Cell. Signal. 17, 1158-1173 (2005).
78. Taskén, K. A. et al. Phosphodiesterase 4D and protein kinase a type II constitute a signaling unit in the centrosomal area. J. Biol. Chem. 276, 21999-22002 (2001).
79. Chandrasekaran, A. et al. Identification and characterization of novel mouse PDE4D isoforms: molecular cloning, subcellular distribution and detection of isoform-specific intracellular localization signals. Cell. Signal. 20, 139-153 (2008).
80. Williams, J. A. et al. Identification of a small molecule inhibitor of the hedgehog signaling pathway: effects on basal cell carcinoma-like lesions. Proc. Natl. Acad. Sci. U.S.A. 100, 4616-4621 (2003).
81. Yauch, R. L. et al. Smoothened mutation confers resistance to a Hedgehog pathway inhibitor in medulloblastoma. Science 326, 572-574 (2009).
82. Yauch, R. L. et al. Science 326, 572-574 (2009).

83. Hyman, J. M. et al. Small-molecule inhibitors reveal multiple strategies for Hedgehog pathway blockade. *Proc. Natl. Acad. Sci. U.S.A.* 106, 14132-14137 (2009).
84. Berman, D. M. et al. Medulloblastoma growth inhibition by hedgehog pathway blockade. *Science* 297, 1559-1561 (2002).
85. Goldhoff, P. et al. Targeted inhibition of cyclic AMP phosphodiesterase-4 promotes brain tumor regression. *Clin. Cancer Res.* 14, 7717-7725 (2008).
86. Hao J, Williams C H, Webb M E, Hong C C. Large scale zebrafish-based in vivo small molecule screen. *J Vis Exp.* 2010(46). Available at: http://www.ncbi.nlm.nih.gov/pubmed/21248690. Accessed Nov. 8, 2011.
87. Yu P B, Hong C C, Sachidanandan C, et al. Dorsomorphin inhibits BMP signals required for embryogenesis and iron metabolism. *Nat. Chem. Biol.* 2008; 4(1):33-41.
88. Hong C C. Large-scale small-molecule screen using zebrafish embryos. *Methods Mol. Biol.* 2009; 486:43-55.
89. Westerfield M. *The Zebrafish Book: A Guide for the Laboratory use of Zebrafish*. University of Oregon Press; 1995.
90. Concordet J P, Lewis K E, Moore J W, et al. Spatial regulation of a zebrafish patched homologue reflects the roles of sonic hedgehog and protein kinase A in neural tube and somite patterning. *Development.* 1996; 122(9): 2835-2846.
91. Pauls S, Zecchin E, Tiso N, Bortolussi M, Argenton F. Function and regulation of zebrafish nkx2.2a during development of pancreatic islet and ducts. *Dev Biol.* 2007 Apr. 15; 304(2):875-90.
93. Zilberberg L, ten Dijke P, Sakai L Y, Rifkin D B. A rapid and sensitive bioassay to measure bone morphogenetic protein activity. *BMC Cell Biol.* 2007; 8:41.
94. Fabian M A, Biggs W H, Treiber D K, et al. A small molecule-kinase interaction map for clinical kinase inhibitors. *Nat Biotech.* 2005; 23(3):329-336.
95. Karaman M W, Herrgard S, Treiber D K, et al. A quantitative analysis of kinase inhibitor selectivity. *Nat. Biotechnol.* 2008; 26(1): 127-132.
96. Ekholm, D. et al. Cyclic nucleotide phosphodiesterases (PDE) 3 and 4 in normal, malignant, and HTLV-I transformed human lymphocytes. *Biochem. Pharmacol.* 58, 935-950 (1999).
97. Sun, Y., Li, L., Lau, F., Beavo, J. A. & Clark, E. A. Infection of CD4+ memory T cells by HIV-1 requires expression of phosphodiesterase 4. *J. Immunol.* 165, 1755-1761 (2000).
98. McEwan, D. G. et al. Chemoresistant KM12C colon cancer cells are addicted to low cyclic AMP levels in a phosphodiesterase 4-regulated compartment via effects on phosphoinositide 3-kinase. *Cancer Res.* 67, 5248-5257 (2007).
99. Sengupta, R., Sun, T., Warrington, N. M. & Rubin, J. B. Treating brain tumors with PDE4 inhibitors. *Trends Pharmacol. Sci.* 32, 337-344 (2011).
100. Pullamnsetti, S. S. et al. Phosphodiesterase-4 promotes proliferation and angiogenesis of lung cancer by crosstalk with HIF. *Oncogene* (2012).doi: 10. 1038/onc.2012.136.
101. Burgin, A. B. et al. Design of phosphodiesterase 4D (PDE4D) allosteric modulators for enhancing cognition with improved safety. *Nature Biotechnology* 28, 63-70 (2010).
102. Huang, Y.; Wolf, S.; Bista, M.; Meireles, L.; Camacho, C.; Holak, T. A; Dömling, A. "1,4-Thienodiazepine-2,5-diones via MCR (I): Synthesis, Virtual Space and p53-Mdm2 Activity" *Chemical Biology & Drug Design,* 2010, 76, 116-129.
103. Ivachtchenko, A.; Kovalenko, S.; Tkachenko, O. V.; Parkhomenko, O. "Synthesis of Substituted Thienopyrimidine-4-ones" *Journal of Combinatorial Chemistry,* 2004, 6, 573-583.
104. Alagarsamy, V.; Meena, S.; Ramnseshu, K. V.; Solomon, V. R.; Thirumurugan, K.; Dhanabal, K.; Murugan, M. "Synthesis, Analgesic, Anti-Inflammatory, Ulcerogenic Index and Antibacterial Activities of Novel 2-Methylthio-3-substituted-5,6,7,8-tetrahydrobenzo (b) thieno[2,3-d]pyrimidin-4(3H)-ones" *European Journal of Medicinal Chemistry,* 2006, 41, 1293-1300.
105. Cohen, M. M., Jr. Hedgehog signaling update. *Am. J. Med. Genet. A* 152A, 1875-1914 (2010).
106. Ryan, K. E. & Chiang, C. Hedgehog secretion and signal transduction in vertebrates. *J. Biol. Chem.* 287, 17905-17913 (2012).
107. Corbit, K. C. et al. Vertebrate Smoothened functions at the primary cilium. *Nature* 437, 1018-1021 (2005).
108. Rohatgi, R., Milenkovic, L. & Scott, M. P. Patched1 regulates hedgehog signaling at the primary cilium. *Science* 317, 372-376 (2007).
109. Haycraft, C. J. et al. Gli2 and Gli3 localize to cilia and require the intraflagellar transport protein polaris for processing and function. *PLoS Genet.* 1, e53 (2005).
110. Liu, A., Wang, B. & Niswander, L. A. Mouse intraflagellar transport proteins regulate both the activator and repressor functions of Gli transcription factors. *Development* 132, 3103-3111 (2005).
112. Wang, B., Fallon, J. F. & Beachy, P. A. Hedgehog-regulated processing of Gli3 produces an anterior/posterior repressor gradient in the developing vertebrate limb. *Cell* 100, 423-434 (2000).
113. Pan, Y., Bai, C. B., Joyner, A. L. & Wang, B. Sonic hedgehog signaling regulates Gli2 transcriptional activity by suppressing its processing and degradation. *Mol. Cell. Biol.* 26, 3365-3377 (2006).
114. Ayers, K. L. & Thérond, P. P. Evaluating Smoothened as a G-protein-coupled receptor for Hedgehog signalling. *Trends Cell Biol.* 20, 287-298 (2010).
115. Firestone, A. J. et al. Small-molecule inhibitors of the AAA+ ATPase motor cytoplasmic dynein. *Nature* 484, 125-129 (2012).
116. Hirsinger, E., Stellabotte, F., Devoto, S. H. & Westerfield, M. Hedgehog signaling is required for commitment but not initial induction of slow muscle precursors. *Dev. Biol.* 275, 143-157 (2004).
117. Souness, J. E. et al. Evidence that cyclic AMP phosphodiesterase inhibitors suppress TNF alpha generation from human monocytes by interacting with a 'low-affinity' phosphodiesterase 4 conformer. *Br. J. Pharmacol.* 118, 649-658 (1996).
118. Klarenbeek, J. B., Goedhart, J., Hink, M. A., Gadella, T. W. J. & Jalink, K. A mTurquoise-Based cAMP Sensor for Both FLIM and Ratiometric Read-Out Has Improved Dynamic Range. *PLoS ONE* 6, e 19170 (2011).
119. Terrin, A. et al. PKA and PDE4D3 anchoring to AKAP9 provides distinct regulation of cAMP signals at the centrosome. *J. Cell Biol.* 198, 607-621 (2012).
120. Zhao, Y., Zhang, H.-T. & O'Donnell, J. M. Inhibitor binding to type 4 phosphodiesterase (PDE4) assessed using [3H]piclamilast and [3H]rolipram. *J. Pharmacol. Exp. Ther.* 305, 565-572 (2003).
121. Rocque, W. J. et al. Human recombinant phosphodiesterase 4B2B binds (R)-rolipram at a single site with two affinities. *Biochemistry* 36, 14250-14261 (1997).
122. Rocque, W. J. et al. Detailed characterization of a purified type 4 phosphodiesterase, HSPDE4B2B: differ- 123. Schneider, H. H., Schmiechen, R., Brezinski, M. & Seidler, J. Stereospecific binding of the antidepressant rolipram to brain protein structures. *Eur. J. Pharmacol.* 127, 105-115 (1986).
124. Torphy, T. J. et al. Coexpression of human cAMP-specific phosphodiesterase activity and high affinity rolipram binding in yeast. *J. Biol. Chem.* 267, 1798-1804 (1992).
125. Jacobitz, S., McLaughlin, M. M., Livi, G. P., Burman, M. & Torphy, T. J. Mapping the functional domains of human recombinant phosphodiesterase 4A: structural requirements for catalytic activity and rolipram binding. *Mol. Pharmacol.* 50, 891-899 (1996).
126. Ashton, M. J. et al. Selective type IV phosphodiesterase inhibitors as antiasthmatic agents. The syntheses and biological activities of 3-(cyclopentyloxy)-4-methoxybenzamides and analogues. *J. Med. Chem.* 37, 1696-1703 (1994).
127. Houslay, M. D., Schafer, P. & Zhang, K. Y. J. Keynote review: phosphodiesterase-4 as a therapeutic target. *Drug Discov. Today* 10, 1503-1519 (2005).
128. Houslay, M. D. & Adams, D. R. Putting the lid on phosphodiesterase 4. *Nat. Biotechnol.* 28, 38-40 (2010).
129. Ryan, K. E.; Chiang, C. *Journal of Biological Chemistry* 2012, 287, 17905-17913.
130. Taipale, J.; Cooper, M. K.; Maiti, T.; Beachy, P. A. *Nature* 2002, 418, 892-896.
131. Sharpe, H. J.; Wang, W.; Hannoush, R. N.; de Sauvage, F. J. *Nat Chem Biol* 2015, 11, 246-255.
132. Hui, C.-C.; Angers, S. *Annu. Rev. Cell Dev. Biol.* 2011, 27, 513-537.
133. Chen, J. K.; Taipale, J.; Cooper, M. K.; Beachy, P. A. *Genes Dev.* 2002, 16, 2743-2748.
134. Ng, J. M. Y.; Curran, T. *Nature Reviews Cancer* 2011, 11, 493-501.
135. Kar, S.; Deb, M.; Sengupta, D.; Shilpi, A.; Bhutia, S. K.; Patra, S. K. *Exp. Cell Res.* 2012, 318, 1959-1972.
136. Kasper, M.; Regl, G.; Frischauf, A.-M.; Aberger, F. *Eur. J. Cancer* 2006, 42, 437-445.
137. Mahindroo, N.; Punchihewa, C.; Fujii, N. *Journal of Medicinal Chemistry* 2009, 52, 3829-3845.
138. Hoff, Von, D. D.; LoRusso, P. M.; Rudin, C. M.; Reddy, J. C.; Yauch, R. L.; Tibes, R.; Weiss, G. J.; Borad, M. J.; Hann, C. L.; Brahmer, J. R.; Mackey, H. M.; Lum, B. L.; Darbonne, W. C.; Marsters, J. C., Jr.; de Sauvage, F. J.; Low, J. A. *N Engl J Med* 2009, 361, 1164-1172.
139. Berman, D. M.; Karhadkar, S. S.; Hallahan, A. R.; Pritchard, J. I.; Eberhart, C. G.; Watkins, D. N.; Chen, J. K.; Cooper, M. K.; Taipale, J.; Olson, J. M.; Beachy, P. A. *Science* 2002, 297, 1559-1561.
140. Rudin, C. M.; Hann, C. L.; Laterra, J.; Yauch, R. L.; Callahan, C. A.; Fu, L.; Holcomb, T.; Stinson, J.; Gould, S. E.; Coleman, B.; LoRusso, P. M.; Hoff, Von, D. D.; de Sauvage, F. J.; Low, J. A. *N Engl J Med* 2009, 361, 1173-1178.
141. Rosow, D. E.; Liss, A. S.; Strobel, O.; Fritz, S.; Bausch, D.; Valsangkar, N. P.; Alsina, J.; Kulemann, B.; Park, J. K.; Yamaguchi, J.; LaFemina, J.; Thayer, S. P. *Surgery* 2012, 152, S19-S32.
142. Robarge, K. D.; Brunton, S. A.; Castanedo, G. M.; Cui, Y.; Dina, M. S.; Goldsmith, R.; Gould, S. E.; Guichert, O.; Gunzner, J. L.; Halladay, J.; Jia, W.; Khojasteh, C.; Koehler, M. F. T.; Kotkow, K.; La, H.; LaLonde, R. L.; Lau, K.; Lee, L.; Marshall, D.; Marsters, J. C., Jr.; Murray, L. J.; Qian, C.; Rubin, L. L.; Salphati, L.; Stanley, M. S.; Stibbard, J. H. A.; Sutherlin, D. P.; Ubhayaker, S.; Wang, S.; Wong, S.; Xie, M. *Bioorganic & Medicinal Chemistry Letters* 2009, 19, 5576-5581.
143. Pan, S.; Wu, X.; Jiang, J.; Gao, W.; Wan, Y.; Cheng, D.; Han, D.; Liu, J.; Englund, N. P.; Wang, Y.; Peukert, S.; Miller-Moslin, K.; Yuan, J.; Guo, R.; Matsumoto, M.; Vattay, A.; Jiang, Y.; Tsao, J.; Sun, F.; Pferdekamper, A. C.; Dodd, S.; Tuntland, T.; Maniara, W.; Kelleher, J. F.; Yao, Y.-M.; Warmuth, M.; Williams, J.; Dorsch, M. *ACS Med Chem Lett* 2010, 1, 130-134.
144. Munchhof, M. J.; Li, Q.; Shavnya, A.; Borzillo, G. V.; Boyden, T. L.; Jones, C. S.; LaGreca, S. D.; Martinez-Alsina, L.; Patel, N.; Pelletier, K.; Reiter, L. A.; Robbins, M. D.; Tkalcevic, G. T. *ACS Med Chem Lett* 2012, 3, 106-111.
145. Tremblay, M. R.; Lescarbeau, A.; Grogan, M. J.; Tan, E.; Lin, G.; Austad, B. C.; Yu, L.-C.; Behnke, M. L.; Nair, S. J.; Hagel, M.; White, K.; Conley, J.; Manna, J. D.; Alvarez-Diez, T. M.; Hoyt, J.; Woodward, C. N.; Sydor, J. R.; Pink, M.; MacDougall, J.; Campbell, M. J.; Cushing, J.; Ferguson, J.; Curtis, M. S.; McGovern, K.; Read, M. A.; Palombella, V. J.; Adams, J.; Castro, A. C. *Journal of Medicinal Chemistry* 2009, 52, 4400-4418.
146. Ohashi, T.; Oguro, Y.; Tanaka, T.; Shiokawa, Z.; Tanaka, Y.; Shibata, S.; Sato, Y.; Yamakawa, H.; Hattori, H.; Yamamoto, Y.; Kondo, S.; Miyamoto, M.; Nishihara, M.; Ishimura, Y.; Tojo, H.; Baba, A.; Sasaki, S. *Bioorg Med Chem* 2012, 20, 5507-5517.
147. Kim, J.; Aftab, B. T.; Tang, J. Y.; Kim, D.; Lee, A. H.; Rezaee, M.; Kim, J.; Chen, B.; King, E. M.; Borodovsky, A.; Riggins, G. J.; Epstein, E. H.; Beachy, P. A.; Rudin, C. M. *Cancer Cell* 2013, 23, 23-34.
148. Low, J. A.; de Sauvage, F. J. *J. Clin. Oncol.* 2010, 28, 5321-5326.
149. Metcalfe, C.; de Sauvage, F. J. *Cancer Research* 2011, 71, 5057-5061.
150. Atwood, S. X.; Sarin, K. Y.; Whitson, R. J.; Li, J. R.; Kim, G.; Rezaee, M.; Ally, M. S.; Kim, J.; Yao, C.; Chang, A. L. S.; Oro, A. E.; Tang, J. Y. *Cancer Cell* 2015, 27, 342-353.
151. Sharpe, H. J.; Pau, G.; Dijkgraaf, G. J.; Basset-Seguin, N.; Modrusan, Z.; Januario, T.; Tsui, V.; Durham, A. B.; Dlugosz, A. A.; Haverty, P. M.; Bourgon, R.; Tang, J. Y.; Sarin, K. Y.; Dirix, L.; Fisher, D. C.; Rudin, C. M.; Sofen, H.; Migden, M. R.; Yauch, R. L.; de Sauvage, F. J. *Cancer Cell* 2015, 27, 327-341.
152. Yauch, R. L.; Dijkgraaf, G. J. P.; Alicke, B.; Januario, T.; Ahn, C. P.; Holcomb, T.; Pujara, K.; Stinson, J.; Callahan, C. A.; Tang, T.; Bazan, J. F.; Kan, Z.; Seshagiri, S.; Hann, C. L.; Gould, S. E.; Low, J. A.; Rudin, C. M.; de Sauvage, F. J. *Science* 2009, 326, 572-574.
153. Williams, C. H.; Hempel, J. E.; Hao, J.; Frist, A. Y.; Williams, M. M.; Fleming, J. T.; Sulikowski, G. A.; Cooper, M. K.; Chiang, C.; Hong, C. C. *Cell Reports* 2015, 11, 43-50.
154. Infante, P.; Alfonsi, R.; Botta, B.; Mori, M.; Di Marcotullio, L. *Trends in Pharmacological Sciences* 2015, 36, 547-558.
155. Tang, Y.; Gholamin, S.; Schubert, S.; Willardson, M. I.; Lee, A.; Bandopadhayay, P.; Bergthold, G.; Masoud, S.; Nguyen, B.; Vue, N.; Balansay, B.; Yu, F.; Oh, S.; Woo, P.; Chen, S.; Ponnuswami, A.; Monje, M.; Atwood, S. X.; Whitson, R. J.; Mitra, S.; Cheshier, S. H.; Qi, J.; Beroukhim, R.; Tang, J. Y.; Wechsler-Reya, R.; Oro, A. E.; Link, B. A.; Bradner, J. E.; Cho, Y.-J. *Nat. Med.* 2014, 20, 732-740.

156. Long, J.; Li, B.; Rodriguez-Blanco, J.; Pastori, C.; Volmar, C.-H.; Wahlestedt, C.; Capobianco, A.; Bai, F.; Pei, X.-H.; Ayad, N. G.; Robbins, D. J. Journal of Biological Chemistry 2014, 289, 35494-35502.

157. Powers, G. L.; Hammer, K. D. P.; Domenech, M.; Frantskevich, K.; Malinowski, R. L.; Bushman, W.; Beebe, D. J.; Marker, P. C. Mol. Cancer Res. 2015, 13, 149-160.

158. Ge, X.; Milenkovic, L.; Suyama, K.; Hard, T.; Purzner, T.; Winans, A.; Meyer, T.; Scott, M. P. eLife Sciences 2015, 4, e07068.

159. Fondjo, E. S.; Döpp, D.; Henkel, G. Tetrahedron 2006, 62, 7121-7131.

160. Alagarsamy, V.; Rajesh, R.; Ramaseshu, M.; Vijaykumar, S.; Ramseshu, K. V.; Duraianandakumar, T. Biol. Pharm. Bull. 2004, 27, 652-656.

161. Ivachtchenko, A.; Kovalenko, S.; Tkachenko, O. V.; Parkhomenko, O. J Comb Chem 2004, 6, 573-583.

162. Miller-Moslin, K.; Peukert, S.; Jain, R. K.; McEwan, M. A.; Karki, R.; Llamas, L.; Yusuff, N.; He, F.; Li, Y.; Sun, Y.; Dai, M.; Perez, L.; Michael, W.; Sheng, T.; Lei, H.; Zhang, R.; Williams, J.; Bourret, A.; Ramamurthy, A.; Yuan, J.; Guo, R.; Matsumoto, M.; Vattay, A.; Maniara, W.; Amaral, A.; Dorsch, M.; Kelleher, J. F., III. Journal of Medicinal Chemistry 2009, 52, 3954-3968.

163. Shultz, M. D. Bioorganic & Medicinal Chemistry Letters 2013, 23, 5980-5991.

164. Lauth, M.; BergstrOm, A.; Shimokawa, T.; Toftgård, R. Proceedings of the National Academy of Sciences 2007, 104, 8455-8460.

165. Hesse, S.; Perspicace, E.; Kirsch, G. Tetrahedron Lett 2007, 48, 5261-5264.

166. Svard, J.; Heby-Henricson, K.; Henricson, K. H.; Persson-Lek, M.; Rozell, B.; Lauth, M.; BergstrOm, A.; Ericson, J.; Toftgård, R.; Teglund, S. Developmental Cell 2006, 10, 187-197.

167. Dockendorff, C.; Nagiec, M. M.; Weïwer, M.; Buhrlage, S.; Ting, A.; Nag, P. P.; Germain, A.; Kim, H.-J.; Youngsaye, W.; Scherer, C.; Bennion, M.; Xue, L.; Stanton, B. Z.; Lewis, T. A.; MacPherson, L.; Palmer, M.; Foley, M. A.; Perez, J. R.; Schreiber, S. L. ACS Med Chem Lett 2012, 3, 808-813.

168. Still, W. C.; Kahn, M.; Mitra, A. J. Org. Chem. 1978, 43 (14), 2923-2925.

169. International Patent Application No. PCT/US15/50024, entitled "Compounds and Methods for Inhibition of Hedgehog Signaling and Phosphodiesterase."

What is claimed is:

1. A compound according to a formula selected from the group consisting of:

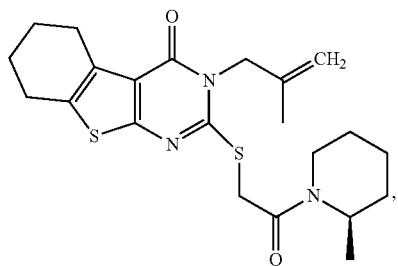

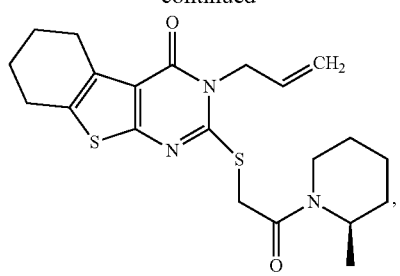

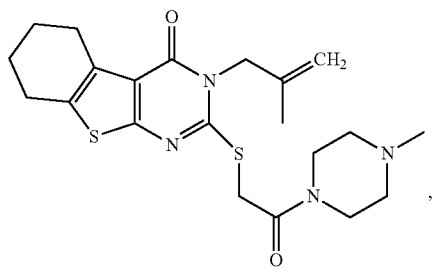

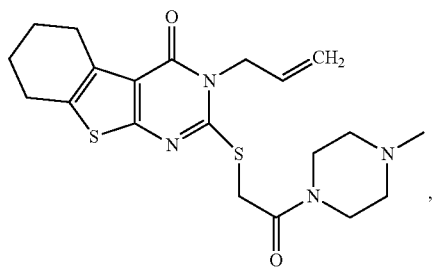

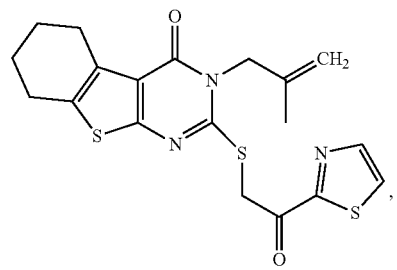

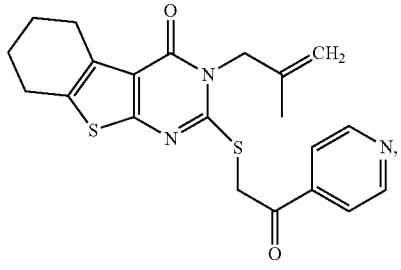

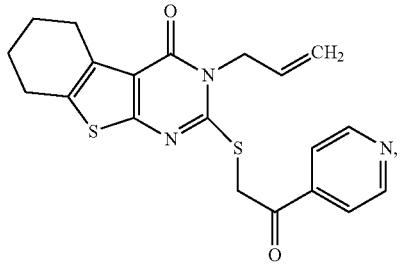

267
-continued
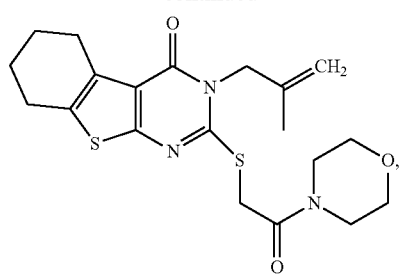
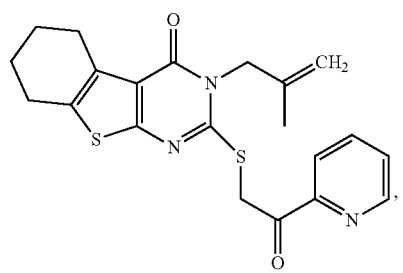
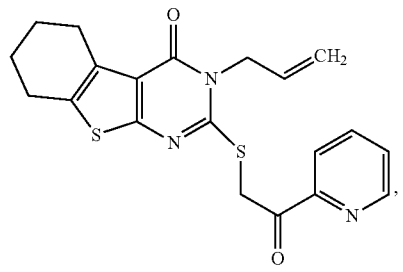
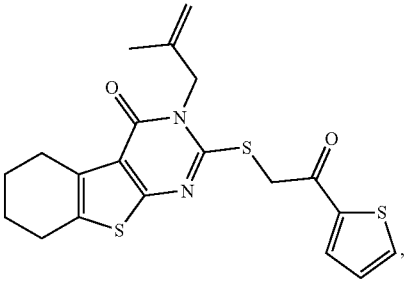
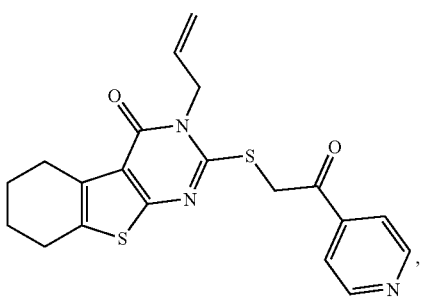
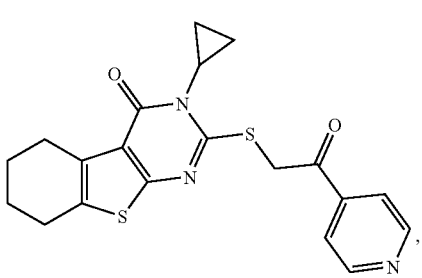
268
-continued
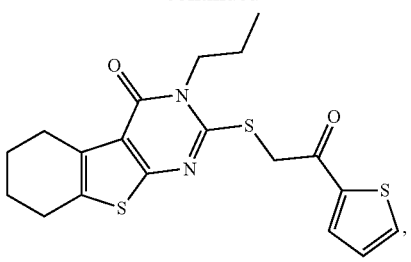
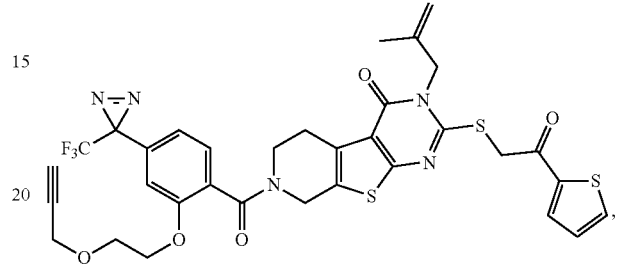
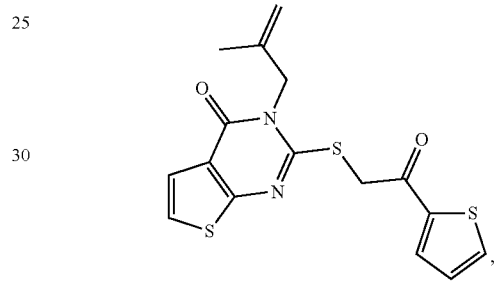
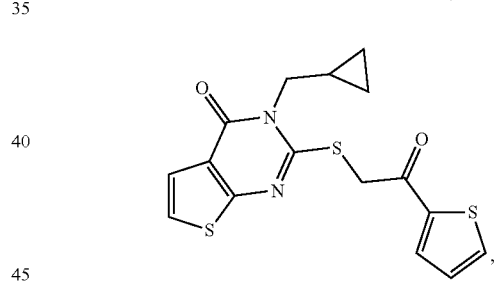
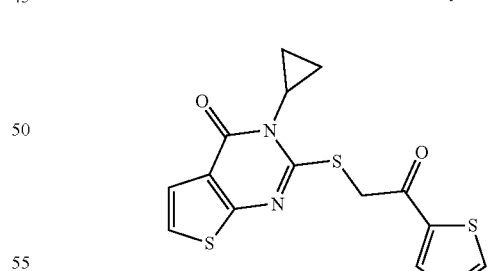
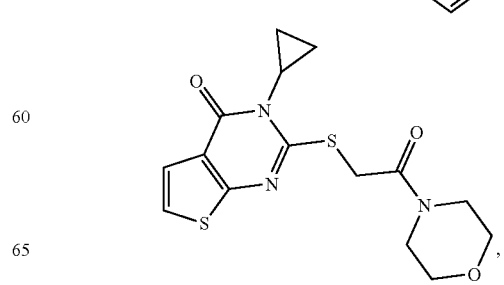

269
-continued
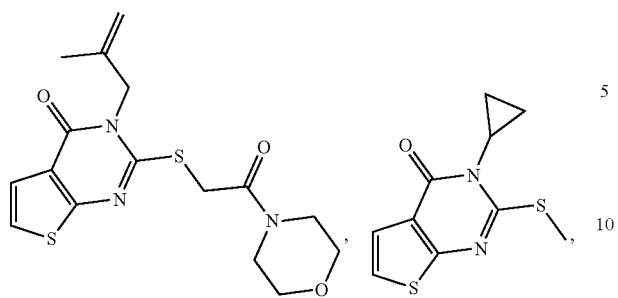
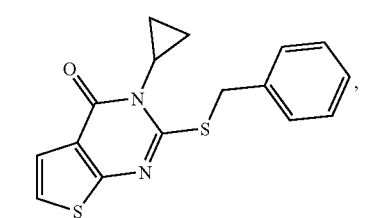
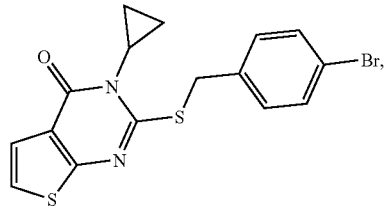
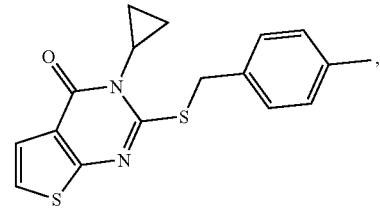
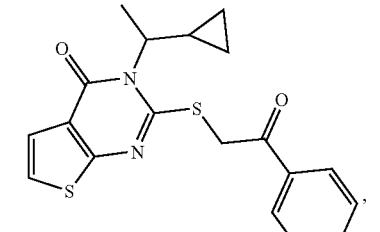
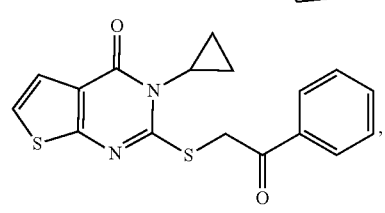
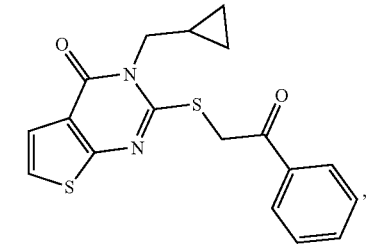
270
-continued
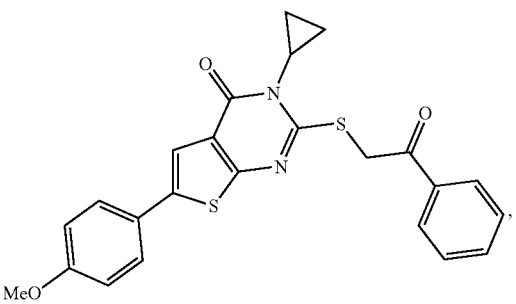
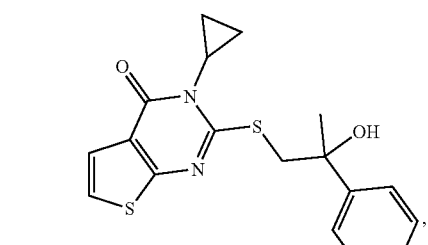
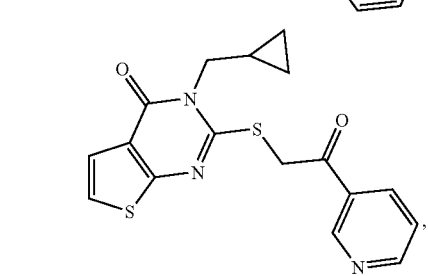
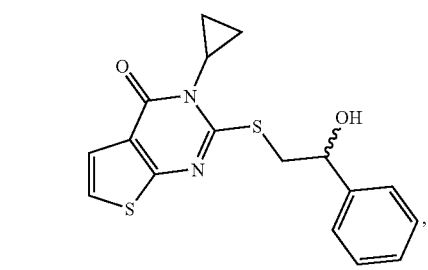
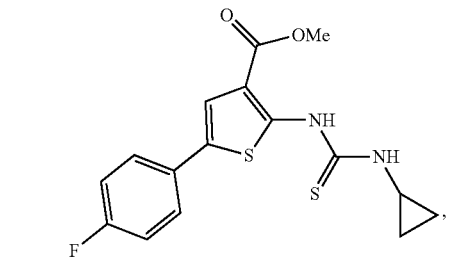
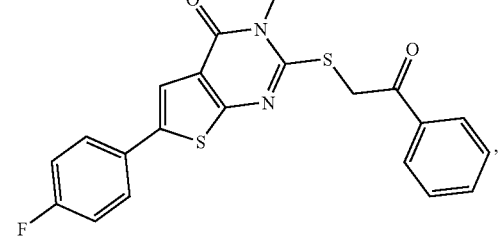

-continued
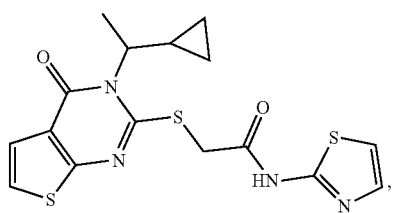
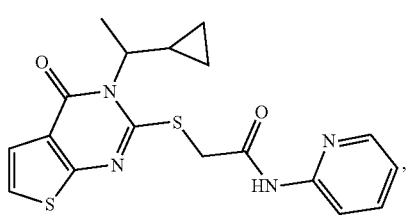
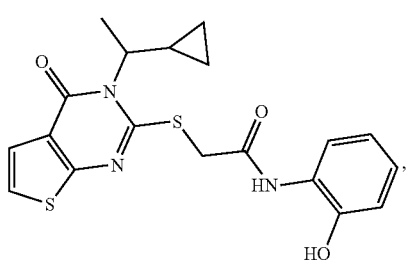
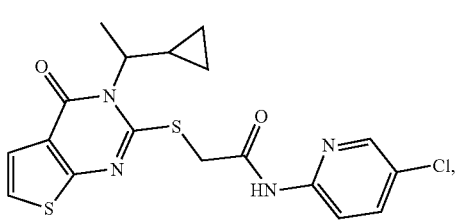
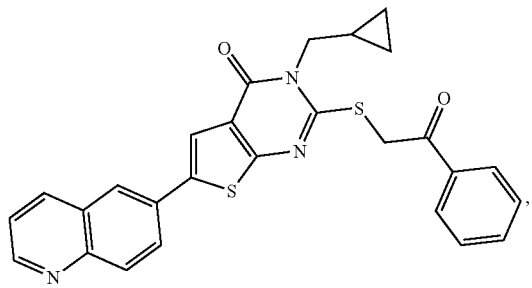
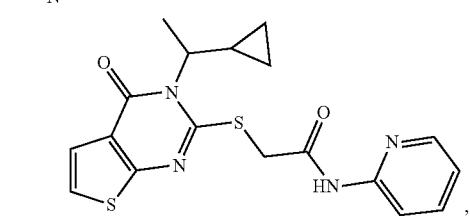
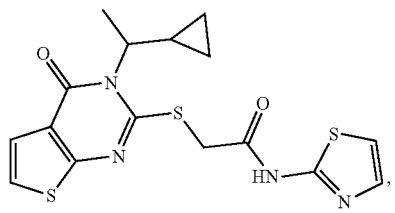
-continued
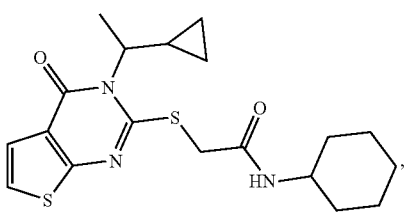
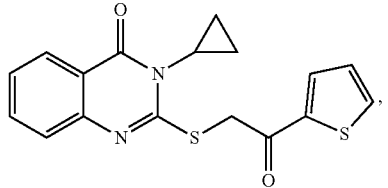
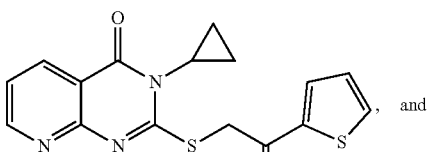
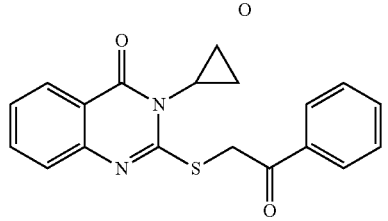
or pharmaceutically-acceptable salts thereof; or
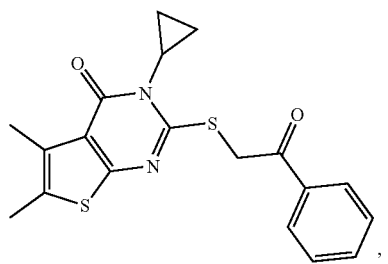
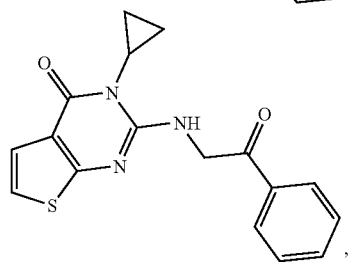
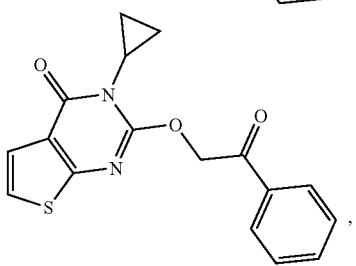

273
-continued
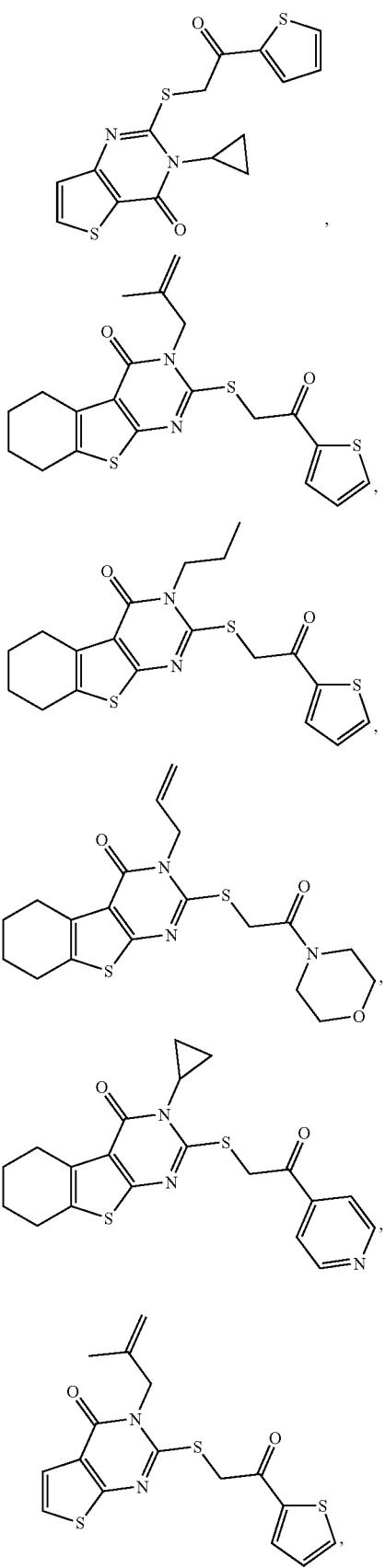
274
-continued
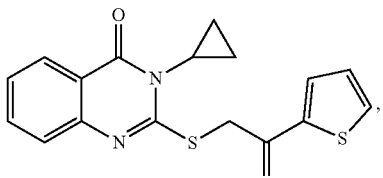
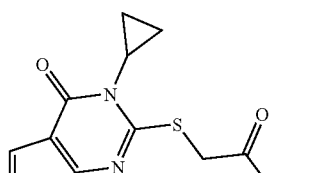
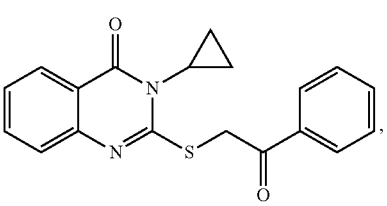
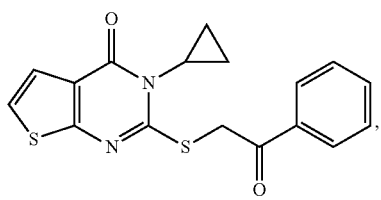
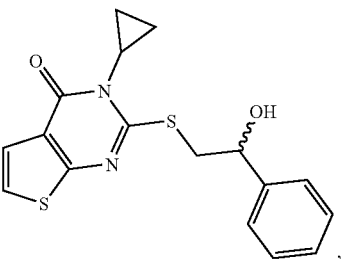, or
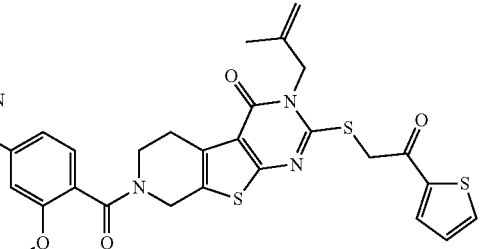
or pharmaceutically-acceptable salts thereof; or

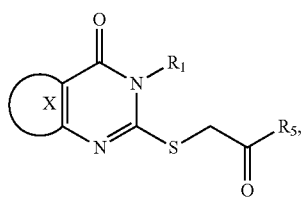

or pharmaceutically-acceptable salts thereof, wherein
(i) X is selected from

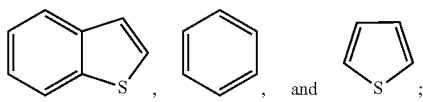

(ii) R₁ is selected from

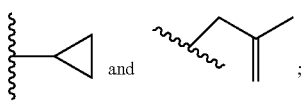

and
(iii) R₅ is selected from

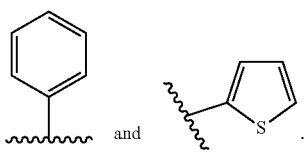 [SMILES: *c1ccccc1 ; *c1cccs1]

2. A pharmaceutical composition, comprising a pharmaceutically-acceptable carrier; and the compound of claim 1, and further comprising a second compound or composition having Hh signaling inhibition activity, PDE4 inhibition activity, anti-cancer or anti-tumor activity, anti-angiogenic activity, anti-metastatic activity, anti-heart failure activity, and/or anti-inflammation activity, or wherein the second compound or composition is useful for treating a condition of interest, and wherein the second compound is a Smo antagonist.

3. The pharmaceutical composition of claim 2, wherein the Smo antagonist is Vismodegib (GDC-0449, 1), Sonidegib (NVP-LDE225, 2), PF-04449913, IPI-926, BMS-833923, TAK-441, LY2940680, or itraconazole.

4. A kit, comprising a compound according to claim 1; and a device for administration of the compound or composition.

5. The kit of claim 4, wherein the device for administration of the compound or composition is a nebulizer.

6. A kit, comprising a compound according to claim 1; and further comprising a second compound or composition having Hh signaling inhibition activity, PDE4 inhibition activity, anti-cancer or anti-tumor activity, anti-viral activity, anti-angiogenic activity, anti-metastatic activity, anti-heart failure activity, and/or anti-inflammation activity, or wherein the second compound or composition is useful for treating a condition of interest.

7. The kit of claim 6, and further comprising a device for administration of the compound or composition and/or a device for administration of the second compound or composition.

8. A pharmaceutical composition, comprising a pharmaceutically-acceptable carrier; and a compound or pharmaceutically-acceptable salts thereof, and a Smo antagonist, wherein the compound is of the formula:

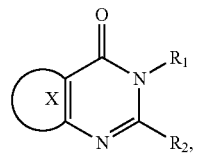

or a pharmaceutically-acceptable salt thereof, wherein
(i) X is selected from

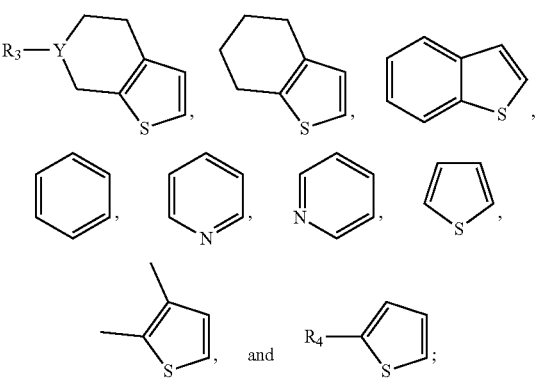

(ii) Y is selected from C, N, O, and S;
(iii) R₁ is selected from H, CH₂CH₃, (CH₂)₂CH₃,

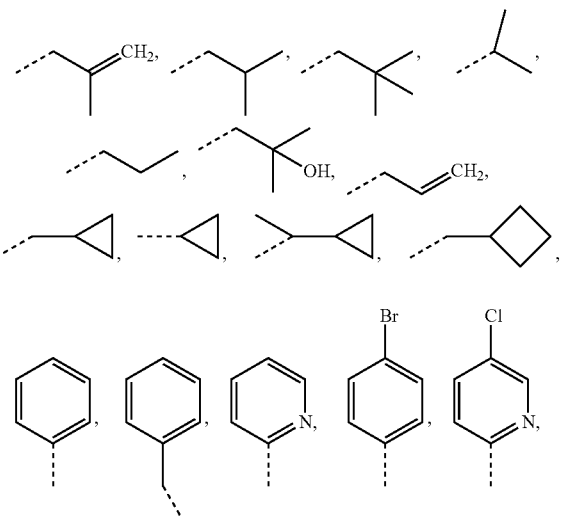

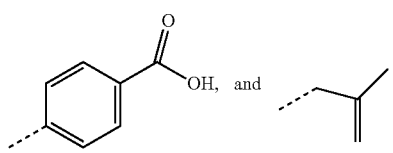

(iv) R₂ is selected from
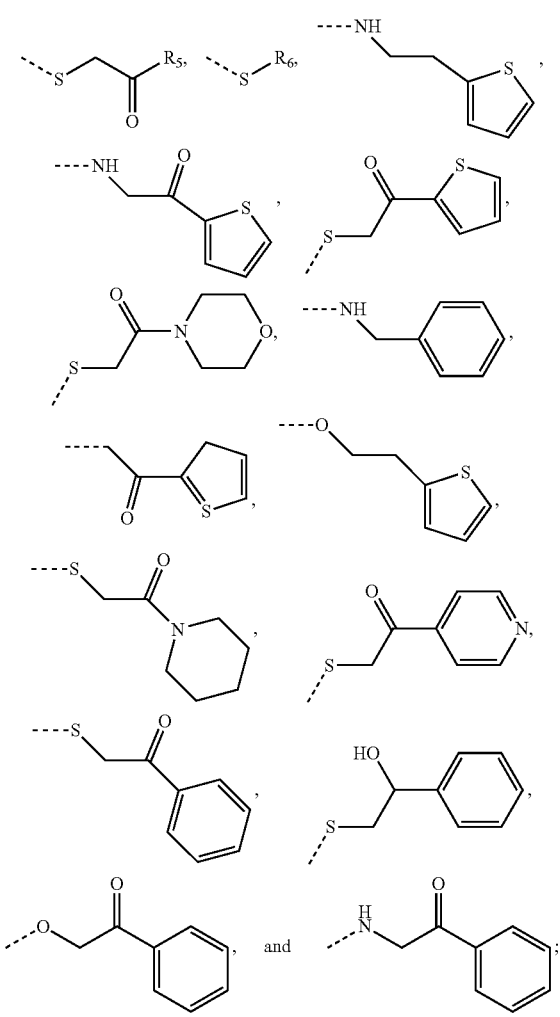
(v) R₃ is selected from H, CH₃,
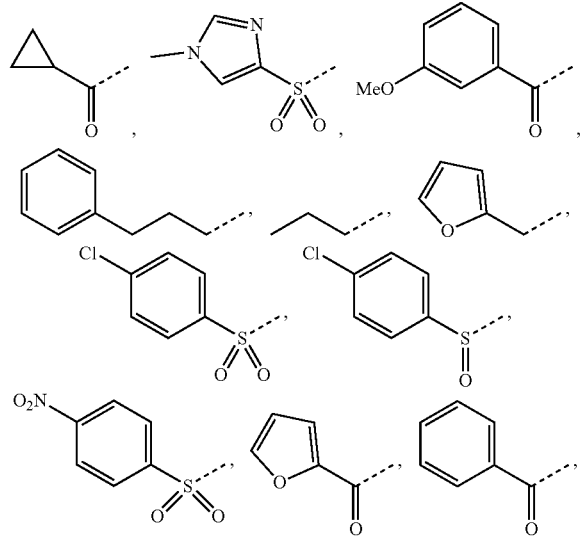
(vi) R₄ is selected from H,
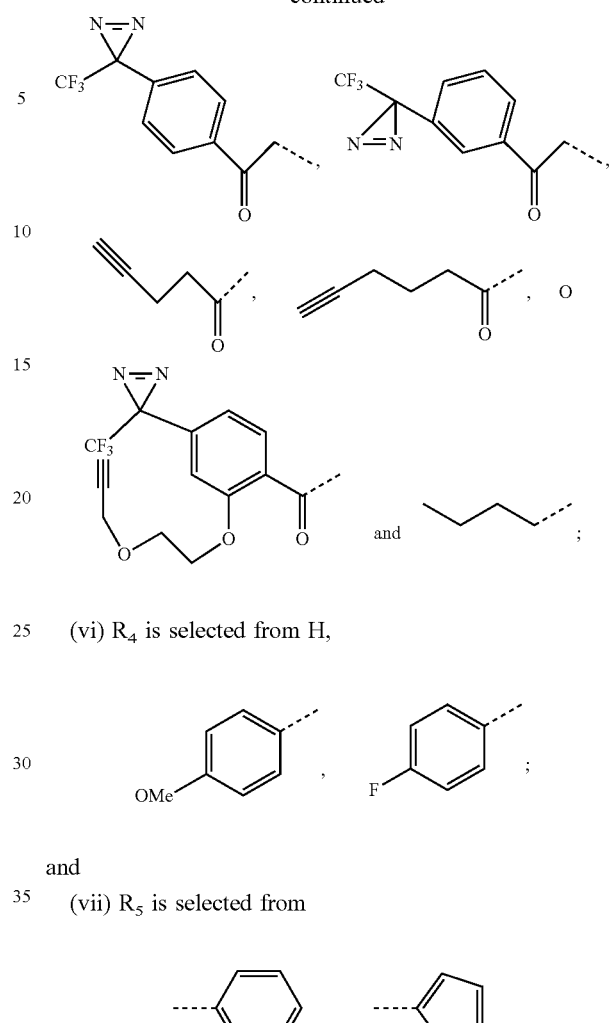
and
(vii) R₅ is selected from
and
(viii) R₆ is selected from CH₃, -continued
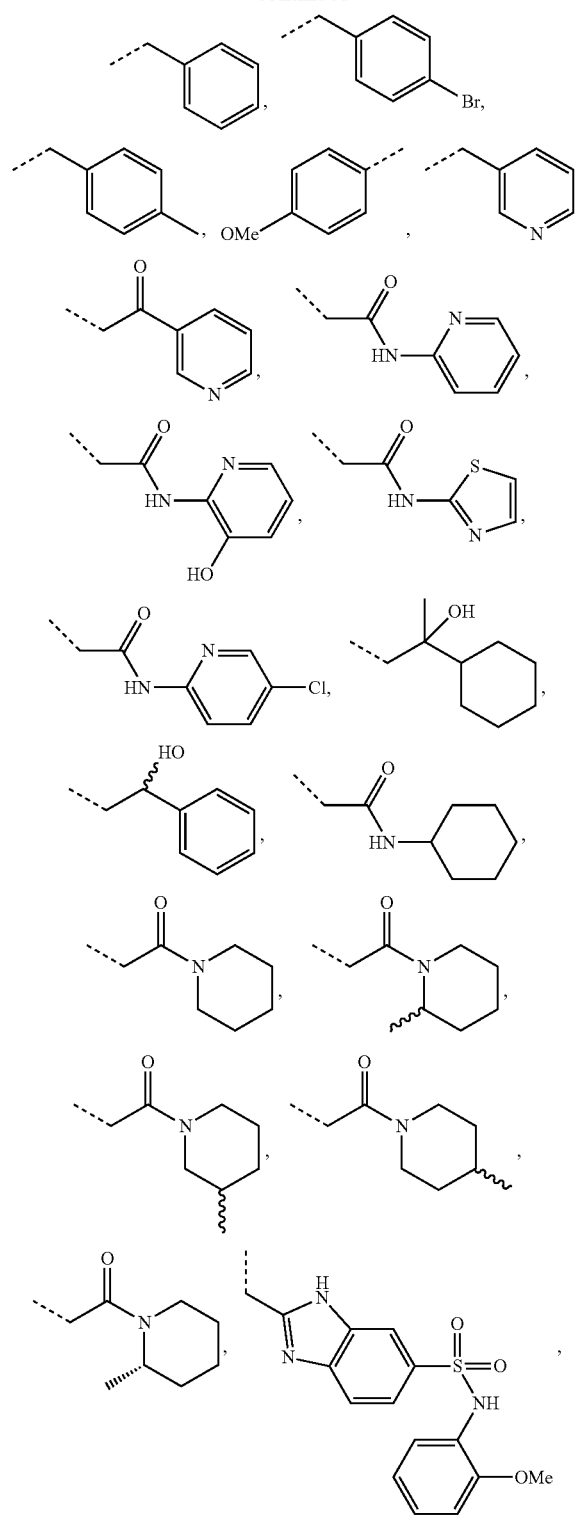
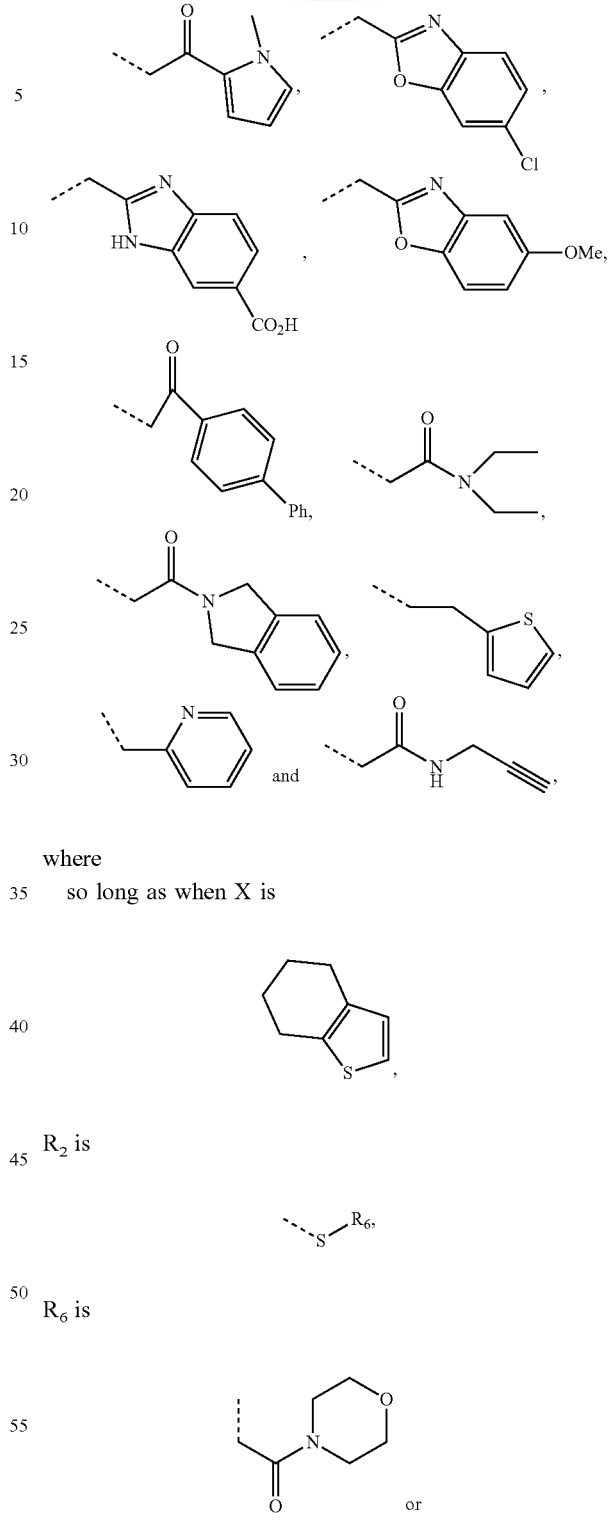
where
so long as when X is
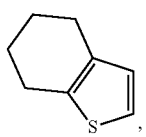
$R_2$ is
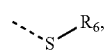
$R_6$ is
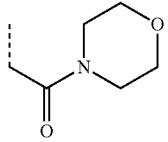
or
then $R_1$ is not
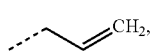
and so long as when X is
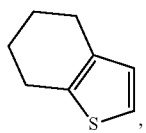
$R_2$ is
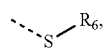
$R_6$ is
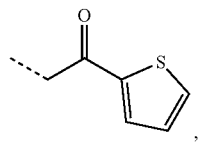
then $R_1$ is not
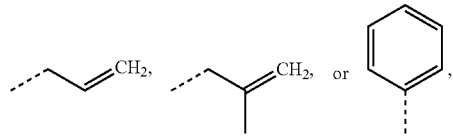
and
so long as when X is
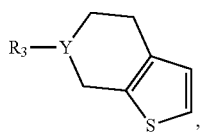
Y is C, $R_3$ is $CH_3$, $R_2$ is
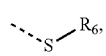
and $R_6$ is
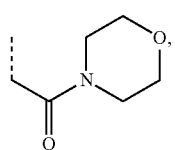
then $R_1$ is not
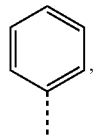
and
so long as when X is
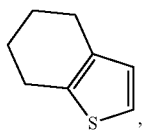
$R_2$ is
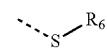
$R_6$ is
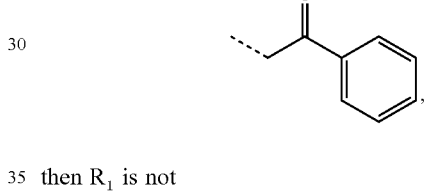
then $R_1$ is not
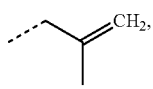
and
so long as when X is
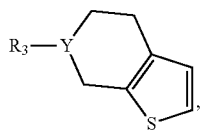
Y is C, $R_3$ is $CH_3$, $R_2$ is
and $R_6$ is
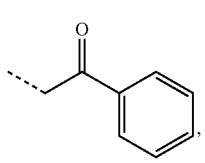

then R₁ is not

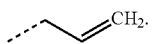

9. The pharmaceutical composition of claim 8, wherein the Smo antagonist is Vismodegib (GDC-0449, 1), Sonidegib (NVP-LDE225, 2), PF-04449913, IPI-926, BMS-833923, TAK-441, LY2940680, or itraconazole.

10. A kit, comprising a compound; and a device for administration of the compound or composition containing the compound, wherein the compound is of the formula

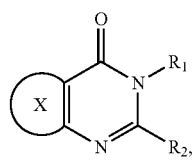

or a pharmaceutically-acceptable salt thereof, wherein
(i) X is selected from

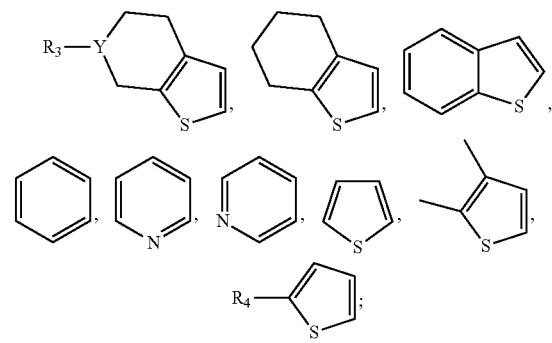

(ii) Y is selected from C, N, O, and S;
(iii) R₁ is selected from H, CH₂CH₃, (CH₂)₂CH₃,

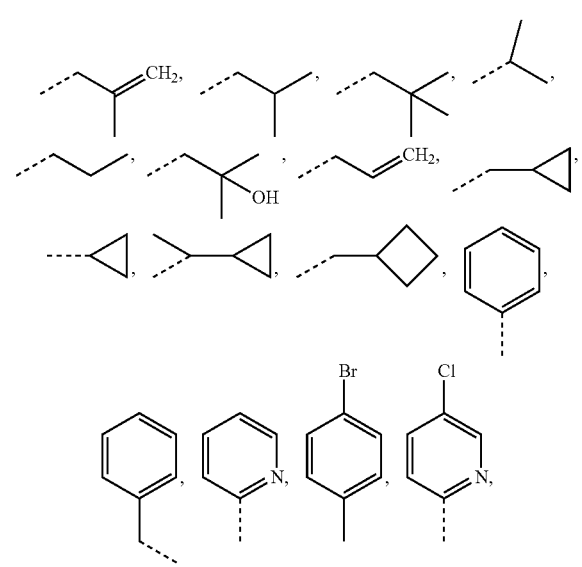

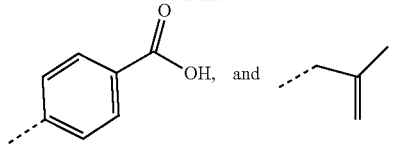

(iv) R₂ is selected from

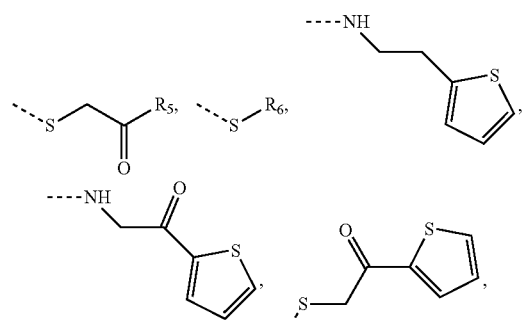

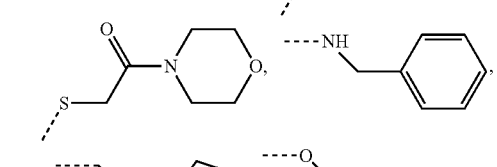

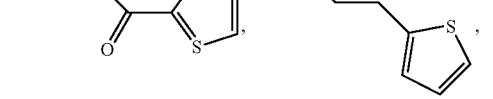

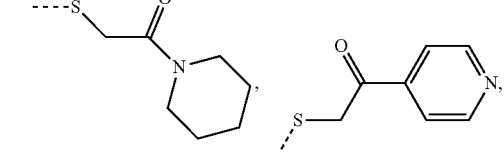

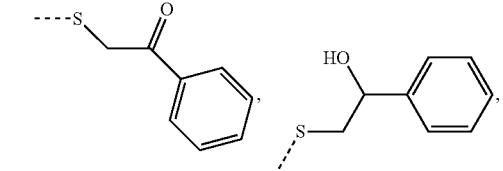

(v) R₃ is selected from H, CH₃,

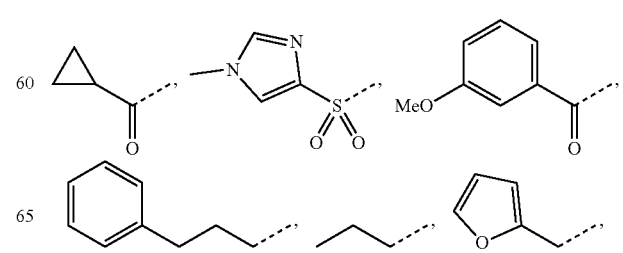

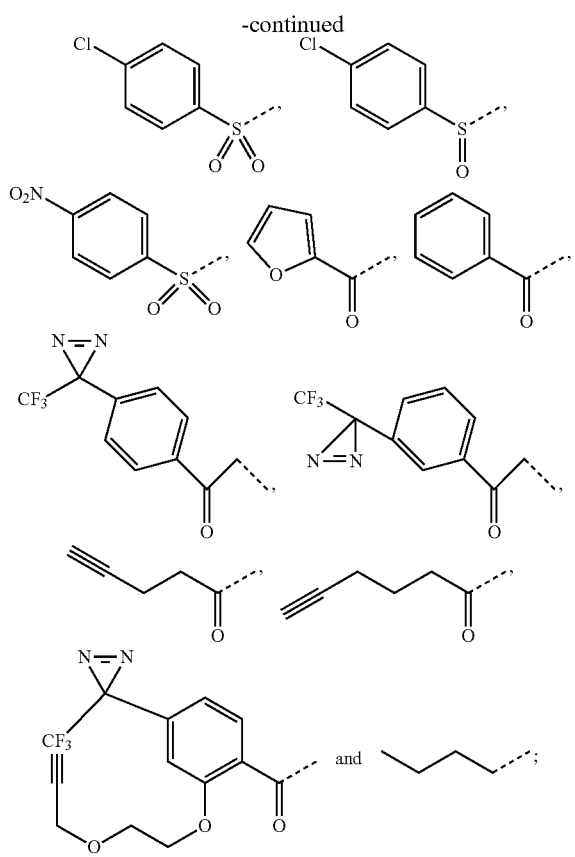
(vi) $R_4$ is selected from H,
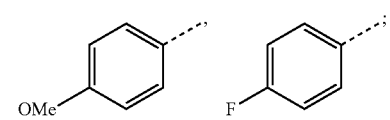
and
(vii) $R_5$ is selected from
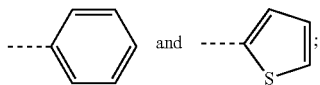
and
(viii) $R_6$ is selected from $CH_3$,
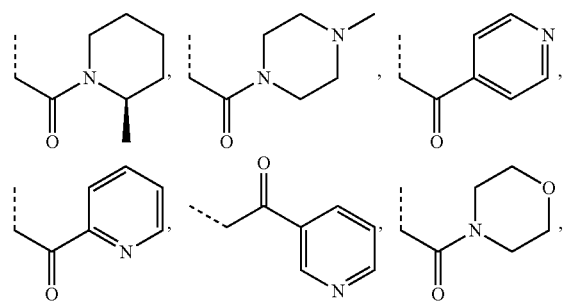
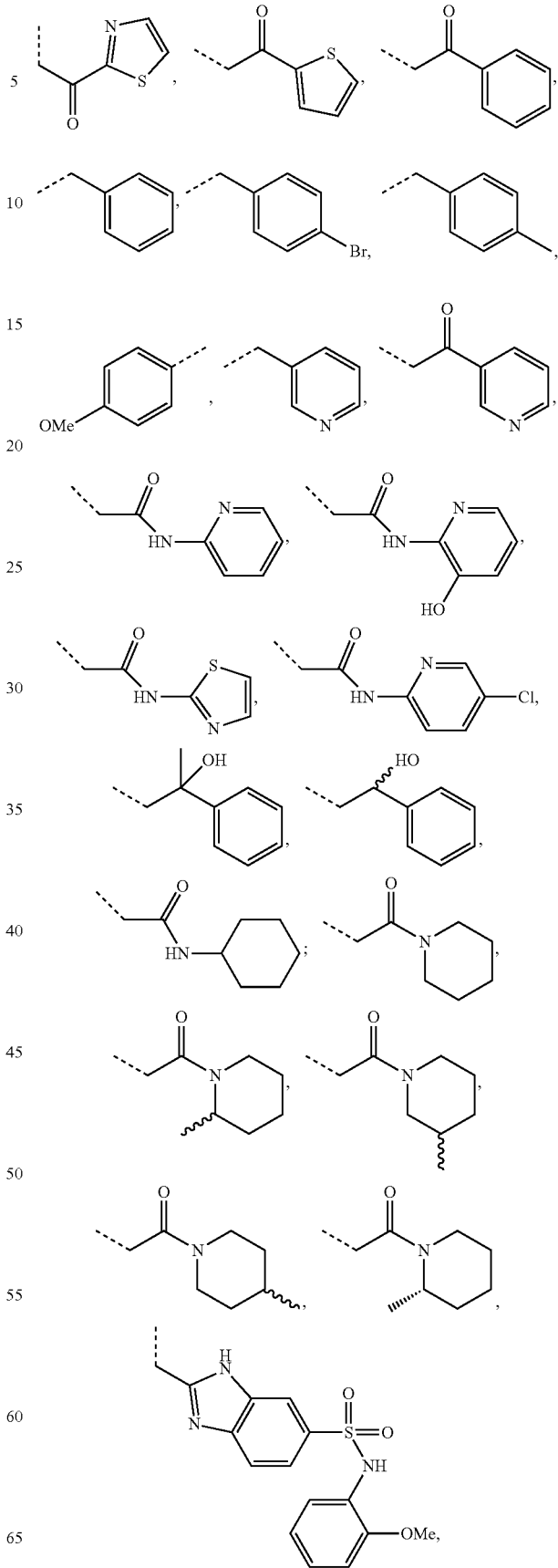

-continued
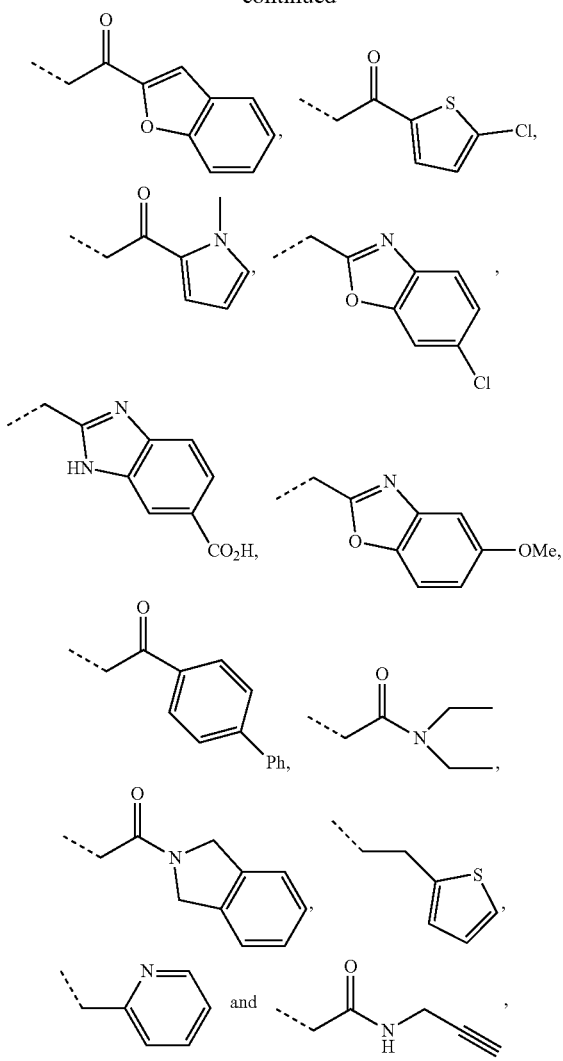
where
  so long as when X is
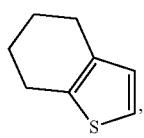
$R_2$ is
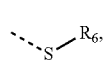
$R_6$ is
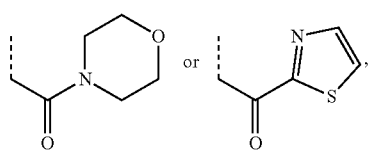
then $R_1$ is not
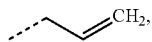
and
  so long as when X is
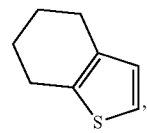
$R_2$ is
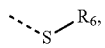
$R_6$ is
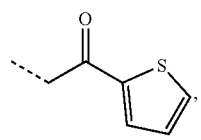
then $R_1$ is not
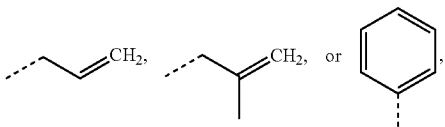
and
  so long as when X is
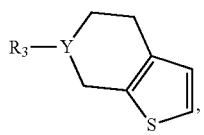
Y is C, $R_3$ is $CH_3$, $R_2$ is
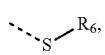
and $R_6$ is
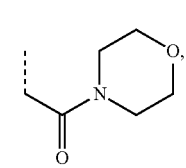

then R₁ is not

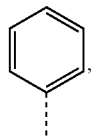

and
  so long as when X is

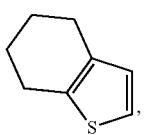

R₂ is

and R₆ is

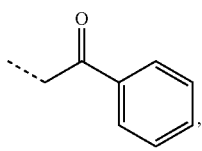

then R₁ is not

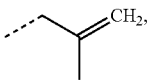

and
  so long as when X is

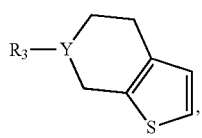

Y is C, R₃ is CH₃, R₂ is

and R₆ is

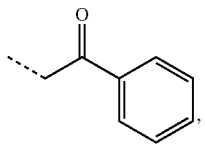

then R₁ is not

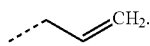

11. The kit of claim 4, wherein the device for administration of the compound or composition is a nebulizer.

12. A kit, comprising a first compound; and further comprising a second compound or composition having Hh signaling inhibition activity, PDE4 inhibition activity, anti-cancer or anti-tumor activity, anti-viral activity, anti-angiogenic activity, anti-metastatic activity, anti-heart failure activity, and/or anti-inflammation activity, or wherein the second compound or composition is useful for treating a condition of interest, wherein the first compound is of the formula

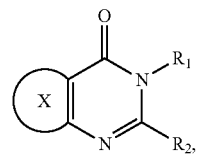

or a pharmaceutically-acceptable salt thereof, wherein
  (i) X is selected from

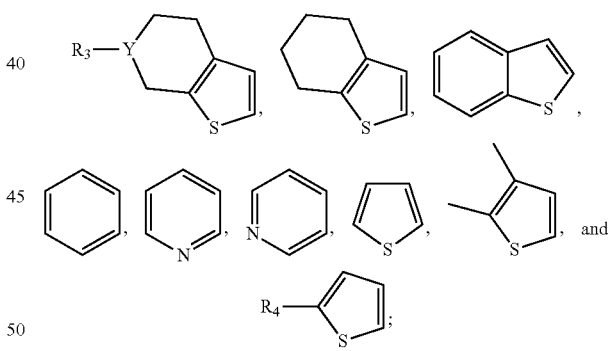

(ii) Y is selected from C, N, O, and S;
  (iii) R₁ is selected from H, CH₂CH₃ (CH₂)₂CH₃,

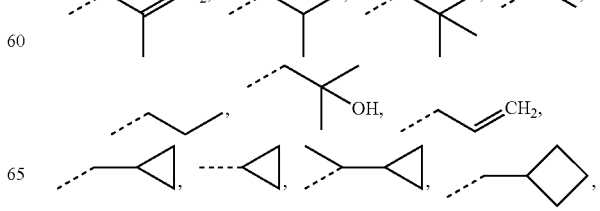

-continued
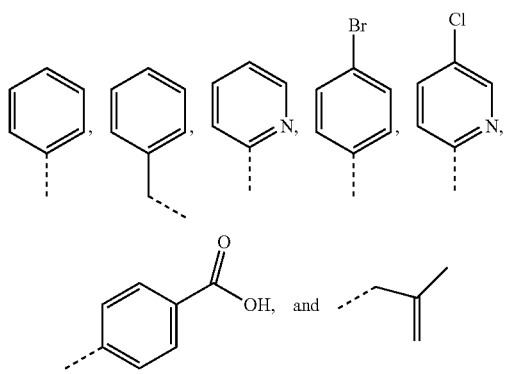
(iv) R₂ is selected from
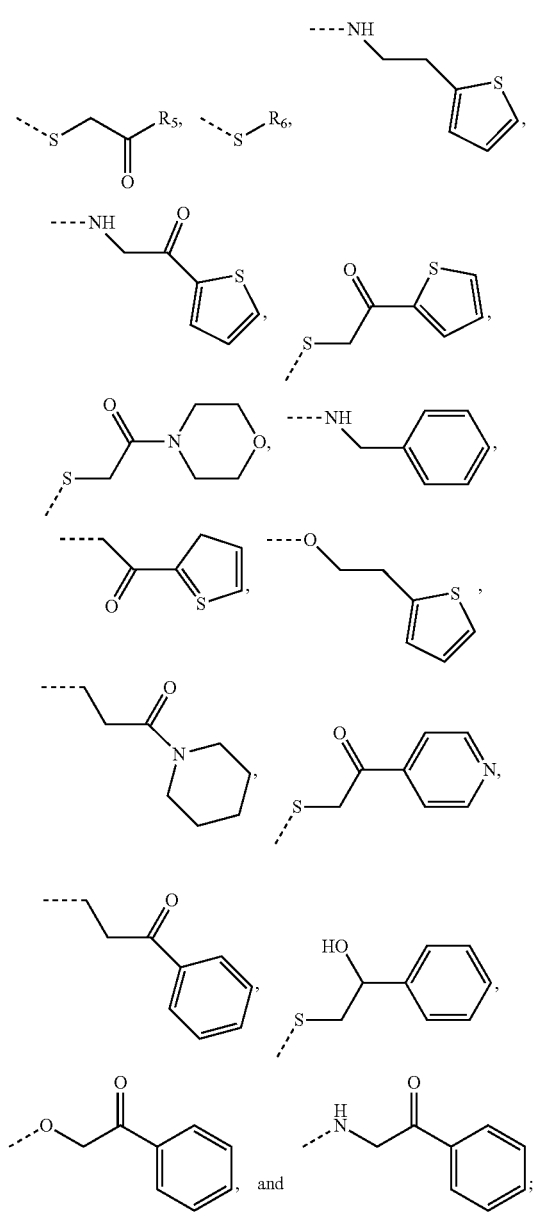
(v) R₃ is selected from H, CH₃,
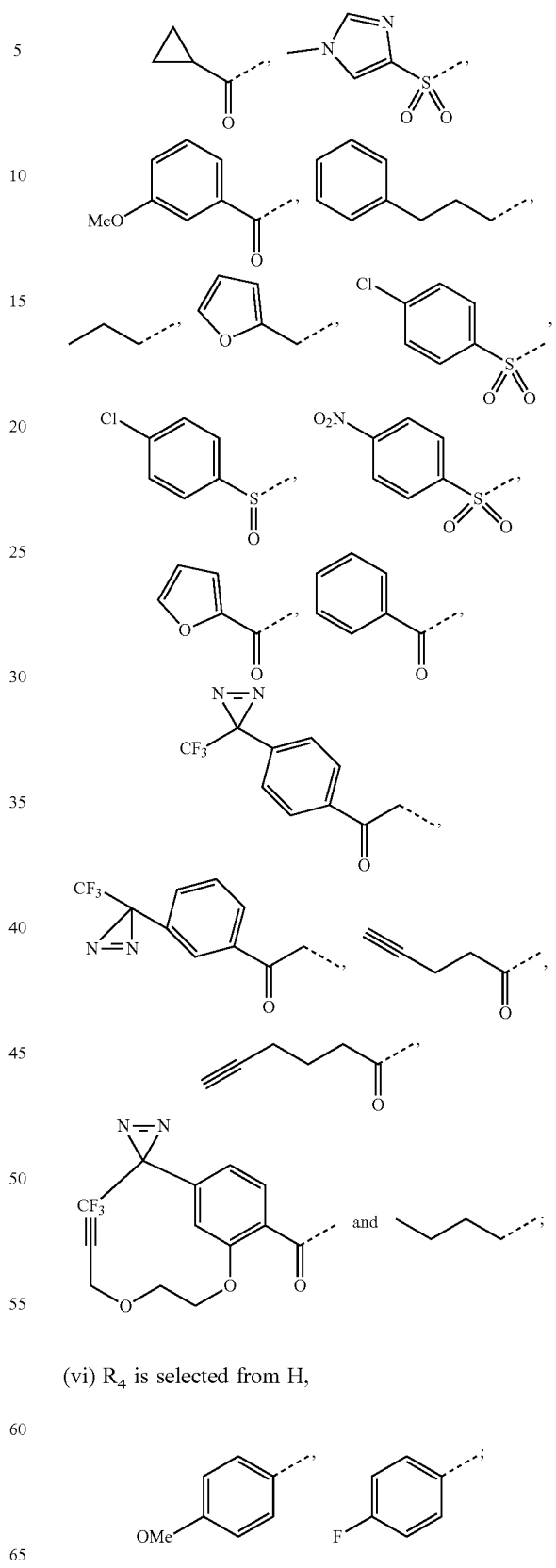
(vi) R₄ is selected from H,
and (vii) R₅ is selected from
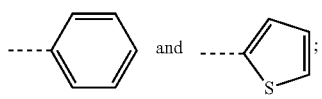
and
(viii) R₆ is selected from CH₃,
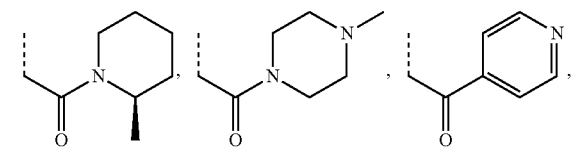
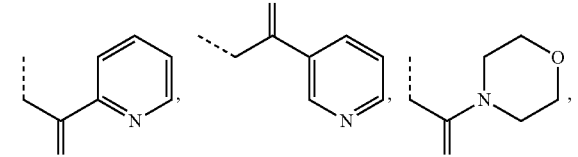
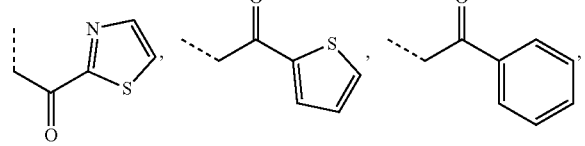
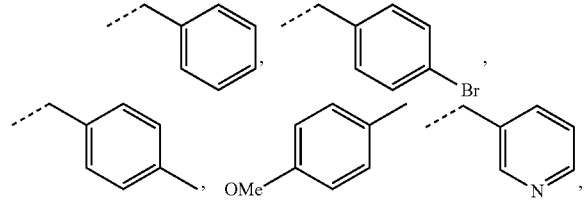
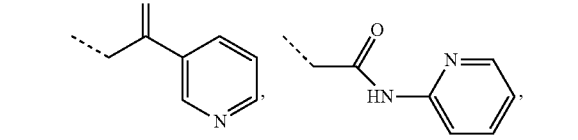
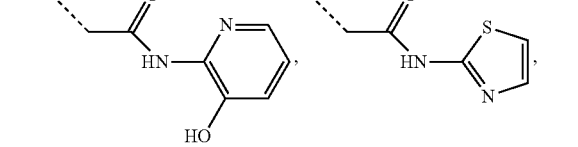
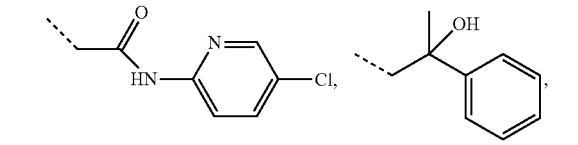
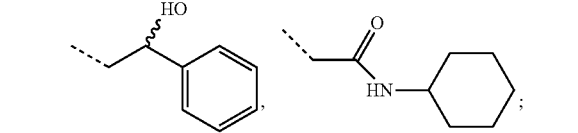
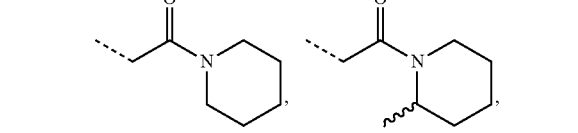
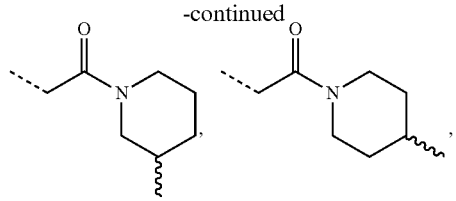
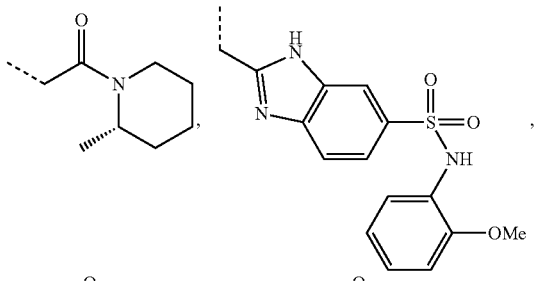
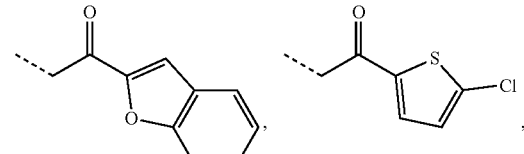
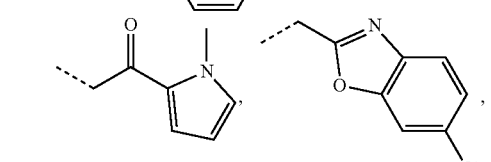
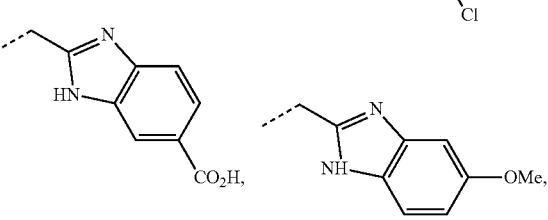
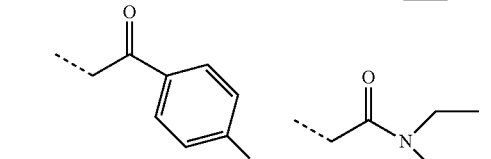
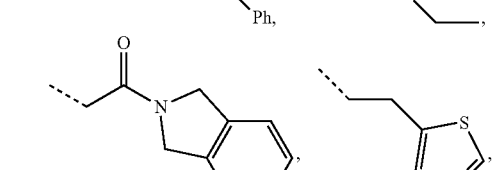
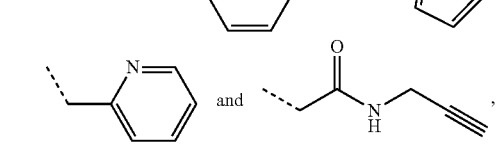
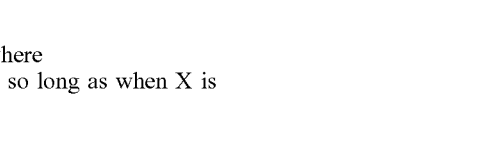
and 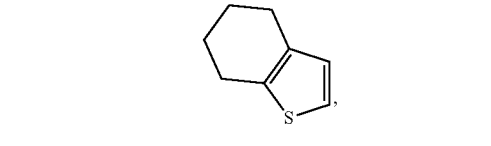,
where
so long as when X is
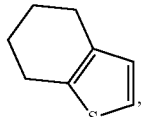

R₂ is
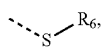
and R₆ is
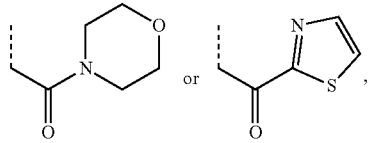
then R₁ is not
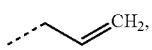
and
so long as when X is
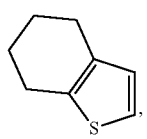
R₂ is
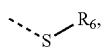
R₆ is
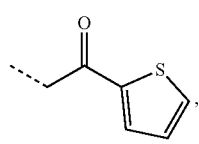
then R₁ is not
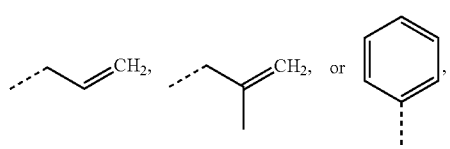
and
so long as when X is
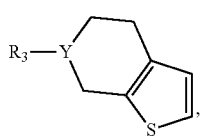
Y is C, R₃ is CH₃, R₂ is
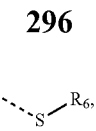
and R₆ is
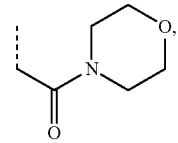
then R₁ is not
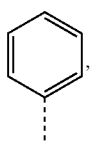
and
so long as when X is
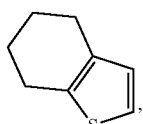
R₂ is
and R₆ is
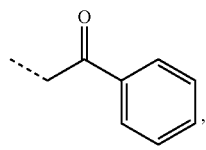
then R₁ is not
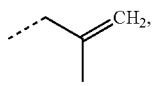
and
so long as when X is
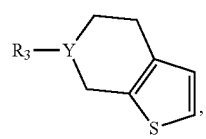
Y is C, R₃ is CH₃, R₂ is

and $R_6$ is
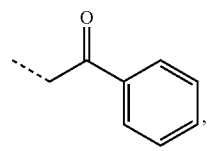
then $R_1$ is not
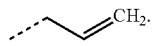
13. The kit of claim 12, and further comprising a device for administration of the compound or composition and/or a device for administration of the second compound or composition.
* * * * *